United States Patent
Wang et al.

(10) Patent No.: US 9,914,732 B2
(45) Date of Patent: Mar. 13, 2018

(54) DIAZABICYCLO[4.3.1]DECANE DERIVATIVES FOR TREATMENT OF PSYCHIATRIC DISORDERS

(71) Applicant: Max-Planck-Gesellschaft zur Forderung der Wissenschaften e.V., Munich (DE)

(72) Inventors: Yansong Wang, Sichaun (CN); Felix Hausch, Munich (DE); Matthias Bischoff, Munich (DE); Sebastian Pomplun, Munich (DE)

(73) Assignee: Max-Planck-Gesellschaft zur Forderung der Wissensc haften e.V., Munich (DE)

( * ) Notice: Subject to any disclaimer, the term of this patent is extended or adjusted under 35 U.S.C. 154(b) by 0 days.

(21) Appl. No.: 15/113,529

(22) PCT Filed: Jan. 26, 2015

(86) PCT No.: PCT/EP2015/000176
§ 371 (c)(1),
(2) Date: Jul. 22, 2016

(87) PCT Pub. No.: WO2015/110271
PCT Pub. Date: Jul. 30, 2015

(65) Prior Publication Data
US 2017/0002003 A1  Jan. 5, 2017

(30) Foreign Application Priority Data
Jan. 24, 2014  (EP) .................................... 14152567
Sep. 25, 2014  (EP) .................................... 14186483

(51) Int. Cl.
| | |
|---|---|
| *C07D 471/08* | (2006.01) |
| *A61K 31/551* | (2006.01) |
| *A61K 31/635* | (2006.01) |
| *A61K 45/06* | (2006.01) |
| *C07D 211/60* | (2006.01) |
| *C07D 303/36* | (2006.01) |

(52) U.S. Cl.
CPC .......... *C07D 471/08* (2013.01); *A61K 31/551* (2013.01); *A61K 31/635* (2013.01); *A61K 45/06* (2013.01); *C07D 211/60* (2013.01); *C07D 303/36* (2013.01)

(58) Field of Classification Search
CPC ............................. A61K 31/551; C07D 471/08
USPC .......................................... 540/500; 514/221
See application file for complete search history.

(56) References Cited

U.S. PATENT DOCUMENTS

| | | | |
|---|---|---|---|
| 6,630,472 B1 | 10/2003 | Katoh et al. | |
| 6,818,643 B1 | 11/2004 | Dubowchik et al. | |
| 9,371,322 B2 * | 6/2016 | Wang .................. | C07D 471/08 |

FOREIGN PATENT DOCUMENTS

WO   WO 2014/015993 A1 *  1/2014  ........... C07D 471/08

OTHER PUBLICATIONS

International Search Report for International Patent Application No. PCT/EP2015/000176 dated Mar. 20, 2015, 5 pages.
Written Opinion for International Patent Application No. PCT/EP2015/000176 dated Mar. 20, 2015, 4 pages.
Elisabeth B. Binder, The role of FKBP5, a co-chaperone of the glucocorticoid receptor in the pathogenesis and therapy of affective and anxiety disorders, Psychoneuroendocrinology (2009).
Galigniana, et al., Regulation of Glucocorticoid Response to Stress-Related Disorders by the Hsp90-binding immunophilin, Journal of Neurochemistry, 2012.
Li Ni, et al, FKBP51Promotes Assembly of the Hsp90 Chaperone Complex and Regulates Cancer Cells Androgen Receptor Signaling in Prostate, Mol. Cell. Biol. 2010, 30(5).
S Romano, et al., Role of FK506-binding protein 51 in the control of apoptosis of irradiated melanoma cells, Cell Death and Differentiation (2010) 17, 145-157.
Edwin R. Sanchez, Chaperoning steroidal physiology: Lessons from mouse genetic models of Hsp90 and its cochaperones, Center for Diabetes and Endocrine Research, Department of Physiology & Pharmacology, University of Toledo College of Medicine, 2011.
Manya Warrier, Role of FKBP51 and FKBP52 in Glucocorticoid Receptor Regulated Metabolism, The University of Toledo, Health Science Campus, Jul. 2008.

* cited by examiner

*Primary Examiner* — Charanjit Aulakh
(74) *Attorney, Agent, or Firm* — Amin, Turocy & Watson LLP

(57) ABSTRACT

The present invention relates to diazabicyclo[4.3.1]decane derivatives, pharmaceutically acceptable salts of these compounds and pharmaceutical compositions containing at least one of these compounds together with pharmaceutically acceptable carrier, excipient and/or diluents. Said diazabicyclo[4.3.1]decane derivatives can be used for prophylaxis and/or treatment of psychiatric disorders and neurodegenerative diseases, disorders and conditions.

12 Claims, 4 Drawing Sheets

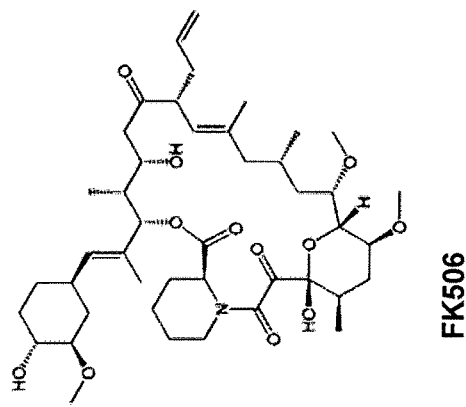
Figure 1 continued
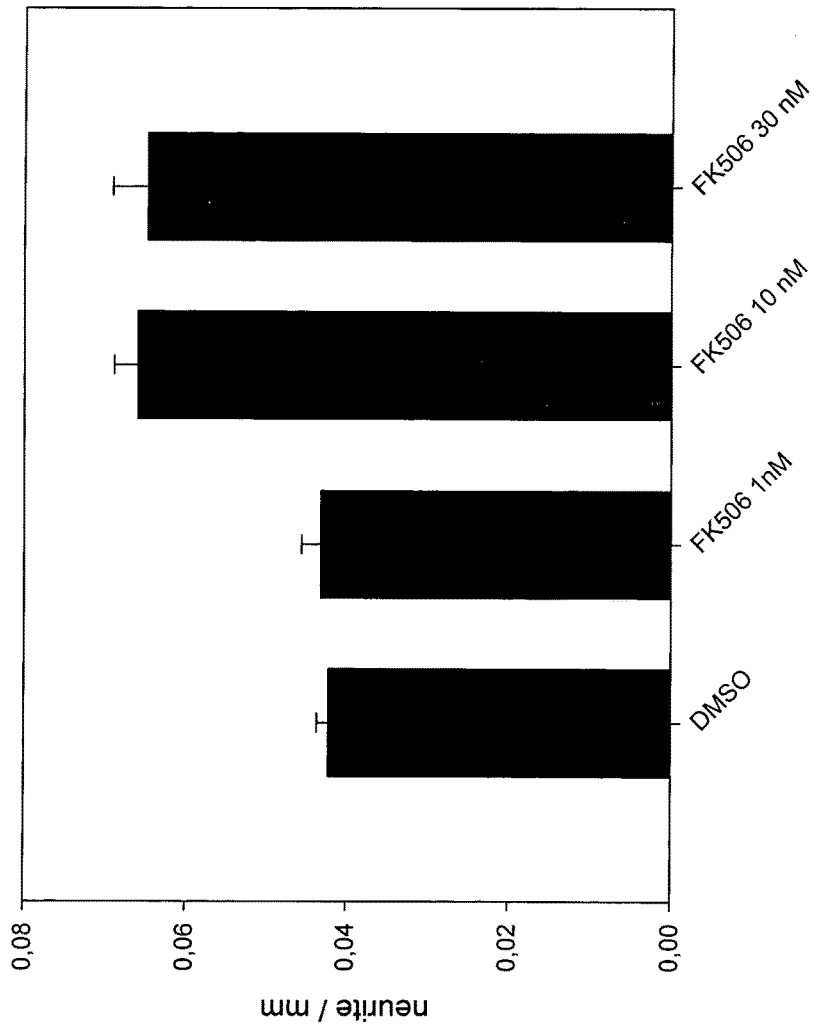

DIAZABICYCLO[4.3.1]DECANE DERIVATIVES FOR TREATMENT OF PSYCHIATRIC DISORDERS

The present invention relates to diazabicyclo[4.3.1]decane derivatives and stereoisomeric forms, solvates, hydrates and/or pharmaceutically acceptable salts of these compounds as well as pharmaceutical compositions containing at least one of these bicyclic aza-amides derivatives together with pharmaceutically acceptable carrier, excipient and/or diluents. Said diazabicyclo[4.3.1]decane derivatives have been identified as specific inhibitors of the FK506 binding proteins (FKBP's), especially FKBP51 and FKBP52, and are useful for the treatment of psychiatric disorders and neurodegenerative diseases, disorders and conditions, for treating vision disorders and/or improving vision; for treating memory impairment and/or enhancing memory performance, for treating alopecia and promoting hair growth, for treating metabolic disorders and obesity, or for treating prostate cancer or malignant melanoma.

BACKGROUND OF THE INVENTION

The FK506-binding protein (FKBP) family of immunophilins consists of proteins with a variety of protein-protein interaction domains and versatile cellular functions. This highly conserved protein family binds with immunosuppressive drugs, such as FK506 and rapamycin. This protein family displays peptidyl propyl isomerase (PPIase) activity as seen with cyclophilins and parvulins. FKBP12, a 12 kD protein is the most widely studied member of this family.

The immunosuppressant drugs FK506, rapamycin, and cyclosporin are well known as potent T-cell specific immunosuppressants, and are effective against autoimmunity, transplant or graft rejection, inflammation, allergic responses, other autoimmune or immune-mediated diseases, and infectious diseases.

FK506 and rapamycin apart from binding to FKBP12 also interact and inhibit calcineurin (CaN) and mTOR respectively thereby mediating their immunosuppressive action.

The high molecular weight multidomain homologs of FKBP12, FKBP51 and FKBP 52, act as cochaperones for the heat shock protein 90 (Hsp90) and modulate the signal transduction of the glucocorticoid receptor, by participating in the Heat shock protein 90 (Hsp90)-steroid receptor complex.

In this complex, FKBP51 and FKBP52 modulate the binding competence and signalling of steroid hormone receptors and thereby regulate the cellular responsiveness to circulating hormone levels. This is supported by a natural animal model (squirrel monkey) and by knockout mice, where the crucial role of FKBP51 and FKBP52 on the Glucocorticoid Receptor (GR) Progesterone Receptor (PR) or Androgen Receptor (AR) activity have been clearly demonstrated. Moreover, polymorphisms in the FKBP51-encoding gene of psychiatric patients have been associated with numerous stress-related psychiatric disorders (Schmidt et al., ChemMedChem 2012, 7, 1351-1359).

The immunosuppressive compounds disclosed in the prior art suppress the immune system, by definition, and also exhibit other toxic side effects. Accordingly, there is a need for non-immunosuppressant, small molecule compounds, and compositions and methods for use of such compounds, that are useful in treating psychiatric disorders and neurodegenerative diseases, disorders and conditions.

Further studies led to α-ketoamide analogs of FK506 devoid of immunosuppressive activity. So far there has been only few investigations on the activity of monocyclic, pipecolate or proline-based compounds concerning the larger FKBP's (FKBP51 and 52).

Also, the main physiological role of FKBP51 is believed to be the inhibition of glucocorticoid receptor signaling, especially in stressful situations. However, the FKBP51-GR interplay (glucocorticoid receptor interplay) has been difficult to assess pharmacologically, largely due to lack of appropriate chemical probes.

Therefore, it is the object of the present invention to provide compounds and/or pharmaceutically acceptable salts thereof which inhibit FKBP 51 and/or FKBP 52 more effectively based on significantly increased affinity to FKBP 51 and/or FKBP 52.

Another aspect of the invention is to provide compounds and/or pharmaceutically acceptable salts thereof which can be used as pharmaceutically active agents, especially for the treatment of psychiatric disorders and neurodegenerative diseases, disorders and conditions, for treating vision disorders and/or improving vision; for treating memory impairment and/or enhancing memory performance and for treating alopecia, as well as compositions comprising at least one of those compounds and/or pharmaceutically acceptable salts thereof as pharmaceutically active ingredients.

A further aspect of the invention is to provide methods for preparing said compounds.

The object of the present invention is solved by the teaching of the independent claims. Further advantageous features, aspects and details of the invention are evident from the dependent claims, the description, and the examples of the present application.

DESCRIPTION OF THE INVENTION

Thus the present invention relates to the compound of the general formula (I):

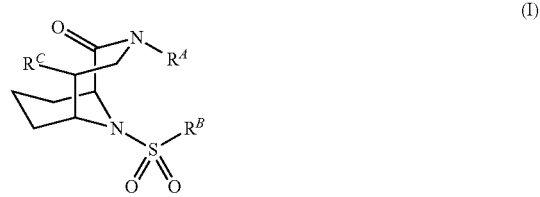

(I)

wherein
$R^A$ represents —H, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_7$H$_{15}$, —C$_8$H$_{17}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —CH$_2$OH, —C$_2$H$_4$OH, —C$_3$H$_6$OH, —C$_4$H$_8$OH, —CH(CH$_3$)—C$_2$H$_4$OH, —C$_5$H$_{10}$OH, —CH$_2$OCH$_3$, —C$_2$H$_4$OCH$_3$, —C$_3$H$_6$OCH$_3$, —C$_4$H$_8$OCH$_3$, —CH(CH$_3$)—C$_2$H$_4$OCH$_3$, —C$_5$H$_{10}$OCH$_3$, —CH$_2$NH$_2$, —C$_2$H$_4$NH$_2$, —C$_3$H$_6$NH$_2$, —C$_4$H$_8$NH$_2$, —CH(CH$_3$)—C$_2$H$_4$NH$_2$, —C$_5$H$_{10}$NH$_2$, —C$_2$H$_4$NHCH$_3$, —C$_2$H$_4$N(CH$_3$)$_2$, —C$_2$H$_4$N(CH$_3$)$_2$, —C$_2$H$_4$NHCH(CH$_3$)$_2$, —C$_2$H$_4$NH(CH$_2$CH$_3$), —C$_2$H$_4$N(CH$_2$CH$_3$)$_2$, —CH═CH$_2$, —CH₂—CH=CH₂, —C(CH₃)=CH₂, —CH=CH—CH₃, —C₂H₄—CH=CH₂, —CH₂—CH=CH—CH₃, —CH=CH—C₂H₅, —CH₂—C(CH₃)=CH₂, —CH(CH₃)—CH=CH, —CH=C(CH₃)₂, —C(CH₃)=CH—CH₃, —C₃H₆—CH=CH₂, —C₂H₄—CH=CH—CH₃, —CH₂—CH=CH—C₂H₅, —CH=CH—C₃H₇, —CH₂—CH=CH—CH₂, —CH=CH—CH=CH—CH₃, —CH=CH—CH₂—CH=CH₂, —C(CH₃)=CH—CH=CH₂, —CH=C(CH₃)—CH=CH₂, —CH=CH—C(CH₃)=CH₂, —C₂H₄—C(CH₃)=CH₂, —CH₂—CH(CH₃)—CH=CH₂, —CH(CH₃)—CH₂—CH=CH₂, —CH₂—CH=C(CH₃)₂, —CH₂—C(CH₃)=CH—CH₃, —CH(CH₃)—CH=CH—CH₃, —CH=CH—CH(CH₃)₂, —CH=C(CH₃)—C₂H₅, —C(CH₃)=CH—C₂H₅, —C(CH₃)=C(CH₃)₂, —C(CH₃)₂—CH=CH₂, —CH(CH₃)—C(CH₃)=CH₂, —C(CH₃)=CH—CH=CH₂, —CH=C(CH₃)—CH=CH₂, —CH=CH—C(CH₃)=CH₂, —C₄H₈—CH=CH₂, —C₃H₆—CH=CH—CH₃, —C₂H₄—CH=CH—C₂H₅, —CH₂—CH=CH—C₃H₇, —CH=CH—C₄H₉, —C₃H₆—C(CH₃)=CH₂, —C₂H₄—CH(CH₃)—CH=CH₂, —CH₂—CH(CH₃)—CH₂—CH=CH₂, —C₂H₄—CH=C(CH₃)₂, —CH(CH₃)—C₂H₄—CH=CH₂, —C₂H₄—C(CH₃)=CH—CH₃, —CH₂—CH(CH₃)—CH=CH—CH₃, —CH (CH₃)—CH₂—CH=CH—CH₃, —CH₂—CH=CH—CH(CH₃)₂, —CH₂—CH=C(CH₃)—C₂H₅, —CH₂—C(CH₃)=CH—C₂H₅, —CH(CH₃)—CH=CH—C₂H₅, —CH=CH—CH₂—CH(CH₃)₂, —CH=CH—CH(CH₃)—C₂H₅, —CH=C(CH₃)—C₃H₇, —C(CH₃)=CH—C₃H₇, —CH₂—CH(CH₃)—C(CH₃)=CH₂, —C[C(CH₃)₃]=CH₂, —CH(CH₃)—CH₂—C(CH₃)=CH₂, —CH(CH₃)—CH (CH₃)—CH=CH₂, —CH=CH—C₂H₄—CH=CH₂, —CH₂—C(CH₃)₂—CH=CH₂, —C(CH₃)₂—CH₂—CH=CH₂, —CH₂—C(CH₃)=C(CH₃)₂, —CH(CH₃)—CH=C(CH₃)₂, —C(CH₃)₂—CH=CH—CH₃, —CH=CH—CH₂—CH=CH—CH₃, —CH(CH₃)—C(CH₃)=CH—CH₃, —CH=C(CH₃)—CH(CH₃)₂, —C(CH₃)=CH—CH(CH₃)₂, —C(CH₃)=C(CH₃)—C₂H₅, —CH=CH—C(CH₃)₃, —C(CH₃)₂—C(CH₃)=CH₂, —CH(C₂H₅)—C(CH₃)=CH₂, —C(CH₃)(C₂H₅)—CH=CH₂, —CH(CH₃)—C(C₂H₅)=CH₂, —CH₂—C(C₃H₇)=CH₂, —CH₂—C(C₂H₅)=CH—CH₃, —CH(C₂H₅)—CH=CH—CH₃, —C(C₄H₉)=CH₂, —C(C₃H₇)=CH—CH₃, —C(C₂H₅)=CH—C₂H₅, —C(C₂H₅)=C(CH₃)₂, —C[CH(CH₃)(C₂H₅)]=CH₂, —C[CH₂—CH(CH₃)₂]=CH₂, —C₂H₄—CH=CH—CH₂, —CH₂—CH=CH—CH₂—CH=CH₂, —C₃H₆—C≡C—CH₃, —CH₂—CH=CH—CH=CH—CH₃, —CH=CH—CH=CH—C₂H₅, —CH₂—CH=CH—C(CH₃)=CH₂, —CH₂—CH=C(CH₃)—CH=CH₂, —CH₂—C(CH₃)=CH—CH=CH₂, —CH(CH₃)—CH₂—C≡CH, —CH(CH₃)—CH=CH—CH=CH₂, —CH=CH—CH₂—C(CH₃)=CH₂, —CH(CH₃)—C≡C—CH₃, —CH=CH—CH(CH₃)—CH=CH₂, —CH=C(CH₃)—CH₂—CH=CH₂, —C₂H₄—CH(CH₃)—C≡CH, —C(CH₃)=CH—CH₂—CH=CH₂, —CH=CH—CH=C(CH₃)₂, —CH₂—CH(CH₃)—CH₂—C≡CH, —CH=CH—C(CH₃)=CH—CH₃, —CH=C(CH₃)—CH=CH—CH₃, —CH₂—CH(CH₃)—C≡CH, —C(CH₃)=CH—CH=CH—CH₃, —CH=C(CH₃)—C(CH₃)=CH₂, —C(CH₃)=CH—C(CH₃)=CH₂, —C(CH₃)=C(CH₃)—CH=CH₂, —CH=CH—CH=CH—CH=CH₂, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —C₄H₈—C≡CH, —C₂H₄—C≡C—C₂H₅, —CH₂—C≡C—C₃H₇, —C≡C—C₄H₉, —C≡C—C(CH₃)₃, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —C≡C—CH₂—CH(CH₃)₂, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —CH₂-Ph, —CH₂-L₁-R^D,

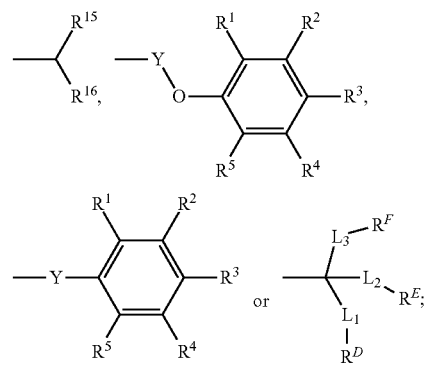

Y represents —CH₂—, —CH₂—CH₂—, —CH₂—CH₂—CH₂—, —CH=CH—, —CH=CH—CH₂—, —CH₂—CH=CH—, —CH(CH₃)—, —CH(CH₃)—CH₂—, —CH₂—CH(CH₃)—, —CH₂—CH(CH₃)—CH₂—, or —CH₂—O—CH₂—;

$R^D$ represents: $R^{22}$ or

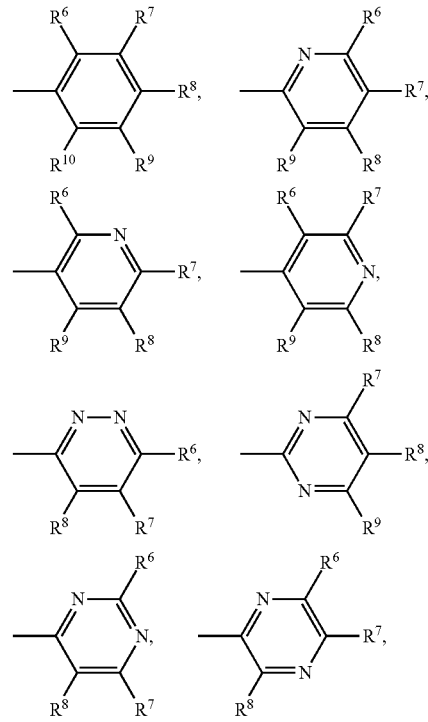

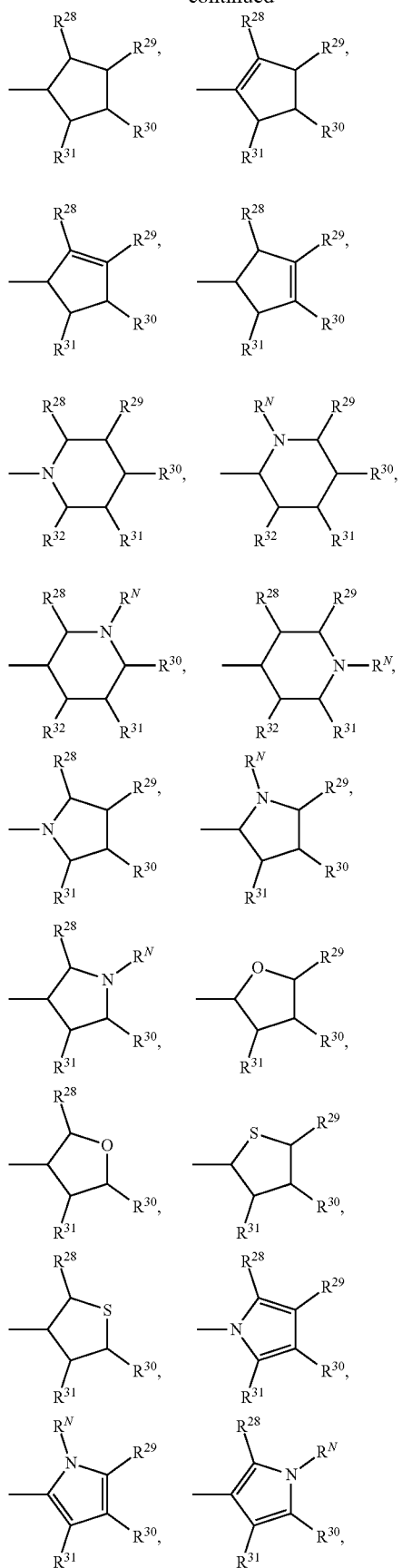
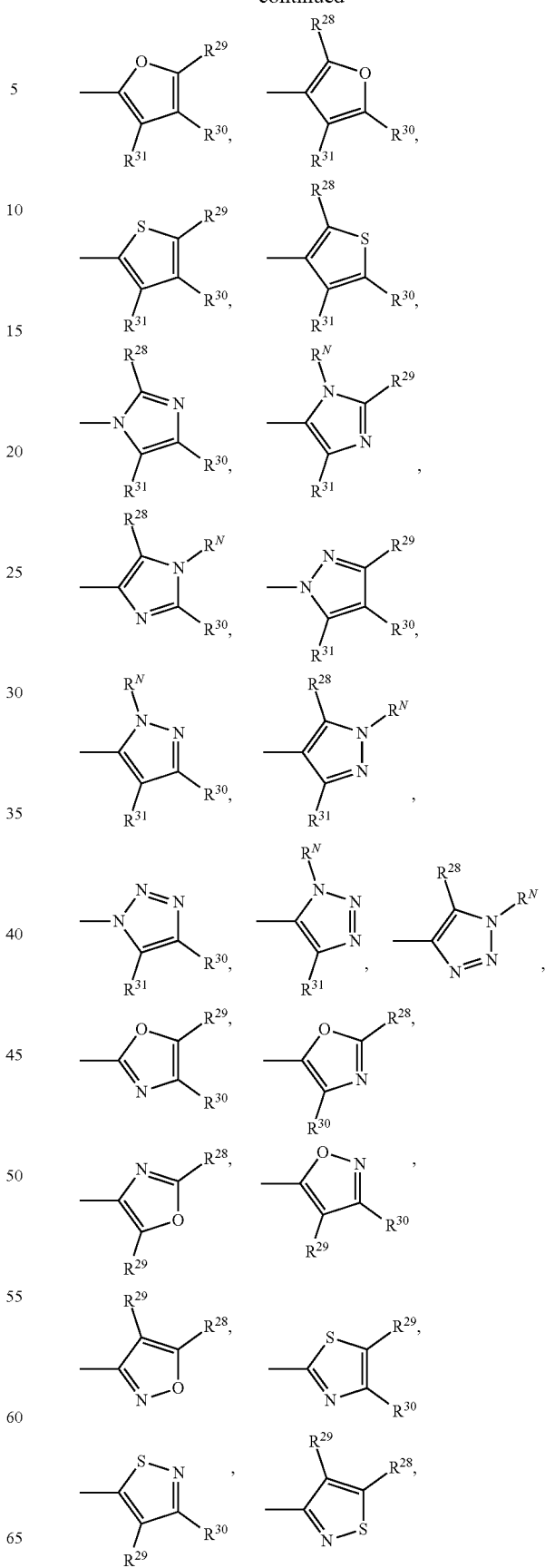

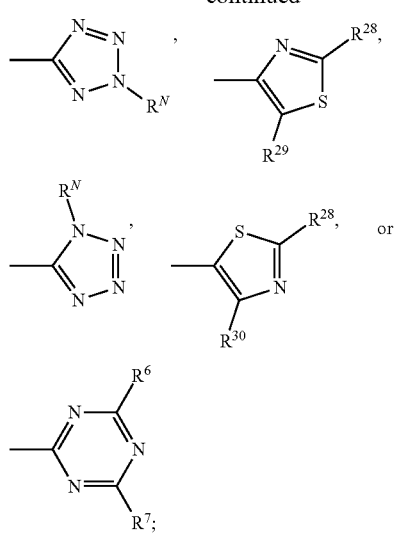
$R^E$ represents: $R^{23}$ or
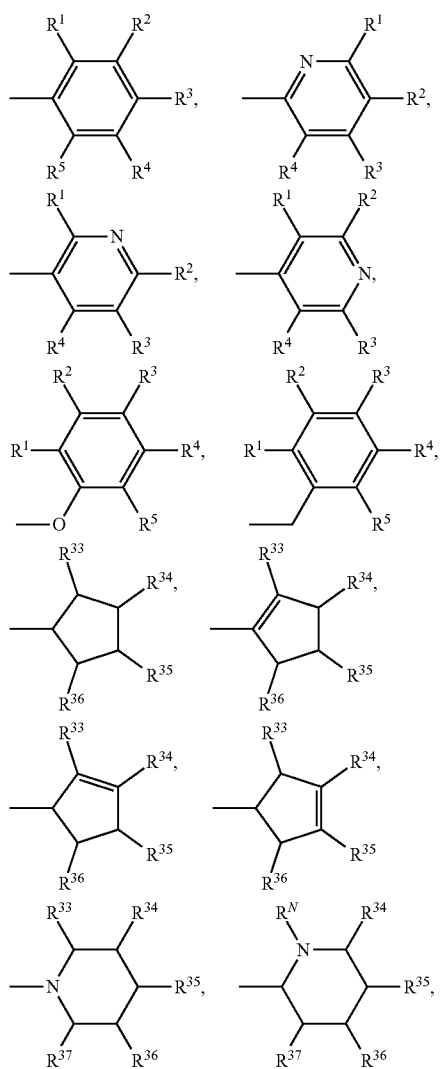
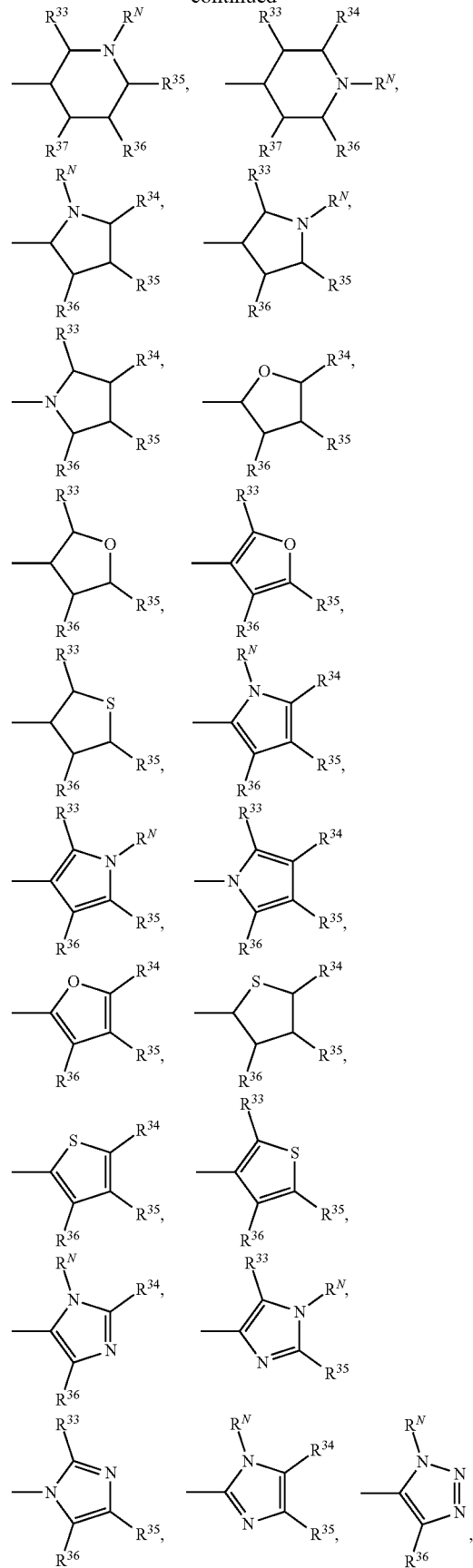

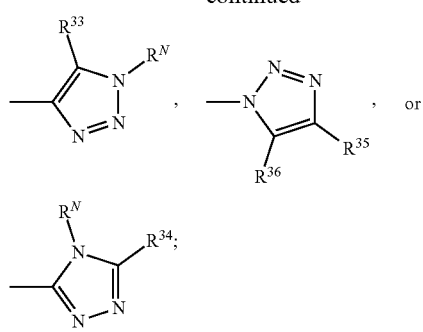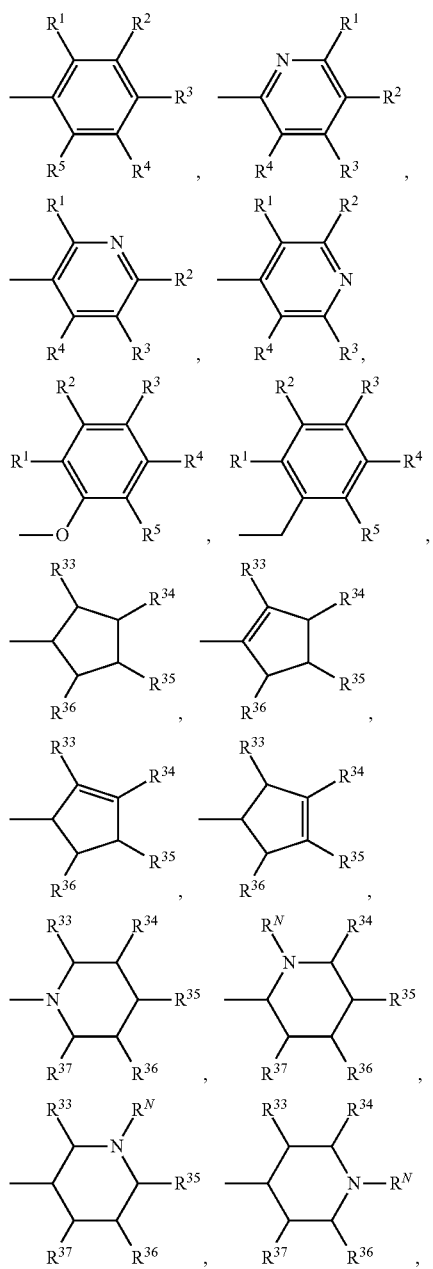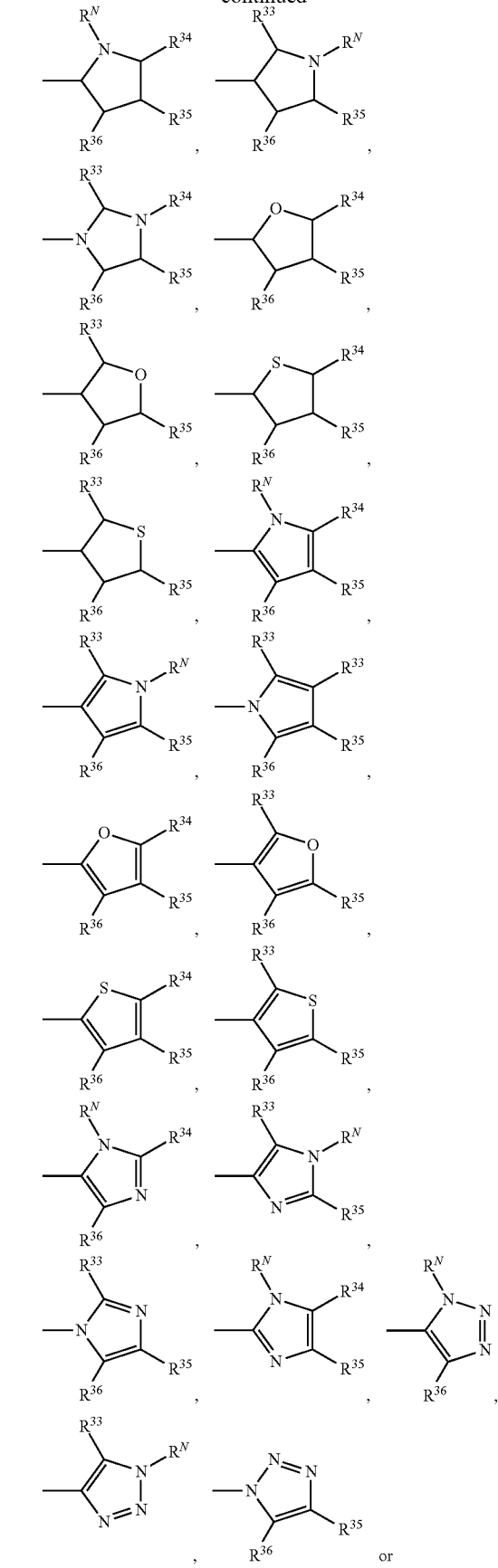

-continued

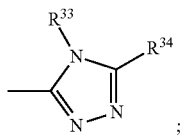

L₁, L₂ and L₃ represent independently of each other:
a bond, —CH₂—, —C₂H₄—, —C₃H₆—, —C₄H₈—, —C₅H₁₀—, —C₆H₁₂—, —C₇H₁₄—, —C₈H₁₆—, —C₉H₁₈—, —C₁₀H₂₀—, —CH(CH₃)—, —C[(CH₃)₂]—, —CH₂—CH(CH₃)—, —CH(CH₃)—CH₂—, —CH(CH₃)—C₂H₄—, —CH₂—CH(CH₃)—CH₂—, —C₂H₄—CH(CH₃)—, —CH₂—C[(CH₃)₂]—, —C[(CH₃)₂]—CH₂—, —CH(CH₃)—CH(CH₃)—, —C[(C₂H₅)(CH₃)]—, —CH(C₃H₇)—, —(CH₂)ₘO—, —(CH₂)ₚOCH₂—, —(CH₂—CH₂—O)ₙ—CH₂—CH₂—, —CH═CH—, —C(CH₃)═CH—, —CH═C(CH₃)—, —CH₂—CH═CH—, —CH₂—C(CH₃)═CH—, —CH₂—CH═C(CH₃)—, —CH═CH—CH₂—, —C(CH₃)═CH—CH₂—, —CH═C(CH₃)—CH₂—, —C(CH₃)═CH—C(CH₃)═CH—, —C₂H₄—CH═CH—CH═CH—, —CH₂—CH═CH—CH₂—CH═CH—, —C₃H₆—C≡C—CH₂—, —CH₂—CH═CH—CH═CH—CH₂—, —CH═CH—CH═CH—C₂H₄—, —CH₂—CH═CH—C(CH₃)═CH—, —CH₂—CH═C(CH₃)—CH═CH—, —CH₂—C(CH₃)═CH—CH═CH—, —CH(CH₃)—CH═CH—CH═CH—, —CH═CH—CH₂—C(CH₃)═CH—, —CH(CH₃)—C≡C—CH₂—, —CONH—, —NHCO—, —CH₂—CONH—, —CONH—CH₂—, —NHCO—CH₂—, —CH₂—NHCO—;
wherein n, m, p are independently an integer from 1 to 10;
or
L₁-R^D and L₂-R^E or L₁-R^D and L₃-R^F or L₂-R^E and L₃-R^F can form together a cyclic ring selected from the group consisting of:

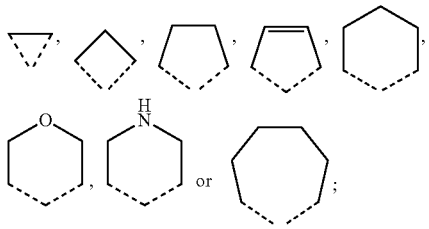

R^N represents —H, —CH₂—OCH₃, —C₂H₄—OCH₃, —C₃H₆—OCH₃, —CH₂—OC₂H₅, —C₂H₄—OC₂H₅, —C₃H₆—OC₂H₅, —CH₂—OC₃H₇, —C₂H₄—OC₃H₇, —C₃H₆—OC₃H₇, —CH₂—O-cyclo-C₃H₅, —C₂H₄—O-cyclo-C₃H₅, —C₃H₆—O-cyclo-C₃H₅, —CH₂—OCH(CH₃)₂, —C₂H₄—OCH(CH₃)₂, —C₃H₆—OCH(CH₃)₂, —CH₂—OC(CH₃)₃, —C₂H₄—OC(CH₃)₃, —C₃H₆—OC(CH₃)₃, —CH₂—OC₄H₉, —C₂H₄—OC₄H₉, —C₃H₆—OC₄H₉, —CH₂—OPh, —C₂H₄—OPh, —C₃H₆—OPh, —CH₂—OCH₂-Ph, —C₂H₄—OCH₂-Ph, —C₃H₆—OCH₂-Ph, —CHO, —COCH₃, —COC₂H₅, —COC₃H₇, —CO-cyclo-C₃H₅, —COCH(CH₃)₂, —COC(CH₃)₃, —COPh, —COCN, —COOCH₃, —COOC₂H₅, —COOC₃H₇, —COO-cyclo-C₃H₅, —COOCH(CH₃)₂, —COOC(CH₃)₃, —COCH₂Ph, —CONH₂, —CONHCH₃, —CONHC₂H₅, —CONHC₃H₇, —CONH-cyclo-C₃H₅, —CONH[CH(CH₃)₂], —CONH[C(CH₃)₃], —CON(CH₃)₂, —CON(C₂H₅)₂, —CON(C₃H₇)₂, —CON(cyclo-C₃H₅)₂, —CON[CH(CH₃)₂]₂, —CON[C(CH₃)₃]₂, —SO₂CH₃, —SO₂C₂H₅, —SO₂CH₂Ph, —SO₂C₃H₇, —SO₂-cyclo-C₃H₅, —SO₂CH(CH₃)₂, —SO₂C(CH₃)₃, —SO₂Ph, —CH₂—OCF₃, —C₂H₄—OCF₃, —C₃H₆—OCF₃, —OC₂F₅, —CH₂—OC₂F₅, —C₂H₄—OC₂F₅, —C₃H₆—OC₂F₅, —CH₂F, —CHF₂, —CF₃, —CH₂Cl, —CH₂Br, —CH₂I, —CH₂F, —CH₂—CHF₂, —CH₂—CF₃, —CH₂—CH₂Cl, —CH₂—CH₂Br, —CH₂—CH₂I, -cyclo-C₈H₁₅, -Ph, —CH₂-Ph, —CH₂—CH₂-Ph, —CH═CH-Ph, —CPh₃, —CH₃, —C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₇H₁₅, —C₈H₁₇, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —CH═CH₂, —CH₂—CH═CH₂, —C(CH₃)═CH₂, —CH═CH—CH₃, —C₂H₄—CH═CH₂, —CH₂—CH═CH—CH₃, —CH═CH—C₂H₅, —CH₂—C(CH₃)═CH₂, —CH(CH₃)—CH═CH, —CH═C(CH₃)₂, —C(CH₃)═CH—CH₃, —CH═CH—CH═CH₂, —C₃H₆—CH═CH₂, —C₂H₄—CH═CH—CH₃, —CH₂—CH═CH—C₂H₅, —CH═CH—C₃H₇, —CH₂—CH═CH—CH₂, —CH═CH—CH═CH—CH₃, —CH═CH—CH₂—CH═CH₂, —C(CH₃)═CH—CH═CH₂, —CH═C(CH₃)—CH═CH₂, —CH═CH—C(CH₃)═CH₂, —C₂H₄—C(CH₃)═CH₂, —CH₂—CH(CH₃)—CH═CH₂, —CH(CH₃)—CH₂—CH═CH₂, —CH₂—CH═C(CH₃)₂, —CH₂—C(CH₃)═CH—CH₃, —CH(CH₃)—CH═CH—CH₃, —CH═CH—CH(CH₃)₂, —CH═C(CH₃)—C₂H₅, —C(CH₃)═CH—C₂H₅, —C(CH₃)═C(CH₃)₂, —C(CH₃)₂—CH═CH₂, —CH(CH₃)—C(CH₃)═CH₂, —C(CH₃)═CH—CH₂, —CH═C(CH₃)—CH═CH₂, —CH═CH—C(CH₃)═CH₂, —C₄H₈—CH═CH₂, —C₃H₆—CH═CH—CH₃, —C₂H₄—CH═CH—C₂H₅, —CH₂—CH═CH—C₃H₇, —CH₂—CH(CH₃)—CH═CH₂, —CH═CH—C₄H₉, —C₃H₆—C(CH₃)═CH₂, —C₂H₄—CH(CH₃)—CH═CH₂, —C₂H₄—CH═C(CH₃)₂, —CH(CH₃)—C₂H₄—CH═CH₂, —C₂H₄—C(CH₃)═CH—CH₃, —CH₂—CH(CH₃)—CH═CH—CH₃, —CH₂—CH═CH—CH(CH₃)₂, —CH(CH₃)—CH═CH—CH₃, —CH₂—CH═CH—CH═CH—CH(CH₃)₂, —CH₂—CH═C(CH₃)—C₂H₅, —CH₂—C(CH₃)═CH—C₂H₅, —CH(CH₃)—CH═CH—C₂H₅, —CH═CH—CH₂—CH(CH₃)₂, —CH═CH—CH(CH₃)—C₂H₅, —CH₂—CH(CH₃)—C(CH₃)═CH₂, —CH═C(CH₃)—C₃H₇, —C(CH₃)═CH—C₃H₇, —C[C(CH₃)₃]═CH₂, —CH(CH₃)—CH₂—C(CH₃)═CH₂, —CH(CH₃)—CH(CH₃)—CH═CH₂, —CH═CH—C₂H₄—CH═CH₂, —CH₂—C(CH₃)₂—CH═CH₂, —C(CH₃)₂—CH₂—CH═CH₂, —CH₂—C(CH₃)═C(CH₃)₂, —CH(CH₃)—CH═C(CH₃)₂, —C(CH₃)₂—CH═CH—CH₃, —CH═CH—CH₂—CH═CH—CH₃, —CH(CH₃)—C(CH₃)═CH—CH₃, —CH═C(CH₃)—CH(CH₃)₂, —C(CH₃)═CH—CH(CH₃)₂, —C(CH₃)═C(CH₃)—C₂H₅, —CH═CH—C(CH₃)₃, —C(CH₃)₂—C(CH₃)═CH₂, —CH(C₂H₅)—C(CH₃)═CH₂, —C(CH₃)(C₂H₅)—CH═CH₂, —CH(CH₃)—C(C₂H₅)═CH₂, —CH₂—C(C₃H₇)═CH₂, —CH₂—C(C₂H₅)═CH—CH₃, —CH(C₂H₅)—CH═CH—CH₃, —C(C₄H₉)═CH₂, —C(C₃H₇)═CH—CH₃, —C(C₂H₅)═CH—C₂H₅, —C(C₂H₅)═C(CH₃)₂, —C[CH(CH₃)(C₂H₅)]═CH₂, —C[CH₂—CH(CH₃)₂]═CH₂, —C₂H₄—CH═CH—CH═CH₂, —CH₂—CH═CH—CH₂—CH═CH₂, —C₃H₆—C≡C—CH₃, —CH₂—

—CH═CH—CH═CH—CH₃, —CH═CH—CH═CH—C₂H₅, —CH₂—CH═CH—C(CH₃)═CH₂, —CH₂—CH═C(CH₃)—CH═CH₂, —CH₂—C(CH₃)═CH—CH═CH₂, —CH(CH₃)—CH₂—C≡CH, —CH(CH₃)—CH═CH—CH═CH₂, —CH═CH—CH₂—C(CH₃)═CH₂, —CH═C—C═C—CH₃, —CH═CH—CH(CH₃)—CH═CH₂, —CH═C(CH₃)—CH₂—CH═CH₂, —C₂H₄—CH(CH₃)—C≡CH, —C(CH₃)═CH—CH₂—CH═CH₂, —CH₂—C═C—C₂H₅, —CH═CH—CH═C(CH₃)₂, —CH₂—CH(CH₃)—CH₂—C≡CH, —C₂H₄—C≡C—CH₃, —CH═CH—C(CH₃)═CH—CH₃, —CH═C(CH₃)—CH═CH—CH₃, —CH₂—CH(CH₃)—C≡CH, —C(CH₃)═CH—CH═CH—CH₃, —CH═C(CH₃)—C(CH₃)═CH₂, —C(CH₃)═CH—C(CH₃)═CH₂, —C(CH₃)═C(CH₃)—CH═CH₂, —CH═CH—CH═CH—CH═CH₂, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C≡C—C₃H₇, —CH(CH₃)—C≡CH, —C₄H₈—C≡CH, —C₂H₄—C≡C—C₂H₅, —CH₂—C≡C—C₃H₇, —C≡C—C₄H₉, —C≡C—C(CH₃)₃, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —C≡C—CH₂—CH(CH₃)₂, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —CH₂—CH(C≡CH)₂, —C≡C—C≡CH, —CH₂—C≡C—C≡CH, —C≡C—C≡C—CH₃, —CH(C≡CH)₂, —C₂H₄—C≡C—C≡CH, —CH₂—C≡C—CH₂—C≡CH, —C≡C—C₂H₄—C≡CH, —CH₂—C≡C—C≡C—CH₃, —C≡C—CH₂—C≡C—CH₃, —C≡C—C≡C—C₂H₅, —C(C≡CH)₂—CH₃, —C≡C—CH(CH₃)—C≡CH, —CH(CH₃)—C≡C—C≡CH, —CH(C≡CH)—CH₂—C≡CH, or —CH(C≡CH)—C≡C—CH₃;

R^B represents

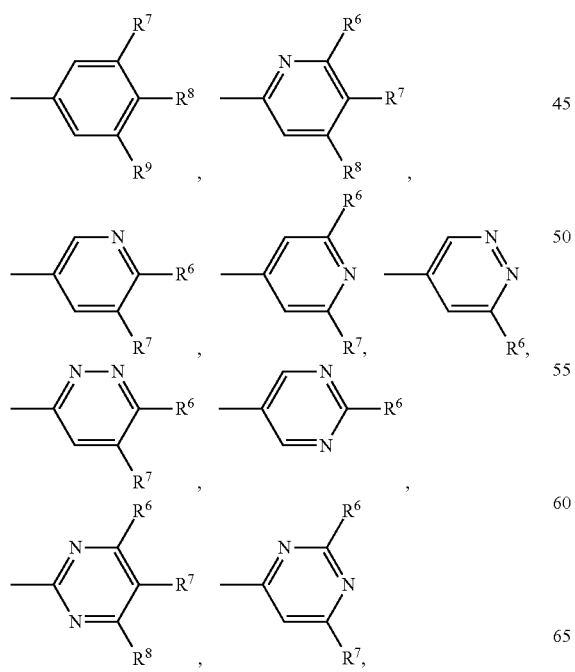

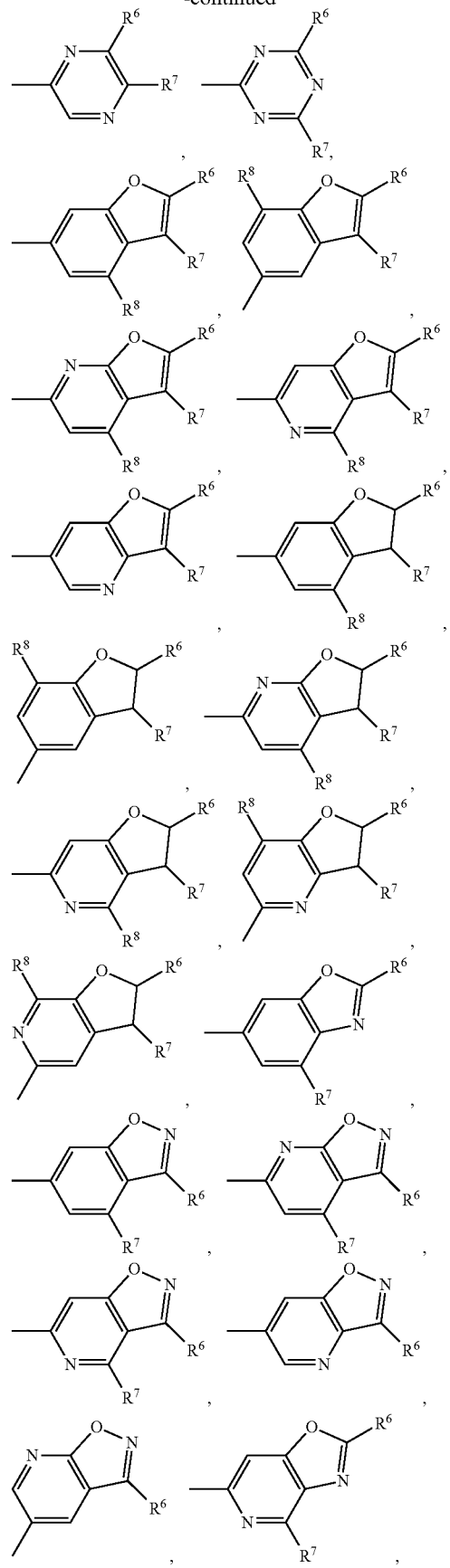

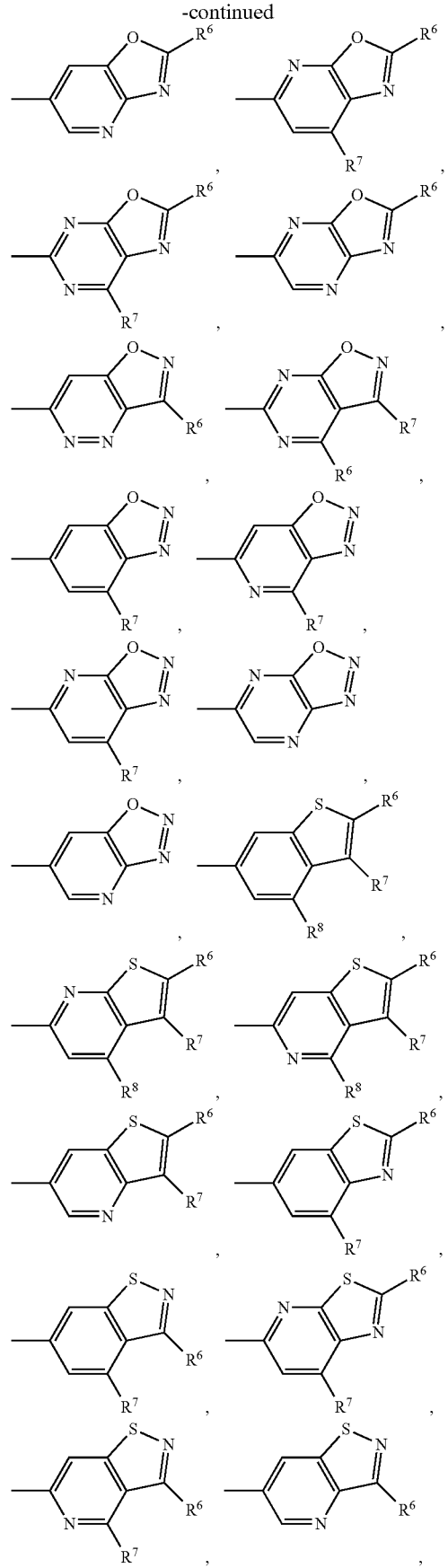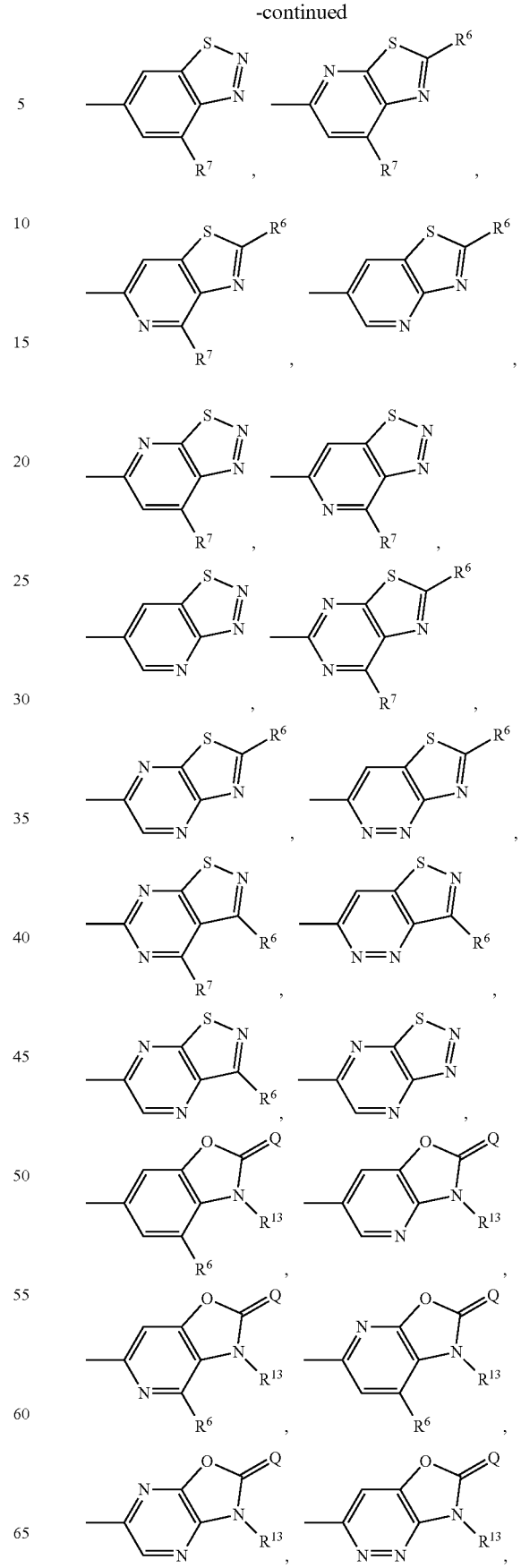

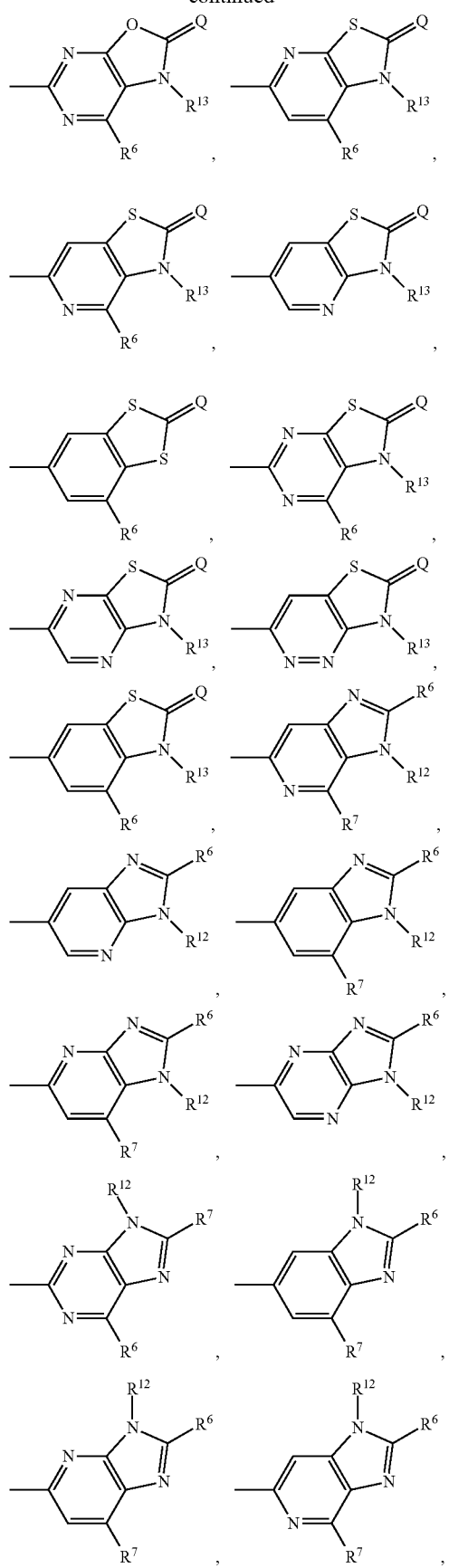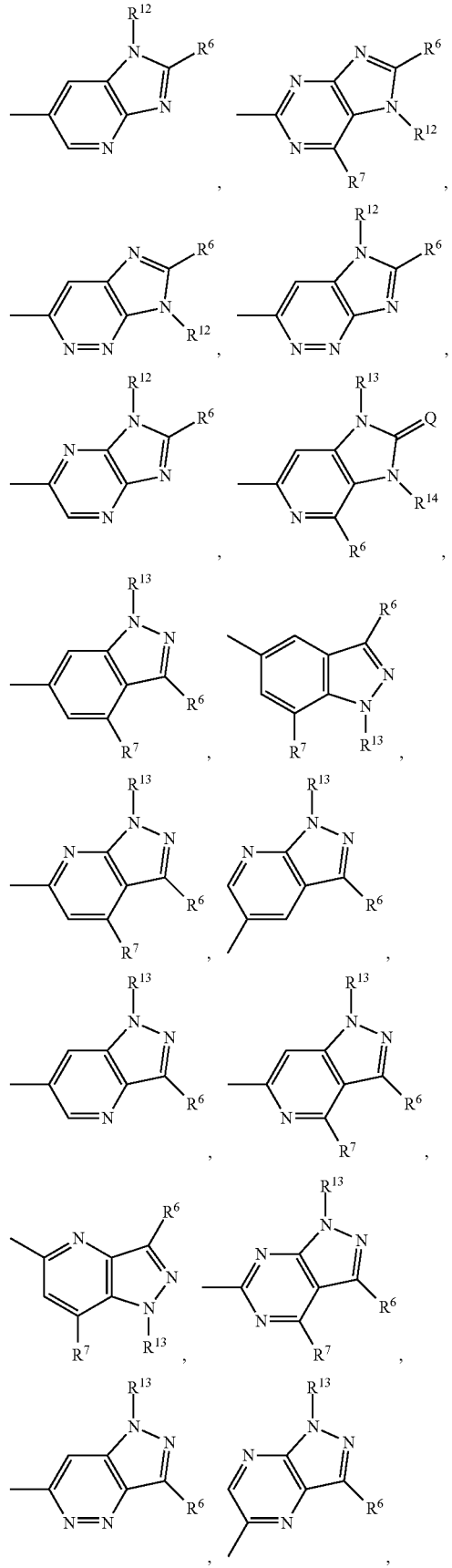

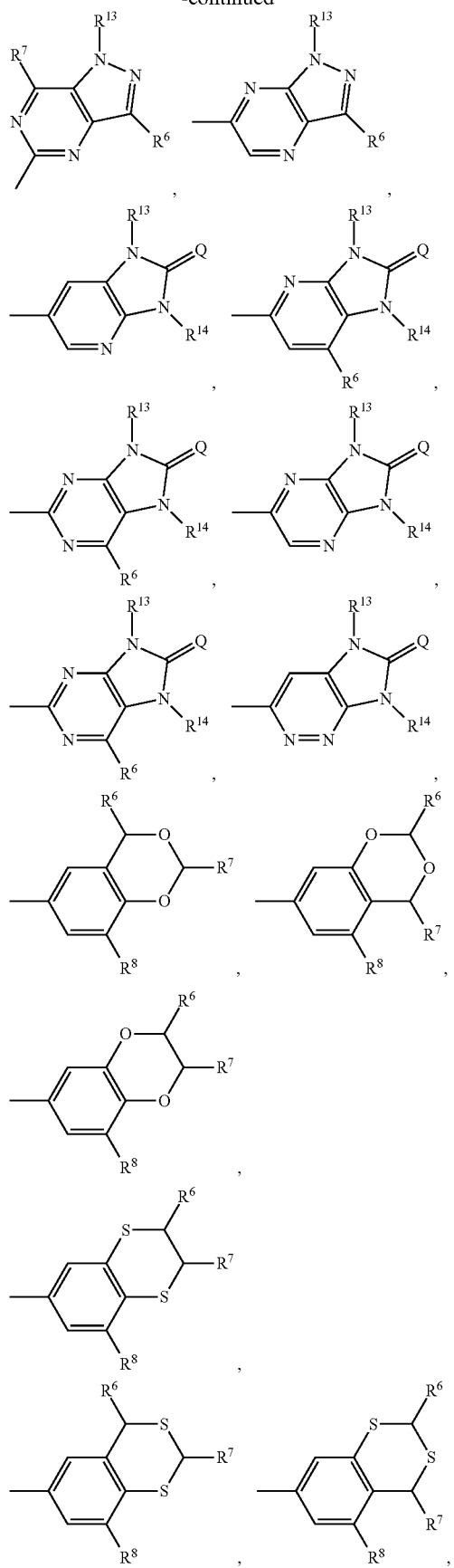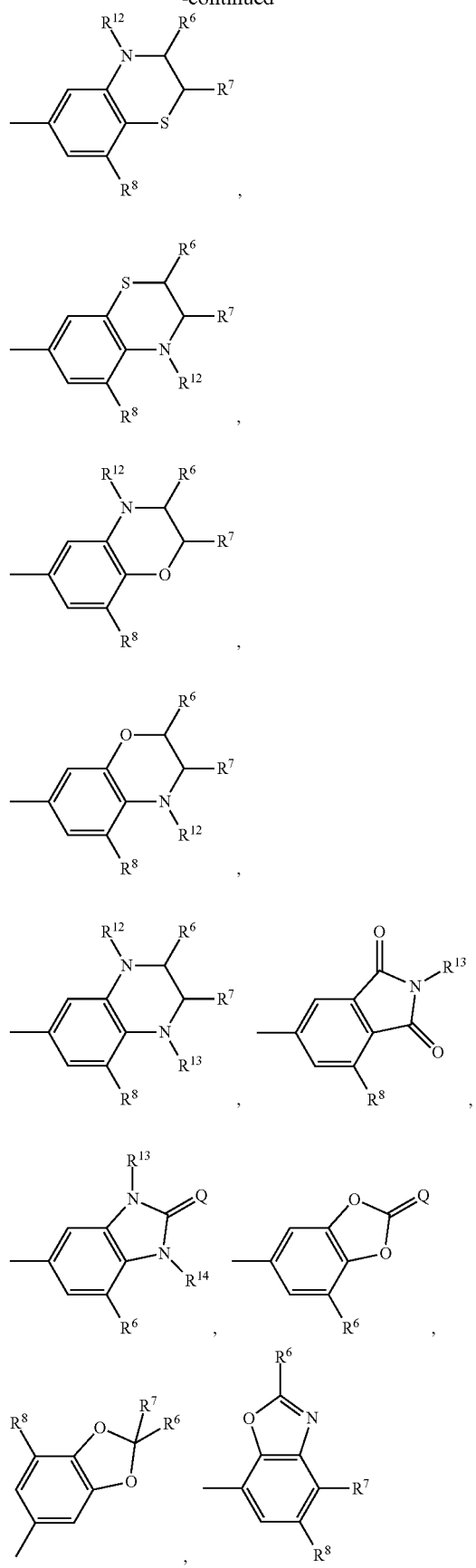

-continued

[Chemical structures showing various heterocyclic ring systems: benzoxazole, benzothiazole, thiazolopyridine, oxazolopyridine derivatives, benzimidazole, and methyl-substituted variants, with substituents R⁶, R⁷, R⁸, R⁹, R¹⁰]

Q represents =O, =S, or =N—R¹²;
$R^C$ represents —OH, —CH₂—OH, —CHO, —CH₂CHO, —CH₂CH₂CHO, —C₂H₄—OH, —C₃H₆—OH, —O—CH₃, —O—C₂H₅, —O—CH₂—OH, —O—CH(CH₃)₂, —O—CH₂—O—CH₃, —O—C₂H₄—O—CH₃, —CH₂—O—CH₃, —CH₂—O—CH₂—OH, —CH₂O—C₂H₅, —CH₂—O—CH(CH₃)₂, —CH₂—O—C₃H₇, —CO—CH₃, —CH₂—CO—CH₃, —CO—CH₂—OH, —CH(OH)—CH₃, —C(OH)(CH₃)₂, —CH(CH₃)CH₂OH, —CH(OH)—CH₂—OH, —CH₂—CH(OH)—CH₃, —CH₂—CH(OH)—CH₂—OH, —CH(OCH₃)—CH₂OH, —CH(OC₂H₅)—CH₂OH, —CH(OCH₃)—CH₂OCH₃, —CH(OC₂H₅)—CH₂OCH₃, —CH(OC₂H₅)—CH₂OC₂H₅, —CH(OAc)—CH₂OH, —CH(OAc)—CH₂OAc, —CH(OH)—CH₂OAc, —CH(OH)—CH₂—NH₂, —CH₂—CH(OH)—CH₂—NH₂, —CH(OCH₃)—CH₂—NH₂, —CH(OC₂H₅)—CH₂—NH₂, —CH₂—CH(OCH₃)—CH₂—NH₂, —CH₂—CH(OC₂H₅)—CH₂—NH₂, —CH(OH)—CH₂—NHCH₃, —CH(OH)—CH₂—NHC₂H₅, —CH₂—CH(OH)—CH₂—NHCH₃, —CO—C₃H₇, —CH₂—CH(OH)—CH₂—NHC₂H₅, —CH(OCH₃)—CH₂NHCH₃, —CO—C₂H₅, —CO—CH(CH₃)₂, —CH(OC₂H₅)—CH₂NHCH₃, —CH₂—CH(OCH₃)—CH₂—NHCH₃, —O—C₃H₇, —CH₂—CH(OC₂H₅)—CH₂—NHCH₃, —CH(OCH₃)—CH₂NHC₂H₅, —CH(OC₂H₅)—CH₂NHC₂H₅, —CH(OCH₃)—CH₂N(CH₃)₂, —CH(OC₂H₅)—CH₂N(CH₃)₂, —NH₂, —NHCH₃, —N(CH₃)₂, —CH₂—NH₂, —CH₂—NHCH₃, —CH₂—N(CH₃)₂, —C₂H₄—NH₂, —C₂H₄—NHCH₃, —C₂H₄—N(CH₃)₂, —CH(NHCH₃)CH₃, —CH(NHC₂H₅)CH₃, —CH(N(CH₃)₂)CH₃, —CH(N(C₂H₅)₂)CH₃, —CH(NH₂)CH₂OH, —CH(NHCH₃)CH₂OH, —CH(NHC₂H₅)CH₂OH, —CH(N(CH₃)₂)CH₂OH, —CH(N(C₂H₅)₂)CH₂OH, —CH(NH₂)CH₂OCH₃, —CH(NHCH₃)CH₂OCH₃, —CH(NHC₂H₅)CH₂OCH₃, —CH(N(CH₃)₂)CH₂OCH₃, —CH(N(C₂H₅)₂)CH₂OCH₃, —CH(NH₂)CH₂OC₂H₅, —CH(NHCH₃)CH₂OC₂H₅, —CH(NHC₂H₅)CH₂OC₂H₅, —CH(N(CH₃)₂)CH₂OC₂H₅, —CH(N(C₂H₅)₂)CH₂OC₂H₅, —CH(NH₂)CH₂OAc, —CH(NHCH₃)CH₂OAc, —CH(NHC₂H₅)CH₂OAc, —CH(N(CH₃)₂)CH₂OAc, —CH(N(C₂H₅)₂)CH₂OAc, —CH₂—CH(NHAc)CH₂OH, —CH₂—CH(NHAc)CH₂OCH₃, —CH₂—CH(NHAc)CH₂OC₂H₅, —CH₂—CH(NHCH₃)CH₃, —CH₂—CH(NHC₂H₅)CH₃, —CH₂—CH(N(CH₃)₂)CH₃, —CH₂—CH(N(C₂H₅)₂)CH₃, —CH₂—CH(NH₂)CH₂OH, —CH₂—CH(NHCH₃)CH₂OH, —CH₂—CH(NHC₂H₅)CH₂OH, —CH₂—CH(N(CH₃)₂)CH₂OH, —CH₂—CH(N(C₂H₅)₂)CH₂OH, —CH₂—CH(NH₂)CH₂OCH₃, —CH₂—CH(NHCH₃)CH₂OCH₃, —CH₂—CH(NHC₂H₅)CH₂OCH₃, —CH₂—CH(N(CH₃)₂)CH₂OCH₃, —CH₂—CH(N(C₂H₅)₂)CH₂OCH₃, —CH₂—CH(NH₂)CH₂OC₂H₅, —CH₂—CH(NHCH₃)CH₂OC₂H₅, —CH₂—CH(NHC₂H₅)CH₂OC₂H₅, —CH₂—CH(N(CH₃)₂)CH₂OC₂H₅, —CH₂—CH(N(C₂H₅)₂)CH₂OC₂H₅, —CH₂—CH(NH₂)CH₂OAc, —CH₂—CH(NHCH₃)CH₂OAc, —CH₂—CH(NHC₂H₅)CH₂OAc, —CH₂—CH(N(CH₃)₂)CH₂OAc, —CH₂—CH(N(C₂H₅)₂)CH₂OAc, —CH₂—CH(NHAc)CH₂OH, —CH₂—CH(NHAc)CH₂OCH₃, —CH₂—CH(NHAc)CH₂OC₂H₅, —NHCOCH₃, —CH₂—NHCOCH₃, —C₂H₄—NHCOCH₃, —NHCHO, —CH₂—NHCHO, —C₂H₄—NHCHO, —NHSO₂CH₃, —NHSO₂CF₃, —NHSO₂CH₂CF₃, —CH₂—NHSO₂CH₃, —CH₂—NHSO₂CF₃, —CH₂—NHSO₂CH₂CF₃, —C₂H₄—NHSO₂CH₃, —C₂H₄—NHSO₂CF₃, —C₂H₄—NHSO₂CH₂CF₃, —CONH₂, —CONHCH₃, —CONHC₂H₅, —CONHC₃H₇, —NH(C₂H₅), —N(C₂H₅)₂, —CH₂—NH(C₂H₅), —CH₂—N(C₂H₅)₂, —C₂H₄—NH(C₂H₅), —C₂H₄—N(C₂H₅)₂, —NO₂, —CH₂—NO₂, —C₂H₄—NO₂, —CH(OH)—NO₂, —CH(NO₂)—OH, —CO₂H, —CH₂—CO₂H, —C₂H₄—CO₂H, —CH=CH—CO₂H, —CO₂CH₃, —CO₂C₂H₅, —CO₂CH(CH₃)₂, —CH₂—CO₂CH₃, —CH₂—CO₂C₂H₅, —CH₂—CO₂CH(CH₃)₂, —C₂H₄—CO₂CH₃, —C₂H₄—CO₂C₂H₅, —C₂H₄—CO₂CH(CH₃)₂, —CO₂NH₂, —CO₂NHCH₃, —CO₂N(CH₃)₂, —CH₂—CO₂NH₂, —CH₂—CO₂NHCH₃, —CH₂—CO₂N(CH₃)₂, —C₂H₄—CO₂NH₂, —C₂H₄—CO₂NHCH₃, —C₂H₄—CO₂N(CH₃)₂, —O—Si(CH₃)₃, —O—Si(C₂H₅)₃, —CO—CHO, —CO—CO—CH₃, —C(OH)—CO—CH₃, —CO—C(OH)—CH₃, —CO—CH₂—CO—CH₃, —C(OH)—CH₂—CO—CH₃, —CO—CH₂—C(OH)—CH₃, —C(OH)—CH₂—C(OH)—CH₃, —F, —Cl, —Br, —CH₂—F, —CHF₂, —CF₃, —C₂H₄—F, —CH₂—CF₃, —CF₂—CF₃, —O—CHF₂, —O—CF₃, —O—CH₂—CF₃, —O—C₂F₅, —CH₃, —CH₂CH₃, —C₃H₇, —CH(CH₃)₂, —CH=CH₂, —C≡CH, —CH₂—CH=CH₂, or —CH₂—C≡CH;
$R^1$-$R^{10}$ represent independently of each other —H, —OH, —OCH₃, —OC₂H₅, —OC₃H₇, —O-cyclo-C₃H₅, —OCH —(CH₃)₂, —OC(CH₃)₃, —OC₄H₉, —OCH₂—COOH, —OPh, —OCH₂-Ph, —OCPh₃, —CH₂—OCH₃, —CH₂—OH, —C₂H₄—OCH₃, —C₃H₆—OCH₃, —CH₂—OC₂H₅, —C₂H₄—OC₂H₅, —C₃H₆—OC₂H₅, —CH₂—OC₃H₇, —C₂H₄—OC₃H₇, —C₃H₆—OC₃H₇, —CH₂—O-cyclo-C₃H₅, —C₂H₄—O-cyclo-C₃H₅, —C₃H₆—O-cyclo-C₃H₅, —CH₂—OCH(CH₃)₂, —C₂H₄—OCH(CH₃)₂, —C₃H₆—OCH(CH₃)₂, —CH₂—OC(CH₃)₃, —C₂H₄—OC(CH₃)₃, —C₃H₆—OC(CH₃)₃, —CH₂—OC₄H₉, —C₂H₄—OC₄H₉, —C₃H₆—OC₄H₉, —CH₂—OPh, —C₂H₄—OPh, —C₃H₆—OPh, —CH₂—OCH₂-Ph, —C₂H₄—OCH₂-Ph, —C₃H₆—OCH₂-Ph, —SH, —SCH₃, —SC₂H₅, —SC₃H₇, —S-cyclo-C₃H₅, —SCH(CH₃)₂, —SC(CH₃)₃, —NO₂, —F, —Cl, —Br, —I, —P(O)(OH)₂, —P(O)(OCH₃)₂, —P(O)(OC₂H₅)₂, —P(O)(OCH(CH₃)₂)₂, —C(OH)[P(O)(OH)₂]₂, —Si(CH₃)₂(C(CH₃)₃), —Si(C₂H₅)₃, —Si(CH₃)₃, —N₃, —CN, —OCN, —NCO, —SCN, —NCS, —CHO, —COCH₃, —COC₂H₅, —COC₃H₇, —CO-cyclo-C₃H₅, —COCH(CH₃)₂, —COC(CH₃)₃, —COOH, —COCN, —COOCH₃, —COOC₂H₅, —COOC₃H₇, —COO-cyclo-C₃H₅, —COOCH(CH₃)₂, —COOC(CH₃)₃, —OOC—CH₃, —OOC—C₂H₅, —OOC—C₃H₇, —OOC-cyclo-C₃H₅, —OOC—CH(CH₃)₂, —OOC—C(CH₃)₃, —CONH₂, —CONHCH₃, —CONHC₂H₅, —CONHC₃H₇, —CONH-cyclo-C₃H₅, —CONH[CH(CH₃)₂], —CONH[C(CH₃)₃], —CON(CH₃)₂, —CON(C₂H₅)₂, —CON(C₃H₇)₂, —CON(cyclo-C₃H₅)₂, —CON[CH(CH₃)₂]₂, —CON[C(CH₃)₃]₂, —NHCOCH₃, —NHCOC₂H₅, —NHCOC₃H₇, —NHCO-cyclo-C₃H₅, —NHCO—CH(CH₃)₂, —NHCO—C(CH₃)₃, —NHCO—OCH₃, —NHCO—OC₂H₅, —NHCO—OC₃H₇, —NHCO—O-cyclo-C₃H₅, —NHCO—OCH(CH₃)₂, —NHCO—OC(CH₃)₃, —NH₂, —NHCH₃, —NHC₂H₅, —NHC₃H₇, —NH-cyclo-C₃H₅, —NHCH(CH₃)₂, —NHC(CH₃)₃, —N(CH₃)₂, —N(C₂H₅)₂, —N(C₃H₇)₂, —N(cyclo-C₃H₅)₂, —N[CH(CH₃)₂]₂, —N[C(CH₃)₃]₂, —SOCH₃, —SOC₂H₅, —SOC₃H₇, —SO-cyclo-C₃H₅, —SOCH(CH₃)₂, —SOC(CH₃)₃, —SO₂CH₃, —SO₂C₂H₅, —SO₂C₃H₇, —SO₂-cyclo-C₃H₅, —SO₂CH(CH₃)₂, —SO₂C(CH₃)₃, —SO₃H, —SO₃CH₃, —SO₃C₂H₅, —SO₃C₃H₇, —SO₃-cyclo-C₃H₅, —SO₃CH(CH₃)₂, —SO₃C(CH₃)₃, —SO₂NH₂, —SO₂NHCH₃, —SO₂NHC₂H₅, —SO₂NHC₃H₇, —SO₂NH-cyclo-C₃H₅, —SO₂NHCH(CH₃)₂, —SO₂NHC(CH₃)₃, —SO₂N(CH₃)₂, —SO₂N(C₂H₅)₂, —SO₂N(C₃H₇)₂, —SO₂N(cyclo-C₃H₅)₂, —SO₂N[CH(CH₃)₂]₂, —SO₂N[C(CH₃)₃]₂, —O—S(=O)CH₃, —O—S(=O)C₂H₅, —O—S(=O)C₃H₇, —O—S(=O)-cyclo-C₃H₅, —O—S(=O)CH(CH₃)₂, —O—S(=O)C(CH₃)₃, —S(=O)(=NH)CH₃, —S(=O)(=NH)C₂H₅, —S(=O)(=NH)C₃H₇, —S(=O)(=NH)-cyclo-C₃H₅, —S(=O)(=NH)CH(CH₃)₂, —S(=O)(=NH)C(CH₃)₃, —NH—SO₂—CH₃, —NH—SO₂—C₂H₅, —NH—SO₂—C₃H₇, —NH—SO₂-cyclo-C₃H₅, —NH—SO₂—CH(CH₃)₂, —NH—SO₂—C(CH₃)₃, —O—SO₂—CH₃, —O—SO₂—C₂H₅, —O—SO₂—C₃H₇, —O—SO₂-cyclo-C₃H₅, —O—SO₂—CH(CH₃)₂, —O—SO₂—C(CH₃)₃, —OCF₃, —CH₂—OCF₃, —C₂H₄—OCF₃, —C₃H₆—OCF₃, —OC₂F₅, —CH₂—OC₂F₅, —C₂H₄—OC₂F₅, —C₃H₆—OC₂F₅, —O—COOCH₃, —O—COOC₂H₅, —O—COOC₃H₇, —O—COO-cyclo-C₃H₅, —O—COOCH(CH₃)₂, —O—COOC(CH₃)₃, —NH—CO—NH₂, —NH—CO—NHCH₃, —NH—CO—NHC₂H₅, —NH—CS—N(C₃H₇)₂, —NH—CO—NHC₃H₇, —NH—CO—N(C₃H₇)₂, —NH—CO—NH[CH(CH₃)₂], —NH—CO—NH[C(CH₃)₃], —NH—CO—N(CH₃)₂, —NH—CO—N(C₂H₅)₂, —NH—CO—NH-cyclo-C₃H₅, —NH—CO—N(cyclo-C₃H₅)₂, —NH—CO—N[CH(CH₃)₂]₂, —NH—CO—N[C(CH₃)₃]₂, —NH—CS—NH₂, —NH—CS—NHCH₃, —NH—CS—N(CH₃)₂, —NH—CS—NHC₂H₅, —NH—CS—NHC₃H₇, —NH—CS—NH-cyclo-C₃H₅, —NH—CS—NH[CH(CH₃)₂], —NH—CS—NH[C(CH₃)₃], —NH—CS—N(cyclo-C₃H₅)₂, —NH—CS—N[CH(CH₃)₂]₂, —NH—CS—N[C(CH₃)₃]₂, —NH—C(=NH)—NH₂, —NH—C(=NH)—NHCH₃, —NH—C(=NH)—NHC₂H₅, —NH—C(=NH)—NHC₃H₇, —O—CO—NH-cyclo-C₃H₅, —NH—C(=NH)—NH-cyclo-C₃H₅, —NH—C(=NH)—NH[CH(CH₃)₂], —O—CO—NH[CH(CH₃)₂], —NH—C(=NH)—NH[C(CH₃)₃], —NH—C(=NH)—N(CH₃)₂, —NH—C(=NH)—N(C₂H₅)₂, —NH—C(=NH)—N(C₃H₇)₂, —NH—C(=NH)—N(cyclo-C₃H₅)₂, —O—CO—NHC₃H₇, —NH—C(=NH)—N[CH(CH₃)₂]₂, —NH—C(=NH)—N[C(CH₃)₃]₂, —O—CO—NH₂, —O—CO—NHCH₃, —O—CO—NHC₂H₅, —O—CO—NH[C(CH₃)₃], —O—CO—N(CH₃)₂, —O—CO—N(C₂H₅)₂, —O—CO—N(C₃H₇)₂, —O—CO—N(cyclo-C₃H₅)₂, —O—CO—N[CH(CH₃)₂]₂, —O—CO—N[C(CH₃)₃]₂, —O—CO—OCH₃, —O—CO—OC₂H₅, —O—CO—OC₃H₇, —O—CO—O-cyclo-C₃H₅, —O—CO—OCH(CH₃)₂, —O—CO—OC(CH₃)₃, —CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, -cyclo-C₃H₅, -cyclo-C₄H₇, -cyclo-C₅H₉, -cyclo-C₆H₁₁, -cyclo-C₇H₁₃, -cyclo-C₈H₁₅, -Ph, —CH₂-Ph, —CH₂—CH₂-Ph, —CH=CH-Ph, —CPh₃, —CH₃, —C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₇H₁₅, —C₈H₁₇, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —CH=CH₂, —CH₂—CH=CH₂, —C(CH₃)=CH₂, —CH=CH—CH₃, —C₂H₄—CH=CH₂, —CH₂—CH=CH—CH₃, —CH=CH—C₂H₅, —CH₂—C(CH₃)=CH₂, —CH(CH₃)—CH=CH, —CH=C(CH₃)₂, —C(CH₃)=CH—CH₃, —CH=CH—CH=CH₂, —C₃H₆—CH=CH₂, —C₂H₄—CH=CH—CH₃, —CH₂—CH=CH—C₂H₅, —CH=CH—C₃H₇, —CH₂—CH=CH—CH=CH₂, —CH=CH—CH=CH—CH₃, —CH=CH—CH₂—CH=CH₂, —C(CH₃)=CH—CH=CH₂, —CH=C(CH₃)—CH=CH₂, —CH=CH—C(CH₃)=CH₂, —C₂H₄—C(CH₃)=CH₂, —CH₂—CH(CH₃)—CH=CH₂, —CH(CH₃)—CH₂—CH=CH₂, —CH₂—CH=C(CH₃)₂, —CH₂—C(CH₃)=CH—CH₃, —CH(CH₃)—CH=CH—CH₃, —CH=CH—CH(CH₃)₂, —CH=C(CH₃)—C₂H₅, —C(CH₃)=CH—C₂H₅, —C(CH₃)=C(CH₃)₂, —C(CH₃)₂—CH=CH₂, —CH(CH₃)—C(CH₃)=CH₂, —C(CH₃)=CH—CH=CH₂, —CH=C(CH₃)—CH=CH₂, —CH=CH—C(CH₃)=CH₂, —C₄H₈—CH=CH₂, —C₃H₆—CH=CH—CH₃, —C₂H₄—CH=CH—C₂H₅, —CH₂—CH=CH—C₃H₇, —CH=CH—C₄H₉, —C₃H₆—C(CH₃)=CH₂, —C₂H₄—CH(CH₃)—CH=CH₂, —CH₂—CH(CH₃)—CH₂—CH=CH₂, —C₂H₄—CH=C(CH₃)₂, —CH(CH₃)—C₂H₄—CH=CH₂, —C₂H₄—C(CH₃)=CH—CH₃, —CH₂—CH(CH₃)—CH=CH—CH₃, —CH(CH₃)—CH₂—CH=CH—CH₃, —CH₂—CH=CH—CH(CH₃)₂, —CH₂—CH=C(CH₃)—C₂H₅, —CH₂—C(CH₃)=CH—C₂H₅, —C₂H₅—CH(CH₃)—CH=CH—C₂H₅, —CH=CH—CH₂—CH(CH₃)₂, —CH=CH—CH(CH₃)—C₂H₅, —C(CH₃)=CH—C₃H₇, —C(CH₃)=CH—C₃H₇, —CH₂—CH(CH₃)—C(CH₃)=CH₂, —C[C(CH₃)₃]=CH₂, —CH(CH₃)—CH₂—C(CH₃)=CH₂, —CH(CH₃)—CH(CH₃)—CH=CH₂, —CH₂—C(CH₃)₂—CH=CH₂, —C(CH₃)₂—CH₂—CH=CH₂, —CH₂—C(CH₃)=C(CH₃)₂, —CH(CH₃)—CH=C(CH₃)₂, —C(CH₃)₂—CH=CH—CH₃, —CH(CH₃)—C(CH₃)=CH—CH₃, —CH=C(CH₃)—CH(CH₃)₂, —C(CH₃)=CH—CH(CH₃)₂, —C(CH₃)=C(CH₃)—C₂H₅, —CH=CH—C(CH₃)₃, —C(CH₃)₂—C(CH₃)=CH₂, —CH(C₂H₅)—C(CH₃)=CH₂, —C(CH₃)(C₂H₅)—CH=CH₂, —CH(CH₃)—C(C₂H₅)=CH₂, —CH₂—C(C₃H₇)=CH₂, —CH₂—C(C₂H₅)=CH—CH₃, —CH(C₂H₅)—CH=CH—CH₃, —C(C₄H₉)=CH₂, —C(C₃H₇)=CH—CH₃, —C(C₂H₅)=CH—C₂H₅, —C(C₂H₅)=C(CH₃)₂, —C[CH(CH₃)(C₂H₅)]=CH₂, —C[CH₂—CH(CH₃)₂]=CH₂, —CH(CH₃)—CH₂—C≡CH, —CH(CH₃)—C≡C—CH₃, —C₂H₄—CH(CH₃)—C≡CH, —CH₂—CH(CH₃)—CH₂—C≡CH, —CH₂—CH(CH₃)—C≡CH, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —C₄H₈—C≡CH, —C₂H₄—C≡C—C₂H₅, —CH₂—C≡C—C₃H₇, —C≡C—C(CH₃)₃, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —C≡C—CH₂—CH(CH₃)₂, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —CH₂—CH(C≡CH)₂,

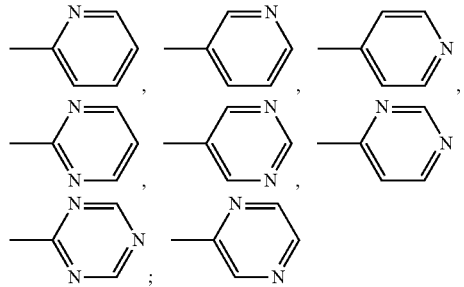

$R^{15}$ represents —$R^{20}$, —CN, —CH₂—CN, —CH₂—OR¹⁷, —CH₂—CH₂—OR¹⁷, —CH₂—NR¹⁷R¹⁸, —CH₂—NR¹⁷COR¹⁹, —CH₂—CH₂—NR¹⁷R¹⁸, —CH₂—CH₂—NR¹⁷COR¹⁹, —CO₂R¹⁷, —CO—NR¹⁷R¹⁸, —CH₂—CO₂R¹⁷, or —CH₂—CO—NR¹⁷R¹⁸;

$R^{16}$ represents —$R^{21}$, —H, —CH₃, —C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₇H₁₅, —C₈H₁₇, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —CH₂OH, —CH₂—SH, —CH(OH)CH₃, —C₂H₄OH, —C₃H₆OH, —C₄H₈OH, —CH(CH₃)—C₂H₄OH, —C₅H₁₀OH, —CH₂—S—CH₃, —CH₂—S—CH₃, —C₃H₆—S—CH₃, —CH₂OCH₃, —C₂H₄OCH₃, —C₃H₆OCH₃, —C₄H₈OCH₃, —CH(CH₃)—C₂H₄OCH₃, —C₅H₁₀OCH₃, —CH₂NH₂, —C₂H₄NH₂, —C₃H₆NH₂, —C₄H₈NH₂, —CH(CH₃)—C₂H₄NH₂, —C₅H₁₀NH₂, —CH₂—CH₂—CH₂—NH—C(NH)NH₂, —CH₂—CO₂H, —CH₂—CONH₂, —CH₂—CH₂—CO₂H, —CH₂—CH₂—CONH₂, —CH₂—CO₂CH₃, —CH₂—CONHCH₃, —CH₂—CON(CH₃)₂, —CH₂—CH₂—CO₂CH₃, —CH₂—CH₂—CONHCH₃, —CH₂—CH₂—CONH(CH₃)₂, —CH=CH—CO₂H, —CH=CH—CO₂CH₃, —CH=CH—CONHCH₃, —CH=CH—CONHC₂H₅, —CH=CH—CON(CH₃)₂, —CH=CH—CON(C₂H₅)₂, —CH₂—CH=CH—CO₂H, —CH₂—CH=CH—CO₂CH₃, —CH₂—CH=CH—CONHCH₃, —CH₂—CH=CH—CON(CH₃)₂, —CH₂—CH=CH—CONHC₂H₅, —CH₂—CH=CH—CON(C₂H₅)₂, —CH=CH₂, —CH₂—CH=CH₂, —C(CH₃)=CH₂, —CH=CH—CH₃, —C₂H₄—CH=CH₂, —CH₂—CH=CH—CH₃, —CH=CH—C₂H₅, —CH₂—C(CH₃)=CH₂, —CH(CH₃)—CH=CH, —CH=C(CH₃)₂, —C(CH₃)=CH—CH₃, —CH=CH—CH=CH₂, —C₃H₆—CH=CH₂, —C₂H₄—CH=CH—CH₃, —CH₂—CH=CH—C₂H₅, —CH=CH—C₃H₇, —CH₂—CH=CH—CH₂, —CH=CH—CH=CH—CH₃, —CH=CH—CH₂—CH=CH₂, —C(CH₃)=CH—CH=CH₂, —CH=C(CH₃)—CH=CH₂, —C₂H₄—C(CH₃)=CH₂, —CH₂—CH(CH₃)—CH=CH₂, —CH(CH₃)—CH₂—CH=CH₂, —CH₂—CH=C(CH₃)₂, —CH₂—C(CH₃)=CH—CH₃, —CH(CH₃)—CH=CH—CH₃, —CH=CH—CH(CH₃)₂, —CH=C(CH₃)—C₂H₅, —C(CH₃)=CH—C₂H₅, —C(CH₃)=C(CH₃)₂, —C(CH₃)₂—CH=CH₂, —CH(CH₃)—C(CH₃)=CH₂, —C(CH₃)=CH—CH=CH₂, —CH=C(CH₃)—CH=CH₂, —CH=CH—C(CH₃)=CH₂, —C₄H₈—CH=CH₂, —C₃H₆—CH=CH—CH₃, —C₂H₄—CH=CH—C₂H₅, —CH₂—CH=CH—C₃H₇, —CH=CH—C₄H₉, —C₃H₆—C(CH₃)=CH₂, —C₂H₄—CH(CH₃)—CH=CH₂, —CH₂—CH(CH₃)—CH₂—CH=CH₂, —C₂H₄—CH=C(CH₃)₂, —CH(CH₃)—C₂H₄—CH=CH₂, —C₂H₄—C(CH₃)=CH—CH₃, —CH₂—CH(CH₃)—CH=CH—CH₃, —CH(CH₃)—CH₂—CH=CH—CH₃, —CH₂—CH=CH—CH(CH₃)₂, —CH₂—CH=C(CH₃)—C₂H₅, —CH₂—C(CH₃)=CH—C₂H₅, —CH(CH₃)—CH=CH—C₂H₅, —CH=CH—CH₂—CH(CH₃)₂, —CH=CH—CH(CH₃)—C₂H₅, —CH=C(CH₃)—C₃H₇, —C(CH₃)=CH—C₃H₇, —CH₂—CH(CH₃)—C(CH₃)=CH₂, —C[C(CH₃)₃]=CH₂, —CH(CH₃)—CH₂—C(CH₃)=CH₂, —CH(CH₃)—CH(CH₃)—CH=CH₂, —CH=CH—C₂H₄—CH=CH₂, —CH₂—C(CH₃)₂—CH=CH₂, —C(CH₃)₂—CH₂—CH=CH₂, —CH₂—C(CH₃)=C(CH₃)₂, —CH(CH₃)—CH=C(CH₃)₂, —C(CH₃)₂—CH=CH—CH₃, —CH(CH₃)—C(CH₃)=CH—CH₃, —CH=C(CH₃)—CH(CH₃)₂, —C(CH₃)=CH—CH(CH₃)₂, —C(CH₃)=C(CH₃)—C₂H₅, —CH=CH—C(CH₃)₃, —C(CH₃)₂—C(CH₃)=CH₂, —CH(C₂H₅)—C(CH₃)=CH₂, —C(CH₃)(C₂H₅)—CH=CH₂, —CH(CH₃)—C(C₂H₅)=CH₂, —CH₂—C(C₃H₇)=CH₂, —CH₂—C(C₂H₅)=CH—CH₃, —CH(C₂H₅)—CH=CH—CH₃, —C(C₄H₉)=CH₂, —C(C₃H₇)=CH—CH₃, —C(C₂H₅)=CH—C₂H₅, —C(C₂H₅)=C(CH₃)₂, —C[CH(CH₃)(C₂H₅)]=CH₂, —C[CH₂—CH(CH₃)₂]=CH₂, —C₂H₄—CH=CH—CH=CH₂, —CH₂—CH=CH—CH₂—CH=CH₂, —C₃H₆—C≡C—CH₃, —CH₂—CH=CH—CH=CH—CH₃, —CH=CH—CH=CH—C₂H₅, —CH₂—CH=CH—C(CH₃)=CH₂, —CH=C(CH₃)—CH=CH—CH₃, —CH₂—C(CH₃)=CH—CH=CH₂, —CH(CH₃)—CH₂—C≡CH, —CH(CH₃)—C≡C—CH₃, —CH=CH—CH₂—C(CH₃)=CH₂, —CH(CH₃)—C≡C—CH₃, —CH=CH—CH (CH$_3$)—CH=CH$_2$, —CH=C(CH$_3$)—CH$_2$—CH=CH$_2$, —C$_2$H$_4$—CH(CH$_3$)—C≡CH, —C(CH$_3$)=CH—CH$_2$—CH=CH$_2$, —CH=CH—CH=C(CH$_3$)$_2$, —CH$_2$—CH(CH$_3$)—CH$_2$—C≡CH, —CH=CH—C(CH$_3$)=CH—CH$_3$, —CH=C(CH$_3$)—CH=CH—CH$_3$, —CH$_2$—CH(CH$_3$)—C≡CH, —C(CH$_3$)=CH—CH=CH—CH$_3$, —CH=C(CH$_3$)—C(CH$_3$)=CH$_2$, —C(CH$_3$)=CH—C(CH$_3$)=CH$_2$, —C(CH$_3$)=C(CH$_3$)—CH=CH$_2$, —CH=CH—CH=CH—CH=CH$_2$, —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —C$_3$H$_6$—C≡CH, —C$_2$H$_4$—C≡C—CH$_3$, —CH$_2$—C≡C—C$_2$H$_5$, —C≡C—C$_3$H$_7$, —CH(CH$_3$)—C≡CH, —C$_4$H$_8$—C≡CH, —C$_2$H$_4$—C≡C—C$_2$H$_5$, —CH$_2$—C≡C—C$_3$H$_7$, —C≡C—C$_4$H$_9$, —C≡C—C(CH$_3$)$_3$, —CH(CH$_3$)—C$_2$H$_4$—C≡CH, —CH$_2$—CH(CH$_3$)—C≡C—CH$_3$, —CH(CH$_3$)—CH$_2$—C≡C—CH$_3$, —CH(CH$_3$)—C≡C—C$_2$H$_5$, —CH$_2$—C≡C—CH(CH$_3$)$_2$, —C≡C—CH(CH$_3$)—C$_2$H$_5$, —C≡C—CH$_2$—CH(CH$_3$)$_2$, —CH(C$_2$H$_5$)—C≡C—CH$_3$, —C(CH$_3$)$_2$—C≡C—CH$_3$, —CH(C$_2$H$_5$)—CH$_2$—C≡CH, —CH$_2$—CH(C$_2$H$_5$)—C≡CH, —C(CH$_3$)$_2$—CH$_2$—C≡CH, —CH$_2$—C(CH$_3$)$_2$—C≡CH, —CH(CH$_3$)—CH(CH$_3$)—C≡CH, —CH(C$_3$H$_7$)—C≡CH, —C(CH$_3$)(C$_2$H$_5$)—C≡CH, —CH$_2$-Ph,

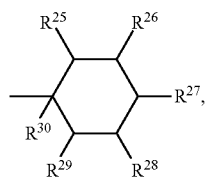
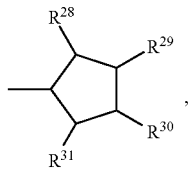
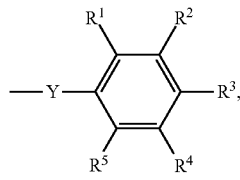
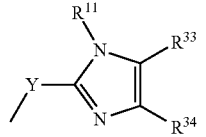
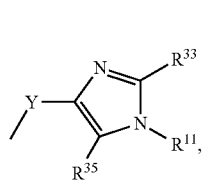
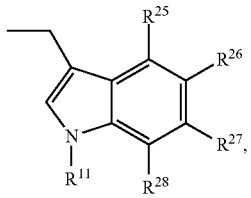
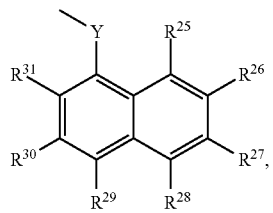
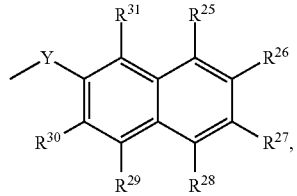

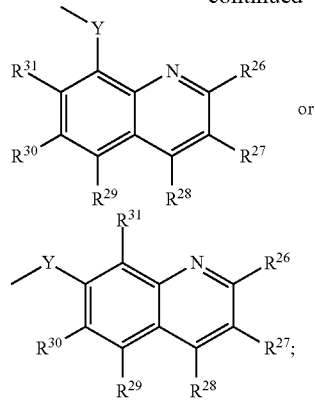

$R^{11}$-$R^{14}$ and $R^{17}$-$R^{21}$ represent independently of each other —H, —CH$_2$F, —CHF$_2$, —CH$_2$—OCH$_3$, —CH$_2$—OH, —C$_2$H$_4$—OCH$_3$, —C$_3$H$_6$—OCH$_3$, —CH$_2$—OC$_2$H$_5$, —C$_2$H$_4$—OC$_2$H$_5$, —C$_3$H$_6$—OC$_2$H$_5$, —CH$_2$—OC$_3$H$_7$, —C$_2$H$_4$—OC$_3$H$_7$, —C$_3$H$_6$—OC$_3$H$_7$, —CH$_2$—O-cyclo-C$_3$H$_5$, —C$_2$H$_4$—O-cyclo-C$_3$H$_5$, —C$_3$H$_6$—O-cyclo-C$_3$H$_5$, —CH$_2$—OCH(CH$_3$)$_2$, —C$_2$H$_4$—OCH(CH$_3$)$_2$, —C$_3$H$_6$—OCH(CH$_3$)$_2$, —CH$_2$—OC(CH$_3$)$_3$, —C$_2$H$_4$—OC(CH$_3$)$_3$, —C$_3$H$_6$—OC(CH$_3$)$_3$, —CH$_2$—OC$_4$H$_9$, —C$_2$H$_4$—OC$_4$H$_9$, —C$_3$H$_6$—OC$_4$H$_9$, —CH$_2$—OPh, —C$_2$H$_4$—OPh, —C$_3$H$_6$—OPh, —CH$_2$—OCH$_2$-Ph, —C$_2$H$_4$—OCH$_2$-Ph, —C$_3$H$_6$—OCH$_2$-Ph, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, -cyclo-C$_3$H$_5$, -cyclo-C$_4$H$_7$, -cyclo-C$_5$H$_9$, -cyclo-C$_6$H$_{11}$, -cyclo-C$_7$H$_{13}$, -cyclo-C$_8$H$_{15}$, -Ph, —CH$_2$-Ph, —CH$_2$—CH$_2$-Ph, —CH=CH-Ph, —CPh$_3$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_7$H$_{15}$, —C$_8$H$_{17}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$, —CH=CH—C$_2$H$_5$, —CH$_2$—C(CH$_3$)=CH$_2$, —CH(CH$_3$)—CH=CH, —CH=C(CH$_3$)$_2$, —C(CH$_3$)=CH—CH$_3$, —CH=CH—CH=CH$_2$, —C$_3$H$_6$—CH=CH$_2$, —C$_2$H$_4$—CH=CH—CH$_3$, —CH$_2$—CH=CH—C$_2$H$_5$, —CH=CH—C$_3$H$_7$, —CH$_2$—CH=CH—CH=CH$_2$, —CH=CH—CH=CH—CH$_3$, —CH=CH—CH$_2$—CH=CH$_2$, —C(CH$_3$)=CH—CH=CH$_2$, —CH=C(CH$_3$)—CH=CH$_2$, —CH=CH—C(CH$_3$)=CH$_2$, —C$_2$H$_4$—C(CH$_3$)=CH$_2$, —CH$_2$—CH(CH$_3$)—CH=CH$_2$, —CH(CH$_3$)—CH$_2$—CH=CH$_2$, —CH$_2$—CH=C(CH$_3$)$_2$, —CH$_2$—C(CH$_3$)=CH—CH$_3$, —CH(CH$_3$)—CH=CH—CH$_3$, —CH=CH—CH(CH$_3$)$_2$, —CH=C(CH$_3$)—C$_2$H$_5$, —C(CH$_3$)=CH—C$_2$H$_5$, —C(CH$_3$)=C(CH$_3$)$_2$, —C(CH$_3$)$_2$—CH=CH$_2$, —CH(CH$_3$)—C(CH$_3$)=CH$_2$, —C(CH$_3$)=CH—CH=CH$_2$, —CH=C(CH$_3$)—CH=CH$_2$, —CH=CH—C(CH$_3$)=CH$_2$, —C$_4$H$_8$—CH=CH$_2$, —C$_3$H$_6$—CH=CH—CH$_3$, —C$_2$H$_4$—CH=CH—C$_2$H$_5$, —CH$_2$—CH=CH—C$_3$H$_7$, —CH=CH—C$_4$H$_9$, —C$_3$H$_6$—C(CH$_3$)=CH$_2$, —C$_2$H$_4$—CH(CH$_3$)—CH=CH$_2$, —CH$_2$—CH(CH$_3$)—CH$_2$—

—CH=CH$_2$, —C$_2$H$_4$—CH=C(CH$_3$)$_2$, —CH(CH$_3$)—C$_2$H$_4$—CH=CH$_2$, —C$_2$H$_4$—C(CH$_3$)=CH—CH$_3$, —CH$_2$—CH(CH$_3$)—CH=CH—CH$_3$, —CH(CH$_3$)—CH$_2$—CH=CH—CH$_3$, —CH$_2$—CH=CH—CH(CH$_3$)$_2$, —CH$_2$—CH=C(CH$_3$)—C$_2$H$_5$, —CH$_2$—C(CH$_3$)=CH—C$_2$H$_5$, —CH(CH$_3$)—CH=CH—C$_2$H$_5$, —CH=CH—CH$_2$—CH(CH$_3$)$_2$, —CH=CH—CH(CH$_3$)—C$_2$H$_5$, —CH=C(CH$_3$)—C$_3$H$_7$, —C(CH$_3$)=CH—C$_3$H$_7$, —CH$_2$—CH(CH$_3$)—C(CH$_3$)=CH$_2$, —C[C(CH$_3$)$_3$]=CH$_2$, —CH(CH$_3$)—CH$_2$—C(CH$_3$)=CH$_2$, —CH(CH$_3$)—CH(CH$_3$)—CH=CH$_2$, —CH$_2$—C(CH$_3$)$_2$—CH=CH$_2$, —C(CH$_3$)$_2$—CH$_2$—CH=CH$_2$, —CH$_2$—C(CH$_3$)=C(CH$_3$)$_2$, —CH(CH$_3$)—CH=C(CH$_3$)$_2$, —C(CH$_3$)$_2$—CH=CH—CH$_3$, —CH(CH$_3$)—C(CH$_3$)=CH—CH$_3$, —CH=C(CH$_3$)—CH(CH$_3$)$_2$, —C(CH$_3$)=CH—CH(CH$_3$)$_2$, —C(CH$_3$)=C(CH$_3$)—C$_2$H$_5$, —CH=CH—C(CH$_3$)$_3$, —C(CH$_3$)$_2$—C(CH$_3$)=CH$_2$, —CH(C$_2$H$_5$)—C(CH$_3$)=CH$_2$, —C(CH$_3$)(C$_2$H$_5$)—CH=CH$_2$, —CH(CH$_3$)—C(C$_2$H$_5$)=CH$_2$, —CH$_2$—C(C$_3$H$_7$)=CH$_2$, —CH$_2$—C(C$_2$H$_5$)=CH—CH$_3$, —CH(C$_2$H$_5$)—CH=CH—CH$_3$, —C(C$_4$H$_9$)=CH$_2$, —C(C$_3$H$_7$)=CH—CH$_3$, —C(C$_2$H$_5$)=CH—C$_2$H$_5$, —C(C$_2$H$_5$)=C(CH$_3$)$_2$, —C[CH(CH$_3$)(C$_2$H$_5$)]=CH$_2$, —C[CH$_2$—CH(CH$_3$)$_2$]=CH$_2$, —C$_3$H$_6$—C≡C—CH$_3$, —CH(CH$_3$)—CH$_2$—C≡CH, —CH(CH$_3$)—C≡C—CH$_3$, —C$_2$H$_4$—CH(CH$_3$)—C≡CH, —CH$_2$—CH(CH$_3$)—CH$_2$—C≡CH, —CH$_2$—CH(CH$_3$)—C≡CH, —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —C$_3$H$_6$—C≡CH, —C$_2$H$_4$—C≡C—CH$_3$, —CH$_2$—C≡C—C$_2$H$_5$, —C≡C—C$_3$H$_7$, —CH(CH$_3$)—C≡CH, —C$_4$H$_8$—C≡CH, —C$_2$H$_4$—C≡C—C$_2$H$_5$, —CH$_2$—C≡C—C$_3$H$_7$, —C≡C—C$_4$H$_9$, —C≡C—C(CH$_3$)$_3$, —CH(CH$_3$)—C$_2$H$_4$—C≡CH, —CH$_2$—CH(CH$_3$)—C≡C—CH$_3$, —CH(CH$_3$)—CH$_2$—C≡C—CH$_3$, —CH(CH$_3$)—C≡C—C$_2$H$_5$, —CH$_2$—C≡C—CH(CH$_3$)$_2$, —C≡C—CH(CH$_3$)—C$_2$H$_5$, —C≡C—CH$_2$—CH(CH$_3$)$_2$, —CH(C$_2$H$_5$)—C≡C—CH$_3$, —C(CH$_3$)$_2$—C≡C—CH$_3$, —CH(C$_2$H$_5$)—CH$_2$—C≡CH, —CH$_2$—CH(C$_2$H$_5$)—C≡CH, —C(CH$_3$)$_2$—CH$_2$—C≡CH, —CH$_2$—C(CH$_3$)$_2$—C≡CH, —CH(CH$_3$)—CH(CH$_3$)—C≡CH, —CH(C$_3$H$_7$)—C≡CH, —C(CH$_3$)(C$_2$H$_5$)—C≡CH, or —CH$_2$—CH(C≡CH)$_2$;

R$^{22}$-R$^{37}$ represent independently of each other —H, —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OCH$_2$—COOH, —OPh, —OCH$_2$-Ph, —OCPh$_3$, —CH$_2$—OH, —C$_2$H$_4$—OH, —C$_3$H$_6$—OH, —CH(OH)—CH$_2$—OH, —CH$_2$—OCH$_3$, —C$_2$H$_4$—OCH$_3$, —C$_3$H$_6$—OCH$_3$, —CH$_2$—OC$_2$H$_5$, —C$_2$H$_4$—OC$_2$H$_5$, —C$_3$H$_6$—OC$_2$H$_5$, —CH$_2$—OC$_3$H$_7$, —C$_2$H$_4$—OC$_3$H$_7$, —C$_3$H$_6$—OC$_3$H$_7$, —CH$_2$—O-cyclo-C$_3$H$_5$, —C$_2$H$_4$—O-cyclo-C$_3$H$_5$, —C$_3$H$_6$—O-cyclo-C$_3$H$_5$, —CH$_2$—OCH(CH$_3$)$_2$, —C$_2$H$_4$—OCH(CH$_3$)$_2$, —C$_3$H$_6$—OCH(CH$_3$)$_2$, —CH$_2$—OC(CH$_3$)$_3$, —C$_2$H$_4$—OC(CH$_3$)$_3$, —C$_3$H$_6$—OC(CH$_3$)$_3$, —CH$_2$—OC$_4$H$_9$, —C$_2$H$_4$—OC$_4$H$_9$, —C$_3$H$_6$—OC$_4$H$_9$, —CH$_2$—OPh, —C$_2$H$_4$—OPh, —C$_3$H$_6$—OPh, —CH$_2$—OCH$_2$-Ph, —C$_2$H$_4$—OCH$_2$-Ph, —C$_3$H$_6$—OCH$_2$-Ph, —SH, —SCH$_3$, —SC$_2$H$_5$, —SC$_3$H$_7$, —S-cyclo-C$_3$H$_5$, —SCH(CH$_3$)$_2$, —SC(CH$_3$)$_3$, —NO$_2$, —F, —Cl, —Br, —I, —P(O)(OH)$_2$, —P(O)(OCH$_3$)$_2$, —P(O)(OC$_2$H$_5$)$_2$, —P(O)(OCH(CH$_3$)$_2$)$_2$, —C(OH)[P(O)(OH)$_2$]$_2$, —Si(CH$_3$)$_2$(C(CH$_3$)$_3$), —Si(C$_2$H$_5$)$_3$, —Si(CH$_3$)$_3$, —N$_3$, —CN, —OCN, —NCO, —SCN, —NCS, —CHO, —COCH$_3$, —COC$_2$H$_5$, —COC$_3$H$_7$, —CO-cyclo-C$_3$H$_5$, —COCH(CH$_3$)$_2$, —COC(CH$_3$)$_3$, —COOH, —COCN, —COOCH$_3$, —COOC$_2$H$_5$, —COOC$_3$H$_7$, —COO-cyclo-C$_3$H$_5$, —COOCH(CH$_3$)$_2$, —COOC(CH$_3$)$_3$, —OOC—CH$_3$, —OOC—C$_2$H$_5$, —OOC—C$_3$H$_7$, —OOC-cyclo-C$_3$H$_5$, —OOC—CH(CH$_3$)$_2$, —OOC—C(CH$_3$)$_3$, —CONH$_2$, —CH$_2$—CONH$_2$, —CONHCH$_3$, —CONHC$_2$H$_5$, —CONHC$_3$H$_7$, —CONH-cyclo-C$_3$H$_5$, —CONH[CH(CH$_3$)$_2$], —CONH[C(CH$_3$)$_3$], —CON(CH$_3$)$_2$, —CON(C$_2$H$_5$)$_2$, —CON(C$_3$H$_7$)$_2$, —CON(cyclo-C$_3$H$_5$)$_2$, —CON[CH(CH$_3$)$_2$]$_2$, —CON[C(CH$_3$)$_3$]$_2$, —NHCOCH$_3$, —NHCOC$_2$H$_5$, —NHCOC$_3$H$_7$, —NHCO-cyclo-C$_3$H$_5$, —NHCO—CH(CH$_3$)$_2$, —NHCO—C(CH$_3$)$_3$, —NHCO—OCH$_3$, —NHCO—OC$_2$H$_5$, —NHCO—OC$_3$H$_7$, —NHCO—O-cyclo-C$_3$H$_5$, —NHCO—OCH(CH$_3$)$_2$, —NHCO—OC(CH$_3$)$_3$, —NH$_2$, —NHCH$_3$, —NHC$_2$H$_5$, —NHC$_3$H$_7$, —NH-cyclo-C$_3$H$_5$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$, —N[C(CH$_3$)$_3$]$_2$, —SOCH$_3$, —SOC$_2$H$_5$, —SOC$_3$H$_7$, —SO-cyclo-C$_3$H$_5$, —SOCH(CH$_3$)$_2$, —SOC(CH$_3$)$_3$, —SO$_2$CH$_3$, —SO$_2$C$_2$H$_5$, —SO$_2$C$_3$H$_7$, —SO$_2$-cyclo-C$_3$H$_5$, —SO$_2$CH(CH$_3$)$_2$, —SO$_2$C(CH$_3$)$_3$, —SO$_3$H, —SO$_3$CH$_3$, —SO$_3$C$_2$H$_5$, —SO$_3$C$_3$H$_7$, —SO$_3$-cyclo-C$_3$H$_5$, —SO$_3$CH(CH$_3$)$_2$, —SO$_3$C(CH$_3$)$_3$, —SO$_2$NH$_2$, —SO$_2$NHCH$_3$, —SO$_2$NHC$_2$H$_5$, —SO$_2$NHC$_3$H$_7$, —SO$_2$NH-cyclo-C$_3$H$_5$, —SO$_2$NHCH(CH$_3$)$_2$, —SO$_2$NHC(CH$_3$)$_3$, —SO$_2$N(CH$_3$)$_2$, —SO$_2$N(C$_2$H$_5$)$_2$, —SO$_2$N(C$_3$H$_7$)$_2$, —SO$_2$N(cyclo-C$_3$H$_5$)$_2$, —SO$_2$N[CH(CH$_3$)$_2$]$_2$, —SO$_2$N[C(CH$_3$)$_3$]$_2$, —O—S(=O)CH$_3$, —O—S(=O)C$_2$H$_5$, —O—S(=O)C$_3$H$_7$, —O—S(=O)-cyclo-C$_3$H$_5$, —O—S(=O)CH(CH$_3$)$_2$, —O—S(=O)C(CH$_3$)$_3$, —S(=O)(=NH)CH$_3$, —S(=O)(=NH)C$_2$H$_5$, —S(=O)(=NH)C$_3$H$_7$, —S(=O)(=NH)-cyclo-C$_3$H$_5$, —S(=O)(=NH)CH(CH$_3$)$_2$, —S(=O)(=NH)C(CH$_3$)$_3$, —NH—SO$_2$—CH$_3$, —NH—SO$_2$—C$_2$H$_5$, —NH—SO$_2$—C$_3$H$_7$, —NH—SO$_2$-cyclo-C$_3$H$_5$, —NH—SO$_2$—CH(CH$_3$)$_2$, —NH—SO$_2$—C(CH$_3$)$_3$, —O—SO$_2$—CH$_3$, —O—SO$_2$—C$_2$H$_5$, —O—SO$_2$—C$_3$H$_7$, —O—SO$_2$-cyclo-C$_3$H$_5$, —O—SO$_2$—CH(CH$_3$)$_2$, —O—SO$_2$—C(CH$_3$)$_3$, —OCF$_3$, —CH$_2$—OCF$_3$, —C$_2$H$_4$—OCF$_3$, —C$_3$H$_6$—OCF$_3$, —OC$_2$F$_5$, —CH$_2$—OC$_2$F$_5$, —C$_2$H$_4$—OC$_2$F$_5$, —C$_3$H$_6$—OC$_2$F$_5$, —O—COOCH$_3$, —O—COOC$_2$H$_5$, —O—COOC$_3$H$_7$, —O—COO-cyclo-C$_3$H$_5$, —O—COOCH(CH$_3$)$_2$, —O—COOC(CH$_3$)$_3$, —NH—CO—NH$_2$, —NH—CO—NHCH$_3$, —NH—CO—NHC$_2$H$_5$, —NH—CS—N(C$_3$H$_7$)$_2$, —NH—CO—NHC$_3$H$_7$, —NH—CO—N(C$_3$H$_7$)$_2$, —NH—CO—NH[CH(CH$_3$)$_2$], —NH—CO—NH[C(CH$_3$)$_3$], —NH—CO—N(CH$_3$)$_2$, —NH—CO—N(C$_2$H$_5$)$_2$, —NH—CO—NH-cyclo-C$_3$H$_5$, —NH—CO—N(cyclo-C$_3$H$_5$)$_2$, —NH—CO—N[CH(CH$_3$)$_2$]$_2$, —NH—CS—N(C$_2$H$_5$)$_2$, —NH—CO—N[C(CH$_3$)$_3$]$_2$, —NH—CS—NH$_2$, —NH—CS—NHCH$_3$, —NH—CS—N(CH$_3$)$_2$, —NH—CS—NHC$_2$H$_5$, —NH—CS—NHC$_3$H$_7$, —NH—CS—NH-cyclo-C$_3$H$_5$, —NH—CS—NH[CH(CH$_3$)$_2$], —NH—CS—NH[C(CH$_3$)$_3$], —NH—CS—N(cyclo-C$_3$H$_5$)$_2$, —NH—CS—N[CH(CH$_3$)$_2$]$_2$, —NH—CS—N[C(CH$_3$)$_3$]$_2$, —NH—C(=NH)—NH$_2$, —NH—C(=NH)—NHCH$_3$, —NH—C(=NH)—NHC$_2$H$_5$, —NH—C(=NH)—NHC$_3$H$_7$, —O—CO—NH-cyclo-C$_3$H$_5$, —NH—C(=NH)—NH-cyclo-C$_3$H$_5$, —NH—C(=NH)—NH[CH(CH$_3$)$_2$]—O—CO—NH[CH(CH$_3$)$_2$], —NH—C(=NH)—NH[C(CH$_3$)$_3$], —NH—C(=NH)—N(CH$_3$)$_2$, —NH—C(=NH)—N(C$_2$H$_5$)$_2$, —NH—C(=NH)—N(C$_3$H$_7$)$_2$, —NH—C(=NH)—N(cyclo-C$_3$H$_5$)$_2$, —O—CO—NHC$_3$H$_7$, —NH—C(=NH)—N[CH(CH$_3$)$_2$]$_2$, —NH—C(=NH)—N[C(CH$_3$)$_3$]$_2$, —O—CO—NH$_2$, —O—CO—NHCH$_3$, —O—CO—NHC$_2$H$_5$, —O—CO—NH[C(CH$_3$)$_3$], —O—CO—N(CH$_3$)$_2$, —O—CO—N(C$_2$H$_5$)$_2$, —O—CO—N(C$_3$H$_7$)$_2$, —O—CO—N(cyclo-C$_3$H$_5$)$_2$, —O—CO—N[CH(CH$_3$)$_2$]$_2$, —O—CO—N[C(CH$_3$)$_3$]$_2$, —O—CO—OCH$_3$, —O—CO—OC$_2$H$_5$, —O—CO—OC$_3$H$_7$, —O—CO—O-cyclo-C$_3$H$_5$, —O—CO—OCH(CH$_3$)$_2$, —O—CO—OC(CH$_3$)$_3$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH₂—CH₂Cl, —CH₂—CH₂Br, —CH₂—CH₂I, -cyclo-C₅H₉, -cyclo-C₆H₁₁, —CH₂-cyclo-C₆H₁₁, —CH₂—CH₂-cyclo-C₆H₁₁, -cyclo-C₇H₁₃, -cyclo-C₈H₁₅, -Ph, —CH₂-Ph, —CH₂—CH₂-Ph, —CH═CH-Ph, —CPh₃, —CH₃, —C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₇H₁₅, —C₈H₁₇, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —CH═CH₂, —CH₂—CH═CH₂, —C(CH₃)═CH₂, —CH═CH—CH₃, —C₂H₄—CH═CH₂, —CH₂—CH═CH—CH₃, —CH═CH—C₂H₅, —CH₂—C(CH₃)═CH₂, —CH(CH₃)—CH═CH, —CH═C(CH₃)₂, —C(CH₃)═CH—CH₃, —CH═CH—CH═CH₂, —C₃H₆—CH═CH₂, —C₂H₄—CH═CH—CH₃, —CH₂—CH═CH—C₂H₅, —CH═CH—C₃H₇, —CH₂—CH═CH—CH═CH₂, —CH═CH—CH═CH—CH₃, —CH═CH—CH₂—CH═CH₂, —C(CH₃)═CH—CH═CH₂, —CH═C—CH═CH—C(CH₃)═CH₂, —C₂H₄—C(CH₃)═CH₂, —CH₂—CH(CH₃)—CH═CH₂, —CH(CH₃)—CH₂—CH═CH₂, —CH₂—CH═C(CH₃)₂, —CH₂—C(CH₃)═CH—CH₃, —CH(CH₃)—CH═CH—CH₃, —CH═CH—CH(CH₃)₂, —CH═C(CH₃)—C₂H₅, —C(CH₃)═CH—C₂H₅, —C(CH₃)═C(CH₃)₂, —C(CH₃)₂—CH═CH₂, —CH(CH₃)—C(CH₃)═CH₂, —C(CH₃)═CH—CH—CH═CH₂, —CH═C(CH₃)—CH═CH₂, —CH═CH—C(CH₃)═CH₂, —C₄H₈—CH═CH₂, —C₃H₆—CH═CH—CH₃, —C₂H₄—CH═CH—C₂H₅, —CH₂—CH═CH—C₃H₇, —CH═CH—C₄H₉, —C₃H₆—C(CH₃)═CH₂, —C₂H₄—CH(CH₃)—CH═CH₂, —CH₂—CH(CH₃)—CH₂—CH═CH₂, —C₂H₄—CH═C(CH₃)₂, —CH(CH₃)—C₂H₄—CH═CH₂, —C₂H₄—C(CH₃)═CH—CH₃, —CH₂—CH(CH₃)—CH═CH—CH₃, —CH(CH₃)—CH₂—CH═CH—CH₃, —CH₂—CH═CH—CH(CH₃)₂, —CH₂—CH═C(CH₃)—C₂H₅, —CH₂—C(CH₃)═CH—C₂H₅, —CH(CH₃)—CH═CH—C₂H₅, —CH═CH—CH₂—CH(CH₃)₂, —CH═CH—CH(CH₃)—C₂H₅, —CH═C(CH₃)—C₃H₇, —C(CH₃)═CH—C₃H₇, —CH₂—CH═C(CH₃)—CH═CH₂, —C[C(CH₃)₃]═CH₂, —CH(CH₃)—CH₂—C(CH₃)═CH₂, —CH(CH₃)—CH═CH₂, —CH═CH—C₂H₄—CH═CH₂, —CH₂—C(CH₃)₂—CH═CH₂, —C(CH₃)₂—CH₂—CH═CH₂, —CH₂—C(CH₃)═C(CH₃)₂, —CH(CH₃)—CH═C(CH₃)₂, —C(CH₃)₂—CH═CH—CH₃, —CH═CH—CH₂—CH═CH—CH₃, —CH(CH₃)—C(CH₃)═CH—CH₃, —CH═C(CH₃)—CH(CH₃)₂, —C(CH₃)═CH—CH(CH₃)₂, —C(CH₃)═C(CH₃)—C₂H₅, —CH═CH—C(CH₃)₃, —C(CH₃)₂—C(CH₃)═CH₂, —CH(C₂H₅)—C(CH₃)═CH₂, —C(CH₃)(C₂H₅)—CH═CH₂, —CH(CH₃)—C(C₂H₅)═CH₂, —CH₂—C(C₃H₇)═CH₂, —CH₂—C(C₂H₅)═CH—CH₃, —CH(C₂H₅)—CH═CH—CH₃, —C(C₄H₉)═CH₂, —C(C₃H₇)═CH—CH₃, —C(C₂H₅)═CH—C₂H₅, —C(C₂H₅)═C(CH₃)₂, —C[CH(CH₃)(C₂H₅)]═CH₂, —C[CH₂—CH(CH₃)₂]═CH₂, —C₂H₄—CH═CH—CH═CH₂, —CH₂—CH═CH—CH₂—CH═CH₂, —C₃H₆—C≡C—CH₃, —CH₂—CH═CH—CH═CH—CH₃, —CH═CH—CH═CH—C₂H₅, —CH₂—CH═CH—C(CH₃)═CH₂, —CH₂—C(CH₃)═CH—CH₂, —CH═C(CH₃)—CH═CH₂, —CH═CH—CH═CH₂, —CH(CH₃)—CH₂—C≡CH, —CH(CH₃)—CH═CH—CH═CH₂, —CH═CH—CH₂—C(CH₃) ═CH₂, —CH(CH₃)—C≡C—CH₃, —CH═CH—CH (CH₃)—CH═CH₂, —CH═C(CH₃)—CH₂—CH═CH₂, —C₂H₄—CH(CH₃)—C≡CH, —C(CH₃)═CH—CH═CH₂, —CH═CH—CH═C(CH₃)₂, —CH₂—CH(CH₃)—CH₂—C≡CH, —CH═CH—C(CH₃)═CH—CH₃, —CH═C(CH₃)—CH═CH—CH₃, —CH₂—CH(CH₃)—C≡CH, —C(CH₃)═CH—CH═CH—CH₃, —CH═C(CH₃)—C(CH₃)═CH₂, —C(CH₃)═CH—C(CH₃)═CH₂, —C(CH₃)═C(CH₃)—CH═CH₂, —CH═CH—CH═CH—CH═CH₂, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —C₄H₈—C≡CH, —C₂H₄—C≡C—C₂H₅, —CH₂—C≡C—C₃H₇, —C≡C—C₄H₉, —C≡C—C(CH₃)₃, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —C≡C—CH₂—CH(CH₃)₂, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —CH₂—CH(C≡CH)₂, —C≡C—C≡CH, —CH₂—C≡C—C≡CH, —C≡C—C≡C—CH₃, —CH(C≡CH)₂, —C₂H₄—C≡C—C≡CH, —CH₂—C≡C—CH₂—C≡CH, —C≡C—C₂H₄—C≡CH, —CH₂—C≡C—C≡C—CH₃, —C≡C—CH₂—C≡C—CH₃, —C≡C—C≡C—C₂H₅, —C(C≡CH)₂—CH₃, —C≡C—CH(CH₃)—C≡CH, —CH(CH₃)—C≡C—C≡CH, —CH(C≡CH)—CH₂—C≡CH, —CH(C≡CH)—C≡C—CH₃,

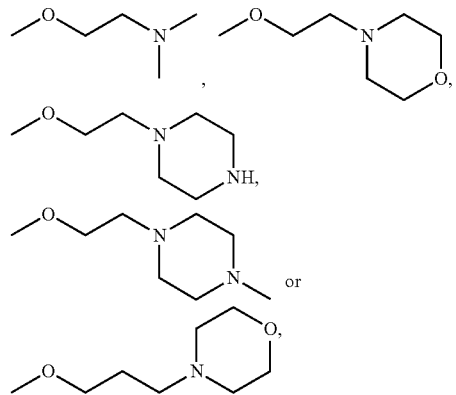

and enantiomers, stereoisomeric forms, mixtures of enantiomers, anomers, deoxy-forms, diastereomers, mixtures of diastereomers, prodrugs, tautomers, hydrates, solvates and racemates of the above mentioned compounds and pharmaceutically acceptable salts;
with the proviso that the compound is not (1S,5S,6R)-10-(3,5-dichlorophenylsulfonyl)-3-(2-(3,4-dimethoxyphenoxy)ethyl)-5-vinyl-3,10-diazabicyclo[4.3.1]decan-2-one.

The expression prodrug is defined as a pharmacological substance, a drug, which is administered in an inactive or significantly less active form. Once administered, the prodrug is metabolized in the body in vivo into the active compound.

The expression tautomer is defined as an organic compound that is interconvertible by a chemical reaction called tautomerization. Tautomerization can be catalyzed preferably by bases or acids or other suitable compounds.

In regard to diazabicyclic compounds as FKBP51/52 ligands which have respectively 3,10-diazabicyclo[4.3.1]decan-2-one or 3,9-diazabicyclo[3.3.1]nonan-2-one as back bone structure, the compounds of the present invention are characterized by better affinity. These bicyclic back bones are useful for fixing the conformation of FKBP51/52 ligands. Thus, these bicyclic compounds have usually better affinity to FKBP51/52 than the monocyclic compounds which have piperidine as back bone structure. Further, it was found that the diazabicyclo[4.3.1]decan-2-one derivatives have higher affinity compared to the 3,9-diazabicyclo[3.3.1]nononan-2-one derivates, because the sulfonamide nitrogen of the diazabicyclo[4.3.1]decan-2-one derivatives can accept an unusual hydrogen bond from Tyr113 that mimics the putative FKBP transition state. However, in addition to these advantages, the compounds of the present invention are characterized by a high affinity and/or selectivity, to FKBP 51 and FKBP 52.

Preferred substituents for $R^4$ are

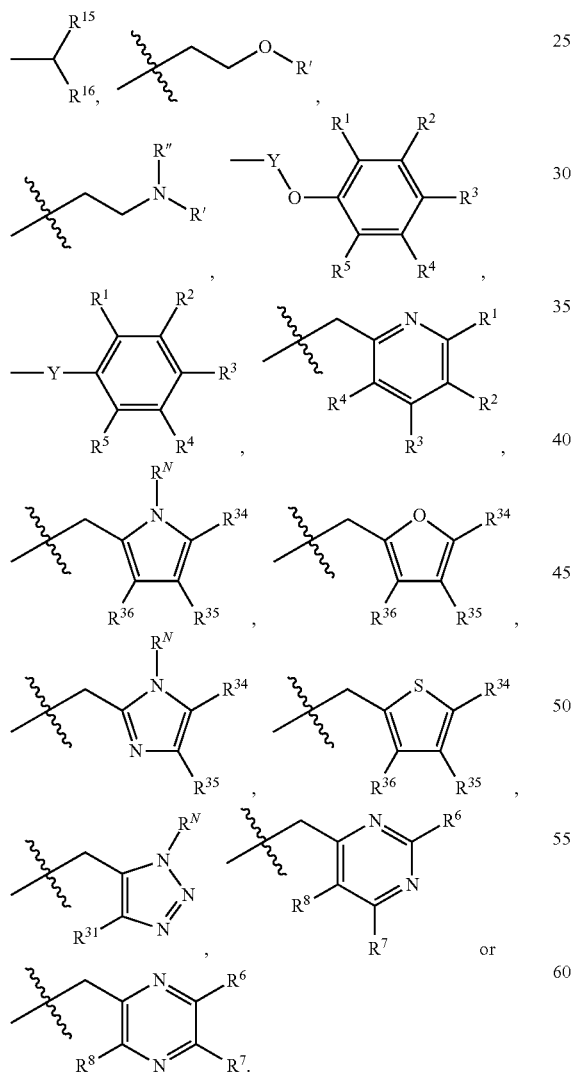

wherein $R^1$-$R^8$, $R^{15}$-$R^{16}$, $R^{31}$, $R^{34}$-$R^{36}$, $R^N$ and Y have the meanings as defined in the general formula (I) and R' and R" represent independently of each other —H, —$CH_3$, —$C_2H_5$, —$CH(CH_3)_2$, —$CF_3$, or —$COCH_3$.

More preferred are compounds of the formula (I) having one of the following substituents $R^4$:

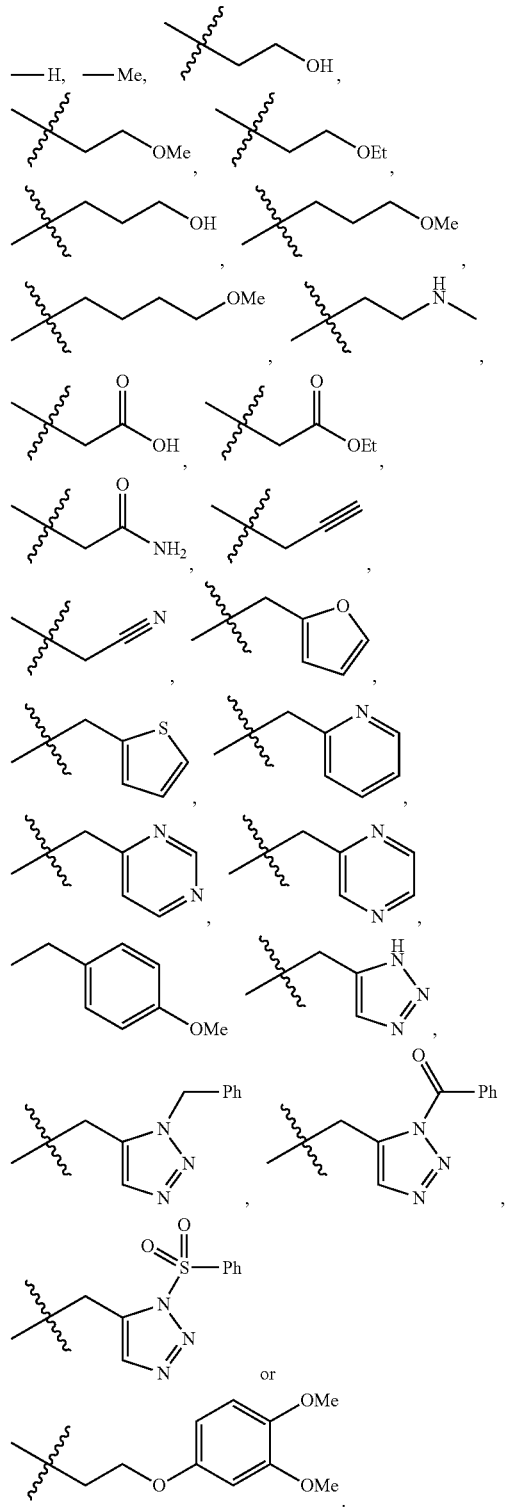

Especially preferred $R^4$ is selected from the following group:

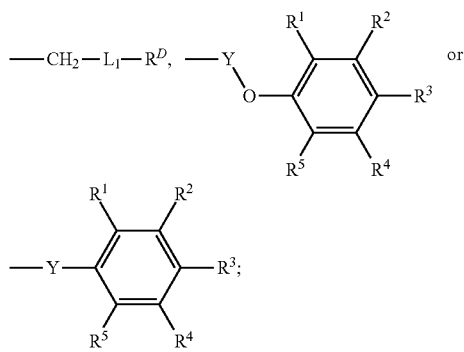

wherein
Y represents —CH$_2$—, —C$_2$H$_4$—, or —C$_3$H$_6$—;
L$_1$ represents a bond, —CH$_2$—, —C$_2$H$_4$—, or —C$_3$H$_6$—, and preferably a bond, —CH$_2$—, or —C$_2$H$_4$—;
R$^1$-R$^5$ represent independently of each other —H or —OCH$_3$;
R$^D$ represents —H, —OH, —OCH$_3$, —OCF$_3$, —OC$_2$H$_5$, —OC$_3$H$_7$, —OPh, —OCH$_2$-Ph, —COOH, —COOCH$_3$, —COOC$_2$H$_5$, —COOC$_3$H$_7$, —CN, —NH$_2$, —NHCH$_3$, —NHC$_2$H$_5$, —NHC$_3$H$_7$, —N(CH$_3$)$_2$, —N(C$_2$H$_5$)$_2$, —N(C$_3$H$_7$)$_2$, —CONH$_2$, —CONHCH$_3$, —CONHC$_2$H$_5$, —CONHC$_3$H$_7$, —CON(CH$_3$)$_2$, —CON(C$_2$H$_5$)$_2$, —CON(C$_3$H$_7$)$_2$, —CH=CH$_2$, —C(CH$_3$)=CH$_2$, —CH=CH—CH$_3$, —CH=CH—C$_2$H$_5$, —C≡CH, —C≡C—CH$_3$, —C≡C—C$_2$H$_5$,

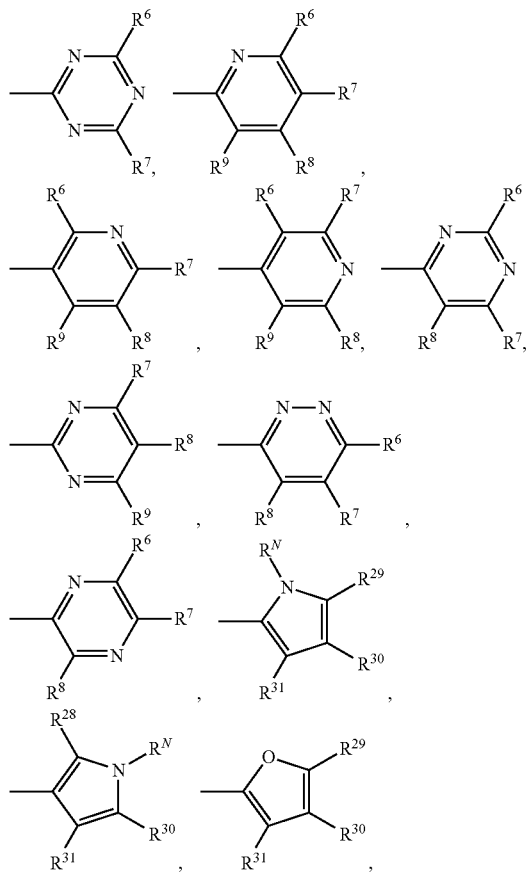

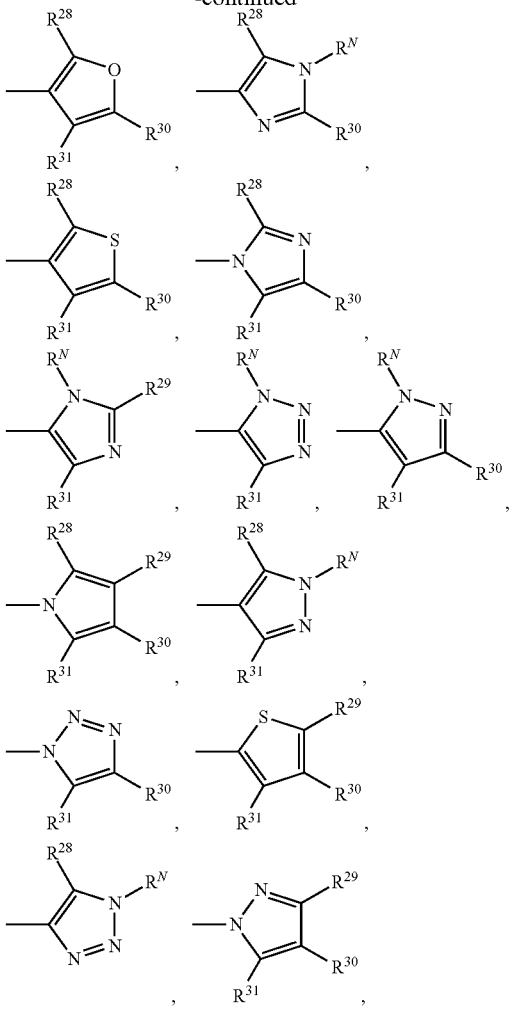

and preferably —OH, —OCH$_3$, —OC$_2$H$_5$, —OCH$_2$-Ph, —COOH, —COOC$_2$H$_5$, —CN, —NHCH$_3$, —CONH$_2$, —C≡CH,

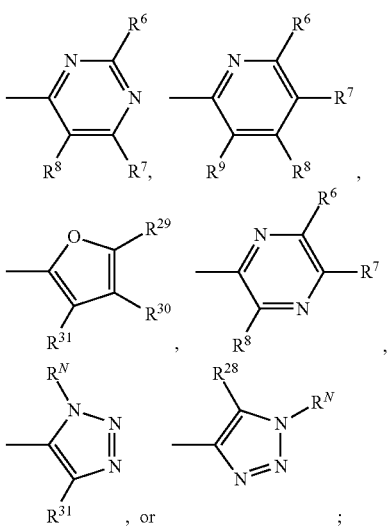

$R^6$-$R^9$ and $R^{28}$-$R^{31}$ represent independently of each other —H or —$CH_3$ and more preferably —H;

$R^N$ represents —H, —$COCH_3$, —$COC_2H_5$, —COPh, —$COCH_2Ph$, —$SO_2Ph$, —$SO_2CH_2Ph$, —$CH_3$, —$C_2H_5$, —$C_3H_7$, —$CH(CH_3)_2$, -Ph, or —$CH_2$-Ph, and more preferably —H, —COPh, —$SO_2Ph$, -Ph, or —$CH_2$-Ph.

In an alternative definition preferred are compounds of the formula (I) having a substituent $R^A$ with a molecular weight of <200 g/mole, more preferable <100 g/mole, and most preferable <50 g/mole.

Preferred substituents for $R^B$ are:

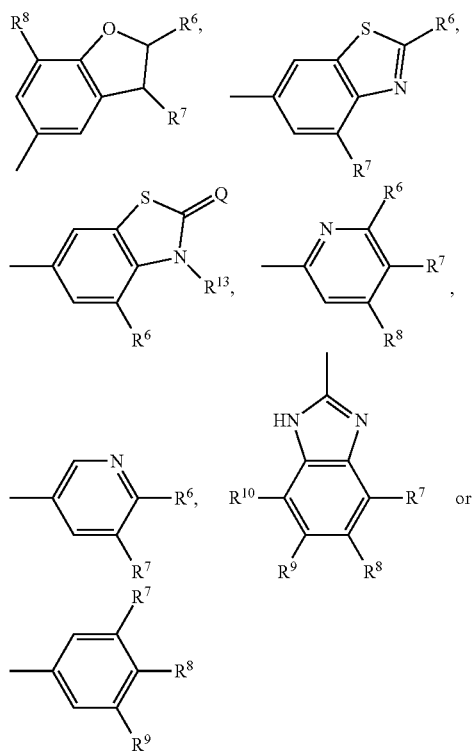

wherein $R^6$-$R^{10}$, $R^{13}$ and Q have the meanings as defined in the general formula (I), and more preferably have the following meanings:

Q represents =O;

$R^6$-$R^9$ represent independently of each other —H, —F, —Cl, —Br, —I, —OH, —$OCH_3$, —$OC_2H_5$, —$OC_3H_7$, —CN, —$CONH_2$, —$NHCOCH_3$, —$NHCOC_2H_5$, —$NHCOC_3H_7$, —COOH, —$COOCH_3$, —$COOC_2H_5$, —$COOC_3H_7$, -Ph,

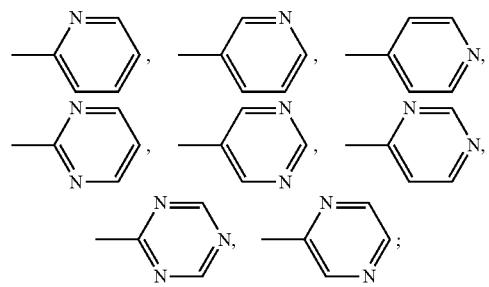

and preferably —F, —Cl, —Br, —OH, —$OCH_3$, —CN, —$CONH_2$, —NHCOCH_3$, —$COOCH_3$, -Ph, or

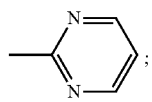

$R^{10}$ represents —H;

$R^{13}$ represents —H, —$CH_3$, or —$C_2H_5$, and more preferably —H;

and preferably one of $R^7$-$R^9$ is different from hydrogen.

Particularly preferred are compounds of the formula (I) having one of the following substituents $R^B$:

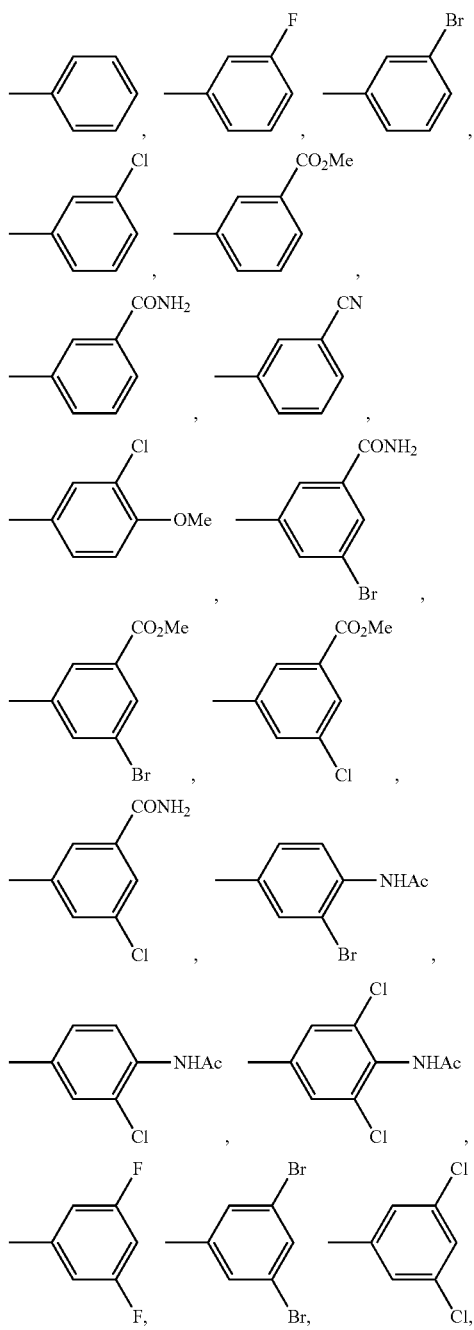

-continued

[Structures shown: 3,5-dichloro-4-hydroxyphenyl; 3,4,5-trimethoxyphenyl; benzothiazol-6-yl; 2-methylbenzothiazol-6-yl; 2-oxo-2,3-dihydrobenzothiazol-6-yl; 2,3-dihydrobenzofuran-5-yl; pyridin-4-yl; pyridin-3-yl; 6-phenylpyridin-3-yl; 5-(pyrimidin-2-yl)phenyl; 2-methyl-1H-benzimidazol-5-yl]

Preferred substituents for $R^1$-$R^{10}$ are: —H, —OH, —OCH$_3$, —OC$_2$H$_5$, —OC$_3$H$_7$, —OCH(CH$_3$)$_2$, —OCPh$_3$, —CH$_2$—OCH$_3$, —CH$_2$—OH, —OC$_3$H$_7$, —OC(CH$_3$)$_3$, —OCH$_2$—COOH, —CO$_2$Me, —CO$_2$Et, —CONH$_2$, —NHCOCH$_3$, —NHSO$_2$CH$_3$, —CH$_3$, —CH$_2$—OH, —C$_2$H$_5$, —C$_3$H$_7$, —CH(CH$_3$)$_2$, —CN, —F, —Cl, —Br, —I,

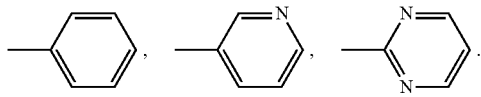

In an alternative definition preferred are compounds of the formula (I) having a substituent $R^B$ with a molecular weight of <300 g/mole, more preferable <200 g/mole, and most preferable <130 g/mole.

Preferred are compounds of the formula (I) having one of the following substituents $R^C$: —CH$_2$—OH, —CHO, —CH$_2$CHO, —CH$_2$CH$_2$CHO, —C$_2$H$_4$—OH, —C$_3$H$_6$—OH, —OH, —O—CH$_3$, —O—C$_2$H$_5$, —O—CH$_2$—OH, —O—CH(CH$_3$)$_2$, —O—CH$_2$—O—CH$_3$, —O—C$_2$H$_4$—O—CH$_3$, —CH$_2$—O—CH$_3$, —CH$_2$—O—CH$_2$—OH, —CH$_2$O—C$_2$H$_5$, —CH$_2$—O—CH(CH$_3$)$_2$, —CH$_2$—O—C$_3$H$_7$, —CO—CH$_3$, —CH$_2$—CO—CH$_3$, —CO—CH$_2$—OH, —CH(OH)—CH$_3$, —C(OH)(CH$_3$)$_2$, —CH(CH$_3$)CH$_2$OH, —CH(OH)—CH$_2$—OH, —CH$_2$—CH(OH)—CH$_3$, —CH$_2$—CH(OH)—CH$_2$—OH, —CH(OCH$_3$)—CH$_2$OH, —CH(OC$_2$H$_5$)—CH$_2$OH, —CH(OCH$_3$)—CH$_2$OCH$_3$, —CH(OC$_2$H$_5$)—CH$_2$OCH$_3$, —CH(OC$_2$H$_5$)—CH$_2$OC$_2$H$_5$, —CH(OAc)—CH$_2$—OH, —CH(OAc)—CH$_2$OAc, —CH(OH)—CH$_2$OAc, —CH(OH)—CH$_2$—NH$_2$, —CH$_2$—CH(OH)—CH$_2$—NH$_2$, —CH(OCH$_3$)—CH$_2$—NH$_2$, —CH(OC$_2$H$_5$)—CH$_2$—NH$_2$, —CH$_2$—CH(OCH$_3$)—CH$_2$—NH$_2$, —CH$_2$—CH(OC$_2$H$_5$)—CH$_2$—NH$_2$, —CH(OH)—CH$_2$—NHCH$_3$, —CH(OH)—CH$_2$—NHC$_2$H$_5$, —CH$_2$—CH(OH)—CH$_2$—NHCH$_3$, —CO—C$_3$H$_7$, —CH$_2$—CH(OH)—CH$_2$—NHC$_2$H$_5$, —CH(OCH$_3$)—CH$_2$NHCH$_3$, —CO—C$_2$H$_5$, —CO—CH(CH$_3$)$_2$, —CH(OC$_2$H$_5$)—CH$_2$NHCH$_3$, —CH$_2$—CH(OCH$_3$)—CH$_2$—NHCH$_3$, —O—C$_3$H$_7$, —CH$_2$—CH(OC$_2$H$_5$)—CH$_2$—NHCH$_3$, —CH(OCH$_3$)—CH$_2$NHC$_2$H$_5$, —CH(OC$_2$H$_5$)—CH$_2$NHC$_2$H$_5$, —CH(OCH$_3$)—CH$_2$N(CH$_3$)$_2$, —CH(OC$_2$H$_5$)—CH$_2$N(CH$_3$)$_2$, —NH$_2$, —NHCH$_3$, —N(CH$_3$)$_2$, —CH$_2$—NH$_2$, —CH$_2$—NHCH$_3$, —CH$_2$—N(CH$_3$)$_2$, —C$_2$H$_4$—NH$_2$, —C$_2$H$_4$—NHCH$_3$, —C$_2$H$_4$—N(CH$_3$)$_2$, —CH(NHCH$_3$)CH$_3$, —CH(NHC$_2$H$_5$)CH$_3$, —CH(N(CH$_3$)$_2$)CH$_3$, —CH(N(C$_2$H$_5$)$_2$)CH$_3$, —CH(NH$_2$)CH$_2$OH, —CH(NHCH$_3$)CH$_2$OH, —CH(NHC$_2$H$_5$)CH$_2$OH, —CH(N(CH$_3$)$_2$)CH$_2$OH, —CH(N(C$_2$H$_5$)$_2$)CH$_2$OH, —CH(NH$_2$)CH$_2$OCH$_3$, —CH(NHCH$_3$)CH$_2$OCH$_3$, —CH(NHC$_2$H$_5$)CH$_2$OCH$_3$, —CH(N(CH$_3$)$_2$)CH$_2$OCH$_3$, —CH(N(C$_2$H$_5$)$_2$)CH$_2$OCH$_3$, —CH(NH$_2$)CH$_2$OC$_2$H$_5$, —CH(NHCH$_3$)CH$_2$OC$_2$H$_5$, —CH(NHC$_2$H$_5$)CH$_2$OC$_2$H$_5$, —CH(N(CH$_3$)$_2$)CH$_2$OC$_2$H$_5$, —CH(N(C$_2$H$_5$)$_2$)CH$_2$OC$_2$H$_5$, —CH(NH$_2$)CH$_2$OAc, —CH(NHCH$_3$)CH$_2$OAc, —CH(NHC$_2$H$_5$)CH$_2$OAc, —CH(N(CH$_3$)$_2$)CH$_2$OAc, —CH(N(C$_2$H$_5$)$_2$)CH$_2$OAc, —CH$_2$—CH(NHAc)CH$_2$OH, —CH$_2$—CH(NHAc)CH$_2$OCH$_3$, —CH$_2$—CH(NHAc)CH$_2$OC$_2$H$_5$, —CH$_2$—CH(NHCH$_3$)CH$_3$, —CH$_2$—CH(NHC$_2$H$_5$)CH$_3$, —CH$_2$—CH(N(CH$_3$)$_2$)CH$_3$, —CH$_2$—CH(N(C$_2$H$_5$)$_2$)CH$_3$, —CH$_2$—CH(NH$_2$)CH$_2$OH, —CH$_2$—CH(NHCH$_3$)CH$_2$OH, —CH$_2$—CH(NHC$_2$H$_5$)CH$_2$OH, —CH$_2$—CH(N(CH$_3$)$_2$)CH$_2$OH, —CH$_2$—CH(N(C$_2$H$_5$)$_2$)CH$_2$OH, —CH$_2$—CH(NH$_2$)CH$_2$OCH$_3$, —CH$_2$—CH(NHCH$_3$)CH$_2$OCH$_3$, —CH$_2$—CH(NHC$_2$H$_5$)CH$_2$OCH$_3$, —CH$_2$—CH(N(CH$_3$)$_2$)CH$_2$OCH$_3$, —CH$_2$—CH(N(C$_2$H$_5$)$_2$)CH$_2$OCH$_3$, —CH$_2$—CH(NH$_2$)CH$_2$OC$_2$H$_5$, —CH$_2$—CH(NHCH$_3$)CH$_2$OC$_2$H$_5$, —CH$_2$—CH(NHC$_2$H$_5$)CH$_2$OC$_2$H$_5$, —CH$_2$—CH(N(CH$_3$)$_2$)CH$_2$OC$_2$H$_5$, —CH$_2$—CH(N(C$_2$H$_5$)$_2$)CH$_2$OC$_2$H$_5$, —CH$_2$—CH(NH$_2$)CH$_2$OAc, —CH$_2$—CH(NHCH$_3$)CH$_2$OAc, —CH$_2$—CH(NHC$_2$H$_5$)CH$_2$OAc, —CH$_2$—CH(N(CH$_3$)$_2$)CH$_2$OAc, —CH$_2$—CH(N(C$_2$H$_5$)$_2$)CH$_2$OAc, —CH$_2$—CH(NHAc)CH$_2$OH, —CH$_2$—CH(NHAc)CH$_2$OCH$_3$, —CH$_2$—CH(NHAc)CH$_2$OC$_2$H$_5$, —NHCOCH$_3$, —CH$_2$—NHCOCH$_3$, —C$_2$H$_4$—NHCOCH$_3$, —NHCHO, —CH$_2$—NHCHO, —C$_2$H$_4$—NHCHO, —CONH$_2$, —CONHCH$_3$, —CONHC$_2$H$_5$, —CONHC$_3$H$_7$, —NH(C$_2$H$_5$), —N(C$_2$H$_5$)$_2$, —CH$_2$—NH(C$_2$H$_5$), —CH$_2$—N(C$_2$H$_5$)$_2$, —C$_2$H$_4$—NH(C$_2$H$_5$), —C$_2$H$_4$—N(C$_2$H$_5$)$_2$, —CO$_2$H, —CH$_2$—CO$_2$H, —C$_2$H$_4$—CO$_2$H, —CH═CH—CO$_2$H, —CO$_2$CH$_3$, —CO$_2$C$_2$H$_5$, —CO$_2$CH(CH$_3$)$_2$, —CH$_2$—CO$_2$CH$_3$, —CH$_2$—CO$_2$C$_2$H$_5$, —CH$_2$—CO$_2$CH(CH$_3$)$_2$, —C$_2$H$_4$—CO$_2$CH$_3$, —C$_2$H$_4$—CO$_2$C$_2$H$_5$, —C$_2$H$_4$—CO$_2$CH(CH$_3$)$_2$, —CO$_2$NH$_2$, —CO$_2$NHCH$_3$, —CO$_2$N(CH$_3$)$_2$, —CH$_2$—CO$_2$NH$_2$, —CH$_2$—CO$_2$NHCH$_3$, —CH$_2$—CO$_2$N(CH$_3$)$_2$, —C$_2$H$_4$—CO$_2$NH$_2$, —C$_2$H$_4$—CO$_2$NHCH$_3$, —C$_2$H$_4$—CO$_2$N(CH$_3$)$_2$, —CH$_2$—F, —CHF$_2$, —CF$_3$, —C$_2$H$_4$—F, —CH$_2$—CF$_3$, —CF$_2$—CF$_3$, —O—CHF$_2$, —O—CF$_3$, —CH$_3$, —CH$_2$CH$_3$, —C$_3$H$_7$, —CH(CH$_3$)$_2$, —CH═CH$_2$, —C≡CH, —CH$_2$—CH═CH$_2$, or —CH$_2$—C≡CH.

More preferably $R^C$ represents: —OH, —CH$_2$—OH, —C$_2$H$_4$—OH, —C$_3$H$_6$—OH, —CHO, —CH$_2$CHO, —CH$_2$CH$_2$CHO, —O—CH$_3$, —O—C$_2$H$_5$, —O—C$_3$H$_7$, —O—CH(CH$_3$)$_2$, —CONH$_2$, —CONHCH$_3$, —CONHC$_2$H$_5$, —CONHC$_3$H$_7$, —CO—CH$_3$, —CO—C$_2$H$_5$, —CO—C$_3$H$_7$, —CO—CH(CH$_3$)$_2$, —CO$_2$H, —CH$_2$—CO$_2$H, —C$_2$H$_4$—CO$_2$H, —O—CH$_2$—OH, —O—CH$_2$—O—CH$_3$, —O—C$_2$H$_4$—O—CH$_3$, —CH$_2$—O—CH$_3$, —CH$_2$—O—CH$_2$—OH, —CH$_2$O—C$_2$H$_5$, —CH$_2$—O—CH(CH$_3$)$_2$, —CH$_2$—O—C$_3$H$_7$, —CH$_2$—CO—CH$_3$, —CO—CH$_2$—OH, —CH(OH)—CH$_3$, —C(OH)(CH₃)₂, —CH(CH₃)CH₂OH, —CH(OH)—CH₂—OH, —CH₂—CH(OH)—CH₃, —CH₂—CH(OH)—CH₂—OH, —CH(OCH₃)—CH₂OH, —CH(OC₂H₅)—CH₂OH, —CH(OCH₃)—CH₂OCH₃, —CH(OC₂H₅)—CH₂OCH₃, —CH(OC₂H₅)—CH₂OC₂H₅, —NH₂, —NHCH₃, —N(CH₃)₂, —CH₂—NH₂, —CH₂—NHCH₃, —CH₂—N(CH₃)₂, —C₂H₄—NH₂, —C₂H₄—NHCH₃, —C₂H₄—N(CH₃)₂, —NH(C₂H₅), —N(C₂H₅)₂, —CH₂—NH(C₂H₅), —CH₂—N(C₂H₅)₂, —C₂H₄—NH(C₂H₅), —C₂H₄—N(C₂H₅)₂, —CH₂—F, —CHF₂, —CF₃, —C₂H₄—F, —CH₂—CF₃, —CF₂—CF₃, —CH₃, —CH₂CH₃, —C₃CH₇, —CH(CH₃)₂, —CH=CH₂, —C≡CH, —CH₂—CH=CH₂, or —CH₂—C≡CH.

Most preferably $R^C$ represents: —OH, —NH₂, —CH₂F, —CHF₂, —CH₂CH₃, —CH=CH₂, —CH₂OH, —CHO, —CO₂H, —CONH₂, —COCH₃, —OCH₃, —OCH₂CH₃, —OCH(CH₃)₂, —OCH₂OCH₃, —OC₂H₄OCH₃, —CH₂OCH₃, —CH₂OCH₂CH₃, —CH₂CH₂OH, —CH₂CHO, —CH₂CH₂CHO, —CH₂NH₂, —CH₂NHCH₃, —CH₂N(CH₃)₂, —CH(OH)CH₃, —C(OH)(CH₃)₂, —CH₂CH(OH)CH₃ or —CH(OH)CH₂OH.

Also most preferably $R^C$ represents: —OH, —NH₂, —CH₂F, —CHF₂, —CH₂CH₃, —CH₂OH, —CHO, —CO₂H, —CONH₂, —COCH₃, —OCH₃, —OCH₂CH₃, —OCH(CH₃)₂, —OCH₂OCH₃, —OC₂H₄OCH₃, —CH₂OCH₃, —CH₂OCH₂CH₃, —CH₂CH₂OH, —CH₂CHO, —CH₂CH₂CHO, —CH₂NH₂, —CH₂NHCH₃, —CH₂N(CH₃)₂, —CH(OH)CH₃, —C(OH)(CH₃)₂, —CH₂CH(OH)CH₃ or —CH(OH)CH₂OH. Especially preferred are $R^C$ residues which comprise a hydroxyl group or an alkoxy group such as —CH₂OH, —CH₂CH₂OH, —CH(OH)CH₃, —C(OH)(CH₃)₂, —CH₂CH(OH)CH₃, —CH(OH)CH₂OH and —CH₂OCH₃.

In an alternative definition preferred are compounds of the formula (I) having a substituent $R^C$ with a molecular weight of <200 g/mole, more preferable <100 g/mole, and most preferable <50 g/mole.

In an alternative definition preferred are compounds of the formula (I) having substituents $R^A$, $R^B$ and $R^C$ with a combined molecular weight of <400 g/mole, more preferable <300 g/mole, and most preferable <250 g/mole.

Preferred are the compounds of the formula (I) with a proviso that the compounds having $R^C$=—CH=CH₂ and $R^A$=—H, —CH₂—C≡CH, —C₂H₄—OMe, —C₃H₆—OMe, —C₃H₆—O—CH₂Ph, —C₄H₈—OCH₃ or 2-(3,4-dimethoxyphenoxy)ethyl and $R^B$=3,5-dichlorophenyl, are excluded.

Also preferred are compounds of the formula (II) and (III):

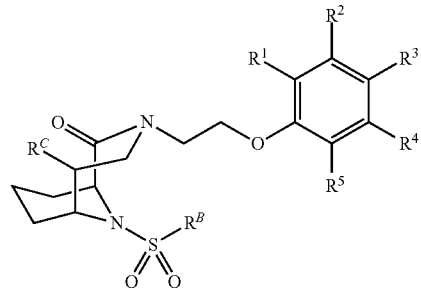

(II)

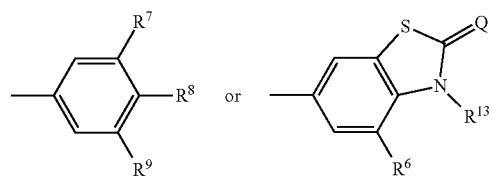

(III)

wherein Y, $R^B$, $R^C$ and the substituents $R^1$-$R^5$ have the meanings as defined in the general formula (I).

In these formulae (II) and (III) $R^B$ represents preferably

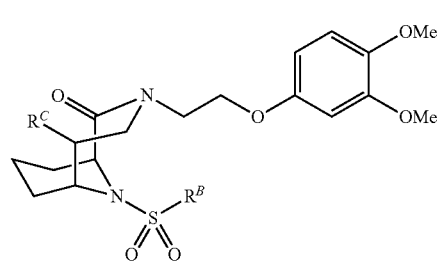

wherein $R^6$-$R^9$, $R^{13}$ and Q have the same meanings as defined in the general formula (I).

Further preferred are the general formulae (IV), (V) and (VI):

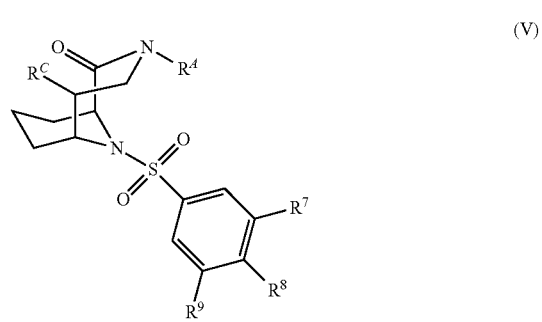

(IV)

(V)

-continued

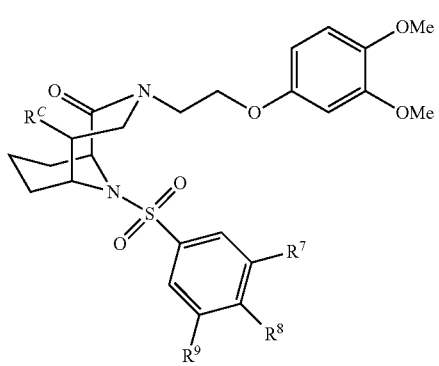
(VI)

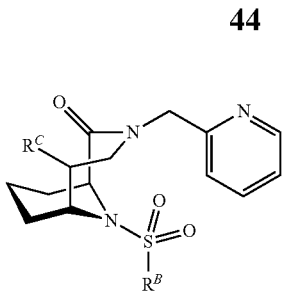
(X)

wherein and the substituents $R^A$ $R^B$, $R^C$ and $R^7$-$R^9$ have the meanings as defined herein.

Yet further preferred are the general formulas (VII) and (VIII):

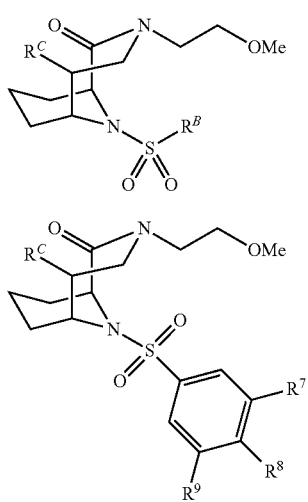
(VII)

(VIII)

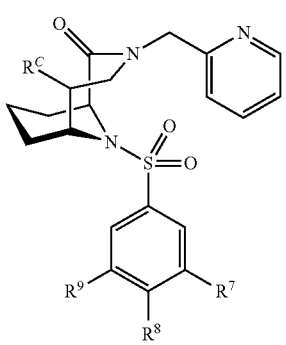
(Xa)

wherein the substituents $R^B$, $R^C$ and $R^7$-$R^9$ have the meanings as defined herein.

Yet further preferred are the general formulas (XI) and (XIa):

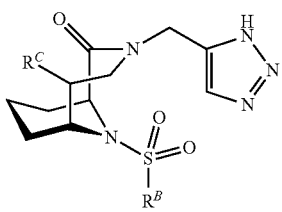
(XI)

wherein the substituents $R^B$, $R^C$ and $R^7$-$R^9$ have the meanings as defined herein.

Further preferred are compounds of general formula (IX):

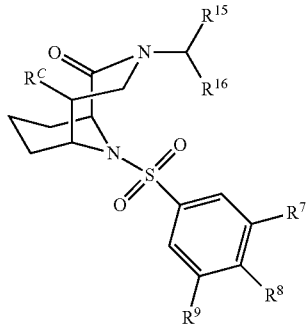
(IX)

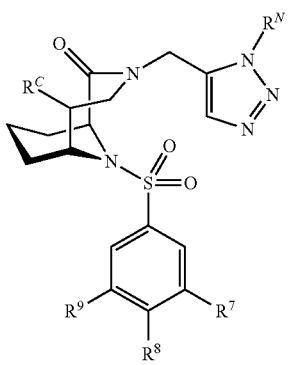
(XIa)

wherein the substituents $R^C$, $R^7$-$R^9$ and $R^{15}$-$R^{16}$ have the meanings as defined herein.

Yet further preferred are the general formulas (X) and (Xa):

wherein the substituents $R^B$, $R^C$, $R^N$ and $R^7$-$R^9$ have the meanings as defined herein.

Further preferred are compounds of general formula (XII):

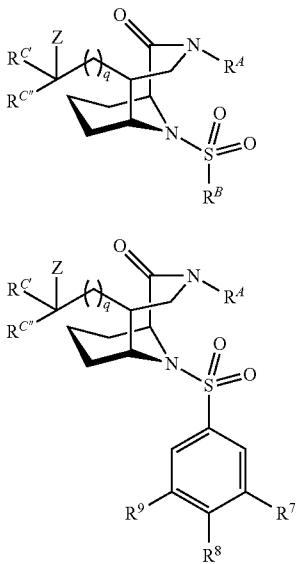

(XII)

(XIII)

wherein the substituents $R^A$, $R^B$ and $R^7$-$R^9$ have the meanings as defined herein;

$R^{C'}$ and $R^{C''}$ represent independently of each other, —H, —CH$_3$, —C$_2$H$_5$, —CH$_2$—OH; Z represents —OH, —OCH$_3$, —OC$_2$H$_5$, —OCH(CH$_3$)$_2$, —NH$_2$, —NH(CH$_3$), —NH(C$_2$H$_5$), —NHCH(CH$_3$)$_2$, —N(CH$_3$)$_2$, or —N(C$_2$H$_5$)$_2$; and q is 0 or 1.

Particularly preferred are compounds of formula (XII) or (XIII), wherein $R^A$ represents —H, —C$_2$H$_4$—OH,

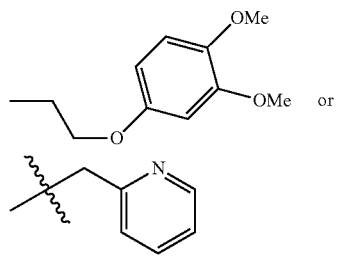

—C$_2$H$_4$—OCH$_3$, and/or compounds of formula (XII) wherein $R^B$ represents

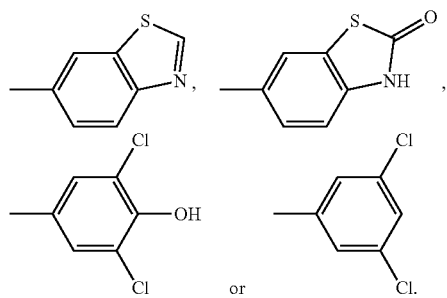

Most preferred are compounds of formula (V),

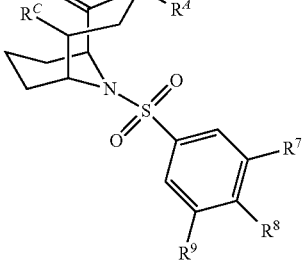

(V)

wherein $R^A$, $R^C$ and $R^7$-$R^9$ have the meanings and especially the preferred meanings as defined herein.

Preferably in general formula (V) and (XIII) $R^7$-$R^9$ represent independently of each other —H, —F, —Cl, —Br, —I, —OH, —OCH$_3$, —OC$_2$H$_5$, —OC$_3$H$_7$, —CN, —CONH$_2$, —NHCOCH$_3$, —NHCOC$_2$H$_5$, —NHCOC$_3$H$_7$, —COOH, —COOCH$_3$, —COOC$_2$H$_5$, —COOC$_3$H$_7$, -Ph,

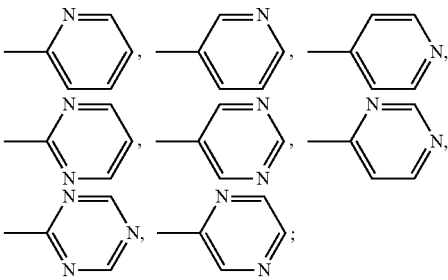

and more preferably —F, —Cl, —Br, —OH, —OCH$_3$, —CN, —CONH$_2$, —NHCOCH$_3$, —COOCH$_3$, -Ph, or

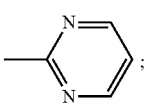

Preferred for any general formula disclosed herein and especially for general formulae (I), (V), (XII) and (XIII) substituents for $R^A$ are preferably selected from:

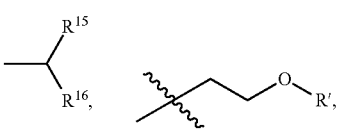

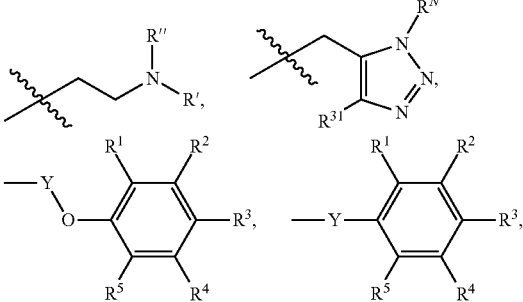

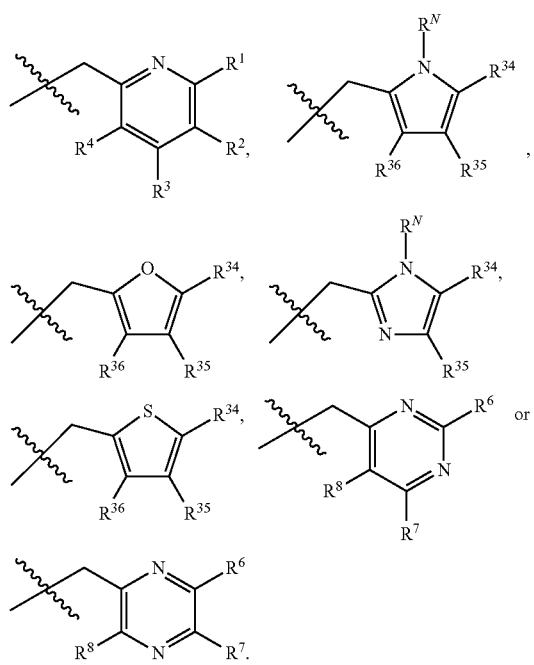

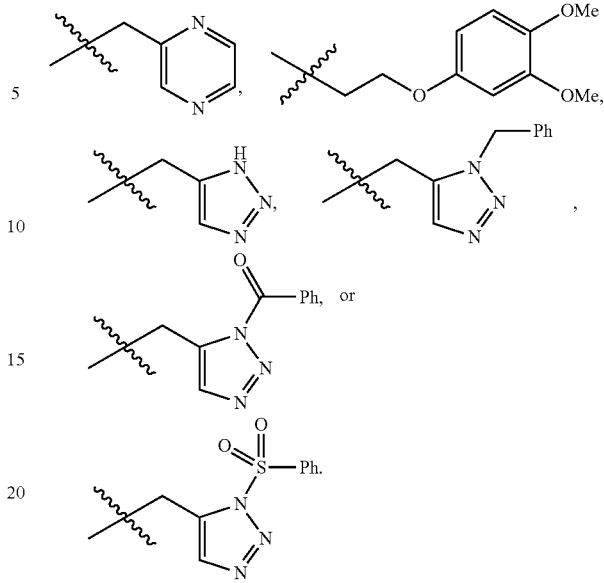

wherein $R^1$-$R^8$, $R^{15}$-$R^{16}$, $R^{31}$, $R^{34}$-$R^{36}$, $R^N$ and Y have the meanings as defined in the general formula (I) and R' and R" represent independently of each other —H, —CH$_3$, —C$_2$H$_5$, —CH(CH$_3$)$_2$, —CF$_3$, —COCH$_3$.

More preferred are compounds of the formula (I) having one of the following substituents $R^4$:

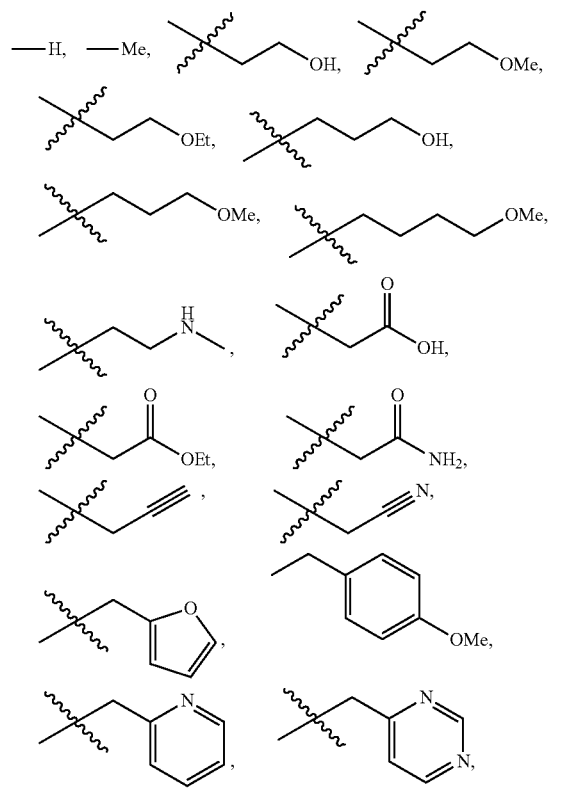

Specifically preferred are compounds of the formula (I) having one of the following substituents $R^A$:

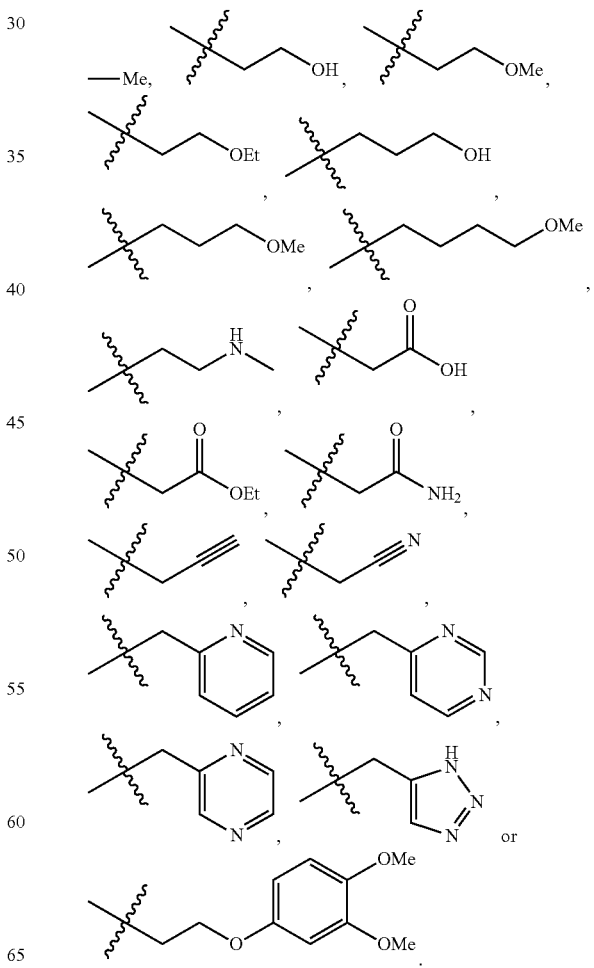

The compounds 10-(3,5-dichlorophenylsulfonyl)-3-(2-(3,4-dimethoxyphenoxy)-ethyl)-5-vinyl-3,10-diazabicyclo[4.3.1]decan-2-one and (1S,5R,6R)-10-(3,5-dichlorophenylsulfonyl)-3-(2-(3,4-dimethoxyphenoxy)ethyl)-5-vinyl-3,10-diazabicyclo[4.3.1]-decan-2-one and (1S,5S,6R)-10-(3,5-dichlorophenylsulfonyl)-3-(2-(3,4-dimethoxyphenoxy)ethyl)-5-vinyl-3,10-diazabicyclo[4.3.1]-decan-2-one are excluded from the scope of the present application.

FKBP inhibitors or FKBP ligands as used herein are defined as compounds that (i) inhibit the peptidyl-prolyl isomerase activity of FKBPs (PPIase inhibitors, also referred to as rotamase inhibitors) or (ii) displace FK506 or FK506 analogs from the PPIase active site of FKBPs or (iii) bind to the FK506-binding domain of FKBPs as determined by isothermal calorimetry, surface plasmon resonance, tryptophan quenching, NMR or x-ray crystallography.

The expression prodrug is defined as a pharmacological substance, a drug, which is administered in an inactive or significantly less active form. Once administered, the prodrug is metabolized in the body in vivo into the active compound.

The expression tautomer is defined as an organic compound that is interconvertible by a chemical reaction called tautomerization. Tautomerization can be catalyzed preferably by bases or acids or other suitable compounds.

In yet another preferred embodiment of the present invention, the compound according to the general formula (I) is selected from the group comprising or consisting of:

| | |
|---|---|
| B1 | (1S,5S,6R)-5-acetyl-10-((3,5-dichlorophenyl)sulfonyl)-3-(2-methoxyethyl)-3,10-diazabicyclo[4.3.1]decan-2-one |
| B2 | 2-((1S,5S,6R)-10-((3,5-dichlorophenyl)sulfonyl)-3-(2-methoxyethyl)-2-oxo-3,10-diazabicyclo[4.3.1]decan-5-yl)acetaldehyde |
| B3 | (1S,5S,6R)-10-((3,5-dichlorophenyl)sulfonyl)-5-(2-hydroxypropan-2-yl)-3-(2-methoxyethyl)-3,10-diazabicyclo[4.3.1]decan-2-one |
| B4 | (1S,5R,6R)-10-((3,5-dichlorophenyl)sulfonyl)-5-((S)-2-hydroxypropyl)-3-(2-methoxyethyl)-3,10-diazabicyclo[4.3.1]decan-2-one |
| B5 | (1S,5R,6R)-10-((3,5-dichlorophenyl)sulfonyl)-5-((R)-2-hydroxypropyl)-3-(2-methoxyethyl)-3,10-diazabicyclo[4.3.1]decan-2-one |
| B6 | (1S,5R,6R)-10-((3,5-dichlorophenyl)sulfonyl)-5-((R)-1-hydroxyethyl)-3-(2-methoxyethyl)-3,10-diazabicyclo[4.3.1]decan-2-one |
| B7 | (1S,5R,6R)-10-((3,5-dichlorophenyl)sulfonyl)-5-((S)-1-hydroxyethyl)-3-(2-methoxyethyl)-3,10-diazabicyclo[4.3.1]decan-2-one |
| B8 | (1S,5S,6R)-10-((3,5-dichlorophenyl)sulfonyl)-5-(2-hydroxyethyl)-3-(2-methoxyethyl)-3,10-diazabicyclo[4.3.1]decan-2-one |
| B9 | (1S,5S,6R)-10-((3,5-dichlorophenyl)sulfonyl)-3-(2-methoxyethyl)-2-oxo-3,10-diazabicyclo[4.3.1]decane-5-carbaldehyde |
| B10 | (1S,5S,6R)-10-((3,5-dichlorophenyl)sulfonyl)-3-(2-methoxyethyl)-2-oxo-3,10-diazabicyclo[4.3.1]decane-5-carboxylic acid |
| B11 | (1S,5S,6R)-10-((3,5-dichlorophenyl)sulfonyl)-3-(2-methoxyethyl)-2-oxo-3,10-diazabicyclo[4.3.1]decane-5-carboxamide |
| B12 | (1S,5S,6R)-10-((3,5-dichlorophenyl)sulfonyl)-3-(2-methoxyethyl)-5-((methylamino)methyl)-3,10-diazabicyclo[4.3.1]decan-2-one |
| B13 | (1S,5R,6R)-10-((3,5-dichlorophenyl)sulfonyl)-5-(hydroxymethyl)-3-(2-methoxyethyl)-3,10-diazabicyclo[4.3.1]decan-2-one |
| B14 | (1S,5R,6R)-10-((3,5-dichlorophenyl)sulfonyl)-3-(2-methoxyethyl)-5-(methoxymethyl)-3,10-diazabicyclo[4.3.1]decan-2-one |
| B15 | (1S,5S,6R)-10-((3,5-dichlorophenyl)sulfonyl)-5-ethyl-3-(2-methoxyethyl)-3,10-diazabicyclo[4.3.1]decan-2-one |
| C1 | (1S,5R,6R)-10-((3,5-dichlorophenyl)sulfonyl)-3-(2-hydroxyethyl)-5-(hydroxymethyl)-3,10-diazabicyclo[4.3.1]decan-2-one |
| C2 | (1S,5S,6R)-10-((3,5-dichlorophenyl)sulfonyl)-5-(1,2-dihydroxyethyl)-3-(2-(3,4-dimethoxyphenoxy)ethyl)-3,10-diazabicyclo[4.3.1]decan-2-one |
| C3 | (1S,5S,6R)-10-((3,5-dichlorophenyl)sulfonyl)-5-(1,2-dihydroxyethyl)-3-(2-ethoxyethyl)-3,10-diazabicyclo[4.3.1]decan-2-one |
| D1 | (1S,5S,6R)-5-acetyl-10-((3,5-dichlorophenyl)sulfonyl)-3-(2-(3,4-dimethoxyphenoxy)ethyl)-3,10-diazabicyclo[4.3.1]decan-2-one |
| D2 | 2-((1S,5S,6R)-10-((3,5-dichlorophenyl)sulfonyl)-3-(2-(3,4-dimethoxyphenoxy)ethyl)-2-oxo-3,10-diazabicyclo[4.3.1]decan-5-yl)acetaldehyde |
| D3 | (1S,5S,6R)-10-((3,5-dichlorophenyl)sulfonyl)-3-(2-(3,4-dimethoxyphenoxy)ethyl)-5-(2-hydroxypropan-2-yl)-3,10-diazabicyclo[4.3.1]decan-2-one |
| D4 | (1S,5S,6R)-10-((3,5-dichlorophenyl)sulfonyl)-3-(2-(3,4-dimethoxyphenoxy)ethyl)-5-(2-hydroxypropyl)-3,10-diazabicyclo[4.3.1]decan-2-one |
| D5 | (1S,5S,6R)-10-((3,5-dichlorophenyl)sulfonyl)-3-(2-(3,4-dimethoxyphenoxy)ethyl)-5-(2-hydroxypropyl)-3,10-diazabicyclo[4.3.1]decan-2-one |
| D6 | (1S,5S,6R)-10-((3,5-dichlorophenyl)sulfonyl)-3-(2-(3,4-dimethoxyphenoxy)ethyl)-5-((R)-1-hydroxyethyl)-3,10-diazabicyclo[4.3.1]decan-2-one |
| D7 | (1S,5S,6R)-10-((3,5-dichlorophenyl)sulfonyl)-3-(2-(3,4-dimethoxyphenoxy)ethyl)-5-((R)-1-hydroxyethyl)-3,10-diazabicyclo[4.3.1]decan-2-one |
| D8 | (1S,5S,6R)-10-((3,5-dichlorophenyl)sulfonyl)-3-(2-(3,4-dimethoxyphenoxy)ethyl)-5-(2-hydroxyethyl)-3,10-diazabicyclo[4.3.1]decan-2-one |
| G6 | (1S,5S,6R)-10-((3,5-dichlorophenyl)sulfonyl)-5-hydroxy-3,10diazabicyclo[4.3.1]decan-2-one |
| H1.2 | (1S,5R,6R)-5-amino-10-((3,5-dichlorophenyl)sulfonyl)-3,10-diazabicyclo[4.3.1]decan-2-one |
| H1.3 | (1S,5S,6R)-10-((3,5-dichlorophenyl)sulfonyl)-5-methoxy-3-methyl-3,10-diazabicyclo[4.3.1]decan-2-one |
| H1.4 | (1S,5R,6R)-10-((3,5-dichlorophenyl)sulfonyl)-5-hydroxy-3,10-diazabicyclo[4.3.1]decan-2-one |
| H2.1 | (1S,5S,6R)-10-((3,5-dichlorophenyl)sulfonyl)-5-(2-methoxyethoxy)-3-(2-methoxy-ethyl)-3,10-diazabicyclo[4.3.1]decan-2-one |

-continued

| | |
|---|---|
| H2.2 | (1S,5S,6R)-10-((3,5-dichlorophenyl)sulfonyl)-5-(methoxymethoxy)-3,10-diaza-bicyclo[4.3.1]decan-2-one |
| H2.3 | (1S,5S,6R)-10-((3,5-dichlorophenyl)sulfonyl)-3-(2-(3,4-dimethoxyphenoxy)ethyl)-5-hydroxy-3,10-diazabicyclo[4.3.1]decan-2-one |
| I7 | (1S,5R,6R)-10-((3,5-dichlorophenyl)sulfonyl)-3-(4-methoxybenzyl)-5-vinyl-3,10-diazabicyclo[4.3.1]decan-2-one |
| I8 | (1S,5R,6R)-10-((3,5-dichlorophenyl)sulfonyl)-5-vinyl-3,10-diazabicyclo[4.3.1]decan-2-one |
| J2 | (1S,5R,6R)-10-((3,5-dichlorophenyl)sulfonyl)-3-(3-methoxypropyl)-5-vinyl-3,10-diazabicyclo[4.3.1]decan-2-one |
| J3 | (1S,5R,6R)-10-((3,5-dichlorophenyl)sulfonyl)-3-(4-methoxybutyl)-5-vinyl-3,10-diazabicyclo[4.3.1]decan-2-one |
| J4 | (1S,5R,6R)-10-((3,5-dichlorophenyl)sulfonyl)-3-(pyridin-2-ylmethyl)-5-vinyl-3,10-diazabicyclo[4.3.1]decan-2-one |
| J5 | (1S,5R,6R)-10-((3,5-dichlorophenyl)sulfonyl)-5-(hydroxymethyl)-3-(3-hydroxypropyl)-3,10-diazabicyclo[4.3.1]decan-2-one |
| J6 | (1S,5R,6R)-10-((3,5-dichlorophenyl)sulfonyl)-5-(hydroxymethyl)-3-(3-methoxypropyl)-3,10-diazabicyclo[4.3.1]decan-2-one |
| J7 | (1S,5R,6R)-10-((3,5-dichlorophenyl)sulfonyl)-5-(hydroxymethyl)-3-(4-methoxybutyl)-3,10-diazabicyclo[4.3.1]decan-2-one |
| J8 | (1S,5R,6R)-10-((3,5-dichlorophenyl)sulfonyl)-5-(hydroxymethyl)-3-(pyridin-2-ylmethyl)-3,10-diazabicyclo[4.3.1]decan-2-one |
| J9 | ethyl 2-((1S,5R,6R)-10-((3,5-dichlorophenyl)sulfonyl)-2-oxo-5-vinyl-3,10-diazabicyclo[4.3.1]decan-3-yl)acetate |
| J10 | 2-((1S,5R,6R)-10-((3,5-dichlorophenyl)sulfonyl)-2-oxo-5-vinyl-3,10-diazabicyclo[4.3.1]decan-3-yl)acetic acid |
| J11 | 2-((1S,5R,6R)-10-((3,5-dichlorophenyl)sulfonyl)-2-oxo-5-vinyl-3,10-diazabicyclo[4.3.1]decan-3-yl)acetamide |
| J12 | (1S,5R,6R)-10-((3,5-dichlorophenyl)sulfonyl)-3-(prop-2-yn-1-yl)-5-vinyl-3,10-diazabicyclo[4.3.1]decan-2-one |
| J13 | (1S,5R,6R)-3-((1H-1,2,3-triazol-4-yl)methyl)-10-((3,5-dichlorophenyl)sulfonyl)-5-vinyl-3,10-diazabicyclo[4.3.1]decan-2-one |
| J14 | (1S,5R,6R)-10-((3,5-dichlorophenyl)sulfonyl)-3-(pyrazin-2-ylmethyl)-5-vinyl-3,10-diazabicyclo[4.3.1]decan-2-one |
| J15 | (1S,5R,6R)-10-((3,5-dichlorophenyl)sulfonyl)-3-(pyrimidin-4-ylmethyl)-5-vinyl-3,10-diazabicyclo[4.3.1]decan-2-one |
| J16 | 2-((1S,5R,6R)-10-((3,5-dichlorophenyl)sulfonyl)-2-oxo-5-vinyl-3,10-diazabicyclo[4.3.1]decan-3-yl)acetonitrile |
| J17 | (1S,5R,6R)-10-((3,5-dichlorophenyl)sulfonyl)-3-(furan-2-ylmethyl)-5-vinyl-3,10-diazabicyclo[4.3.1]decan-2-one |
| J18 | ((1S,5R,6R)-10-((3,5-dichlorophenyl)sulfonyl)-3-(thiophen-2-ylmethyl)-5-vinyl-3,10-diazabicyclo[4.3.1]decan-2-one |
| J19 | (1S,5R,6R)-10-((3,5-dichlorophenyl)sulfonyl)-3-(2-(methylamino)ethyl)-5-vinyl-3,10-diazabicyclo[4.3.1]decan-2-one |
| K4 | 6-(((1S,5R,6R)-2-oxo-3-(pyridin-2-ylmethyl)-5-vinyl-3,10-diazabicyclo[4.3.1]decan-10-yl)sulfonyl)benzo[d]thiazol-2(3H)-one |
| K5 | (1S,5R,6R)-10-((3-bromophenyl)sulfonyl)-3-(pyridin-2-ylmethyl)-5-vinyl-3,10-diazabicyclo[4.3.1]decan-2-one |
| K6 | (1S,5R,6R)-10-((2-methylbenzo[d]thiazol-6-yl)sulfonyl)-3-(pyridin-2-ylmethyl)-5-vinyl-3,10-diazabicyclo[4.3.1]decan-2-one |
| K7 | 3-(((1S,5R,6R)-2-oxo-3-(pyridin-2-ylmethyl)-5-vinyl-3,10-diazabicyclo[4.3.1]decan-10-yl)sulfonyl)benzonitrile |
| K8 | (1S,5R,6R)-10-((3,5-dichloro-4-hydroxyphenyl)sulfonyl)-3-(pyridin-2-ylmethyl)-5-vinyl-3,10-diazabicyclo[4.3.1]decan-2-one |
| K9 | (1S,5R,6R)-10-(benzo[d]thiazol-6-ylsulfonyl)-3-(pyridin-2-ylmethyl)-5-vinyl-3,10-diazabicyclo[4.3.1]decan-2-one |
| K10 | (1S,5R,6R)-10-((3-chloro-4-methoxyphenyl)sulfonyl)-3-(pyridin-2-ylmethyl)-5-vinyl-3,10-diazabicyclo[4.3.1]decan-2-one |
| K11 | (1S,5R,6R)-10-((3-chlorophenyl)sulfonyl)-3-(pyridin-2-ylmethyl)-5-vinyl-3,10-diazabicyclo[4.3.1]decan-2-one |
| K12 | (1S,5R,6R)-10-((2,3-dihydrobenzofuran-5-yl)sulfonyl)-3-(pyridin-2-ylmethyl)-5-vinyl-3,10-diazabicyclo[4.3.1]decan-2-one |
| K13 | (1S,5R,6R)-10-(phenylsulfonyl)-3-(pyridin-2-ylmethyl)-5-vinyl-3,10-diazabicyclo[4.3.1]decan-2-one |
| K14 | (1S,5R,6R)-3-(pyridin-2-ylmethyl)-10-(pyridin-2-ylsulfonyl)-5-vinyl-3,10-diazabicyclo[4.3.1]decan-2-one |
| K15 | (1S,5R,6R)-10-((3-fluorophenyl)sulfonyl)-3-(pyridin-2-ylmethyl)-5-vinyl-3,10-diazabicyclo[4.3.1]decan-2-one |
| K16 | 1S,5R,6R)-10-((3,5-dibromophenyl)sulfonyl)-3-(pyridin-2-ylmethyl)-5-vinyl-3,10-diazabicyclo[4.3.1]decan-2-one |
| K17 | 3-(((1S,5R,6R)-2-oxo-3-(pyridin-2-ylmethyl)-5-vinyl-3,10-diazabicyclo[4.3.1]decan-10-yl)sulfonyl)benzamide |
| K18 | 3-bromo-5-(((1S,5R,6R)-2-oxo-3-(pyridin-2-ylmethyl)-5-vinyl-3,10-diazabicyclo[4.3.1]decan-10-yl)sulfonyl)benzamide |
| K19 | 3-chloro-5-(((1S,5R,6R)-2-oxo-3-(pyridin-2-ylmethyl)-5-vinyl-3,10-diazabicyclo[4.3.1]decan-10-yl)sulfonyl)benzamide |
| K20 | N-(2-bromo-4-(((1S,5R,6R)-2-oxo-3-(pyridin-2-ylmethyl)-5-vinyl-3,10-diazabicyclo[4.3.1]decan-10-yl)sulfonyl)phenyl)acetamide |

| | |
|---|---|
| K21 | N-(2-chloro-4-(((1S,5R,6R)-2-oxo-3-(pyridin-2-ylmethyl)-5-vinyl-3,10-diazabicyclo[4.3.1]decan-10-yl)sulfonyl)phenyl)acetamide |
| K22 | N-(2,6-dichloro-4-(((1S,5R,6R)-2-oxo-3-(pyridin-2-ylmethyl)-5-vinyl-3,10-diazabicyclo[4.3.1]decan-10-yl)sulfonyl)phenyl)acetamide |
| K23 | methyl 3-(((1S,5R,6R)-2-oxo-3-(pyridin-2-ylmethyl)-5-vinyl-3,10-diazabicyclo[4.3.1]decan-10-yl)sulfonyl)benzoate |
| K24 | methyl 3-bromo-5-(((1S,5R,6R)-2-oxo-3-(pyridin-2-ylmethyl)-5-vinyl-3,10-diazabicyclo[4.3.1]decan-10-yl)sulfonyl)benzoate |
| K25 | methyl 3-chloro-5-(((1S,5R,6R)-2-oxo-3-(pyridin-2-ylmethyl)-5-vinyl-3,10-diazabicyclo[4.3.1]decan-10-yl)sulfonyl)benzoate |
| K26 | (1S,5R,6R)-3-(pyridin-2-ylmethyl)-10-(pyridin-3-ylsulfonyl)-5-vinyl-3,10-diazabicyclo[4.3.1]decan-2-one |
| K27 | (1S,5R,6R)-10-((6-phenylpyridin-3-yl)sulfonyl)-3-(pyridin-2-ylmethyl)-5-vinyl-3,10-diazabicyclo[4.3.1]decan-2-one |
| K28 | 1S,5R,6R)-3-(pyridin-2-ylmethyl)-10-((4-(pyrimidin-2-yl)phenyl)sulfonyl)-5-vinyl-3,10-diazabicyclo[4.3.1]decan-2-one |
| K29 | (1S,5R,6R)-10-((1H-benzo[d]imidazol-2-yl)sulfonyl)-3-(pyridin-2-ylmethyl)-5-vinyl-3,10-diazabicyclo[4.3.1]decan-2-one |
| M1 | (1S,5R,6R)-10-((3,5-dichlorophenyl)sulfonyl)-5-ethyl-3-(pyridin-2-ylmethyl)-3,10-diazabicyclo[4.3.1]decan-2-one |
| M2 | (1S,5S,6R)-10-((3,5-dichlorophenyl)sulfonyl)-5-((dimethylamino)methyl)-3-(pyridin-2-ylmethyl)-3,10-diazabicyclo[4.3.1]decan-2-one |
| M3 | (1S,5S,6R)-10-((3,5-dichlorophenyl)sulfonyl)-5-(difluoromethyl)-3-(pyridin-2-ylmethyl)-3,10-diazabicyclo[4.3.1]decan-2-one |
| M4 | (1S,5S,6R)-10-((3,5-dichlorophenyl)sulfonyl)-5-(fluoromethyl)-3-(pyridin-2-ylmethyl)-3,10-diazabicyclo[4.3.1]decan-2-one |
| M5 | (1S,5R,6R)-10-((3,5-dichlorophenyl)sulfonyl)-5-(methoxymethyl)-3-(pyridin-2-ylmethyl)-3,10-diazabicyclo[4.3.1]decan-2-one |
| M6 | (1S,5S,6R)-10-((3,5-dichlorophenyl)sulfonyl)-5-(ethoxymethyl)-3-(pyridin-2-ylmethyl)-3,10-diazabicyclo[4.3.1]decan-2-one |
| N2 | (1S,5S,6R)-10-((3-fluorophenyl)sulfonyl)-5-(methoxymethyl)-3-(prop-2-yn-1-yl)-3,10-diazabicyclo[4.3.1]decan-2-one |
| N3 | (1S,5S,6R)-10-((3,5-dibromophenyl)sulfonyl)-5-(methoxymethyl)-3-(prop-2-yn-1-yl)-3,10-diazabicyclo[4.3.1]decan-2-one |
| N4 | 3-(((1S,5S,6R)-5-(methoxymethyl)-2-oxo-3-(prop-2-yn-1-yl)-3,10-diazabicyclo[4.3.1]decan-10-yl)sulfonyl)benzamide |
| N5 | 3-bromo-5-(((1S,5S,6R)-5-(methoxymethyl)-2-oxo-3-(prop-2-yn-1-yl)-3,10-diazabicyclo[4.3.1]decan-10-yl)sulfonyl)benzamide |
| N6 | 3-chloro-5-(((1S,5S,6R)-5-(methoxymethyl)-2-oxo-3-(prop-2-yn-1-yl)-3,10-diazabicyclo[4.3.1]decan-10-yl)sulfonyl)benzamide |
| N7 | N-(2-bromo-4-(((1S,5S,6R)-5-(methoxymethyl)-2-oxo-3-(prop-2-yn-1-yl)-3,10-diazabicyclo[4.3.1]decan-10-yl)sulfonyl)phenyl)acetamide |
| N8 | N-(2-chloro-4-(((1S,5S,6R)-5-(methoxymethyl)-2-oxo-3-(prop-2-yn-1-yl)-3,10-diazabicyclo[4.3.1]decan-10-yl)sulfonyl)phenyl)acetamide |
| N9 | N-(2,6-dichloro-4-(((1S,5S,6R)-5-(methoxymethyl)-2-oxo-3-(prop-2-yn-1-yl)-3,10-diazabicyclo[4.3.1]decan-10-yl)sulfonyl)phenyl)acetamide |
| N10 | methyl 3-(((1S,5S,6R)-5-(methoxymethyl)-2-oxo-3-(prop-2-yn-1-yl)-3,10-diazabicyclo[4.3.1]decan-10-yl)sulfonyl)benzoate |
| N11 | methyl 3-bromo-5-(((1S,5S,6R)-5-(methoxymethyl)-2-oxo-3-(prop-2-yn-1-yl)-3,10-diazabicyclo[4.3.1]decan-10-yl)sulfonyl)benzoate |
| N12 | methyl 3-chloro-5-(((1S,5S,6R)-5-(methoxymethyl)-2-oxo-3-(prop-2-yn-1-yl)-3,10-diazabicyclo[4.3.1]decan-10-yl)sulfonyl)benzoate |
| N13 | 1S,5S,6R)-5-(methoxymethyl)-3-(prop-2-yn-1-yl)-10-(pyridin-3-ylsulfonyl)-3,10-diazabicyclo[4.3.1]decan-2-one |
| N14 | (1S,5S,6R)-5-(methoxymethyl)-10-((6-phenylpyridin-3-yl)sulfonyl)-3-(prop-2-yn-1-yl)-3,10-diazabicyclo[4.3.1]decan-2-one |
| N15 | (1S,5S,6R)-5-(methoxymethyl)-3-(prop-2-yn-1-yl)-10-((4-(pyrimidin-2-yl)phenyl)sulfonyl)-3,10-diazabicyclo[4.3.1]decan-2-one |
| N16 | (1S,5S,6R)-10-((1H-benzo[d]imidazol-2-yl)sulfonyl)-5-(methoxymethyl)-3-(prop-2-yn-1-yl)-3,10-diazabicyclo[4.3.1]decan-2-one |
| N17 | (1S,5S,6R)-3-((1H-1,2,3-triazol-5-yl)methyl)-10-((3-fluorophenyl)sulfonyl)-5-(methoxymethyl)-3,10-diazabicyclo[4.3.1]decan-2-one |
| N18 | 1S,5S,6R)-3-((1H-1,2,3-triazol-5-yl)methyl)-10-((3,5-dibromophenyl)sulfonyl)-5-(methoxymethyl)-3,10-diazabicyclo[4.3.1]decan-2-one |
| N19 | 3-(((1S,5S,6R)-3-((1H-1,2,3-triazol-5-yl)methyl)-5-(methoxymethyl)-2-oxo-3,10-diazabicyclo[4.3.1]decan-10-yl)sulfonyl)benzamide |
| N20 | 3-(((1S,5S,6R)-3-((1H-1,2,3-triazol-5-yl)methyl)-5-(methoxymethyl)-2-oxo-3,10-diazabicyclo[4.3.1]decan-10-yl)sulfonyl)-5-bromobenzamide |
| N21 | 3-(((1S,5S,6R)-3-((1H-1,2,3-triazol-5-yl)methyl)-5-(methoxymethyl)-2-oxo-3,10-diazabicyclo[4.3.1]decan-10-yl)sulfonyl)-5-chlorobenzamide |
| N22 | N-(4-(((1S,5S,6R)-3-((1H-1,2,3-triazol-5-yl)methyl)-5-(methoxymethyl)-2-oxo-3,10-diazabicyclo[4.3.1]decan-10-yl)sulfonyl)-2-bromophenyl)acetamide |
| N23 | N-(4-(((1S,5S,6R)-3-((1H-1,2,3-triazol-5-yl)methyl)-5-(methoxymethyl)-2-oxo-3,10-diazabicyclo[4.3.1]decan-10-yl)sulfonyl)-2-chlorophenyl)acetamide |
| N24 | N-(4-(((1S,5S,6R)-3-((1H-1,2,3-triazol-5-yl)methyl)-5-(methoxymethyl)-2-oxo-3,10-diazabicyclo[4.3.1]decan-10-yl)sulfonyl)-2,6-dichlorophenyl)acetamide |

-continued

| | |
|---|---|
| N25 | (1S,5S,6R)-3-((1H-1,2,3-triazol-5-yl)methyl)-5-(methoxymethyl)-10-(pyridin-3-ylsulfonyl)-3,10-diazabicyclo[4.3.1]decan-2-one |
| N26 | (1S,5S,6R)-3-((1H-1,2,3-triazol-5-yl)methyl)-5-(methoxymethyl)-10-((6-phenylpyridin-3-yl)sulfonyl)-3,10-diazabicyclo[4.3.1]decan-2-one |
| N27 | (1S,5S,6R)-3-((1H-1,2,3-triazol-5-yl)methyl)-5-(methoxymethyl)-10-((4-(pyrimidin-2-yl)phenyl)sulfonyl)-3,10-diazabicyclo[4.3.1]decan-2-one |
| N28 | (1S,5S,6R)-3-((1H-1,2,3-triazol-5-yl)methyl)-10-((1H-benzo[d]imidazol-2-yl)sulfonyl)-5-(methoxymethyl)-3,10-diazabicyclo[4.3.1]decan-2-one |
| N29 | (1S,5R,6R)-10-((3-fluorophenyl)sulfonyl)-5-(methoxymethyl)-3-((1-phenyl-1H-1,2,3-triazol-5-yl)methyl)-3,10-diazabicyclo[4.3.1]decan-2-one |
| N30 | (1S,5S,6R)-3-((1-benzyl-1H-1,2,3-triazol-5-yl)methyl)-10-((3-fluorophenyl)-sulfonyl)-5-(methoxymethyl)-3,10-diazabicyclo[4.3.1]decan-2-one |
| N31 | (1S,5S,6R)-3-((1-benzoyl-1H-1,2,3-triazol-5-yl)methyl)-10-((3-fluorophenyl)-sulfonyl)-5-(methoxymethyl)-3,10-diazabicyclo[4.3.1]decan-2-one |
| N32 | (1S,5S,6R)-10-((3-fluorophenyl)sulfonyl)-5-(methoxymethyl)-3-((1-(phenylsulfonyl)-1H-1,2,3-triazol-5-yl)methyl)-3,10-diazabicyclo[4.3.1]decan-2-one |

Synthetic Methods

The compounds of the general formula (I) can be prepared according to the following synthetic route in scheme 1. Accordingly, intermediate compound (I-A1) can be prepared by providing 6-carboxy-2-piperidone and a precursor molecule for the moiety $R^A$ which has a suitable leaving group (LG) such as trimethylsilyl (TMS) and a carbon-carbon double bond in allyl position to the $R^A$ amino group. Said $R^A$ amino group is reacted with the carboxy moiety of 6-carboxy-2-piperidone. Subsequently, this compound undergoes a cyclization reaction upon which the leaving group LG is detached from the starting molecule. After deprotecting $PG_1$ from amine, 5-vinyl-3,10-diazabicyclo[4.3.1]decane-2-one derivative (I-B1) is formed. This intermediate can subsequently be reacted with a suitable precursor for the moiety —$SO_2$—$R^B$. By suitable transformation reactions of vinyl group at C-5 position of the resulting sulphonamide compound (I-C), the compound of the general formula (I) can be obtained. Preferred, the vinyl group could be transformed by oxidation reaction with oxygen gas or epoxidation reaction.

In one embodiment of the present invention, a method for preparation of compound of the general formula (I) by synthetic route 1 comprises the following steps:

(a) providing an intermediate compound of the formula (I-A1)

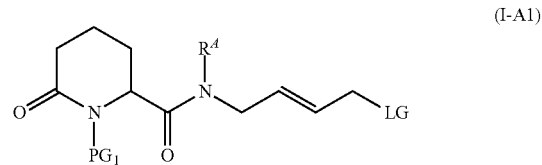

wherein $R^A$ has the meanings as defined herein, LG refers to a leaving group, and $PG_1$ refers to a protecting group for amine;

(b) performing a cyclization reaction and deprotecting $PG_1$ to yield compound of the formula (I-B1)

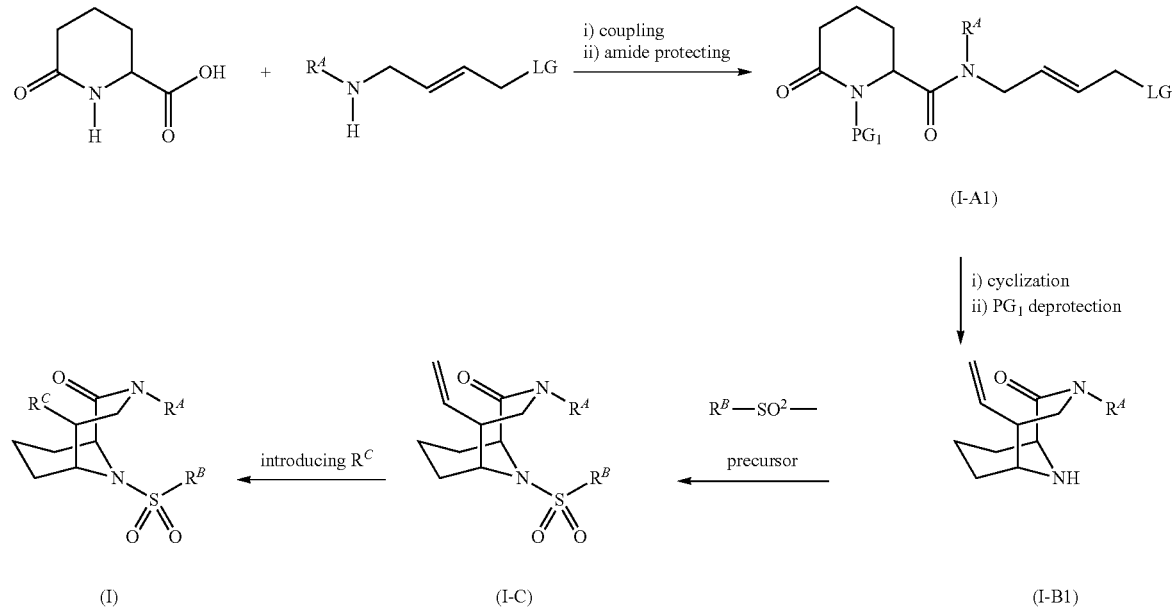

Scheme 1

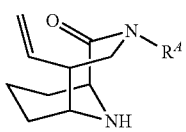
(I-B1)

(c) introducing the moiety —SO₂—R$^B$ to yield compound of the formula (I-C)

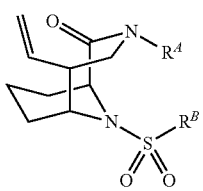
(I-C)

(d) transforming the vinyl group of compound (I-C) into the substituent R$^C$ to yield compound of the formula (I)

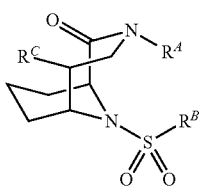
(I)

wherein R$^A$, R$^B$ and R$^C$ have the meanings as defined herein.

As synthetic route 2, intermediate compound (I-A2) can be prepared by providing 6-carboxy-2-piperidone and a butenyl amine protected with a protecting group PG$_6$ which has a suitable leaving group (LG) such as trimethylsilyl (TMS) and a carbon-carbon double bond in allyl position to the amino group. Said protected amino group is reacted with the carboxy moiety of 6-carboxy-2-piperidone. Subsequently, this compound undergoes a cyclization reaction upon which the leaving group LG is detached from the starting molecule. After deprotecting PG$_1$ from amide, 5-vinyl-3,10-diazabicyclo[4.3.1]decane-2-one derivative (I-B2) is formed. A sulphonamide intermediate (I-B3) can be obtained by subsequently reacting (I-B2) with a suitable precursor for the moiety —SO₂—R$^B$. By deprotecting PG$_6$ from amide group of the intermediate (I-B3) and subsequently reacting with a suitable precursor for the moiety R$^{A'}$ a sulphonamide compound (I-C) can be produced. By suitable transformation reactions of vinyl group at C-5 position of the resulting sulphonamide compound (I-C), the compound of the general formula (I) can be obtained. Preferred, the vinyl group could be transformed by oxidation reaction with oxygen gas or ozone, epoxidation reaction or dihydroxylation catalyzed by osmium (VIII) oxide.

Scheme 2

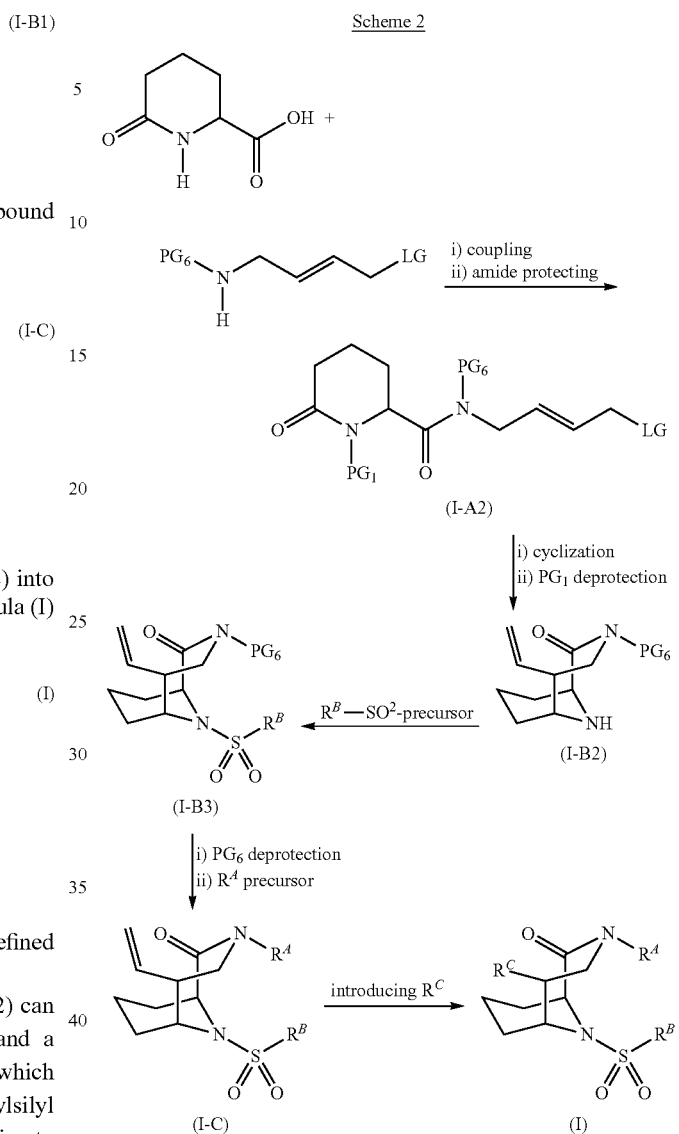

In another embodiment of the present invention, a method for preparation of compound of the general formula (I) by synthetic route 2 comprises the following steps:

(a) providing an intermediate compound of the formula (I-A2)

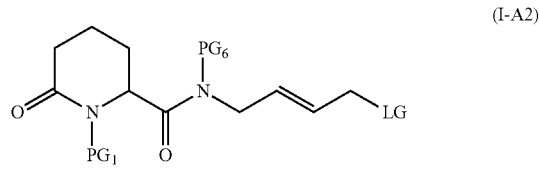
(I-A2)

wherein R$^A$ has the meanings as defined herein, LG refers to a leaving group, and PG$_1$ and PG$_6$ refer to protecting groups for amines;

(b) performing a cyclization reaction and deprotecting PG$_1$ to yield compound of the formula (I-B1)

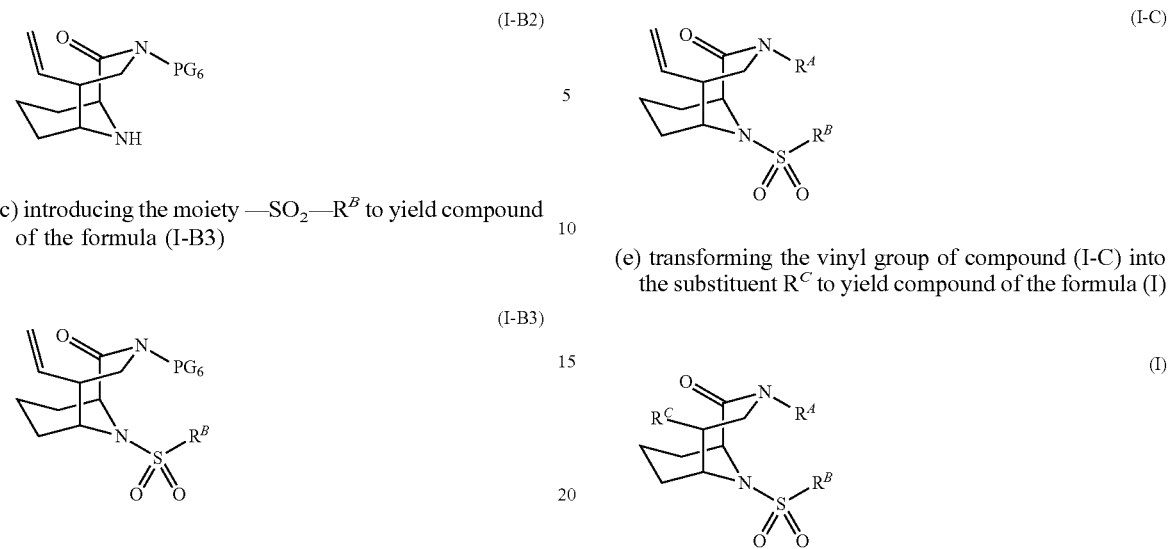

(c) introducing the moiety —SO₂—R^B to yield compound of the formula (I-B3)

(e) transforming the vinyl group of compound (I-C) into the substituent R^C to yield compound of the formula (I)

wherein R^B has the meanings as defined herein;

(d) deprotecting PG₆ and introducing the moiety R^A to yield compound of the formula (I-C)

wherein R^A, R^B and R^C have the meanings as defined herein.

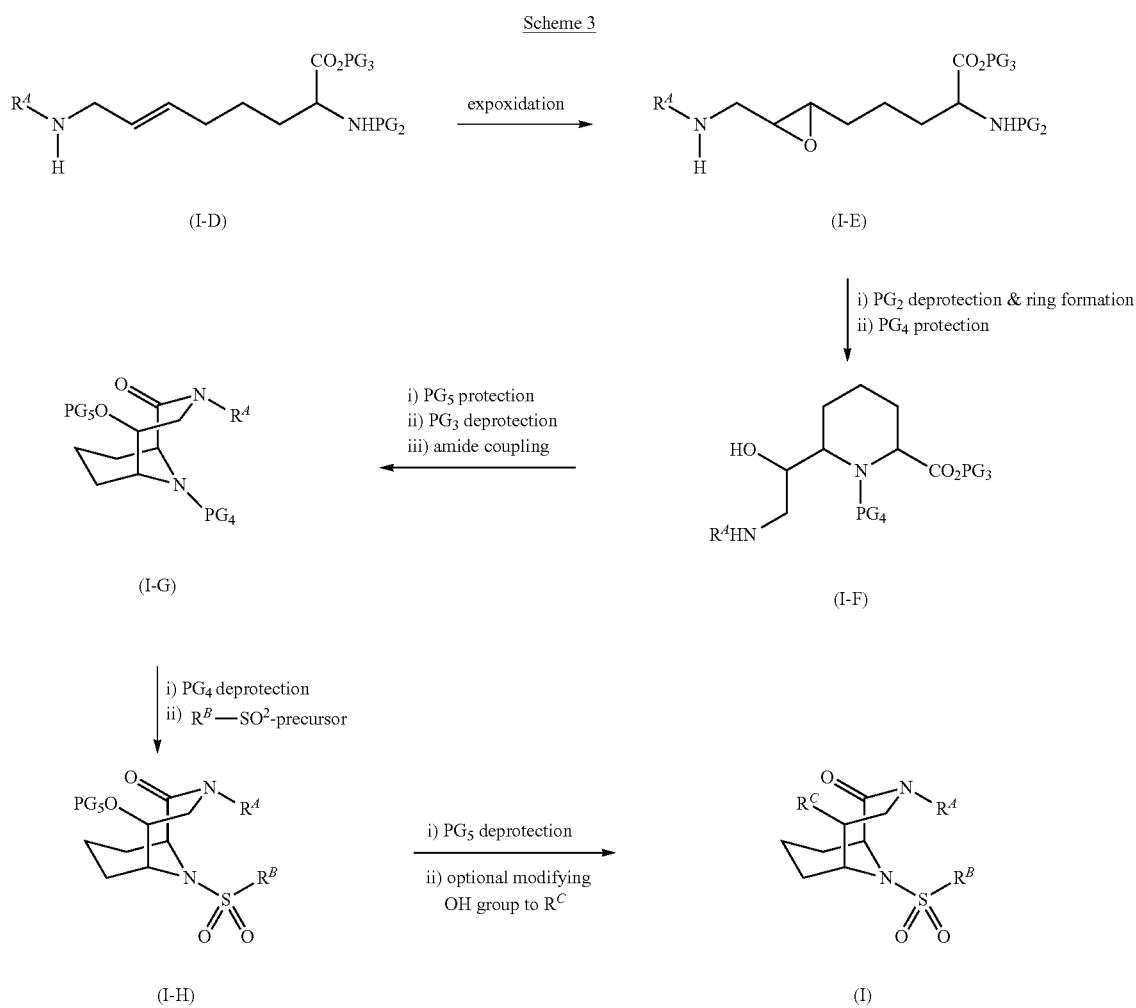

As alternative synthetic route 3, 1-amino-hex-2-en-yl substituted amino acid derivate (I-D) can be used as starting material (scheme 2). Amino group of hexenyl substituent is further substituted with $R^A$. Amino group and carboxy group of said amino acid are also protected respectively with suitable protecting groups $PG_2$ and $PG_3$. After epoxidation of a double bond of starting material, piperidine intermediate (I-F) is formed by deprotecting $PG_2$ and spontaneous ring formation reaction. An amino group of piperidine ring and a hydroxyl group derived from epoxide ring are protected respectively with protecting groups $PG_4$ and $PG_5$. After deprotecting of carboxylic protecting group $PG_3$, 3,10-diazabicyclo[4.3.1]decane-2-one derivative (I-G) is formed by an intramolecular amide coupling reaction between free carboxylic acid and $R^A$ substituted amine.

After deprotecting $PG_4$, the $SO_2$—$R^B$ precursor reacts with the amino group of the above shown intermediate product (I-G) in order to introduce the residue —$SO_2$—$R^B$ by covalent chemical bonding into the intermediate product to obtain the intermediate compound (I-H). The term $SO_2$—$R^B$ precursor has the same meaning as defined in synthetic route 1. The inventive compound is prepared by deprotecting $PG_5$ or further transformation of hydroxy group obtained by deprotecting $PG_5$. Preferred, the Hydroxy group can be transformed into keto, ether, ester or amine functional group.

Thus, in another embodiment of the present invention, a method for preparation of compound of the general formula (I) by alternative synthetic route 2 comprises the following steps:

(a) providing an intermediate compound of the formula (I-E)

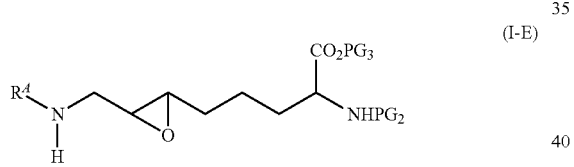

wherein $R^A$ has the meanings as defined herein, $PG_2$ refers to a protecting group for amine, and $PG_3$ refers to a protecting group for carboxylic acid;

(b) deprotecting $PG_2$, performing a piperidine ring formation reaction and introducing $PG_4$ to yield compound of the formula (I-F)

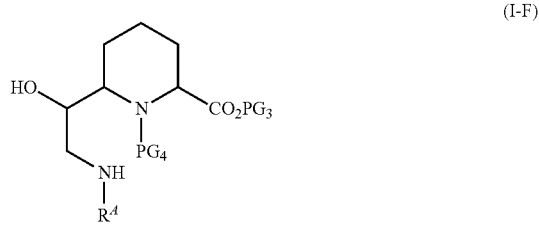

wherein $R^A$ has the meanings as defined herein, $PG_3$ refers to a protecting group for carboxylic acid, and $PG_4$ refers to a protecting group for amine;

(c) introducing $PG_5$, deprotecting $PG_3$ and performing a amide coupling reaction to yield compound of the formula (I-G)

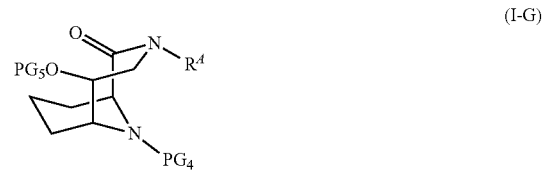

wherein $R^A$ has the meanings as defined herein, $PG_4$ refers to a protecting group for amine, and $PG_5$ refers to a protecting group for hydroxyl group;

(d) deprotecting $PG_4$ and introducing the moiety —$SO_2$—$R^B$ to yield compound of the formula (I-H)

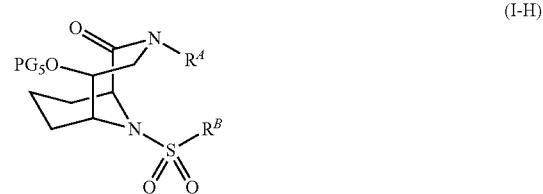

wherein $R^A$ and $R^B$ have the meanings as defined herein, $PG_5$ refers to a protecting group for hydroxyl group;

(e) transforming a hydroxyl group obtained by deprotecting $PG_5$ to yield compound of the formula (I)

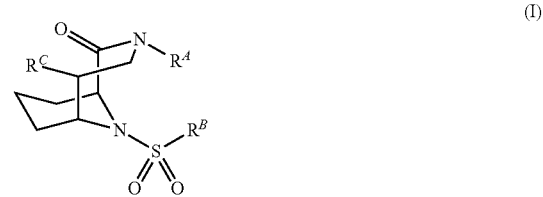

wherein $R^A$, $R^B$ and $R^C$ have the meanings as defined herein.

Said compounds of the formulae (I-E) and (I-F) are important intermediates for preparing the compound of the formula (I). As shown in scheme 4, the intermediate compound of the formula (I-E) has all necessary functional groups to form a diazabicyclo[4.3.1]decane moiety. A protected amine group at C-1 position and an epoxy group at C-5 and C-6 positions form 6-membered piperidine ring of diazabicyclo[4.3.1]decane moiety by nucleophilic epoxide ring opening reaction, as shown in the compound of the formula (I-F). A protected carboxylic acid (ester) group at C-1 position and a secondary amine group at C-7 position further form 7-membered azepane ring of diazabicyclo [4.3.1]decane moiety by amide coupling reaction. Further, said epoxy ring at C-5 and C-6 positions is also a precursor group from which a hydroxyl group is formed at C-6 position and said hydroxyl group can be easily transformed to $R^C$ group of the compound of the formula (I) as shown the step (e). Therefore, said intermediate of the formula (I-E) has important technical meaning for the present invention. The intermediate of the formula (I-F) has a 6-membered piperidine ring and also functional groups, i.e. a protected carboxylic acid (ester) at C-1 position, a secondary amine at C-7 position and a hydroxyl group for introducing $R^C$ group of the compound of the formula (I). Thus, said intermediate of the formula (I-F) is also important for preparing the compound of the present invention.

Scheme 4

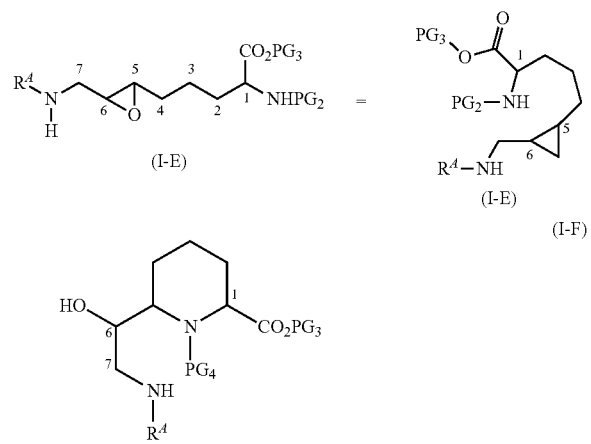

Suitable protecting groups $PG_1$-$PG_4$, and $PG_6$ for amines represent independently of each other carbobenzyloxy (Cbz), p-methoxybenzyl carbonyl (Moz), tert-butyloxycarbonyl (Boc), 9-fluorenylmethyloxycarbonyl (Fmoc), allyloxycarbonyl (Alloc), 2,2,2-trichlorethoxycarbonyl (Troc), trifluoroacetyl, 2-(trimethylsilyl)ethoxycarbonyl (Teoc) p-methoxy-benzyl (PMB) or phthalimide.

Suitable protecting group $PG_3$ for carboxylic acid is selected from the group consisting of methyl, ethyl, isopropyl, tert-butyl (tBu), allyl, and benzyl (Bn).

Suitable protecting group $PG_5$ for hydroxyl group is selected from the group consisting of trimethylsilyl (TMS), triethylsilyl (TES), tert-butyldimethylsilyl (TBDMS), tert-butyldiphenylsilyl (TBDPS), allyl, benzyl, tert-butyl, methoxylmethyl (MOM), methoxyethyl (MEM), tetrahydropyranyl (THP), acetyl (Ac), benzoyl (Bz) and pivalic (Piv).

Influence of Substituent $R^C$ of the General Formula (I) to Affinity to FK506 Domain of FKBP51/52

The compounds of this invention can be distinguished from the closest prior art by having the additional substituent $R^C$.

In the present invention, the influence of substituent $R^C$ at C-5 position of 3,10-diazabicyclo[4.3.1]decan-2-one derivative is proved. In the present invention, in vitro fluorescence polarization assays with the compounds of the general formula (I) were performed to determine the binding affinities to FKBP51 and FKBP52 or to the isolated FK506-binding domains of FKBP51 and FKBP52 (Example 8). Binding to the isolated FK506-binding domains is reliably indicative of binding to the full length proteins. The affinities for the isolated FK506-binding domains and for full-length FKBP51 or FKBP52 are the same for all compounds tested so far (Kozany et al, ChemBioChem 2009, 10, 1402-1410).

Surprisingly, it was found by these assays that substituent $R^C$ of the compounds of the general formula (I) consistently increases affinity to FKBP51 and/or FKBP 52. In Table 1 the binding affinity data of exemplary compounds of the general formula (I) are summarized.

The superiority of the compounds of this invention over the closest prior art is best demonstrated by the direct comparison between Ref. 1 and C2, D3-D8 and H2.3. These compounds share the exact same scaffold and differ only in the $R^C$ position, where Ref. 1 has a simple hydrogen while all inventive compounds have larger substituents. These additional $R^C$ substituents impart a gain in affinity for FKBP51 and FKBP52 by at least 20 fold.

Molecular modelling suggests that the increase in affinity can be caused by additional Van-der-Waals contacts of the inventive $R^C$ substituent with Tyr57, Asp68, Arg73 or Phe77 of FKBP51 or FKBP52 or conserved equivalent residues in other FKBPs. Preferred compounds of this invention have at least one polar heteroatom (N, O, S, F, Cl) in the inventive $R^C$ substituent and thus have the potential to engage in hydrogen bonds with Tyr57, Asp68, or Arg73 of FKBP51 or FKBP52 or conserved equivalent residues in other FKBPs. This is further supported by a direct comparison between compounds J2 and J6, between J3 and J7 and between J4 and J8. These compounds share the exact same scaffold and differ only in the $R^C$ position, where J2-4 have a vinyl group while J6-8 have a $CH_2OH$ group. In each case the latter have the better affinities when pairwise compared with their $R^C$=vinyl counterparts.

As abovementioned, the compounds of the general formula (I) are characterized in that the substituent $R^C$ significantly increases affinity to FKBP51/52. Compared to the compounds (Ref.1-4) of the prior art, the inventive compounds of the general formula (I) have $R^C$ as hydrophilic substituents containing polar functional groups or hetero atoms which can form hydrogen bond(s) with amino acid(s) of FK506 domain.

N2a Cellular Assay

FK506 analogs have repeatedly been described as neuroprotective and neurodegenerative agents in the prior arts. Using a neurite outgrowth assay with N2a neuroblastoma cells, which are a recognized model for neuronal differentiation, compounds C2a and C2b potently enhanced neurite outgrowth(FIG. 1).

Pharmaceutical Composition

The present invention also comprises pharmaceutically acceptable salts of the compounds according to the general formula (I) and the subformulas (II-XIII), all stereoisomeric forms of the compounds according to the general formula (I) and the subformulas (II-XIII) as well as solvates, especially hydrates or prodrugs thereof.

In case, the inventive compounds bear basic and/or acidic substituents, they may form salts with organic or inorganic acids or bases. Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphtholsulfonic acid, sulfanilic acid, camphorsulfonic acid, china acid, mandelic acid, o-methylmandelic acid, hydrogen-benzenesulfonic acid, picric acid, adipic acid, d-o-tolyltartaric acid, tartronic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

Examples for suitable inorganic or organic bases are, for example, NaOH, KOH, $NH_4OH$, tetraalkylammonium hydroxide, lysine or arginine and the like. Salts may be prepared in a conventional manner using methods well known in the art, for example by treatment of a solution of the compound of the general formula (I) and the subformulas (II-XIII) with a solution of an acid, selected out of the group mentioned above.

Some of the compounds of the present invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Certain compounds of the general formula (I) and the subformulas (II-XIII) may exist in the form of optical isomers if substituents with at least one asymmetric center are present, e.g. diastereoisomers and mixtures of isomers in all ratios, e.g. racemic mixtures. The invention includes all such forms, in particular the pure isomeric forms. The different isomeric forms may be separated or resolved one from the other by conventional methods, or any given isomer may be obtained by conventional synthetic methods or by stereospecific or asymmetric syntheses. Where a compound according to the general formula (I) contains an alkene moiety, the alkene can be presented as a cis or trans isomer or a mixture thereof. When an isomeric form of a compound of the invention is provided substantially free of other isomers, it will preferably contain less than 5% w/w, more preferably less than 2% w/w and especially less than 1% w/w of the other isomers.

Another aspect of the present invention relates to the use of the inventive FKBP51/52 ligand derivatives as drugs, i.e. as pharmaceutically active agents applicable in medicine.

Therefore one aspect of the present invention is that the compounds according to the general formula (I) and the subformulas (II-XIII) are suitable for use as inhibitor of FK506-binding proteins (FKBP). It is preferred if said compound is suitable for use as inhibitor of the FK506-binding protein 51 (FKBP51) and/or the FK506-binding protein 52 (FKBP52).

FKBP51 has been implicated in numerous in human diseases (Schmidt et al., ChemMedChem 2012, 7, 1351-1359; Gaali et al, Curr Med Chem 2011, 18, 5355-5379; Galigniana et al, J. Neurochem 2012, 122, 4-18; Erlejman et al, Futue Med Chem 2013, 5, 591-607; Sanchez, biochim Biophys Acta Mol Cell Res 2012r, 1823, 722-729; Zannas, A. S. & Binder, E. B. Gene-environment interactions at the FKBP5 locus: sensitive periods, mechanisms and pleiotropism. Genes Brain Behav, doi: 10.1111/gbb.12104 (2013)). Consequently, FKBP51 is a target which is addressed in order to prevent and/or treat the diseases disclosed in the afore-mentioned literature.

Thus, FKBP51 and/or FKBP 52 ligand compounds of the present invention can be used as pharmaceutically active agent in medicine.

Preferred, the FKBP51/52 ligand compounds of the present invention can be used for treatment, or for the preparation of a pharmaceutical formulation for prophylaxis and/or treatment of these FKBP51/52-associated diseases.

The inventive compound of any one of formula (I) and subformulae (II)-(XIII) is used in the manufacture of a medicament or of a pharmaceutical composition for the treatment and/or prevention of FKBP51/52-associated diseases.

Another aspect of the present invention relates to a method of treating FKBP51/52-associated diseases comprising administration a therapeutically effective amount of at least one inventive compound or a pharmaceutical composition comprising at least one inventive compound.

These FKBP51/52-associated diseases include psychiatric and neurodegenerative diseases, disorders and conditions, for metabolic diseases such as localized adiposity or obesity, for sleep disorders, neuroprotection or neuroregeneration, for the treatment of neurological disorders, for the treatment of diseases relating to neurodegeneration, for the treatment of cancers such as malignant melanoma or acute lymphoblastic leukemia and especially steroid-hormone dependent cancers such as prostate cancer, for the treatment of glucocorticoid hyposensitivity syndromes and for peripheral glucocorticoid resistance, for asthma, especially steroid-resistant asthma, and for the treatment of infectious diseases, for the treatment of alopecia and promoting hair growth, for the treatment or prevention of multi-drug resistance, for stimulating neurite growth or neuroregeneration, for neuroprotection, for the use as wound healing agents for treating wounds resulting from injury or surgery; for the use in antiglaucomatous medications for treating abnormally elevated intraocular pressure; for the use in limiting or preventing hemorrhage or neovascularization for treating macular degeneration, and for treating oxidative damage to eye tissues, for treating a vision disorder, for improving vision, for treating memory impairment or enhancing memory performance.

The FKBP51 and/or FKBP52 ligand compounds of the present invention are preferably suitable for treatment, or for the preparation of a pharmaceutical formulation for prophylaxis and treatment of psychiatric diseases. It is especially preferred if this psychiatric diseases is an affective disorder (ICD-10 classification: F30-F39) or an anxiety disorder.

Affective disorder is a mental disorder characterized by dramatic changes or extremes of mood. The affective disorder according to the invention is selected from the group comprising or consisting of depression, bipolar disorder, mania, substance induced mood disorder and seasonal affective disorder (SAD). Among the psychiatric diseases and disorders, the most preferred is depression, the most commonly diagnosed psychiatric disorder.

The anxiety disorder according to the invention is selected from the group comprising or consisting of generalized anxiety disorder, panic disorder, panic disorder with agoraphobia, phobias, obsessive-compulsive disorder, post-traumatic stress disorder, separation anxiety and childhood anxiety disorders.

Among the hundreds of different neurodegenerative disorders, the attention has been given only to a handful, including Alzheimer's Disease (Blair et al, J Clin Invest 2013, DOI: 10.1172/JCI69003), Parkinson's Disease, and amyotrophic lateral sclerosis.

Among the glucocorticoid hyposensitivity syndromes, the attention has been given to the group of related diseases enclosing resistant asthma (Tajiri et al, PLOS One 2013, 8, e65284), eosinophilic esophagitis (Caldwell et al, J Allerg Clin Immunol 2010, 125, 879-888), AIDS, rheumatoid arthritis, hypertension and diabetes, metabolic syndrome or obesity (Warder, PhD Thesis 2008, University of Toledo, ProQuest LLC, "Role of FKBP51 and FKBP52 in Glucocorticoid Receptor Regulated Metabolism").

Among the cancers, the attention has been given to malignant melanoma (Romano et al, Cell Death Dis 2013, 4, e578), acute lymphoblastic leukemia (Li at al, Br J Cancer, 2013, DOI: 10.1038/bjc.2013.562), gliomas (Jiang et al, Neoplasia 2013, 10, 235-243), idiopathic myelofibrosis (Komura et al, Cancer Res 2005, 65, 3281-3289), pancreatic and breast cancers (Hou & Wang, PLOS One 2012, 7, e36252), steroid-hormone dependent cancers or prostate cancer.

Among the hundreds of infectious diseases, the attention has been given to malaria and the Legionnaires' disease (Gaali et al, Curr Med Chem 2011, 18, 5355-5379).

Among the vision disorders, the attention has been given to visual impairments; orbital disorders; disorders of the lacrimal apparatus; disorders of the eyelids; disorders of the conjunctiva; disorders of the Cornea; cataract; disorders of the uveal tract; disorders of the retina; disorders of the optic nerve or visual pathways; free radical induced eye disorders and diseases; immunologically-mediated eye disorders and diseases; eye injuries; and symptoms and complications of eye disease, eye disorder, or eye injury.

Therefore, another aspect of the present invention is directed to pharmaceutical compositions comprising at least one compound of the present invention as active ingredient, together with at least one pharmaceutically acceptable carrier, excipient and/or diluents. The pharmaceutical compositions of the present invention can be prepared in a conventional solid or liquid carrier or diluent and a conventional pharmaceutically-made adjuvant at suitable dosage level in a known way. The preferred preparations are adapted for oral application. These administration forms include, for example, pills, tablets, film tablets, coated tablets, capsules, powders and deposits.

Furthermore, the present invention also includes pharmaceutical preparations for parenteral application, including dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application, which preparations in addition to typical vehicles and/or diluents contain at least one compound according to the present invention and/or a pharmaceutical acceptable salt thereof as active ingredient.

The pharmaceutical compositions according to the present invention containing at least one compound according to the present invention, and/or a pharmaceutical acceptable salt thereof as active ingredient will typically be administered together with suitable carrier materials selected with respect to the intended form of administration, i.e. for oral administration in the form of tablets, capsules (either solid filled, semi-solid filled or liquid filled), powders for constitution, extrudates, deposits, gels, elixirs, dispersable granules, syrups, suspensions, and the like, and consistent with conventional pharmaceutical practices. For example, for oral administration in the form of tablets or capsules, the active drug component may be combined with any oral non-toxic pharmaceutically acceptable carrier, preferably with an inert carrier like lactose, starch, sucrose, cellulose, magnesium stearate, dicalcium phosphate, calcium sulfate, talc, mannitol, ethyl alcohol (liquid filled capsules) and the like. Moreover, suitable binders, lubricants, disintegrating agents and coloring agents may also be incorporated into the tablet or capsule. Powders and tablets may contain about 5 to about 95 weight % of the benzothiophene-1,1-dioxide derived compound and/or the respective pharmaceutically active salt as active ingredient.

Suitable binders include starch, gelatin, natural sugars, corn sweeteners, natural and synthetic gums such as acacia, sodium alginate, carboxymethylcellulose, polyethylene glycol and waxes. Among suitable lubricants there may be mentioned boric acid, sodium benzoate, sodium acetate, sodium chloride, and the like. Suitable disintegrants include starch, methylcellulose, guar gum, and the like. Sweetening and flavoring agents as well as preservatives may also be included, where appropriate. The disintegrants, diluents, lubricants, binders etc. are discussed in more detail below.

Moreover, the pharmaceutical compositions of the present invention may comprise an additional pharmaceutically active compound or drug. The pharmaceutically active compound or drug may belong to the group of glucocorticoids. Thus an embodiment of the current invention comprises the administration of a compound of the current invention in addition to a co-administration of glucocorticoids.

Moreover, the pharmaceutical compositions of the present invention may be formulated in sustained release form to provide the rate controlled release of any one or more of the components or active ingredients to optimise the therapeutic effect(s), e.g. antihistaminic activity and the like. Suitable dosage forms for sustained release include tablets having layers of varying disintegration rates or controlled release polymeric matrices impregnated with the active components and shaped in tablet form or capsules containing such impregnated or encapsulated porous polymeric matrices.

Liquid form preparations include solutions, suspensions, and emulsions. As an example, there may be mentioned water or water/propylene glycol solutions for parenteral injections or addition of sweeteners and opacifiers for oral solutions, suspensions, and emulsions. Liquid form preparations may also include solutions for intranasal administration. Aerosol preparations suitable for inhalation may include solutions and solids in powder form, which may be present in combination with a pharmaceutically acceptable carrier such as an inert, compressed gas, e.g. nitrogen. For preparing suppositories, a low melting fat or wax, such as a mixture of fatty acid glycerides like cocoa butter is melted first, and the active ingredient is then dispersed homogeneously therein e.g. by stirring. The molten, homogeneous mixture is then poured into conveniently sized moulds, allowed to cool, and thereby solidified.

Also included are solid form preparations which are intended to be converted, shortly before use, to liquid form preparations for either oral or parenteral administration. Such liquid forms include solutions, suspensions, and emulsions.

The compounds according to the present invention may also be delivered transdermally. The transdermal compositions may have the form of a cream, a lotion, an aerosol and/or an emulsion and may be included in a transdermal patch of the matrix or reservoir type as is known in the art for this purpose.

The term capsule as recited herein refers to a specific container or enclosure made e.g. of methyl cellulose, polyvinyl alcohols, or denatured gelatins or starch for holding or containing compositions comprising the active ingredient(s). Capsules with hard shells are typically made of blended of relatively high gel strength gelatins from bones or pork skin. The capsule itself may contain small amounts of dyes, opaquing agents, plasticizers and/or preservatives. Under tablet a compressed or moulded solid dosage form is understood which comprises the active ingredients with suitable diluents. The tablet may be prepared by compression of mixtures or granulations obtained by wet granulation, dry granulation, or by compaction well known to a person of ordinary skill in the art.

Oral gels refer to the active ingredients dispersed or solubilised in a hydrophilic semi-solid matrix. Powders for constitution refers to powder blends containing the active ingredients and suitable diluents which can be suspended e.g. in water or in juice.

Suitable diluents are substances that usually make up the major portion of the composition or dosage form. Suitable diluents include sugars such as lactose, sucrose, mannitol, and sorbitol, starches derived from wheat, corn rice, and potato, and celluloses such as microcrystalline cellulose. The amount of diluent in the composition can range from about 5 to about 95% by weight of the total composition, preferably from about 25 to about 75 weight %, and more preferably from about 30 to about 60 weight %.

The term disintegrants refers to materials added to the composition to support break apart (disintegrate) and release the pharmaceutically active ingredients of a medicament. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium croscarmellose, alginates such as alginic acid and sodium alginate, clays such as bentonites, and effervescent mixtures. The amount of disintegrant in the composition may range from about 2 to about 20 weight % of the composition, more preferably from about 5 to about 10 weight %.

Binders are substances which bind or "glue" together powder particles and make them cohesive by forming granules, thus serving as the "adhesive" in the formulation. Binders add cohesive strength already available in the diluent or bulking agent. Suitable binders include sugars such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate. The amount of binder in the composition may range from about 2 to about 20 weight % of the composition, preferably from about 3 to about 10 weight %, and more preferably from about 3 to about 6 weight %.

Lubricants refer to a class of substances which are added to the dosage form to enable the tablet granules etc. after being compressed to release from the mould or die by reducing friction or wear. Suitable lubricants include metallic stearates such as magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine. Lubricants are usually added at the very last step before compression, since they must be present at the surface of the granules. The amount of lubricant in the composition may range from about 0.2 to about 5 weight % of the composition, preferably from about 0.5 to about 2 weight %, and more preferably from about 0.3 to about 1.5 weight % of the composition.

Glidents are materials that prevent caking of the components of the pharmaceutical composition and improve the flow characteristics of granulate so that flow is smooth and uniform. Suitable glidents include silicon dioxide and talc. The amount of glident in the composition may range from about 0.1 to about 5 weight % of the final composition, preferably from about 0.5 to about 2 weight %.

Coloring agents are excipients that provide coloration to the composition or the dosage form. Such excipients can include food grade dyes adsorbed onto a suitable adsorbent such as clay or aluminum oxide. The amount of the coloring agent may vary from about 0.1 to about 5 weight % of the composition, preferably from about 0.1 to about 1 weight %.

Said pharmaceutical compositions may further comprise at least one FKBP51/52 ligand of the general formulas (I) and subformulas (II-XIII).

The pharmaceutical compositions may further comprise at least one further active agent. It is preferred if this active agent is selected from the group consisting of anti-depressant and other psychotropic drugs. It is further preferred if the anti-depressant is selected from amitriptyline, amioxide clomipramine, doxepine, duloxetine, imipramine trimipramine, mirtazapine, reboxetine, citaloprame, fluoxetine, moclobemide and sertraline.

EXAMPLES

Abbreviations

Figure 1:
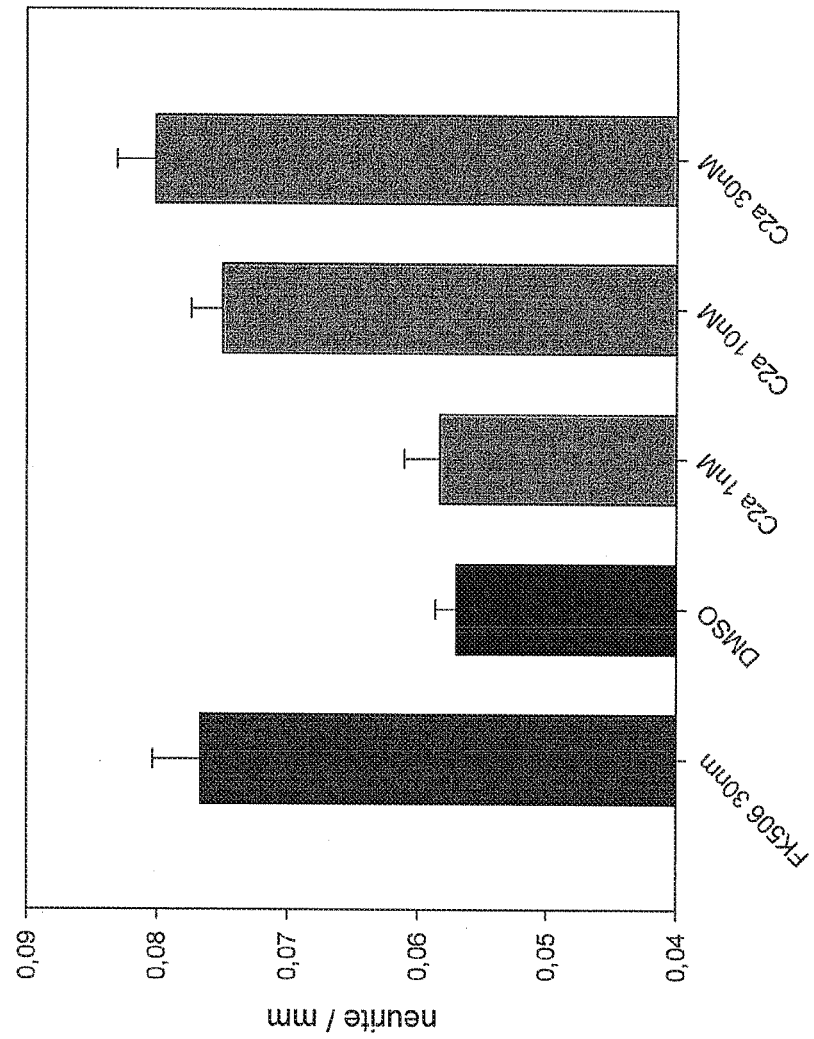
FIG. 1: Effects of FKBP51/52 inhibitors C2a (a) and C2b (b) of the present invention and of FK506 (c) on neurite outgrowth of N2a cells.
Figure 1:
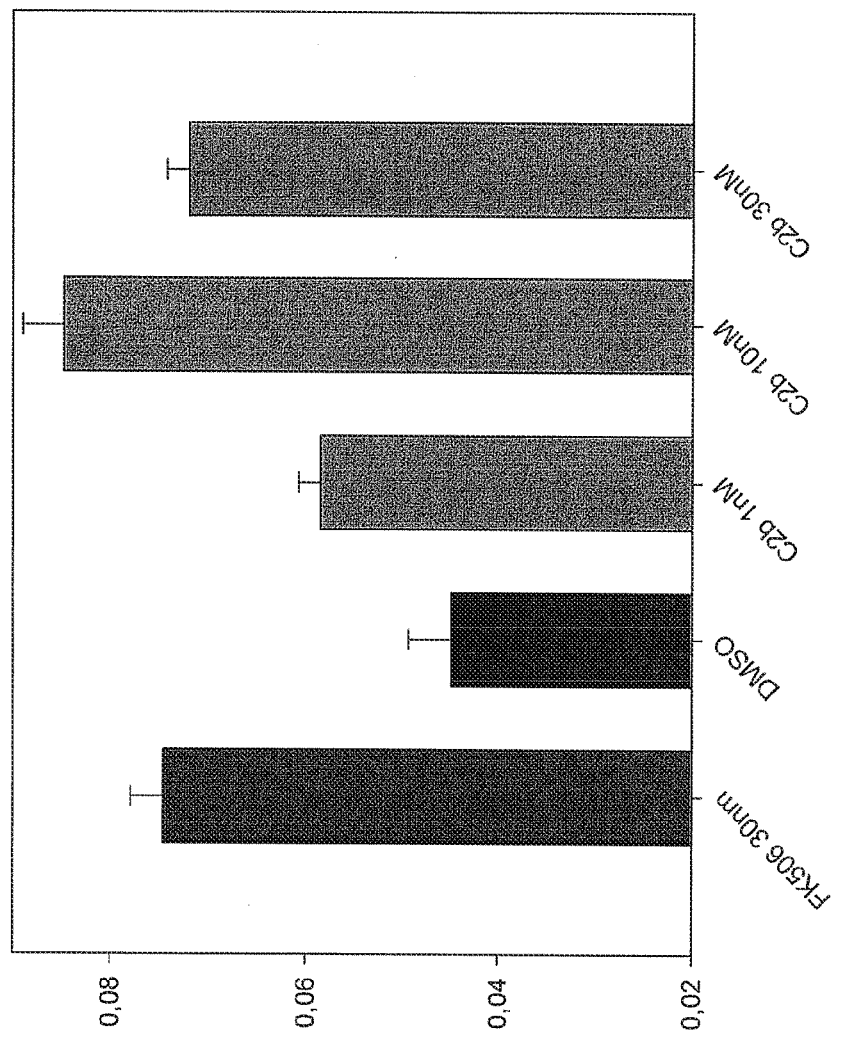
Figure 2:
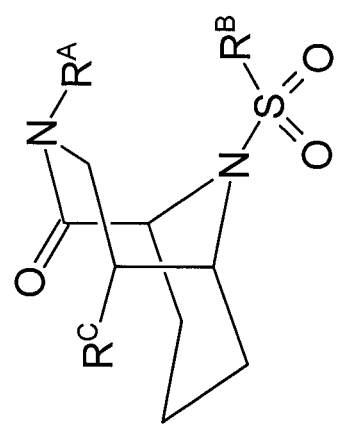
FIG. 2: Represents the general formula of the inventive compounds.

AIBN (azobisisobutyronitrile), Boc (tert-butyloxycarbonyl), CAN (ceric ammonium nitrate), CDI (1,1'-carbonyldiimidazole), DAST (diethylaminosulfur trifluoride), DCM (dichloromethane), dba (dibenzylideneacetone), DIBAL-H (diisobutylaluminum hydride), DIPEA (N,N-diisopropylethylamine), DMAP (4-dimethyl-aminopyridine), DMF (dimethylformamide), DMM (dimethoxymethane), DMSO (dimethyl sulfoxide), EDC (1-ethyl-3-(3-dimethylaminopropyl) carbodiimide), EDTA (ethylenediaminetetraacetic acid), EtOAc (ethylacetate), Fmoc (fluorenylmethyloxycarbonyl), HATU (2-(7-aza-1H-benzotriazole-1-yl)-1,1,3,3-tetramethyluronium hexafluorophosphate), HMDS (hexamethyldisilazane), HOBt (hydroxybenzotriazole), NMO (N-methylmorpholine N-oxide), MOM (methoxymethyl), oNs (2-nitrobenzenesulfonyl), OTf (triflate), oTol (ortho-tolyl), PMB (p-methoxybenzyl), TBAF (tetra-n-butylammonium chloride), tBu (tert-butyl), TEA (triethylamine), TES (triethylsilyl), TFA (trifluoroacetic acid), THF (tetrahydrofuran), TMS (trimethylsilyl).

Synthetic Procedures

The compound of the general formula (I) can be prepared according to the following synthetic procedures.

I. Preparation of Compound A7 as Starting Material

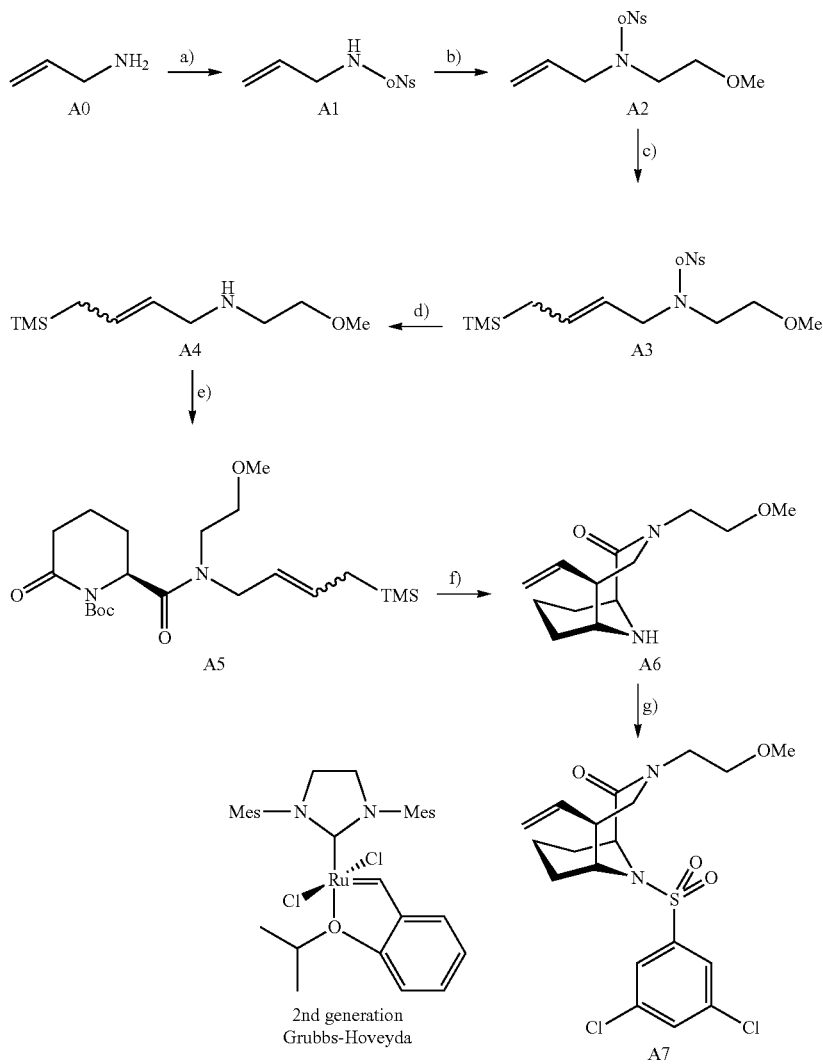

Scheme A.

Reagents and conditions: a) 2-Nibrobenzene-sulfonylchloride, CH₂Cl₂, rt, 1 h, 96%; b) K₂CO₃, 1-Bromo-2-methoxyethane, DMF, 60° C., 2 h, 78%; c) AllylTMS, Grubbs-Hoveyda II, CH₂Cl₂, 60° C., 4 h, 78%; d) K₂CO₃, PhSH, DMF, rt, 14 h, 82%; e) 1.) (S)-6-Oxopiperidine-2-carboxylic acid, HATU, DIPEA, rt, 4 h; 2.) Boc₂O, DIPEA, DMAP, CH₂Cl₂, 6 h, 50% (2 steps); f) 1.) DIBAL, THF, -78° C., 15 min; 2.) HF•yridine, CH₂Cl₂, -78° C., 1 h, 49% (2 steps); g) 3,5-dichlorobenzene-1-sulfonyl chloride, DPEA, DMAP, rt, 24 h, 60%

Example 1-1: Preparation of N-allyl-2-nitrobenzenesulfonamide A1

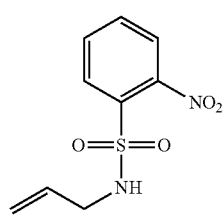

A1

To a solution of Allylamine (7.63 g, 10 mL, 134 mmol) in CH₂Cl₂ (500 mL) was added 2-nitrobenzene-1-sulfonyl chloride (10.0 g, 45.1 mmol). After 1 h stirring at room temperature saturated aqueous NaCl (100 mL) was added to the reaction and washed with CH₂Cl₂ (3×200 mL). The solvent was removed under reduced pressure affording the title compound (10.5 g, 43.3 mmol, 96.1%) as a slightly yellow solid, which was used for the next step without further purification.

$R_f$: 0.24 (Cyclohexane/EtOAc=4:1)

¹H-NMR (300 MHz, CDCl₃): δ=3.72-3.79 (m, 2H), 5.09 (d, J=10.5 Hz, 1H), 5.19 (d, J=17.1 Hz, 1H), 5.40 ($s_{br}$, 1H), 5.65-5.80 (m, 1H), 7.70-7.78 (m, 2H), 7.81-7.88 (m, 1H), 8.08-8.14 (m, 1H).

¹³C-NMR (75.5 MHz, CDCl₃): δ=46.28, 118.0, 125.3, 131.0, 132.5, 132.8, 133.6, 133.9, 147.9.

Example 1-2: Preparation of N-allyl-N-(2-methoxyethyl)-2-nitrobenzenesulfonamide A2

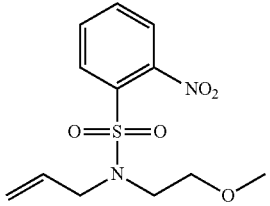

A2

To a solution of N-allyl-2-nitrobenzenesulfonamide (100 mg, 0.413 mmol) in DMF (4 mL) were added K₂CO₃ (114 mg, 0.826 mmol) and 1-Bromo-2-methoxyethane (63.1 mg, 43 µL, 0.454 mmol). The reaction was heated to 60° C. After two hours the reaction was cooled to room temperature, Et₂O (90 mL) was added and washed with sat. aq. NaCl solution (3×10 mL). The organic layer was dried over MgSO₄ and the solvent removed under reduced pressure. Flash column chromatography (10-40% EtOAc in Cyclohexane) afforded the title compound (97.0 mg, 0.323 mmol, 78.2%).

$R_f$: 0.175 (Cyclohexane/EtOAc=4:1)
¹H-NMR (400 MHz, CDCl₃): δ=3.23 (s, 3H), 3.47-3.48 (m, 4H), 4.02 (dt, J=8.0, 1.6 Hz, 2H), 5.16-5.24 (m, 2H), 5.64-5.74 (m, 1H), 7.26-7.68 (m, 3H), 8.04-8.07 (m, 1H).
¹³C-NMR (101 MHz, CDCl₃): δ=46.18, 51.08, 53.43, 58.71, 70.85, 119.2, 124.1, 130.9, 131.6, 132.7, 133.3, 133.9.
MS (ESI): m/z (%)=301.00 [M+H]⁺

Example 1-3: Preparation of N-(2-methoxyethyl)-2-nitro-N-(4-(trimethylsilyl)but-2-en-1-yl)benzenesulfonamide A3

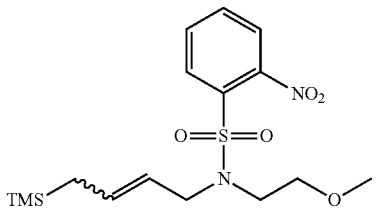

A3

To a solution of N-allyl-N-(2-methoxyethyl)-2-nitrobenzenesulfonamide (10.0 g, 33.3 mmol) in CH₂Cl₂ (350 mL) were added sequentially Allyltrimethylsilane (38.0 g, 52.9 mL, 333 mmol) and Grubbs Hoveyda II generation catalyst (1.46 g, 2.33 mmol). The reaction was stirred at 60° C. for 4 h. Sat. aq. NaCl solution (100 mL) was added to the reaction and the organic phase was separated. The aqueous phase was extracted with CH₂Cl₂ (3×200 mL). The combined organic layers were dried over MgSO₄ and the solvent was removed under reduced pressure. Flash column chromatography over SiO₂ (5-10% EtOAc in Cyclohexane) afforded the title compound (10.1 g, 26.1 mmol, 78.4%).

$R_f$: 0.37 (Cyclohexane/EtOAc=4:1)
¹H-NMR (300 MHz, CDCl₃) δ=−0.06-0.08 (m, 9H), 1.40-1.53 (m, 2H), 3.16-3.56 (m, 7H), 3.86-4.10 (m, 2H), 5.07-5.21 (m, 1H), 5.56-5.70 (m, 1H), 7.59-7.70 (m, 3H), 8.02-8.09 (m, 1H).
¹³C-NMR (75 MHz, CDCl₃) δ=−1.99, 22.91, 45.45, 50.66, 58.69, 70.79, 121.2, 122.0, 124.0, 130.8, 131.4, 133.1, 133.4, 134.2.

Example 1-4: Preparation of N-(2-methoxyethyl)-4-(trimethylsilyl)but-2-en-1-amine A4

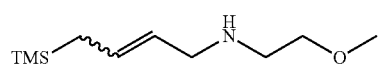

A4

To a solution of N-(2-methoxyethyl)-2-nitro-N-(4-(trimethylsilyl)but-2-en-1-yl) benzenesulfonamide (10.0 g, 25.9 mmol) in DMF (100 mL) was added K₂CO₃ (10.7 g, 78.0 mmol) and thiophenol (2.85 g, 2.65 mL, 25.9 mmol). After 14 hours stirring at room temperature Et₂O (500 mL) was added to the reaction and washed with sat. aq. NaHCO₃ (3×100 mL). The organic phase was dried over MgSO₄ and the solvent was removed under reduced pressure. Column chromatography over SiO₂ (2% TEA and 2% MeOH in EtOAc) afforded the title compound (4.30 g, 21.4 mmol, 82.4%) as a yellow oil. $R_f$: 0.25 (EtOAc+2% TEA (ESI): m/z (%)=201.92 [M+H]⁺

Example 1-5: Preparation of (S)—N-(2-methoxyethyl)-6-oxo-N-(4-(trimethylsilyl)but-2-en-1-yl)piperidine-2-carboxamide A5.1

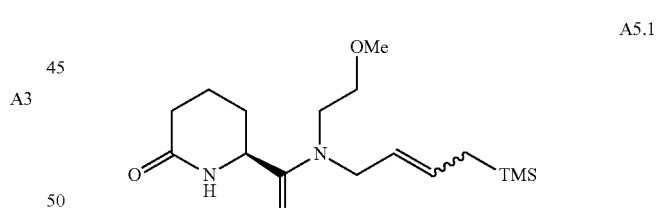

A5.1

To a solution of (S)-6-oxopiperidine-2-carboxylic acid (2.70 g, 18.9 mmol) in CH₂Cl₂ (80 mL) were added sequentially HATU (7.89 g, 20.8 mmol), DIPEA (2.68 g, 3.63 mL, 20.8 mmol) and N-(2-methoxyethyl)-4-(trimethylsilyl)but-2-en-1-amine (3.80 g, 18.9 mmol). The reaction was stirred for 4 h and then saturated sat. aq. NH₄Cl solution (25 mL) was added to the reaction and the organic phase was separated. The aqueous phase was extracted with CH₂Cl₂ (3×100 mL). The combined organic layers were dried over MgSO₄ and the solvent was removed under reduced pressure. The crude product was used for the next step without further purification.

$R_f$: 0.44 (EtOAc+3% MeOH+1% TEA)
MS (ESI): m/z (%)=327.17 [M+H]⁺, 653.02 [2×M+H]⁺, 675.06 [2×M+Na]⁺

Example 1-6: Preparation of (S)-tert-butyl 2-((2-methoxyethyl)(4-(trimethylsilyl)but-2-en-1-yl)carbamoyl)-6-oxopiperidine-1-carboxylate A5.2

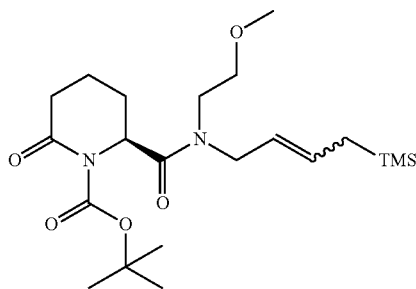

A5.2

Crude mixture of A5.1 was dissolved in CH$_2$Cl$_2$ (150 mL). TEA (3.82 g, 5.23 mL, 38.0 mmol), Boc$_2$O (8.29 g, 38 mmol) and DMAP (3.46 g, 28 mmol) were added. After 6 h stirring at room temperature sat. aq. NaCl solution (25 mL) was added to the reaction and the organic phase was separated. The aqueous phase was extracted with CH$_2$Cl$_2$ (3×100 mL) and the combined organic layers were dried over MgSO$_4$ and the solvent was removed under reduced pressure. Flash column chromatography (10-40% EtOAc in Cyclohexane) afforded the title compound (4.05 g, 9.40 mmol, 50% over two steps) as a yellow resin. R$_f$: 0.56 (Cyclohexane/EtOAc=1:1)

MS (ESI): m/z (%)=327.12 [M-Boc+H]$^+$, 875.12 [2×M+Na]$^+$

Example 1-6: Preparation of (1S,5R,6R)-3-(2-methoxyethyl)-5-vinyl-3,10-diazabicyclo[4.3.1]decan-2-one A6

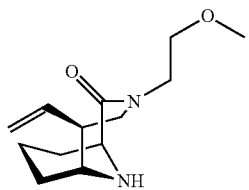

A6

A solution of (6S)-tert-butyl 2-hydroxy-6-((2-methoxyethyl)(4-(trimethylsilyl)but-2-en-1-yl)carbamoyl)piperidine-1-carboxylate (220 mg, 0.516 mmol) in THF (5 mL) was cooled to −78° C. and then DIBAL-H (1 M solution in CH$_2$Cl$_2$, 1.03 mL, 1.03 mmol) was added. After 1 h the solvent was removed under reduced pressure.

The resin resulted from the first step was dissolved in CH$_2$Cl$_2$ (25 mL) and cooled to −78° C. HF (70% in pyridine, 1.25 mL) was added and the reaction was stirred for 1 h. Then Sat. aq. NaHCO$_3$ solution was added. The reaction was extracted three times with CH$_2$Cl$_2$, the combined organic layers were dried over MgSO$_4$ and the solvent removed under reduced pressure. Column chromatography (5% MeOH and 2% TEA in EtOAc) afforded the title compound (60.0 mg, 0.251 mmol, 49.1% over two steps) as an orange resin.

$^1$H-NMR (599 MHz, CDCl$_3$) δ=1.56-1.80 (m, 5H), 2.22-2.38 (m, 1H), 2.58-2.76 (m, 1H), 2.79-2.90 (m, 1H), 3.07 (dd, J=13.9, 2.0 Hz, 1H), 3.31 (m, 1H), 3.34 (s, 3H), 3.50-3.56 (m, 3H), 3.65-3.74 (m, 1H), 3.71-3.86 (m, 1H), 4.08 (dd, J=13.9, 10.7 Hz, 1H), 4.94-5.04 (m, 2H), 5.65 (ddd, J=17.0, 10.2, 8.4 Hz, 1H).

$^{13}$C-NMR (151 MHz, CDCl$_3$) δ=28.04, 29.36, 29.67, 49.61, 51.03, 52.40, 52.57, 57.59, 58.80, 71.32, 114.9, 139.2, 174.2.

MS (ESI): m/z (%)=239.23 [M+H]$^+$, 477.02 [2×M+H]$^+$

Example 1-6: Preparation of (1S,5R,6R)-10-((3,5-dichlorophenyl)sulfonyl)-3-(2-methoxyethyl)-5-vinyl-3,10-diazabicyclo[4.3.1]decan-2-one A7

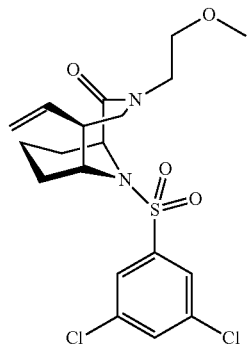

A7

To a solution of (1S,5R,6R)-3-(2-methoxyethyl)-5-vinyl-3,10-diazabicyclo [4.3.1] decan-2-one (600 mg, 2.52 mmol) in CH$_2$Cl$_2$ (25 mL) were added 3,5-dichlorobenzene-1-sulfonyl chloride (618 mg, 2.52 mmol), DMAP (308 mg, 2.52 mmol) and DIPEA (0.879 mL, 5.04 mmol) and the reaction was stirred for 24 hours at room temperature. Sat. aq. NaHCO$_3$ solution (25 mL) was added to the mixture and extracted with CH$_2$Cl$_2$ (250 mL). Flash column chromatography on SiO$_2$ (5-20% EtOAc in Cyclohexane) afforded the title compound (680 mg, 1.52 mmol, 60.3%) as a colorless solid. MS (ESI): m/z (%)=447.17 [M+H]$^+$, 894.44 [2×M+H]$^+$ II. Preparation of Compounds B1-B15

Scheme B.

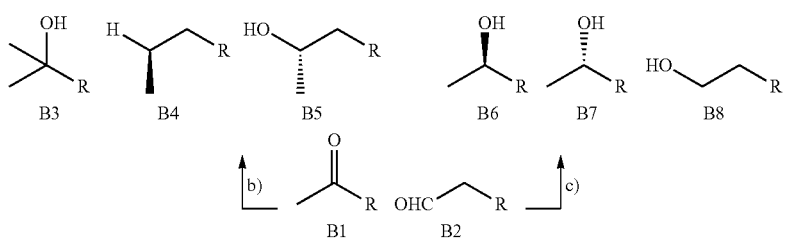

-continued

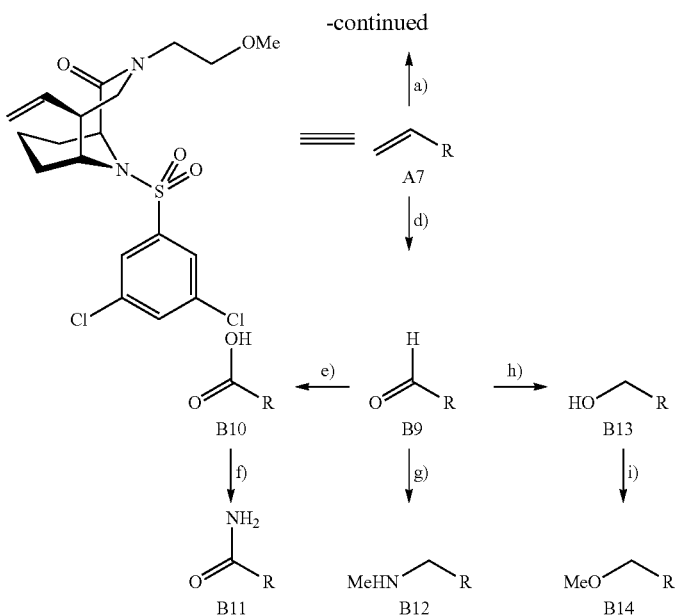

Reagents and conditions: a) PdCl₂, CuCl, O₂, DMF/H₂O, rt, 3 d, 39%; b) MeMgBr, THF, -78° C., 1 h, 62%; c) NaBH₄, EtOH/CH₂Cl₂, rt, 1 h, 36% d) NaIO₄ OsO₄, 2,6-lutidine, dioxane/H₂O, 20 h, rt, 70%; e) 2-methylbutene, NaClO₂, NaH₂PO₄, CHCl₃/tBuOH/H₂O, rt, 16 h, 93%; f) CDI, NH₃ aq., EtOAc, rt, 2 h, 41% g) NH₂Me•HCl, NaBH(OAc)₃, MeOH/AcOH, rt, 4 h, 33%; h) NaBH₄, EtOH, rt, 1 h, 65%; i) NaH, MeI, THF, rt, 5 h, 50%.

Example 2-1: Preparation of (1S,5S,6R)-5-acetyl-10-((3,5-dichlorophenyl)sulfonyl)-3-(2-methoxyethyl)-3,10-diazabicyclo[4.3.1]decan-2-one B1 and 2-((1S,5S,6R)-10-((3,5-dichlorophenyl)sulfonyl)-3-(2-methoxyethyl)-2-oxo-3,10-diazabicyclo[4.3.1]decan-5-yl)acetaldehyde B2

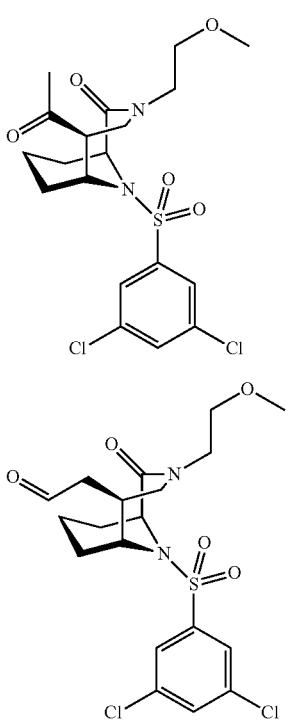

To a solution of (1S,5R,6R)-10-((3,5-dichlorophenyl)sulfonyl)-3-(2-methoxyethyl)-5-vinyl-3,10-diazabicyclo[4.3.1]decan-2-one (450 mg, 1.01 mmol) in DMF/H₂O (0.571 mL, 7:1) was added PdCl₂ (35.7 mg, 0.201 mmol) and CuCl (100 mg, 1.01 mmol). After three days stirring Et₂O was added to the reaction and extracted three times with saturated Na₂S₂O₃. The organic layer was dried over MgSO₄ and the solvent removed under reduced pressure. Column chromatography on SiO₂ (EtOAc/Cyclohexane=1:1) afforded an inseparable mixture of the title compounds (180 mg, 0.388 mmol, 38.6%) as a slightly yellow solid.

$R_f$: 0.6 (Cyclohexan/EtOAc=15:85)

MS (ESI): m/z (%)=463.13 [M+H]⁺

Example 2-2: Preparation of (1S,5S,6R)-10-((3,5-dichlorophenyl)sulfonyl)-5-(2-hydroxypropan-2-yl)-3-(2-methoxyethyl)-3,10-diazabicyclo[4.3.1]decan-2-one B3

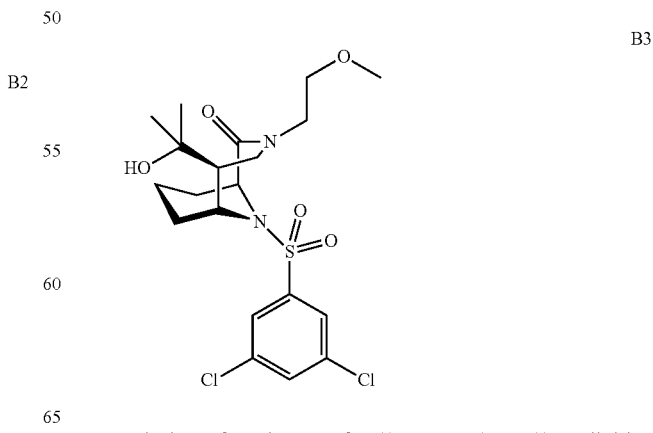

A solution of a mixture of 2-((1S,5S,6R)-10-((3,5-dichlorophenyl)sulfonyl)-3-(2-methoxyethyl)-2-oxo-3,10-diazabicyclo[4.3.1]decan-5-yl)acetaldehyde and (5S)-5-acetyl-10-((3,5-dichlorophenyl)sulfonyl)-3-(2-methoxyethyl)-3,10-diazabicyclo[4.3.1]decan-2-one (58.0 mg, 0.125 mmol) in THF (1.5 mL) was cooled to −78° C. CH₃MgBr (3 M in Et₂O, 0.189 mmol, 63.0 µL) was added and the reaction was stirred for 1 h. Aq. Sat. NH₄Cl solution (10 mL) was added to the reaction and extracted with CH₂Cl₂ (2×90 mL). The organic layer was dried over MgSO₄ and the solvent was evaporated under reduced pressure. Normal phase preparative chromatography (10-30% EtOAc in n-Hexane) afforded the title compound (37.0 mg, 0.0772 mmol, 61.8%) as a colorless solid.

¹H-NMR (600 MHz, Chloroform-d) δ=1.11 (m, 1H), 1.26 (s, 3H), 1.31 (s, 3H), 1.38-1.47 (m, 1H), 1.46-1.57 (m, 3H), 1.65 (d, J=13.4 Hz, 1H), 2.14 (ddd, J=10.3, 6.8, 1.4 Hz, 1H), 2.23 (d, J=13.6 Hz, 1H), 3.27 (dd, J=14.1, 1.6 Hz, 2H), 3.35 (s, 3H), 3.50-3.61 (m, 2H), 3.95 (dd, J=14.3, 10.5 Hz, 1H), 4.06 (ddd, J=14.1, 5.2, 3.6 Hz, 1H), 4.25-4.30 (m, 1H), 4.68 (d, J=5.7 Hz, 1H), 7.56 (t, J=1.8 Hz, 1H), 7.72 (d, J=1.9 Hz, 2H).

¹³C-NMR (150 MHz, Chloroform-d) δ=15.32, 27.10, 27.88, 28.10, 29.72, 49.94, 51.45, 52.01, 53.96, 57.15, 58.80, 71.38, 72.49, 125.0, 132.6, 136.2, 143.9, 169.4.

MS (ESI): m/±(%)=479.11 [M+H]⁺

Example 2-3: Preparation of (1S,5S,6R)-10-((3,5-dichlorophenyl)sulfonyl)-5-((R)-1-hydroxyethyl)-3-(2-methoxyethyl)-3,10-diazabicyclo[4.3.1]decan-2-one B6, (1S,5S,6R)-10-((3,5-dichlorophenyl)sulfonyl)-5-((S)-1-hydroxyethyl)-3-(2-methoxyethyl)-3,10-diazabicyclo[4.3.1]decan-2-one B7, and (1S,5S,6R)-10-((3,5-dichlorophenyl)sulfonyl)-5-(2-hydroxyethyl)-3-(2-methoxyethyl)-3,10-diazabicyclo[4.3.1]decan-2-one B8

B6

B7

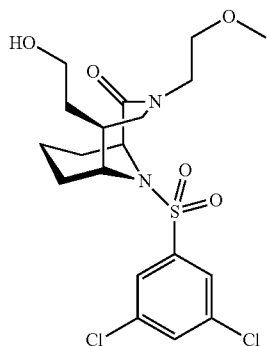

B8

To a solution of a mixture of (1S,5S,6R)-5-acetyl-10-((3,5-dichlorophenyl)sulfonyl)-3-(2-methoxyethyl)-3,10-diazabicyclo[4.3.1]decan-2-one and (2-((1S,5S,6R)-10-((3,5-dichlorophenyl)sulfonyl)-3-(2-methoxyethyl)-2-oxo-3,10-diazabicyclo[4.3.1]decan-5-yl)acetaldehyde (60.0 mg, 0.129 mmol) in EtOH/CH₂Cl₂ (2 mL, 3:1) was added NaBH₄ (7.35 mg, 0.194 mmol) and then stirred for 30 minutes at room temperature. Sat. aq. NaCl solution (10 mL) was added to the reaction and extracted with CH₂Cl₂ (3×50 mL). The organic layer was dried over MgSO₄ and the solvent was evaporated under reduced pressure. Normal phase preparative chromatography on SiO₂ (10-30% EtOAc in n-Hexane) afforded the title compounds (B6: 5.0 mg, 0.011 mmol, B7: 4.2 mg, 0.0090 mmol, B8: 13.0 mg, 0.0279 mmol, 36.9%).

B6

R_f: 0.5 (Cyclohexane/EtOAc=15:85)

¹H-NMR: (600 MHz, CDCl₃) δ=1.28-1.29 (m, 5H), 1.47-1.58 (m, 4H), 2.06-2.13 (m, 1H), 2.21-2.29 (m, 1H), 3.29-3.33 (m, 2H), 3.34 (s, 3H), 3.49-3.60 (m, 2H), 3.78-3.90 (m, 2H), 3.96-4.02 (m, 1H), 4.12-4.17 (m, 1H), 4.66-4.70 (m, 1H), 7.56 (t, J=1.8 Hz, 1H), 7.71 (d, J=1.8 Hz, 2H).

¹³C-NMR: (150 MHz, CDCl₃) δ=20.92, 28.15, 28.51, 29.66, 48.96, 50.55, 51.33, 52.61, 56.96, 58.83, 68.89, 71.24, 124.9, 124.9, 132.6, 132.6, 136.2, 143.9, 169.6.

MS (ESI): m/z (%)=465.14 [M+H]⁺

B7

R_f: 0.5 (Cyclohexane/EtOAc=15:85)

¹H-NMR: (600 MHz, CDCl₃) δ=1.28-1.29 (m, 5H), 1.47-1.58 (m, 4H), 2.06-2.13 (m, 1H), 2.21-2.29 (m, 1H), 3.29-3.33 (m, 2H), 3.34 (s, 3H), 3.49-3.60 (m, 2H), 3.78-3.90 (m, 2H), 3.96-4.02 (m, 1H), 4.12-4.17 (m, 1H), 4.66-4.70 (m, 1H), 7.56 (t, J=1.8 Hz, 1H), 7.71 (d, J=1.8 Hz, 2H).

¹³C-NMR: (150 MHz, CDCl₃) δ=20.92, 28.15, 28.51, 29.66, 48.96, 50.55, 51.33, 52.61, 56.96, 58.83, 68.89, 71.24, 124.9, 124.9, 132.6, 132.6, 136.2, 143.9, 169.6.

MS (ESI): m/z (%)=465.14 [M+H]⁺

B8

R_f: 0.34 (Cyclohexane/EtOAc=15:85)

¹H-NMR: (600 MHz, CDCl₃) δ=1.34-1.41 (m, 2H), 1.47-1.69 (m, 3H), 2.22-2.33 (m, 2H), 3.18-3.25 (m, 1H), 3.37 (s, 3H), 3.46-3.55 (m, 2H), 3.65-3.70 (m, 1H), 3.71-3.75 (m, 2H), 3.83-3.89 (m, 1H), 3.94 (dd, J=14.4, 10.5 Hz, 1H), 4.04-4.11 (m, 1H), 4.68 (d, J=5.8 Hz, 1H), 7.56 (t, J=1.8 Hz, 1H), 7.69 (d, J=1.9 Hz, 2H).

¹³C-NMR: (150 MHz, CDCl₃) δ=26.83, 29.66, 35.59, 40.84, 55.79, 56.72, 59.02, 60.09, 72.05, 124.8, 132.6, 136.3, 144.0, 170.0.

MS (ESI): m/z (%)=465.14 [M+H]⁺

Example 2-4: Preparation of (1S,5S,6R)-10-((3,5-dichlorophenyl)sulfonyl)-3-(2-methoxyethyl)-2-oxo-3,10-diazabicyclo[4.3.1]decane-5-carbaldehyde B9

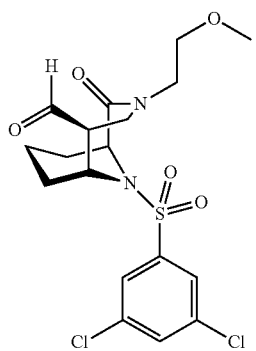
B9

To a solution of (1S,5R,6R)-10-((3,5-dichlorophenyl)sulfonyl)-3-(2-methoxyethyl)-5-vinyl-3,10-diazabicyclo[4.3.1]decan-2-one (250 mg, 0.559 mmol) in Dioxane/H$_2$O (5.6 mL, 3:1) was added NaIO$_4$ (478 mg, 2.23 mmol), OsO$_4$ (2.5% Solution in tert-Butanol, 0.011 mmol, 140 mL) and 2,6-Lutidine. The solution was stirred for 20 h at room temperature, then Et$_2$O (90 mL) was added to the reaction and washed with sat. aq. NaCl solution (3×10 mL). Column chromatography over SiO$_2$ (EtOAc/Cyclohexane 1:1) afforded the title compound (175 mg, 0.389 mmol, 70.0%) as a slightly yellow solid.

R$_f$: 0.21 (Cyclohexane/EtOAc=1:1)

$^1$H-NMR (600 MHz, CDCl$_3$) δ 1.21-1.29 (m, 1H), 1.44-1.50 (m, 3H), 1.53-1.59 (m, 1H), 2.29 (dd, J=13.5, 2.1 Hz, 1H), 3.03 (ddd, J=10.5, 7.0, 1.7 Hz, 1H), 3.36 (s, 3H), 3.37-3.42 (m, 1H), 3.50-3.56 (m, 1H), 3.61-3.66 (m, 1H), 3.68-3.72 (m, 1H), 4.01-4.08 (m, 2H), 4.70 (d, J=7.0 Hz, 1H), 4.72 (d, J=5.9 Hz, 1H), 7.57 (t, J=1.9 Hz, 1H), 7.72 (d, J=1.8 Hz, 2H), 9.65 (s, 1H).

$^{13}$C-NMR (150 MHz, cdcl$_3$) δ=15.20, 28.06, 28.38, 47.66, 48.81, 51.73, 56.97, 57.22, 59.02, 71.53, 124.9, 132.8, 136.4, 143.7, 169.6, 197.7.

MS (ESI): m/z (%)=449.05 [M+H]$^+$

Example 2-5: Preparation of (1S,5S,6R)-10-((3,5-dichlorophenyl)sulfonyl)-3-(2-methoxyethyl)-2-oxo-3,10-diazabicyclo[4.3.1]decane-5-carboxylic acid B10

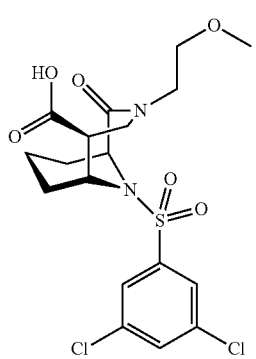
B10

To a solution of (1S,5S,6R)-5-acetyl-10-((3,5-dichlorophenyl)sulfonyl)-3-(2-methoxyethyl)-3,10-diazabicyclo[4.3.1]decan-2-one (25.0 mg, 0.0560 mmol) in CHCl$_3$/t-BuOH/H$_2$O (0.9 ml, 6:2:1) were methylbutene (60 μL), sodium chlorite (19.5 mg, 0.216 mmol) and sodium dihydrogenphosphate (25.9 mg). After 16 h a room temperature the solvent was removed under reduced pressure and the crude mix loaded directly on SiO$_2$. Flash column chromatography (20-60% EtOAc in Cyclohexane) afforded the title compound (24.0 mg, 0.0516 mmol, 92.7%) as a white solid.

MS (ESI): m/z (%)=465.07

Example 2-5: Preparation of (1S,5S,6R)-10-((3,5-dichlorophenyl)sulfonyl)-3-(2-methoxyethyl)-2-oxo-3,10-diazabicyclo[4.3.1]decane-5-carboxamide B11

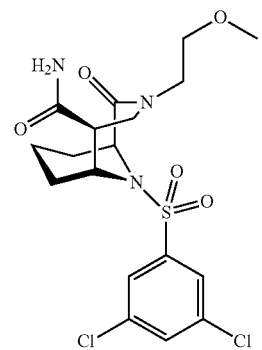
B11

To a solution of (1S,5S,6R)-10-((3,5-dichlorophenyl)sulfonyl)-3-(2-methoxyethyl)-2-oxo-3,10-diazabicyclo[4.3.1]decane-5-carboxylic acid (30.0 mg, 0.0645 mmol) in EtOAc (0.5 ml) was added CDI (15.7 mg, 0.0970 mmol). After one hour stirring at room temperature aqueous ammonia was added (7 M, 184 μL, 1.29 mmol) and the reaction was stirred for two hours. Solvent was removed under reduced pressure and flash column chromatography afforded the title compound (12 mg, 0.026 mmol, 41%).

R$_f$: 0.125 (Cyclohexane/EtOAc=3:7+2% MeOH)

$^1$H-NMR (600 MHz, Chloroform-d) δ=1.42 (s, 2H), 1.45-1.52 (m, 2H), 1.52-1.56 (m, 1H), 2.29 (d, J=13.1 Hz, 1H), 2.98 (ddd, J=10.2, 7.3, 1.5 Hz, 1H), 3.20 (ddd, J=14.2, 9.5, 3.1 Hz, 1H), 3.34-3.38 (m, 1H), 3.40 (s, 3H), 3.51-3.56 (m, 1H), 3.70 (td, J=9.7, 2.5 Hz, 1H), 4.12-4.20 (m, 2H), 4.74 (d, J=5.8 Hz, 1H), 4.77-4.81 (m, 1H), 5.90 (s, 1H), 6.14 (s, 1H), 7.56-7.58 (m, 1H), 7.73-7.75 (m, 2H).

$^{13}$C-NMR (150 MHz, Chloroform-d) δ=15.29, 27.82, 28.03, 51.22, 51.23, 51.58, 51.80, 56.88, 59.10, 72.36, 124.9, 132.8, 136.3, 143.7, 169.7, 172.3.

MS (ESI): m/z (%)=464.07 [M+H]$^+$

Example 2-6: Preparation of (1S,5S,6R)-10-((3,5-dichlorophenyl)sulfonyl)-3-(2-methoxyethyl)-5-((methylamino)methyl)-3,10-diazabicyclo[4.3.1]decan-2-one B12

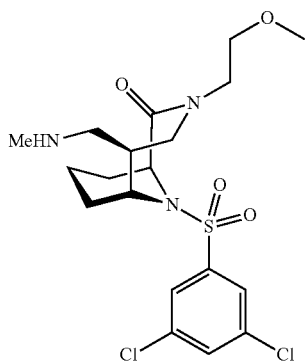

B12

To a solution of (1S,5R,6R)-10-((3,5-dichlorophenyl)sulfonyl)-3-(2-methoxyethyl)-2-oxo-3,10-diazabicyclo[4.3.1]decane-5-carbaldehyde (15.0 mg, 0.0330 mmol) in MeOH/AcOH (0.5 mL, 98:2) were added Methanamine Hydrochlorid (6.80 mg, 0.100 mmol) and NaBH(OAc)$_3$ (14.2 mg, 0.0660 mmol) and the reaction was stirred at room temperature for 4 hours. The solvent was removed under reduced pressure and the crude was loaded directly on SiO$_2$. Column chromatography over SiO$_2$ (EtOAc+2% TEA+2% MeOH) afforded the title compound (5.00 mg, 0.0107 mmol, 32.6%).

R$_f$: 0.16 (EtOAc+2% TEA+2% MeOH)

MS (ESI): m/z (%)=464.36 [M+H]$^+$

Example 2-7: Preparation of (1S,5R,6R)-10-((3,5-dichlorophenyl)sulfonyl)-5-(hydroxymethyl)-3-(2-methoxyethyl)-3,10-diazabicyclo[4.3.1]decan-2-one B13

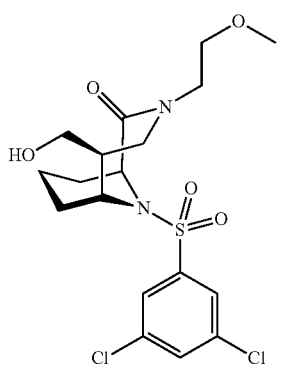

B13

To solution of (1S,5R,6R)-10-((3,5-dichlorophenyl)sulfonyl)-3-(2-methoxyethyl)-2-oxo-3,10-diazabicyclo[4.3.1]decane-5-carbaldehyde (17.0 mg, 0.0378 mmol) in EtOH (1 mL) was added NaBH$_4$ (2.20 mg, 0.0588 mmol). After 1 h stirring at room temperature sat. aq. NaCl solution (10 mL) was added to the reaction and extracted with CH$_2$Cl$_2$ (3×50 mL). The combined organic phases were dried over MgSO$_4$ and the solvent was removed under reduced pressure. Column chromatography on SiO$_2$ (Cyclohexane/EtOAc=1:4) afforded the title compound (11.0 mg, 0.0244 mmol, 64.6%).

R$_f$: 0.2 (Cyclohexane/EtOAc=1:4)

$^1$H-NMR (600 MHz, CDCl$_3$) δ=1.38-1.44 (m, 2H), 1.50-1.57 (m, 3H), 2.24-2.32 (m, 2H), 3.09-3.14 (m, 1H), 3.30 (dd, J=14.4, 1.7 Hz, 1H), 3.35 (s, 3H), 3.41 (dd, J=14.0, 4.0 Hz, 1H), 3.50-3.54 (m, 1H), 3.57 (dd, J=7.2, 3.9 Hz, 1H), 3.59 (dd, J=7.1, 3.5 Hz, 2H), 3.85-3.97 (m, 3H), 4.69-4.72 (m, 1H), 7.56 (t, J=1.8 Hz, 1H), 7.70 (d, J=1.9 Hz, 2H).

$^{13}$C-NMR (150 MHz, CDCl$_3$) δ=15.43, 27.98, 29.66, 46.94, 50.23, 51.19, 52.35, 56.99, 58.90, 63.53, 71.21, 124.8, 132.6, 136.2, 144.0, 169.8.

MS (ESI): m/z (%)=451.15 [M+H]$^+$

Example 2-8: Preparation of (1S,5R,6R)-10-((3,5-dichlorophenyl)sulfonyl)-3-(2-methoxyethyl)-5-(methoxymethyl)-3,10-diazabicyclo[4.3.1]decan-2-one B14

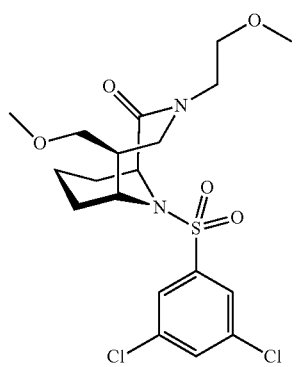

B14

To a solution of (1S,5R,6R)-10-((3,5-dichlorophenyl)sulfonyl)-5-(hydroxymethyl)-3-(2-methoxyethyl)-3,10-diazabicyclo[4.3.1]decan-2-one (25.0 mg, 0.0554 mmol) in THF (1 mL) was added NaH (60% dispersion in mineral oil, 4.7 mg, 0.12 mmol) and stirred for 20 minutes. CH$_3$I (16.8 mg, 7.4 µL, 0.118 mmol) was added. After 5 h the solvent was removed under reduced pressure and column chromatography over SiO$_2$ (EtOAc/Cyclohexane=1:1) afforded the title compound (13.0 mg, 0.0279 mmol, 50.4%) as a yellow oil.

$^1$H-NMR (600 MHz, CDCl$_3$) δ=1.27-1.33 (m, 2H), 1.55-1.65 (m, 3H), 2.27 (d, J=13.1 Hz, 1H), 2.30-2.37 (m, 1H), 3.18 (dd, J=14.3, 1.7 Hz, 1H), 3.23-3.34 (m, 2H), 3.34 (s, 3H), 3.35 (s, 3H), 3.40-3.47 (m, 1H), 3.47-3.57 (m, 2H), 3.75 (dd, J=14.3, 10.6 Hz, 1H), 3.79-3.86 (m, 1H), 3.89-3.95 (m, 1H), 4.70 (d, J=5.9 Hz, 1H), 7.55 (t, J=1.8 Hz, 1H), 7.70 (d, J=1.8 Hz, 2H).

$^{13}$C-NMR (150 MHz, CDCl$_3$) δ 15.45, 22.66, 28.11, 28.16, 29.67, 44.73, 50.31, 51.18, 52.64, 56.99, 70.81, 73.44, 124.9, 132.5, 136.2, 144.0, 169.7.

MS (ESI): m/z (%)=465.12 [M+H]$^+$

Example 2-9: Preparation of (1S,5S,6R)-10-((3,5-dichlorophenyl)sulfonyl)-5-ethyl-3-(2-methoxyethyl)-3,10-diazabicyclo[4.3.1]decan-2-one B15

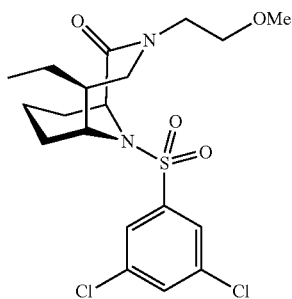

B15

To a solution of (1S,5R,6R)-10-((3,5-dichlorophenyl)sulfonyl)-3-(2-methoxyethyl)-5-vinyl-3,10-diazabicyclo[4.3.1]decan-2-one (20.0 mg, 0.0447 mmol) in MeOH (1.0 mL) was added Pd/C (10% wt, 4.76 mg, 4.47 μmol) and the reaction was stirred for 1 h at room temperature. The mixture was then filtered through celite and washed with MeOH. CH$_2$Cl$_2$ was added to the solution and washed three times with sat. aq. NaCl solution. The organic phase was separated and the solvent was removed under reduced pressure affording the title compound (20.0 mg, 0.0447 mmol, quant.) as a colorless solid.

$^1$H NMR (600 MHz, CDCl$_3$) δ=0.95-0.99 (m, 2H), 1.22-1.26 (m, 3H), 1.30-1.56 (m, 5H), 1.92-1.99 (m, 1H), 2.23 (d, J=13.5 Hz, 1H), 3.07-3.13 (m, 1H), 3.31-3.38 (m, 4H), 3.47-3.56 (m, 2H), 3.79-3.91 (m, 3H), 4.63-4.68 (m, 1H), 7.52-7.56 (m, 1H), 7.67-7.70 (m, 2H).

Example 2-10: Preparation of (1S,5R,6R)-10-((3,5-dichlorophenyl)sulfonyl)-5-((S)-2-hydroxypropyl)-3-(2-methoxyethyl)-3,10-diazabicyclo[4.3.1]decan-2-one B4 and (1S,5R,6R)-10-((3,5-dichlorophenyl)sulfonyl)-5-((R)-2-hydroxypropyl)-3-(2-methoxyethyl)-3,10-diazabicyclo[4.3.1]decan-2-one B5

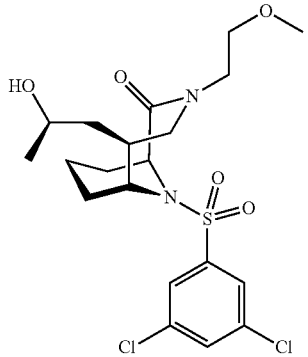

B4

-continued

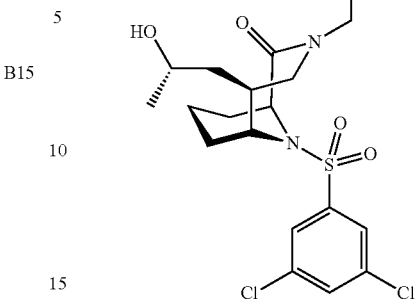

B5

A solution of a mixture of 2-((1S,5S,6R)-10-((3,5-dichlorophenyl)sulfonyl)-3-(2-methoxyethyl)-2-oxo-3,10-diazabicyclo[4.3.1]decan-5-yl)acetaldehyde and (5S)-5-acetyl-10-((3, 5-dichlorophenyl)sulfonyl)-3-(2-methoxyethyl)-3,10-diazabicyclo[4.3.1]decan-2-one (58.0 mg, 0.125 mmol) in THF (1.5 mL) was cooled to −78° C. CH$_3$MgBr (3 M in Et$_2$O, 0.189 mmol, 63.0 μL) was added and the reaction was stirred for 1 h. Aq. Sat. NH$_4$Cl solution (10 mL) was added to the reaction and extracted with CH$_2$Cl$_2$ (2×90 mL). The organic layer was dried over MgSO$_4$ and the solvent was evaporated under reduced pressure. Normal phase preparative chromatography (10-30% EtOAc in n-Hexane) afforded a mixture of the title compounds (12 mg, 0.0250 mmol, 15%) as a colorless oil.

$^1$H NMR (600 MHz, Chloroform-d) δ 1.13-1.20 (m, 1H), 1.31-1.42 (m, 3H), 1.48-1.57 (m, 4H), 2.21-2.27 (m, 2H), 2.30-2.38 (m, 1H), 3.06-3.21 (m, 2H), 3.21-3.26 (m, 1H), 3.29 (dd, J=14.3, 1.7 Hz, 1H), 3.36 (d, J=4.0 Hz, 3H), 3.47-3.53 (m, 1H), 3.60-3.65 (m, 1H), 3.69-3.75 (m, 1H), 3.78 (dt, J=6.7, 3.3 Hz, 1H), 3.96-4.03 (m, 1H), 4.08-4.19 (m, 1H), 4.61-4.70 (m, 1H), 7.53-7.56 (m, 1H), 7.63-7.73 (m, 2H).

MS (ESI): m/z (%)=479.11 [M+H]$^+$

III. Preparation of Compounds C1-C3

Example 3-1: Preparation of (1S,5R,6R)-10-((3,5-dichlorophenyl)sulfonyl)-3-(2-hydroxyethyl)-5-(hydroxymethyl)-3,10-diazabicyclo[4.3.1]decan-2-one C1

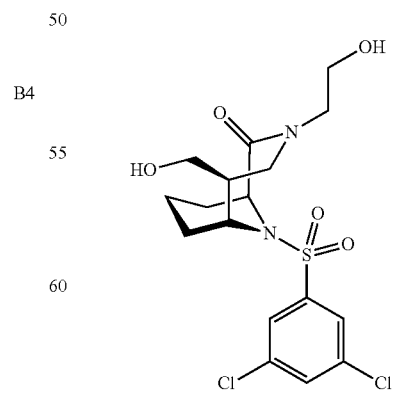

C1

(1S,5R,6R)-10-((3,5-dichlorophenyl)sulfonyl)-3-(2-hydroxyethyl)-5-vinyl-3,10-diazabicyclo[4.3.1]decan-2-one in CH$_2$Cl$_2$/MeOH (5 mL, 1:1) was cooled to −78° C. N$_2$ was bubbled trough the solution for 15 minutes. Then O$_3$ was bubbled through the solution for 5 minutes, until the solution turned blue. The residual O$_3$ was removed with more N$_2$ flux. The reaction was allowed to warm to room temperature, quenched with dimethyl sulfide (13 μL) and then 3.6 mg of NaBH$_4$ (0,096 mmol) were added. After 30 minutes solvent was removed under reduced pressure and column chromatography over SiO$_2$ (ethyl acetate/cyclohexane, 1:1) afforded the title compound (25.0 mg, 0.0569 mmol, 64.9%) as a white solid.

$^1$H-NMR (600 MHz, Chloroform-d) δ=1.37 (s, 2H), 1.51-1.54 (m, 3H), 2.25 (d, J=13.2 Hz, 1H), 2.33 (dt, J=10.3, 5.1 Hz, 1H), 3.33 (dd, J=14.4, 1.7 Hz, 1H), 3.39 (d, J=14.4 Hz, 1H), 3.55-3.62 (m, 2H), 3.78-3.82 (m, 2H), 3.86-3.89 (m, 1H), 3.90-3.95 (m, 1H), 4.69 (d, J=5.9 Hz, 1H), 7.56 (t, J=1.8 Hz, 1H), 7.70 (d, J=1.9 Hz, 2H).

$^{13}$C-NMR (150 MHz, Chloroform-d) δ=15.44, 27.71, 29.67, 30.29, 47.10, 50.07, 52.28, 54.08, 57.04, 61.21, 63.17, 124.9, 132.8, 136.3, 143.9, 171.4.

Example 3-2: Preparation of (1S,5S,6R)-10-((3,5-dichlorophenyl)sulfonyl)-5-(1,2-dihydroxyethyl)-3-(2-(3,4-dimethoxyphenoxy)ethyl)-3, 10-diazabicyclo[4.3.1]decan-2-one C2/C2b To a solution of (1S,5R,6R)-10-((3,5-dichlorophenyl)sulfonyl)-3-(2-(3,4-dimethoxyphenoxy)ethyl)-5-vinyl-3,10-diazabicyclo[4.3.1]decan-2-one (30.0 mg, 0.527 mmol) in t-BuOH/H$_2$O (1 mL, 1:1) was added AD-MIX-β (73.8 mg) and the reaction was stirred at room temperature for 24 h. Saturated NaCl was added to the mixture and extracted three times with CH$_2$Cl$_2$. The combined organic layers were dried over MgSO$_4$ and the solvent was removed under reduced pressure. Column chromatography on SiO$_2$ (Cyclohexane/EtOAc=3:7+1% AcOH) afforded the title compound (24.0 mg, 0.0398 mmol, 75.1%), which were separated by preparative HPLC in pure diastereoisomers.

R$_f$ (C2a): 0.3 (Cyclohexane/EtOAc=3:7+1% AcOH)

R$_f$ (C2b): 0.3 (Cyclohexane/EtOAc=3:7+1% AcOH)

MS (C2a) (ESI): m/z (%)=603.02 [M+H]$^+$; MS (C2b) (ESI): m/z (%)=603.11 [M+H]$^+$

Example 3-3: Preparation of (1S,5S,6R)-10-((3,5-dichlorophenyl)sulfonyl)-5-(1,2-dihydroxyethyl)-3-(2-ethoxyethyl)-3,10-diazabicyclo[4.3.1]decan-2-one C3

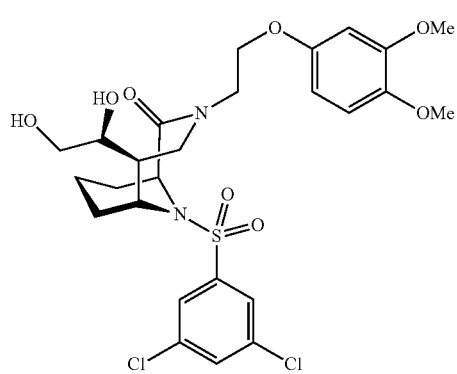

C2a

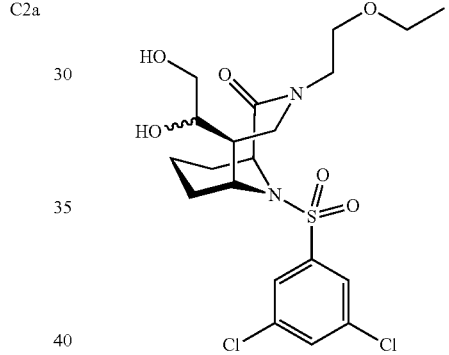

C3

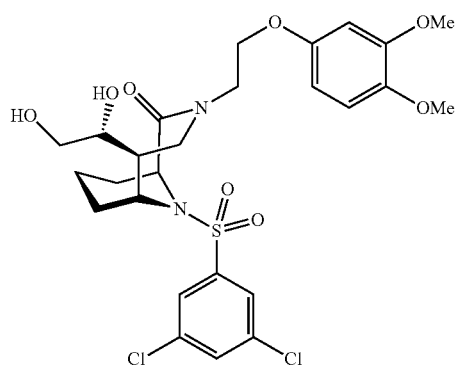

C2b

To a solution of ((1S,5R,6R)-10-((3,5-dichlorophenyl)sulfonyl)-3-(2-ethoxyethyl)-5-vinyl-3,10-diazabicyclo[4.3.1]decan-2-one (30.0 mg, 0.0650 mmol) in THF/H$_2$O (1.5 mL, 2:1) were added NMO (30.5 mg, 0.260 mmol) and OsO$_4$ (2.5% solution in tert-butanol, 2.60 μmol, 33 μL). After 1 h stirring at room temperature saturated sat. aq. NaCl solution (10 mL) was added to the reaction and extracted with CH$_2$Cl$_2$ (3×40 mL). The organic layer was dried over MgSO$_4$ and the solvent removed under reduced pressure. Column chromatography over SiO$_2$ (1% AcOH in cyclohexane/EtOAc=1:4) afforded the title compound (15.0 mg, 0.0303 mmol, 46.6%). R$_f$: 0.22 (Cyclohexane/EtOAc=1:4+1% AcOH)

MS (ESI): m/z (%)=495.29 [M+H]$^+$

IV. Preparation of Compounds D1-D8

Scheme D.

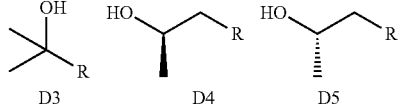

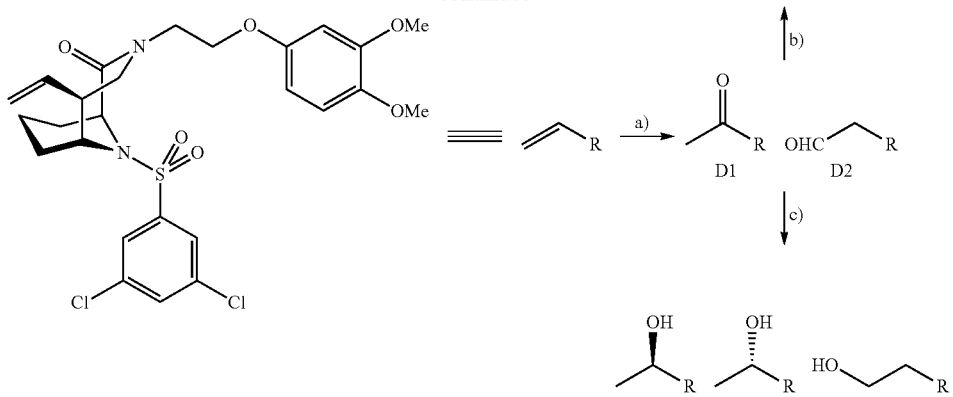

Reagents and conditions: a) PdCl$_2$, CuCl, O$_2$, DMF/H$_2$O, rt, 24 h, 72%; b) MeMgBr, THF, -78° C., 1 h, 75%; c) NaBH$_4$, EtOH/CH$_2$Cl$_2$, rt, 1 h, 68%.

Example 4-1: Preparation of (1S,5S,6R)-5-acetyl-10-((3,5-dichlorophenyl)sulfonyl)-3-(2-(3,4-dimethoxyphenoxy)ethyl)-3,10-diazabicyclo[4.3.1]decan-2-one D1 and 2-((1S,5S,6R)-10-((3,5-dichlorophenyl)sulfonyl)-3-(2-(3,4-dimethoxyphenoxy)ethyl)-2-oxo-3,10-diazabicyclo[4.3.1]decan-5-yl)acetaldehyde D2

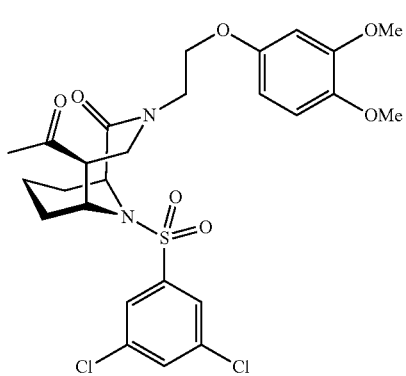

D1

To a solution of (1S,5R,6R)-10-((3,5-dichlorophenyl)sulfonyl)-3-(2-(3,4-dimethoxyphenoxy)ethyl)-5-vinyl-3,10-diazabicyclo[4.3.1]decan-2-one (25.0 mg, 0.0440 mmol) in DMF/H$_2$O (0.229 mL, 7:1) was added PdCl$_2$ (1.57 mg, 8.78 μmol) and CuCl (4.35 mg, 0.440 mmol). After 24 h days stirring Et$_2$O (90 mL) was added to the reaction and washed three times with saturated Na$_2$S$_2$O$_3$ (3×10 mL). The organic layer was dried over MgSO$_4$ and the solvent removed under reduced pressure. Column chromatography on SiO$_2$ (EtOAc/Cyclohexane=1:1) afforded an inseparable mixture of the title compounds (18.0 mg, 0.0307 mmol, 69.8%) as a white solid.

R$_f$: 0.36 (EtOAc/Cyclohexane=1:1)

MS D1: (ESI): m/z (%)=585.09 [M+H]$^+$

MS D2: (ESI): m/z (%)=585.10 [M+H]$^+$

Example 4-2: Preparation of (1S,5S,6R)-10-((3,5-dichlorophenyl)sulfonyl)-3-(2-(3,4-dimethoxyphenoxy)ethyl)-5-(2-hydroxypropan-2-yl)-3,10-diazabicyclo[4.3.1]decan-2-one D3, (1S,5S,6R)-10-((3,5-dichlorophenyl)sulfonyl)-3-(2-(3,4-dimethoxyphenoxy)ethyl)-5-(2-hydroxypropyl)-3,10-diazabicyclo[4.3.1]decan-2-one D4, and (1S,5S,6R)-10-((3,5-dichlorophenyl)sulfonyl)-3-(2-(3,4-dimethoxyphenoxy)ethyl)-5-(2-hydroxypropyl)-3,10-diazabicyclo[4.3.1]decan-2-one D5

D2

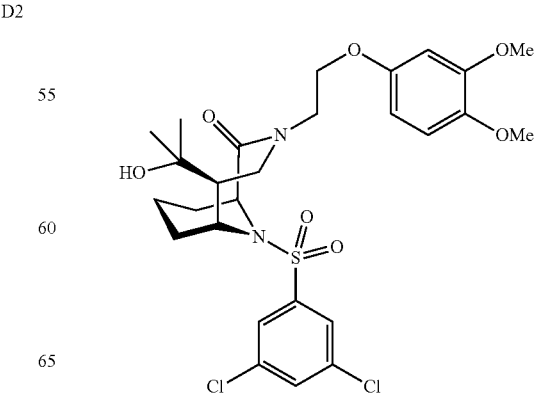

D3

-continued

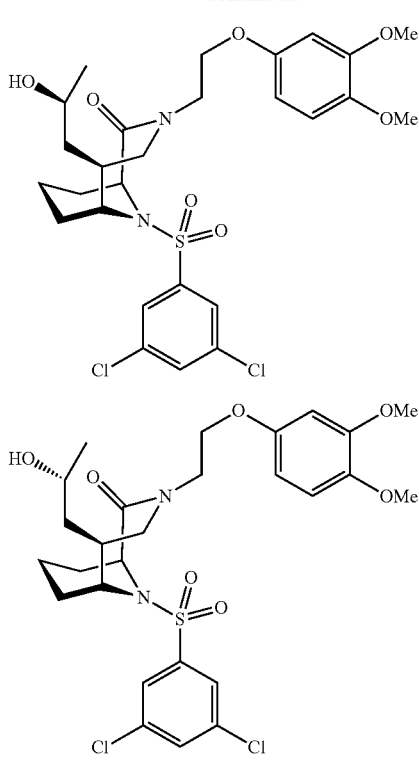

A solution of an inseparable mixture of 2-((1S,5S,6R)-10-((3,5-dichlorophenyl)sulfonyl)-3-(2-(3,4-dimethoxyphenoxy)ethyl)-2-oxo-3, 10-diazabicyclo [4.3.1]decan-5-yl)acetaldehyde and (1S,5S,6R)-5-acetyl-10-((3, 5-dichlorophenyl) sulfonyl)-3-(2-(3,4-dimethoxyphenoxy) ethyl)-3,10-diazabicyclo[4.3.1] decan-2-one (48.0 mg, 0.0820 mmol) in THF (1 mL) was cooled to −78° C. MeMgBr (3 M in Et$_2$O, 0.123 mmol, 41.0 µL) was added and the reaction was stirred for 1 h. Sat. aq. NH$_4$Cl (15 mL) solution was added to the reaction and extracted with CH$_2$Cl$_2$ (3×90 mL). The organic layer was dried over MgSO$_4$ and the solvent was evaporated under reduced pressure. Flash column chromatography on SiO$_2$ (20-50% EtOAc in cyclohexane) afforded the title compound (D3: 23.0 mg, 0.0382 mmol, D4: 6 mg, 0.00998 mmol, D5: 8 mg, 0.0133 mmol, 75.0%).

D3:

$^1$H-NMR: (600 MHz, Chloroform-d) δ=1.25 (s, 3H), 1.27 (s, 3H), 1.44-1.52 (m, 2H), 1.57-1.62 (m, 3H), 2.15 (ddd, J=10.5, 6.7, 1.5 Hz, 1H), 2.23 (d, J=13.4 Hz, 1H), 3.41 (dd, J=14.2, 1.4 Hz, 1H), 3.51-3.59 (m, 1H), 3.83 (s, 3H), 3.84 (s, 3H), 3.98-4.07 (m, 2H), 4.13-4.18 (m, 2H), 4.25-4.30 (m, 1H), 4.69 (d, J=5.7 Hz, 1H), 6.40 (dd, J=8.8, 2.8 Hz, 1H), 6.54 (d, J=2.8 Hz, 1H), 6.77 (d, J=8.8 Hz, 1H), 7.54 (t, J=1.9 Hz, 1H), 7.72 (d, J=1.9 Hz, 2H).

$^{13}$C-NMR: (150 MHz, Chloroform-d) δ=15.33, 27.42, 27.90, 28.11, 29.68, 50.22, 51.73, 51.96, 54.16, 55.84, 56.40, 57.19, 67.13, 72.50, 100.8, 104.2, 111.9, 125.0, 132.7, 136.3, 143.7, 143.9, 149.8, 153.1, 169.8.

MS (ESI): m/z (%)=601.28 [M+H]$^+$

D4:

$^1$H-NMR: (600 MHz, Chloroform-d) δ=1.23-1.29 (m, 5H), 1.49-1.66 (m, 5H), 2.25 (d, J=12.3 Hz, 1H), 2.33-2.41 (m, 1H), 3.31 (dd, J=14.4, 1.7 Hz, 1H), 3.52-3.60 (m, 1H), 3.82-3.87 (m, 7H), 3.93-4.09 (m, 4H), 4.14-4.20 (m, 1H), 4.68 (d, J=5.9 Hz, 1H), 6.42 (dd, J=8.7, 2.8 Hz, 1H), 6.56 (d, J=2.8 Hz, 1H), 6.77 (d, J=8.8 Hz, 1H), 7.54 (t, J=1.8 Hz, 1H), 7.69 (d, J=1.9 Hz, 2H).

$^{13}$C-NMR: (151 MHz, Chloroform-d) δ=15.46, 24.98, 29.68, 41.55, 43.10, 51.77, 54.00, 55.58, 55.89, 56.39, 56.91, 65.69, 67.31, 100.8, 104.1, 111.8, 124.8, 132.6, 136.3, 143.8, 144.1, 149.8, 153.0, 170.0.

MS (ESI): m/z (%)=601.28 [M+H]$^+$

D5:

$^1$H-NMR: (600 MHz, Chloroform-d) δ=1.21-1.27 (m, 5H), 1.45-1.62 (m, 5H), 2.22-2.29 (m, 1H), 2.35-2.41 (m, 1H), 3.29 (dd, J=14.4, 1.8 Hz, 1H), 3.49-3.56 (m, 1H), 3.81-3.88 (m, 7H), 3.93-4.02 (m, 2H), 4.03-4.08 (m, 1H), 4.13-4.24 (m, 2H), 4.69 (dt, J=6.3, 1.9 Hz, 1H), 6.43 (dd, J=8.7, 2.8 Hz, 1H), 6.57 (d, J=2.8 Hz, 1H), 6.78 (d, J=8.8 Hz, 1H), 7.54 (t, J=1.8 Hz, 1H), 7.69 (dd, J=1.9, 0.4 Hz, 2H).

$^{13}$C-NMR: (150 MHz, Chloroform-d) δ=15.50, 24.49, 26.71, 26.90, 27.71, 29.68, 40.96, 42.63, 51.73, 52.46, 55.88, 56.38, 56.80, 64.95, 67.97, 100.8, 104.4, 111.9, 124.8, 132.6, 136.3, 143.9, 144.1, 149.9, 153.1, 170.3.

MS (ESI): m/z (%)=601.32 [M+H]$^+$

Example 4-3: Preparation of (1S,5S,6R)-10-((3,5-dichlorophenyl)sulfonyl)-3-(2-(3,4-dimethoxyphenoxy)ethyl)-5-((R)-1-hydroxyethyl)-3,10-diazabicyclo[4.3.1]decan-2-one D6, (1S,5S,6R)-10-((3, 5-dichlorophenyl)sulfonyl)-3-(2-(3,4-dimethoxyphenoxy)ethyl)-5-((R)-1-hydroxyethyl)-3,10-diazabicyclo[4.3.1]decan-2-one D7, and (1S,5S,6R)-10-((3,5-dichlorophenyl)sulfonyl)-3-(2-(3,4-dimethoxyphenoxy)ethyl)-5-(2-hydroxyethyl)-3,10-diazabicyclo[4.3.1]decan-2-one D8

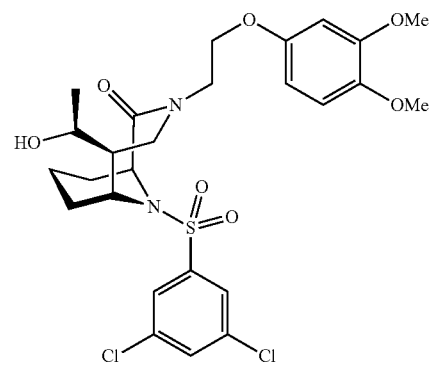

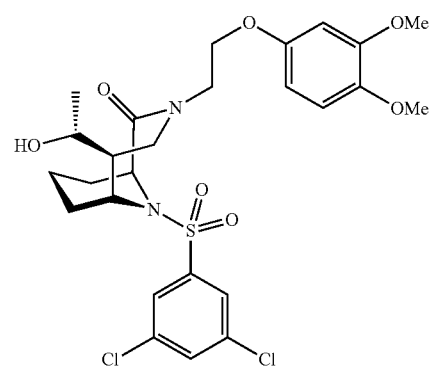

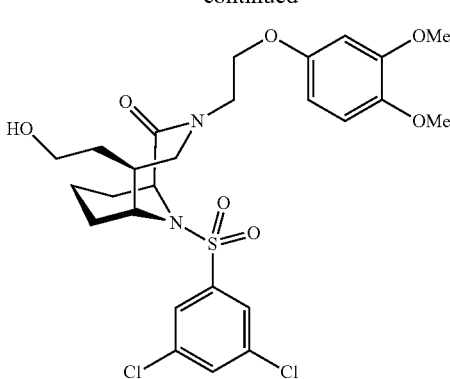

To a solution of an inseparable mixture of 2-((1S,5S,6R)-10-((3,5-dichloro-phenyl)sulfonyl)-3-(2-(3,4-dimethoxy-phenoxy)ethyl)-2-oxo-3,10 diazabicyclo [4.3.1]decan-5-yl) acetaldehyde and (1S,5S,6R)-5-acetyl-10-((3,5-dichlorophenyl) sulfonyl)-3-(2-(3,4-dimethoxyphenoxy) ethyl)-3,10 diazabicyclo[4.3.1]decan-2-one (90.0 mg, 0.154 mmol) in EtOH (1.5 mL) were added of NaBH$_4$ (5.82 mg, 0.154 mmol) and then stirred for 15 minutes at room temperature. EtOAc (90 mL) was added to the reaction and washed with sat. aq. NaCl solution (3×10 mL). The organic layer was dried over MgSO$_4$ and the solvent was evaporated under reduced pressure. Flash column chromatography on SiO$_2$ (20-50% EtOAc in cyclohexane) afforded the title compound (D6: 20.0 mg, 0.0340 mmol, D7: 12.0 mg, 0.0204 mmol, D8: 29.0 mg, 0.0494 mmol, 67.7%).

D6:
R$_f$: 0.53 (Cyclohexane/EtOAc=3:7)
$^1$H-NMR: (600 MHz, Chloroform-d) δ=1.29 (s, 3H), 1.37-1.55 (m, 5H), 2.11-2.18 (m, 1H), 2.26 (d, J=13.4 Hz, 1H), 3.45-3.49 (m, 1H), 3.52-3.58 (m, 1H), 3.83 (s, 3H), 3.84 (s, 3H), 3.86-3.91 (m, 1H), 3.95 (dd, J=14.4, 10.6 Hz, 1H), 4.01-4.06 (m, 1H), 4.13-4.17 (m, 3H), 4.70 (d, J=5.7 Hz, 1H), 6.39 (dd, J=8.7, 2.8 Hz, 1H), 6.54 (d, J=2.8 Hz, 1H), 6.77 (d, J=8.8 Hz, 1H), 7.53 (t, J=1.9 Hz, 1H), 7.69-7.72 (m, 2H).
$^{13}$C-NMR: (150 MHz, Chloroform-d) δ=15.31, 21.09, 28.19, 28.67, 29.67, 49.68, 50.63, 51.67, 52.48, 55.85, 56.40, 57.00, 67.20, 68.91, 100.6, 103.9, 111.8, 124.9, 132.7, 136.3, 143.7, 143.9, 149.8, 153.1, 169.9.
MS (ESI): m/z (%)=587.16 [M+H]$^+$ D7:
R$_f$: 0.5 (Cyclohexane/EtOAc=3:7); MS (ESI): m/z (%)=587.16 [M+H]$^+$
$^1$H-NMR: (600 MHz, Chloroform-d) δ=1.28 (s, 3H), 1.34-1.54 (m, 5H), 2.21 (s, 1H), 2.26 (d, J=13.7 Hz, 1H), 3.33-3.39 (m, 1H), 3.51-3.58 (m, 1H), 3.83 (s, 3H), 3.85 (s, 3H), 3.84-3.90 (m, 1H), 4.04 (dd, J=14.1, 3.3 Hz, 2H), 4.11-4.20 (m, 3H), 4.70 (d, J=5.7 Hz, 1H), 6.40 (dd, J=8.7, 2.8 Hz, 1H), 6.54 (d, J=2.8 Hz, 1H), 6.78 (d, J=8.8 Hz, 1H), 7.53 (t, J=1.9 Hz, 1H), 7.71 (d, J=1.8 Hz, 2H).
$^{13}$C-NMR: (150 MHz, Chloroform-d) δ=15.40, 20.25, 28.13, 28.82, 29.68, 50.44, 50.74, 51.56, 51.66, 55.85, 56.41, 57.01, 67.23, 69.12, 100.5, 103.9, 111.9, 124.9, 124.9, 132.7, 136.3, 143.7, 143.9, 149.9, 153.1, 169.9.

D8:
R$_f$: 0.37 (Cyclohexane/EtOAc=3:7); MS (ESI): m/z (%)=587.15 [M+H]$^+$
$^1$H-NMR: (600 MHz, Chloroform-d) δ=1.42-1.56 (m, 7H), 2.26 (d, J=13.6 Hz, 1H), 2.32-2.36 (m, 1H), 3.29 (d, J=12.6 Hz, 1H), 3.50-3.56 (m, 1H), 3.73-3.78 (m, 2H), 3.83 (s, 3H), 3.86 (s, 3H), 3.94 (s, 1H), 4.02-4.08 (m, 1H), 4.13-4.21 (m, 3H), 4.69 (d, J=5.9 Hz, 1H), 6.42 (dd, J=8.8, 2.8 Hz, 1H), 6.55 (d, J=2.8 Hz, 1H), 6.78 (d, J=8.8 Hz, 1H), 7.55 (t, J=1.8 Hz, 1H), 7.69 (dd, J=1.9, 0.6 Hz, 2H).
$^{13}$C-NMR: (75 MHz, Chloroform-d) δ=15.44, 27.35, 27.84, 29.67, 36.10, 41.09, 51.73, 53.19, 55.42, 55.89, 56.40, 56.85, 59.86, 67.62, 100.7, 104.2, 111.9, 124.8, 132.6, 136.3, 143.8, 144.1, 149.9, 153.1, 170.1.

V. Preparation of Compounds G4-G6

Scheme E.

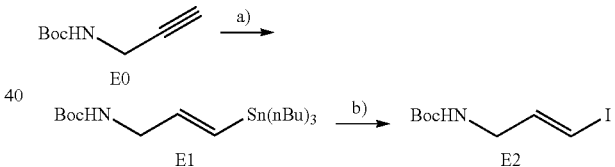

Reagents and conditions: a) (nBu)$_3$SnH, AIBN, toluene, 120° C., 2.5 h, 63%; b) I$_2$, CH$_2$Cl$_2$, rt, 1 h, 97%.

Scheme F.

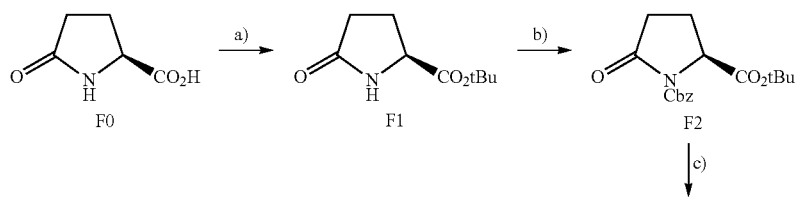

Reagents and conditions: a) tBuOAc, HClO$_4$, rt, 24 h, 74%; b) NaH, CbzCl, THF, rt, 20 h, 90%; C) NaBH$_4$, KH$_2$PO$_4$, MeOH/H$_2$O, rt, 2 h, 66%; d) I$_2$, PPh$_3$ imidazole, CH$_2$Cl$_2$, rt, 1 h, 86%.

Scheme G.

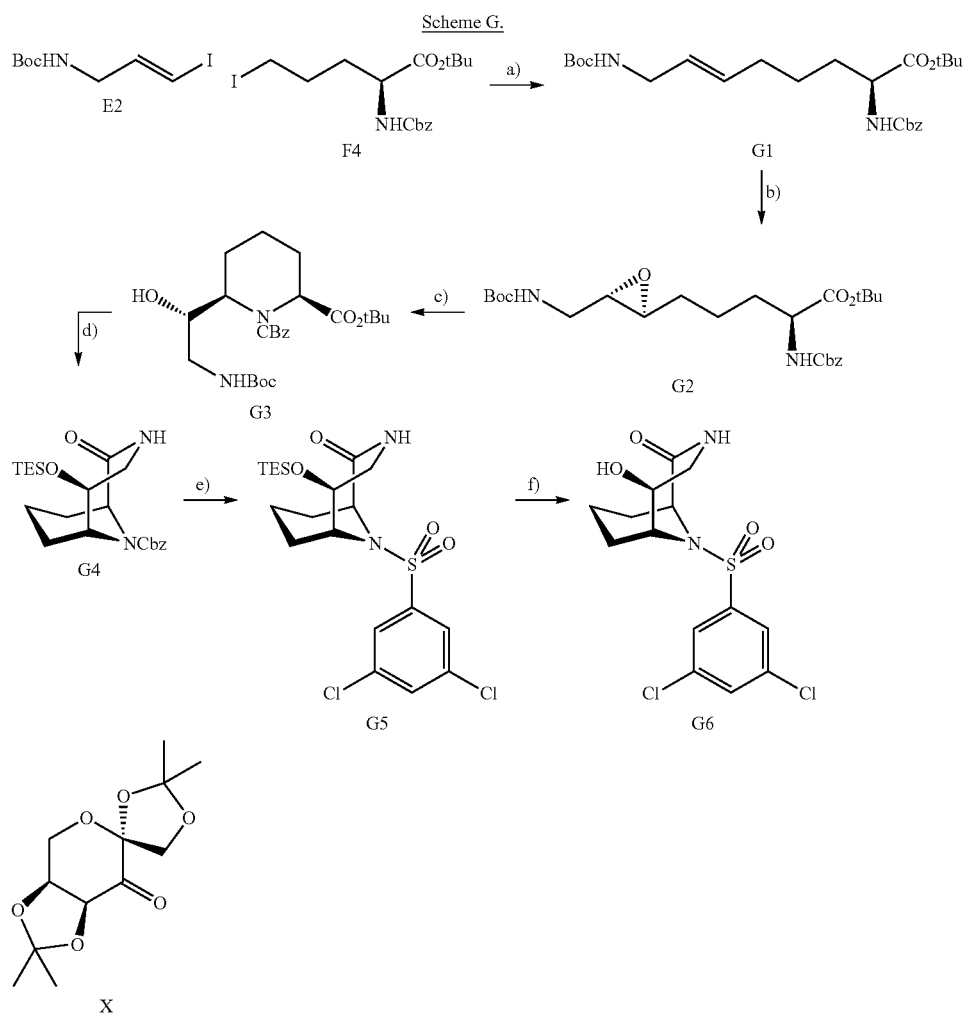

Reagents and conditions: a) 1.) Zn*, DMF, 35° C., 1 h; 2.) Pd₂(dba)₃, P(otol)₃, rt, 16 h, 90%; b) X, Oxone, K₂CO₃, nBu₄NHSO₄, DMM/MeCN, aq. Na₂(EDTA), aq. Na₂B₄O₇, rt, 18 h, 71%, dr 8:1; c) 1.) Pd/C, H₂ EtOH, rt, 2 h; 2.) CbzCl, Na₂CO₃, dioxane/H₂O, rt, 18 h, 83% (2 steps); d) 1.) TESOTf, 2,6-lutidine, CH₂Cl₂, 0° C. to rt, 20 h; 2.) HATU, (iPr)₂NEt, CH₂Cl₂ (c = 5•10⁻³M), rt, 16 h, 50% (2 steps); e) 1.) Pd/C, H₂, EtOAc, rt, 2 h; 2.) 3,5-Dichlorobenzenesulfonyl chloride, DMAP, (iPr)₂NEt, CH₂Cl₂, rt, 20 h, 73% (2 steps); f) TBAF, THF, rt, 1.5 h, 96%.

Example 5-1: Preparation of (E)-N-Boc-3-tributyl-stannyl-2-propen-1-amine E1

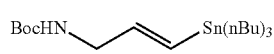

To a solution of N-Boc-propargylamine (818 mg, 5.27 mmol) in toluene (26 mL) was added AIBN (0.2 M in toluene, 1.32 mL, 2.64·10⁻⁵ mol, 0.05 equiv.) and tributyltin hydride (1.56 mL, 5.80 mmol, 1.1 equiv.) and it was stirred for 2.5 h at 120° C. (preheated oil bath). After cooling to room temperature, the solvent was evaporated under reduced pressure. Column chromatography on SiO₂ (cyclohexane/EtOAc 60:1) afforded the title compound (1.48 g, 3.32 mmol, 63%) as colorless liquid.

$R_f$: 0.42 (Cyclohexane/EtOAc 20:1, KMnO₄)

¹H-NMR (600 MHz, CDCl₃): δ=0.85-0.90 (m, 15H, 3×CH₂, 3×CH₃), 1.25-1.33 (m, 6H, 3×CH₂), 1.45 (s, 9H, 3×CH₃), 1.46-1.51 (m, 6H, 3×CH₂), 3.78 ($s_{br}$, 1H, CH₂), 4.60 ($s_{br}$, 1H, NH), 5.95 (dt, J=19.2, 4.8 Hz, 1H, CH), 6.08 (dt, J=19.2, 1.8 Hz, 1H, CH).

¹³C-NMR (150 MHz, CDCl₃): δ=9.65, 13.90, 27.48, 28.62, 29.27, 46.21, 79.45, 129.3, 144.5, 156.0.

Example 5-2: Preparation of (E)-N-Boc-3-iodo-2-propen-1-amine E2

To a solution of E1 (6.96 g, 15.6 mmol) in CH₂Cl₂ (160 mL) was added Iodine (4.16 g, 16.4 mmol, 1.05 equiv.) and the resulting suspension was stirred for 2 h at room temperature. The reaction mixture was washed with 1 M Na₂S₂O₃ solution (150 mL), dried over MgSO₄, filtered and the solvent was evaporated under reduced pressure. Column chromatography on SiO$_2$ (cyclohexane/EtOAc 10:1) afforded the title compound (4.28 g, 15.1 mmol, 97%) as slightly yellow liquid, which solidified upon cooling to 4° C.

R$_f$: 0.17 (Cyclohexane/EtOAc 20:1, KMnO$_4$)

$^1$H-NMR (400 MHz, CDCl$_3$): δ=1.44 (s, 9H, 3×CH$_3$), 3.65-3.73 (m, 2H, CH$_2$), 4.67 (s$_{br}$, 1H, NH), 6.27 (dt, J=14.4, 1.6 Hz, 1H, CH), 6.53 (dt, J=14.4, 4.0 Hz, 1H, CH).

$^{13}$C-NMR (100 MHz, CDCl$_3$): δ=28.56, 44.97, 77.95, 79.99, 142.6, 155.6.

Example 5-3: Preparation of (2S)-tert-Butyl-pyroglutamate F1

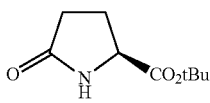

To a suspension of L-Pyroglutamic acid (6.46 g, 50.0 mmol) and tBuOAc (100 mL) in a pressure flask was added HClO$_4$ (70%, 1.51 mL 0.35 equiv.) and the solution was stirred for 24 h at room temperature. It was poured into a sat. aq. NaHCO$_3$ solution (200 mL), the organic phase was separated and the aqueous phase was extracted with CH$_2$Cl$_2$ (2×100 mL). The combined organic phases were dried over MgSO$_4$, filtered and the solvent was evaporated under reduced pressure to afford the title compound (6.87 g, 37.1 mmol, 74%) as a colorless solid.

R$_f$: 0.41 (EtOAc, KMnO$_4$)

$^1$H-NMR (300 MHz, CDCl$_3$): δ=1.44 (s, 9H, 3×CH$_3$), 2.12-2.15 (m, 4H, 2×CH$_2$), 4.08-4.16 (m, 1H, CH), 6.11 (s$_{br}$, 1H, NH).

$^{13}$C-NMR (75.5 MHz, CDCl$_3$): δ=25.08, 28.18, 29.58, 56.25, 82.62, 171.2, 177.9.

Example 5-4: Preparation of (2S)—N-Cbz-tert-Butyl-pyroglutamate F2

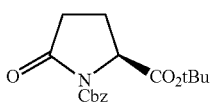

To a solution of F1 (2.29 g, 12.4 mmol) in THF (62 mL) was added NaH (60% oil dispersion, 546 mg, 13.6 mmol, 1.1 equiv.) and it was stirred for 30 min at room temperature. Subsequently Benzyl chloroformate (1.94 mL, 13.6 mmol, 1.1 equiv.) was added and stirring was continued for further 20 h. The solvent was evaporated under reduced pressure, sat. aq. NH$_4$Cl solution (100 mL) was added and extracted with EtOAc (2×100 mL). The organic phase was dried over MgSO$_4$, filtered and the the solvent was evaporated under reduced pressure. Column chromatography on SiO$_2$ (cyclohexane/EtOAc 3:1) afforded the title compound (3.56 g, 11.1 mmol, 90%) as colorless oil.

R$_f$: 0.18 (Cyclohexane/EtOAc 3:1, KMnO$_4$)

$^1$H-NMR (300 MHz, CDCl$_3$): δ=1.39 (s, 9H, 3×CH$_3$), 1.97-2.70 (m, 4H, 2×CH$_2$), 4.54 (dd, J=9.3, 2.7 Hz, 1H, CH), 5.27 (dd, J=16.2, 12.3 Hz, 2H, CH$_2$), 7.27-7.43 (m, 5H, 5×Ar—H).

$^{13}$C-NMR (75.5 MHz, CDCl$_3$): δ=25.11, 27.12, 31.23, 59.60, 68.43, 82.76, 128.4, 128.6, 128.7, 135.3, 151.1, 170.3, 173.3.

Example 5-5: Preparation of tert-Butyl-(S)-2-(benzyloxycarbonylamino)-5-hydroxypentanoate F3

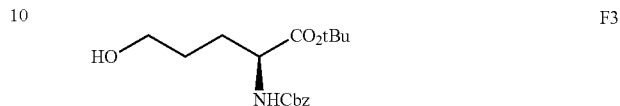

To a suspension of F2 (2.15 g, 6.73 mmol) and KH$_2$PO$_4$ (6.87 g, 50.5 mmol, 7.5 equiv.) in MeOH/H$_2$O (5:1, 67 mL) was added NaBH$_4$ (1.91 g, 50.5 mmol, 7.5 equiv.) in portions. After stirring for 1 h the mixture was filtered and the solvent was evaporated under reduced pressure. Column chromatography on SiO$_2$ (cyclohexane/EtOAc 2:1) afforded the title compound (1.43 g, 4.42 mmol, 66%) as colorless oil.

R$_f$: 0.29 (Cyclohexane/EtOAc 2:1, KMnO$_4$)

$^1$H-NMR (300 MHz, DMSO-d$_6$): δ=1.39 (s, 9H, 3×CH$_3$), 1.41-1.91 (m, 4H, 2×CH$_2$), 3.38 (dd, J=6.3, 1.8 Hz, 2H, CH$_2$), 3.82-3.92 (m, 1H, CH), 5.04 (d, J=2.4 Hz, 2H, CH$_2$), 7.28-7.40 (m, 5H, 5×Ar—H), 7.58 (d$_{br}$, J=7.8 Hz, 1H, NH).

$^{13}$C-NMR (75.5 MHz, DMSO-d$_6$): δ=27.62, 28.83, 54.48, 60.10, 65.32, 80.32, 127.7, 127.8, 128.3, 156.1, 171.6.

MS (ESI): m/z (%)=267.9 (16) [M-tBu+H]$^+$, 324.0 (36) [M+H]$^+$, 346.2 (10) [M+Na]$^+$, 646.9 (100) [2M+H]$^+$, 669.0 (28) [2M+Na]$^+$.

Example 5-6: Preparation of tert-Butyl-(S)-2-(benzyloxycarbonylamino)-5-iodopentanoate F4

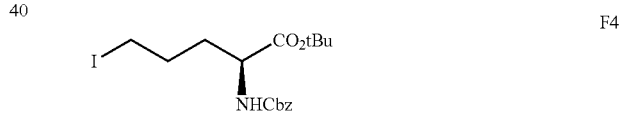

To a suspension of PPh$_3$ (2.30 g, 8.78 mmol, 2.0 equiv.), I$_2$ (2.23 g, 8.78 mmol, 2.0 equiv.) and imidazole (897 mg, 13.2 mmol, 3.0 equiv.) in CH$_2$Cl$_2$ (44 mL) was added F3 (1.42 g, 4.39 mmol) and it was stirred for 1 h at room temperature. H$_2$O was added (30 mL), the organic phase separated, washed with aq. 1 M Na$_2$S$_2$O$_3$ solution (30 mL), dried over MgSO$_4$ and the solvent was evaporated under reduced pressure. Column chromatography on SiO$_2$ (CH$_2$Cl$_2$) afforded the title compound (1.64 g, 3.79 mmol, 86%) as slightly yellow oil, which solidified upon cooling to 4° C.

R$_f$: 0.35 (Cyclohexane/EtOAc 8:1, KMnO$_4$)

$^1$H-NMR (300 MHz, CDCl$_3$): δ=1.47 (s, 9H, 3×CH$_3$), 1.69-2.00 (m, 4H, 2×CH$_2$), 3.08-3.28 (m, 2H, CH$_2$), 4.24-4.33 (m, 1H, CH), 5.11 (s, 2H, CH$_2$), 5.33 (d$_{br}$, J=7.5 Hz, 1H, NH), 7.28-7.38 (m, 5H, 5×Ar—H).

$^{13}$C-NMR (75.5 MHz, CDCl$_3$): δ=5.82, 28.22, 29.20, 34.00, 53.68, 67.18, 82.70, 128.3, 128.4, 128.8, 136.5, 156.0, 171.3.

MS (ESI): m/z (%)=377.8 (74) [M-tBu+H]$^+$, 433.7 (74) [M+H]$^+$, 456.1 (12) [M+Na]$^+$, 810.6 (12) [2M-tBu+H]$^+$, 866.6 (12) [2M+H]$^+$.

Example 5-7: Preparation of (S,E)-tert-Butyl 2-(((benzyloxy)carbonyl)amino)-8-((tert-butoxycarbonyl)amino)oct-6-enoate G1

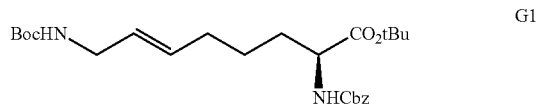 [SMILES: CC(C)(C)OC(=O)NC/C=C/CCC[C@H](NC(=O)OCc1ccccc1)C(=O)OC(C)(C)C]

To a suspension of Zn powder (1.57 g, 24.0 mmol, 6.0 equiv.) in DMF (1.8 mL) was added 1,2-Dibromomethane (103 µL, 1.20 mmol, 0.3 equiv.) and it was stirred for 0.5 h at 60° C. After cooling to room temperature, TMSCl (30 µL, 0.240 mmol, 0.06 equiv.) was added and stirring was continued for further 0.5 h. Then F4 (1.73 g, 4.00 mmol, 1.0 equiv.) was added and the reaction mixture was stirred for 0.5 h. $Pd_2(dba)_3$ (73 mg, 0.080 mmol, 0.02 equiv), $P(otol)_3$ (97 mg, 0.320 mmol, 0.08 equiv.), and E2 (849 mg, 3.00 mmol, 0.75 equiv.) in DMF (1.8 mL), were added and it was stirred for 16 h at room temperature. The resulting green suspension was poured into EtOAc (150 mL) and the organic phase was washed with sat. aq. NaCl solution (3×50 mL), dried over $MgSO_4$ and the solvent was evaporated under reduced pressure. Column chromatography on $SiO_2$ (cyclohexane/EtOAc 8:1→4:1) afforded the title compound (1.25 g, 2.70 mmol, 90%) as yellow oil.

$R_f$: 0.23 (Cyclohexane/EtOAc 4:1, $KMnO_4$)

$^1$H-NMR (400 MHz, $CDCl_3$): δ=1.44 (s, 9H, 3×$CH_3$), 1.45 (s, 9H, 3×$CH_3$), 1.54-1.86 (m, 4H, 2×$CH_2$), 1.95-2.10 (m, 2H, $CH_2$), 3.62-3.72 (m, 2H, $CH_2$), 4.20-4.28 ($m_c$, 1H, CH), 4.57 ($s_{br}$, 1H, NH), 5.10 (s, 2H, $CH_2$), 5.29 ($d_{br}$, J=7.6 Hz, 1H, NH), 5.39-5.48 (m, 1H, CH), 5.49-5.58 (m, 1H, CH), 7.28-7.38 (m, 5H, 5×Ar—H).

$^{13}$C-NMR (100 MHz, $CDCl_3$): δ=24.67, 28.20, 28.61, 31.80, 32.49, 42.74, 54.34, 67.04, 82.21, 127.4, 128.3, 128.3, 128.7, 128.7, 132.1, 136.6, 155.9, 156.0, 171.7.

MS (ESI): m/z (%)=307.3 (28) [M-Boc-tBu+H]$^+$, 363.2 (100) [M-Boc+H]$^+$, 463.0 (64) [M+H]$^+$, 485.2 (16) [M+Na]$^+$, 825.0 (34) [2M-Boc+H]$^+$.

Example 5-8: Preparation of (S)-tert-Butyl 2-(((benzyloxy)carbonyl)amino)-5-((2S,3S)-3-(((tert-butoxycarbonyl)amino)methyl)oxiran-2-yl)pentanoate G2

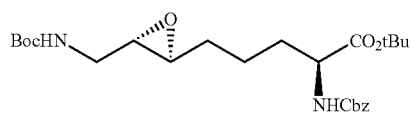

To a solution of G1 (2.00 g, 4.32 mmol) in DMM/MeCN (60 mL, 2:1) was added buffer (40 mL, 0.05 M solution of $Na_2B_4O_7\cdot10H_2O$ in $4\cdot10^{-4}$ M aq. $Na_2$(EDTA)), $nBu_4NHSO_4$ (148 mg, 0.432 mmol, 0.1 equiv.) and L-fructose derived Shi ketone (X) (1.68 g, 2.16 mmol, 0.5 equiv.). Then, a solution of Oxone (3.98 g, 6.48 mmol, 1.5 equiv.) in aq. $Na_2$(EDTA) (40 mL, $4\cdot10^{-4}$ M) and a solution of $K_2CO_3$ (2.39 g, 17.3 mmol, 4.0 equiv.) in $H_2O$ (40 mL) were added dropwise separately over a period of 1.5 h via addition funnels. The reaction was stirred for further 16 h at room temperature. The organic phase was separated and the aqueous phase was extracted with $CH_2Cl_2$ (2×200 mL). The combined organic phases were washed with 1 M aq. $Na_2S_2O_3$ solution (100 mL), dried over $MgSO_4$, and the solvent was removed under reduced pressure. Column chromatography on $SiO_2$ (cyclohexane/EtOAc 5:1→3:1+0.1 $NEt_3$) afforded the title compound (1.46 g, 3.05 mmol, 71%) as colorless oil.

$R_f$: 0.38 (Cyclohexane/EtOAc 2:1, $KMnO_4$)

$^1$H-NMR (300 MHz, $CDCl_3$): δ=1.42 (s, 9H, 3×$CH_3$), 1.45 (s, 9H, 3×$CH_3$), 1.48-1.92 (m, 6H, 3×$CH_2$), 2.70-2.79 (m, 1H, $CH_A$), 2.79-2.85 (m, 1H, $CH_B$), 3.17 (ddd, J=14.8, 6.4, 5.2 Hz, 1H, CH), 3.39-3.53 (m, 1H, CH), 4.24 ($m_c$, 1H, CH), 4.77 ($s_{br}$, 1H, NH), 5.09 (s, 2H, $CH_2$), 5.37 ($d_{br}$, J=8.1 Hz, 1H, NH), 7.28-7.38 (m, 5H, 5×Ar—H).

$^{13}$C-NMR (75.5 MHz, $CDCl_3$): δ=21.78, 28.17, 28.52, 31.18, 32.64, 41.59, 54.39, 56.51, 57.05, 67.05, 79.77, 82.31, 128.3, 128.3, 128.7, 128.7, 136.5, 156.0, 171.6.

MS (ESI): m/z (%)=323.2 (28) [M-Boc-tBu+H]$^+$, 367.1 (58) [M-Boc-tBu-H+2Na]$^+$, 423.0 (100) [M-tBu+H]$^+$, 479.0 (20) [M+H]$^+$, 501.1 (14) [M+Na]$^+$, 957.0 (12) [2M+H]$^+$.

Example 5-9: Preparation of (2S,6R)-1-benzyl 2-tert-butyl 6-((S)-2-((tert-butoxy-carbonyl)amino)-1-hydroxyethyl)piperidine-1,2-dicarboxylate G3

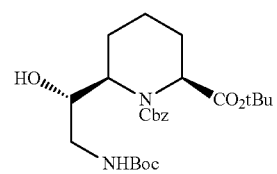

A suspension of G2 (1.45 g, 3.03 mmol) and Pd/C (145 mg, 10 wt. %) in EtOH (30 mL) was stirred for 2 h at room temperature under a $H_2$-atmosphere. The reaction mixture was filtered over Celite, washed with EtOAc and the solvent was evaporated under reduced pressure to give a colorless, crystalline solid.

This solid was dissolved in dioxane/$H_2O$ (30 mL, 2:1), $Na_2CO_3$ (963 mg, 9.09 mmol, 3.0 equiv.) and benzyl chloroformate (646 µL, 4.55 mmol, 1.5 equiv.) were added and it was stirred for 18 h at room temperature. $H_2O$ (50 mL) was added and it was extracted with $CH_2Cl_2$ (2×50 mL), dried over $MgSO_4$, and the solvent was removed under reduced pressure. Column chromatography on $SiO_2$ (cyclohexane/EtOAc 4:1) afforded the title compound (1.20 g, 2.51 mmol, 83% over 2 steps) as colorless oil.

$R_f$: 0.50 (Cyclohexane/EtOAc 2:1, $KMnO_4$)

$^1$H-NMR (400 MHz, DMSO-$d_6$): δ=1.35 ($s_{br}$, 9H, 3×$CH_3$), 1.37 (s, 9H, 3×$CH_3$), 1.40-1.68 (m, 4H, 2×$CH_2$), 1.96-2.12 (m, 2H, $CH_2$), 2.82-2.92 (m, 1H, $CH_A$), 3.28-3.36 (m, 1H, $CH_B$), 3.55-3.63 (m, 1H, CH), 3.96-4.04 (m, 1H, CH), 4.61-4.67 (m, 1H, CH), 4.76 ($d_{br}$, J=5.2 Hz, 1H, OH), 5.03 (d, J=12.4 Hz, 1H, $CH_A$), 5.15 (d, J=12.4 Hz, 1H, $CH_B$), 6.13 ($s_{br}$, 1H, NH), 7.28-7.40 (m, 5H, 5×Ar—H).

$^{13}$C-NMR (100 MHz, DMSO-$d_6$): δ=15.76, 22.96, 25.18, 27.35, 28.19, 53.51, 54.87, 66.64, 68.64, 77.53, 81.00, 126.4, 126.6, 127.3, 136.6, 142.5, 155.6, 171.3.

MS (ESI): m/z (%)=323.2 (70) [M-Boc-tBu+H]$^+$, 379.1 (74) [M-Boc+H]$^+$, 478.9 (26) [M+H]$^+$, 501.2 (42) [M+Na]$^+$, 801.0 (92) [2M-Boc-tBu+H]⁺, 856.9 (100) [2M-Boc+H]⁺, 956.5 (6) [2M+H]⁺, 978.8 (36) [2M+Na]⁺.

Example 5-10: Preparation of (1S,5S,6R)-benzyl 2-oxo-5-((triethylsilyl)oxy)-3,10-diazabicyclo[4.3.1]decane-10-carboxylate G4

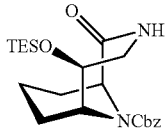

G4

To a solution of G3 (500 mg, 1.04 mmol) and 2,6-lutidine (1.21 mL, 10.4 mmol, 10 equiv.) in $CH_2Cl_2$ (20 mL) at 0° C. was added TESOTf (1.17 mL, 5.20 mol, 5.0 equiv.) dropwise. After 30 minutes the cooling bath was removed and the reaction was stirred for 20 h at room temperature. Sat. aq. $NH_4Cl$ solution (20 mL) was added and stirring was continued for 1 h. The organic phase was separated, the aqueous phase was extracted with $CH_2Cl_2$ (2×50 mL), the combined organic phases were dried over $MgSO_4$, and the solvent was evaporated under reduced pressure. The residue was purified by column chromatography on $SiO_2$ ($CH_2Cl_2$/MeOH 20:1 to 10:1).

The obtained amino acid was dissolved in $CH_2Cl_2$ (25 mL) and the solution was added dropwise at room temperature over 1 h to a solution of HATU (593 mg, 1.56 mmol, 1.5 equiv.) and $(iPr)_2NEt$ (400 µL, 2.23 mmol, 2.2 equiv.) in $CH_2Cl_2$ (200 mL). Stirring was continued for further 16 h, following evaporation of the solvent under reduced pressure. The residue was taken up in $CH_2Cl_2$ (100 mL), washed with $CuSO_4$ solution (10 wt. %, 3×100 mL), dried over $MgSO_4$, and the solvent was evaporated under reduced pressure. Column chromatography on $SiO_2$ (cyclohexane/EtOAc 2:1) afforded the title compound (218 mg, 0.521 mmol, 50% over 2 steps) as a slightly yellow oil.

The compound consists of two carbamate rotamers in a 1:0.7 ratio.

$R_f$: 0.31 (Cyclohexane/EtOAc 1:1, $KMnO_4$)

¹H-NMR (400 MHz, DMSO-d₆): δ=0.58 (q, J=7.6 Hz, 6H, 3×CH₂), 0.90 (t, J=7.6 Hz, 5.4H, 3×CH₃), 0.91 (t, J=7.6 Hz, 3.6H, 3×CH₃), 1.37-1.70 (m, 5H, 2×CH₂, CH), 2.00-2.11 (m, 1H, CH), 2.70-2.79 (m, 1H, CH$_A$), 2.95-3.07 (m, 1H, CH$_B$), 3.83-3.93 (m, 1H, CH), 4.24-4.32 (m, 1H, CH), 4.61-4.66 (m, 1H, CH), 5.05 (d, J=12.8 Hz, 0.6H, CH$_A$), 5.09 (d, J=12.8 Hz, 0.4H, CH$_A$), 5.17 (d, J=12.8 Hz, 0.4H, CH$_B$), 5.26 (d, J=12.8 Hz, 0.6H, CH$_B$), 7.29-7.41 (m, 5H, 3×Ar—H), 7.81-7.86 (m, 0.6H, NH), 7.88-7.93 (m, 0.4H, NH).

¹³C-NMR (100 MHz, DMSO-d₆): δ=4.20 (0.4C), 4.24 (0.6C), 6.62 (0.6C), 6.64 (0.4C), 15.95 (0.4C), 16.01 (0.6C), 26.30, 26.81 (0.4C), 27.14 (0.6C), 44.84 (0.4C), 44.88 (0.6C), 54.64 (0.6C), 54.88 (0.4C), 56.41 (0.4C), 57.27 (0.6C), 66.74 (0.6C), 66.79 (0.4C), 74.45, (0.4C), 74.84 (0.6C), 127.2 (0.6C), 127.4 (0.4C), 127.9 (0.6C), 127.9 (0.4C), 128.3 (0.6C), 128.5 (0.4C), 136.6 (0.6C), 136.7 (0.4C), 155.1 (0.4C), 155.3 (0.6C), 172.2 (0.4C), 172.3 (0.6C).

MS (ESI): m/z (%)=419.2 (34) [M+H]⁺, 837.1 (100) [2M+H]⁺.

Example 5-10: Preparation of (1S,5S,6R)-10-((3,5-dichlorophenyl)sulfonyl)-5-((triethylsilyl)oxy)-3,10-diazabicyclo[4.3.1]decan-2-one G5

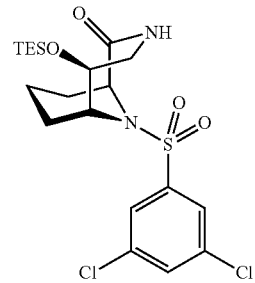

G5

A suspension of G4 (500 mg, 1.19 mmol) and Pd/C (50.0 mg, 10 wt. %) in EtOAc (6 mL) was stirred for 3 h at room temperature under a $H_2$-atmosphere. The reaction mixture was filtered over Celite, washed with EtOAc and the solvent was evaporated under reduced pressure to give a colorless, crystalline solid.

The solid was dissolved in $CH_2Cl_2$ (6 mL), $(iPr)_2NEt$ (624 µL, 3.57 mmol, 3.0 equiv.), DMAP (145 mg, 1.19 mmol, 1.0 equiv.) and 3,5-Dichlorobenzenesulfonyl chloride (584 mg, 2.38 mmol, 2.0 equiv.) were added and the solution was stirred for 20 h at room temperature. Sat. aq. $NH_4Cl$ solution was added (25 mL), the aqueous phase was extracted with $CH_2Cl_2$ (2×25 mL), dried over $MgSO_4$, and the solvent evaporated under reduced pressure. Column chromatography on $SiO_2$ (cyclohexane/EtOAc 3:1) afforded the title compound (420 mg, 0.851 mmol, 72% over 2 steps) as colorless, crystalline solid.

$R_f$: 0.31 (Cyclohexane/EtOAc 2:1)

¹H-NMR (600 MHz, CDCl₃): δ=0.61 (q, J=7.8 Hz, 6H, 3×CH₂), 0.96 (t, J=7.8 Hz, 9H, 3×CH₃), 1.25-1.70 (m, 5H, 2×CH₂, CH), 2.16-2.21 (m, 1H, CH), 2.83-2.91 (m, 1H, CH$_A$), 2.83-2.91 (m, 1H, CH$_A$), 3.59-3.64 (m, 1H, CH$_B$), 3.93-3.97 (m, 1H, CH), 4.12-4.15 (m, 1H, CH), 4.64-4.67 (m, 1H, CH), 6.04-6.09 (m, 1H, NH), 7.57 (t, J=1.8 Hz, 1H, Ar—H), 7.72 (d, J=1.8 Hz, 2H, 2×Ar—H).

¹³C-NMR (75.5 MHz, CDCl₃): δ=4.99, 6.95, 16.26, 26.59, 27.19, 46.88, 56.42, 60.20, 74.89, 125.3, 133.0, 136.5, 144.0, 172.8.

MS (ESI): m/z (%)=493.4 (44) [M+H]⁺, 987.2 (100) [2M+H]⁺.

Example 5-10: Preparation of (1S,5S,6R)-10-((3,5-dichlorophenyl)sulfonyl)-5-hydroxy-3,10-diazabicyclo[4.3.1]decan-2-one G6

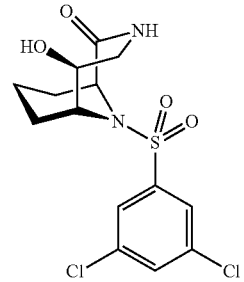

G6

To a solution of G5 (400 mg, 0.811 mmol) in THF (4 mL) was added TBAF (1 M in THF, 892 µL, 0.892 mmol, 1.1 equiv.) and the solution was stirred for 1.5 h at room temperature. Removal of the solvent under reduced pressure and column chromatography on $SiO_2$ ($CH_2Cl_2$/MeOH 20:1) afforded the title compound (294 mg, 0.775 mmol, 96%) as a colorless solid.

$R_f$: 0.30 (EtOAc)

$^1$H-NMR (400 MHz, MeOH-$d_4$): δ=1.27-1.37 (m, 2H, $CH_2$), 1.51-1.59 (m, 2H, $CH_2$), 1.69-1.79 (m, 1H, CH), 2.04-2.11 (m, 1H, CH), 2.99 (dd, J=13.2, 2.8 Hz, 1H, $CH_A$), 3.58 (dd, J=13.2, 10.4 Hz, 1H, $CH_B$), 3.94 (ddd, J=10.4, 5.2, 2.8 Hz, 1H, CH), 4.07 ($m_c$, 1H, CH), 4.66 (dt, J=6.0, 2.0 Hz, 1H, CH), 7.81 (t, J=2.0 Hz, 1H, Ar—H), 7.89 (d, J=2.0 Hz, 2H, 2×Ar—H).

$^{13}$C-NMR (100 MHz, MeOH-$d_4$): δ=16.92, 27.51, 27.94, 47.04, 57.80, 60.52, 74.75, 126.5, 134.1, 137.8, 145.7, 175.0.

MS (ESI): m/z (%)=379.0 (100) $[M+H]^+$, 758.7 (52) $[2M+H]^+$.

VI. Preparation of Compounds H1.1-H1.4 and H2.1-H2.3

Further examples for the compound of the general formula (I) are outlined in scheme H1 and scheme H2:

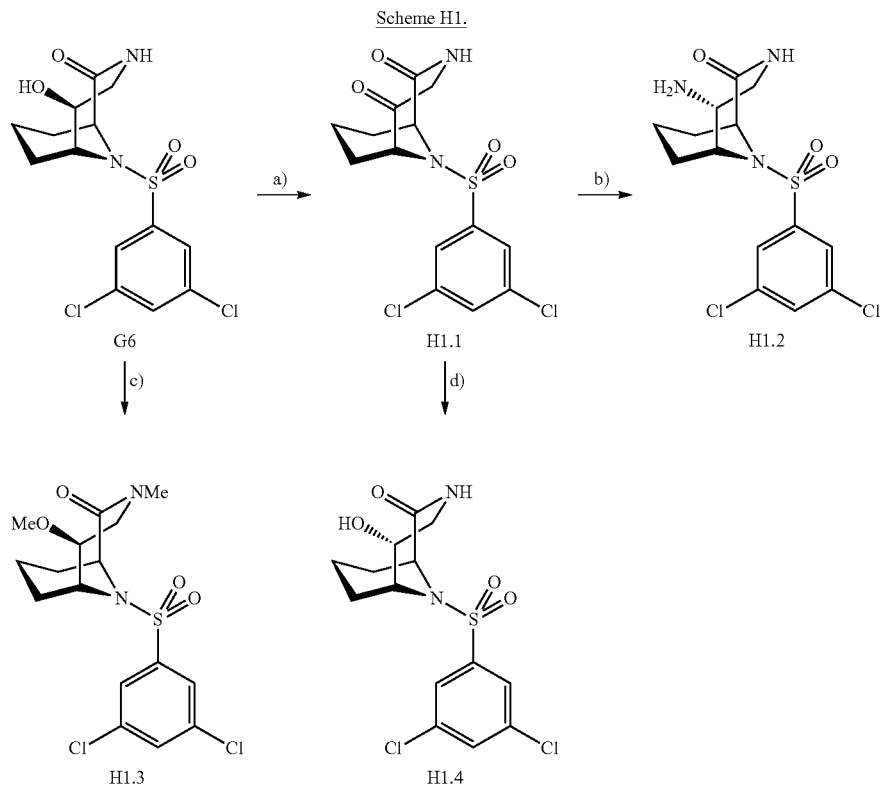

Reagents and conditions: a) Dess-Martin periodinane, $CH_2Cl_2$, rt, 18 h, quant.; b) NH$_4$OTFA, NaBH(OAc)$_3$, THF, rt, 10 h, dr 10:1, quant.; c) NaHMDS, MeI, 0° C. to rt, 16 h, 26%; d) L-Selectride, THF, -78° C., 1 h, quant.

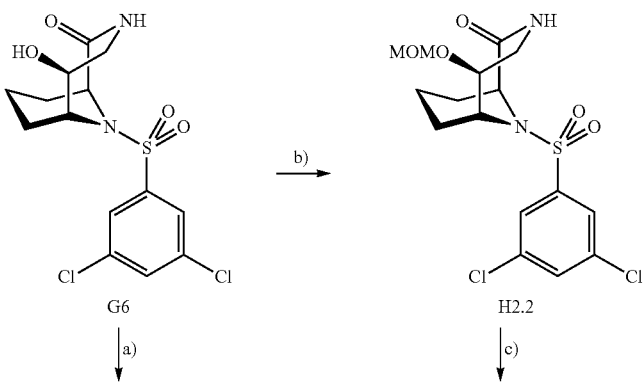

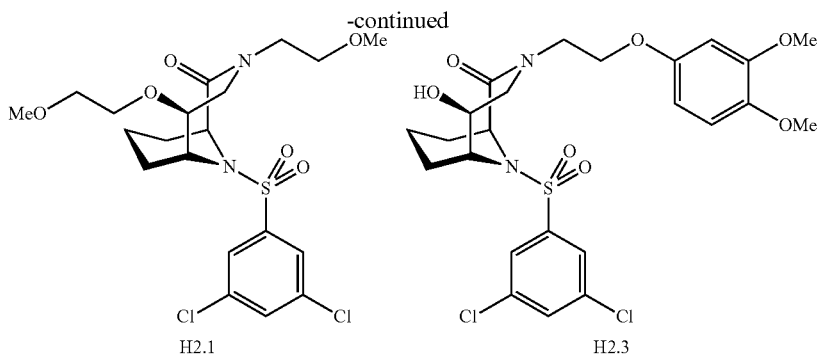

Reagents and conditions: a) NaH, 2-Bromoethyl methyl ether, DMF, 80° C., 6 h, 23%, b) MOMCl, (iPr)₂NEt, DMF, 80° C., 3 h, 39%
c) 1.) NaH, 4-(2-Bromoethoxy)-1,2-dimethoxy benzene, DMF, 80° C., 2 h; 2.) conc. HCl, EtOH, rt, 2 d, 20% (2 steps).

Example 6-1: Preparation of (1S,6R)-10-((3,5-dichlorophenyl)sulfonyl)-3,10-diazabicyclo[4.3.1]decane-2,5-dione H1.1

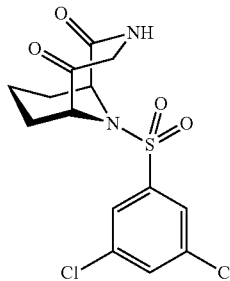

H1.1

To a solution of G6 (100 mg, 0.264 mmol) in CH$_2$Cl$_2$ (6 mL) was added Dess-Martin periodinane (134 mg, 0.317 mmol, 1.2 equiv.) and the solution was stirred for 18 h at room temperature. Removal of the solvent under reduced pressure and column chromatography on SiO$_2$ (CH$_2$Cl$_2$/EtOAc 10:1→5:1) afforded the title compound (100 mg, 0.264 mmol, quant.) as a colorless solid.

R$_f$: 0.28 (Cyclohexane/EtOAc 2:1)

$^1$H-NMR (400 MHz, CDCl$_3$): δ=1.19-1.73 (m, 5H, 2×CH$_2$, CH), 2.20-2.30 (m, 1H, CH), 3.50 (dd, J=13.2, 8.4 Hz, 1H, CH$_A$), 4.64-4.68 (m, 1H, CH), 4.76 (dd, J=13.2, 1.6 Hz, 1H, CH$_B$), 4.78-4.81 (m, 1H, CH), 6.36 (d$_{br}$, J=8.0 Hz, 1H, NH), 7.63 (d, J=2.0 Hz, 1H, Ar—H), 7.72 (d, J=2.0 Hz, 1H, 2×Ar—H).

$^{13}$C-NMR (100 MHz, CDCl$_3$): δ=17.70, 24.74, 27.24, 51.13, 57.14, 62.57, 125.2, 133.7, 137.0, 143.0, 171.5, 205.6.

MS (ESI): m/z (%)=377.0 (100) [M+H]$^+$.

Example 6-2: Preparation of (1S,5R,6R)-5-amino-10-((3,5-dichlorophenyl)sulfonyl)-3,10-diazabicyclo[4.3.1]decan-2-one H1.2

H1.2

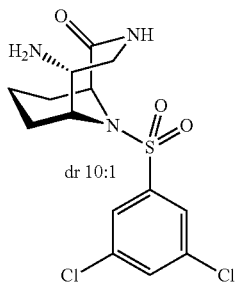

dr 10:1

To a solution of H1.1 (10.0 mg, 2.65·10$^{-5}$ mol) in THF (0.5 mL) was added ammonium trifluoroacetate (34.7 mg, 0.264 mmol, 10 equiv.) and NaBH(OAc)$_3$ (16.8 mg, 7.95·10$^{-5}$ mol, 3.0 equiv.) and the solution was stirred for 10 h at room temperature. 1 M aq. NaOH (15 mL) was added, the aqueous phase was extracted with EtOAc (2×15 mL), dried over MgSO$_4$, and the solvent evaporated under reduced pressure. Column chromatography on SiO$_2$ (cyclohexane/EtOAc 1:2 to 0:1) afforded the title compound (10.0 mg, 2.65·10$^{-5}$ mol, quant.) as a colorless solid.

R$_f$: 0.52 (EtOAc)

$^1$H-NMR (400 MHz, MeOH-d$_4$): δ=1.32-1.52 (m, 3H, CH$_2$, CH), 1.65-1.77 (m, 1H, CH), 2.02-2.12 (m, 1H, CH), 3.28 (dd, J=14.4, 8.0 Hz, 1H, CH$_A$), 3.47 (dd, J=14.4, 3.6 Hz, 1H, CH$_B$), 4.14 (m$_c$, 1H, CH), 4.37 (m$_c$, 1H, CH), 4.62-4.67 (m, 1H, CH), 7.78 (t, J=1.6 Hz, 1H, Ar—H), 7.89 (d, J=1.6 Hz, 2H, 2×Ar—H).

MS (ESI): m/z (%)=379.1 (100) [M+H]$^+$. 758.8 (82) [2M+H]$^+$.

Example 6-3: Preparation of (1S,5S,6R)-10-((3,5-dichlorophenyl)sulfonyl)-5-methoxy-3-methyl-3,10-diazabicyclo[4.3.1]decan-2-one H1.3

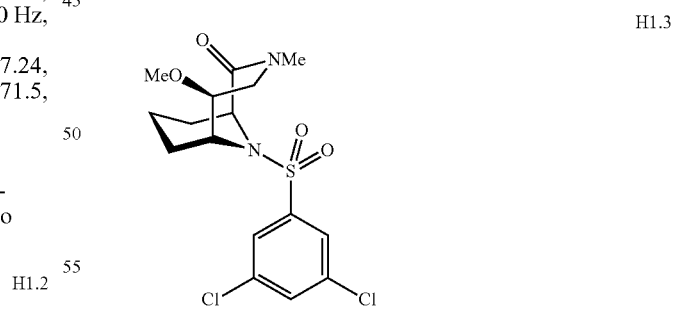

H1.3

To a solution of G6 (40.0 mg, 0.105 mmol) in THF (1 mL) at 0° C. was added NaHMDS (1 M in THF, 126 µL, 0.126 mmol, 1.2 equiv.). After 5 min MeI (7.2 µL, 0.116 mmol, 1.1 equiv.) was added, the cooling bath was removed and the solution was stirred for 16 h at room temperature. Sat. aq. NH$_4$Cl solution (20 mL) was added, the aqueous phase was extracted with EtOAc (2×20 mL), dried over MgSO$_4$, and the solvent removed under reduced pressure. Column chromatography on SiO$_2$ (cyclohexane/EtOAc 1:1→1:2)

afforded the title compound (11.0 mg, 2.70·10⁻⁵ mol, 26%) as a colorless solid.

R$_f$: 0.34 (Cyclohexane/EtOAc 1:1)

¹H-NMR (400 MHz, CDCl$_3$): δ=1.12-1.67 (m, 5H, 2×CH$_2$, CH), 2.19-2.26 (m, 1H, CH), 3.11 (s, 3H, NCH$_3$), 3.15 (dd, J=13.6, 2.4 Hz, 1H, CH$_A$), 3.43 (s, 3H, OCH$_3$), 3.49 (ddd, J=10.4, 4.8, 2.4 Hz, 1H, CH), 3.97 (dd, J=13.6, 10.4 Hz, 1H, CH$_B$), 4.08-4.13 (m, 1H, CH), 4.68 (m$_c$, 1H, CH), 7.56 (t, J=2.0 Hz, 1H, Ar—H), 7.70 (t, J=2.0 Hz, 2H, 2×Ar—H).

¹³C-NMR (100 MHz, CDCl$_3$): δ=16.34, 27.18, 27.50, 50.56, 56.92, 57.08, 58.39, 83.17, 125.3, 133.0, 136.6, 144.1, 170.1.

MS (ESI): m/z (%)=407.0 (100) [M+H]⁺, 814.7 (8) [2M+H]⁺.

Example 6-4: Preparation of (1S,5R,6R)-10-((3,5-dichlorophenyl)sulfonyl)-5-hydroxy-3,10-diazabicyclo[4.3.1]decan-2-one H1.4

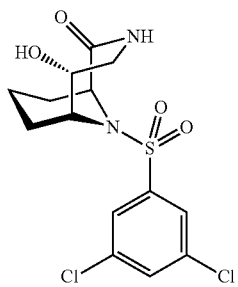

H1.4

To a solution of H1.1 (60.0 mg, 0.159 mmol) in THF (3 mL) at −78° C. was added L-Selectride (1 M in THF, 191 µL, 0.191 mmol, 1.2 equiv.) and the solution was stirred for 1 h at −78° C. The cooling bath was removed, H$_2$O (1 mL) was added and the reaction was allowed to reach room temperature. Sat. aq. NH$_4$Cl solution (20 mL) was added, the aqueous phase was extracted with EtOAc (2×20 mL), dried over MgSO$_4$, and the solvent was evaporated under reduced pressure. Column chromatography on SiO$_2$ (EtOAc) afforded the title compound (59.0 mg, 0.156 mmol, quant.) as a colorless solid.

R$_f$: 0.30 (EtOAc)

¹H-NMR (400 MHz, MeOH-d$_4$): δ=1.21-1.52 (m, 5H, 2×CH$_2$, CH), 2.02-2.11 (m, 1H, CH), 3.28 (dd, J=14.4, 8.0 Hz, 1H, CH$_A$), 3.47 (dd, J=14.4, 3.2 Hz, 1H, CH$_B$), 4.12-4.17 (m, 1H, CH), 4.37 (m$_c$, 1H, CH), 4.63-4.67 (m, 1H, CH), 7.79 (t, J=2.0 Hz, 1H, Ar—H), 7.86 (d, J=2.0 Hz, 2H, 2×Ar—H).

¹³C-NMR (100 MHz, MeOH-d$_4$): δ=19.23, 22.80, 28.42, 46.74, 55.25, 58.59, 71.91, 126.5, 134.0, 137.7, 145.6, 178.1.

MS (ESI): m/z (%)=379.1 (100) [M+H]⁺, 758.7 (94) [2M+H]⁺.

Example 6-5: Preparation of (1S,5S,6R)-10-((3,5-dichlorophenyl)sulfonyl)-5-(2-methoxyethoxy)-3-(2-methoxyethyl)-3,10-diazabicyclo[4.3.1]decan-2-one H2.1

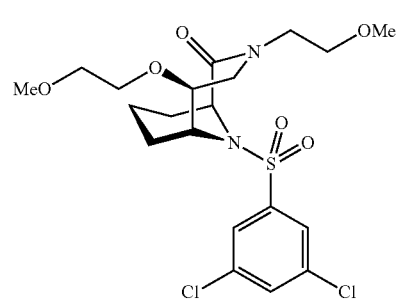

H2.1

To a solution of G6 (10.0 mg, 2.64·10⁻⁵ mol) in DMF (0.25 mL), was added NaH (2.6 mg, 6.60·10⁻⁵ mol, 2.5 equiv.). After stirring for 5 min, 2-Bromoethyl methyl ether (5.40 µL, 5.81·10⁻⁵ mol, 2.2 equiv.) was added and the suspension was stirred at 80° C. for 6 h. After cooling to room temperature, H$_2$O (15 mL) was added and the aqueous phase was extracted with Et$_2$O (2×15 mL), dried over MgSO$_4$, and the solvent was evaporated under reduced pressure. Column chromatography on SiO$_2$ (cyclohexane/EtOAc 1:1→1:2) afforded the title compound (3.0 mg, 6.06·10⁻⁶ mol, 23%) as colorless solid.

R$_f$: 0.26 (Cyclohexane/EtOAc 1:2)

¹H-NMR (600 MHz, CDCl$_3$): δ=1.25-1.60 (m, 5H, CH, 2×CH$_2$), 2.22 (m$_c$, 1H, CH), 3.25-3.30 (m, 1H, CH). 3.35 (s, 3H, OMe), 3.38 (s, 3H, OMe), 3.49-3.55 (m, 4H, 2×CH$_2$), 3.57-3.65 (m, 2H, CH$_2$), 3.72-3.77 (m, 2H, CH$_2$), 3.94 (dd, J=14.4, 10.2 Hz, 1H, CH), 4.01 (dt, J=14.4, 3.6 Hz, 1H, CH), 4.13 (m$_c$, 1H, CH), 4.67 (m$_c$, 1H, CH), 7.56 (t, J=1.8 Hz, 1H, Ar—H), 7.71 (d, J=1.8 Hz, 2H, 2×Ar—H).

MS (ESI): m/z (%)=495.23 (100) [M+H]⁺, 990.32 (28) [2M+H]⁺.

Example 6-6: Preparation of (1S,5S,6R)-10-((3,5-dichlorophenyl)sulfonyl)-5-(methoxymethoxy)-3,10-diazabicyclo[4.3.1]decan-2-one H2.2

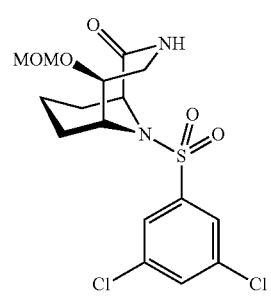

H2.2

To a solution of G6 (25.0 mg, 6.59·10⁻⁵ mol) in DMF (0.5 mL) was added (iPr)$_2$NEt (138 µL, 0.791 mmol, 12 equiv.) and MOMCl (50.0 µL, 0.659 mmol, 10 equiv.) and it was stirred at 80° C. for 3 h. After cooling to room temperature, H$_2$O (15 mL) was added and the aqueous phase was extracted with Et$_2$O (2×15 mL), dried over MgSO$_4$, and the solvent was evaporated under reduced pressure. Column chromatography on SiO$_2$ (cyclohexane/EtOAc 1:1→1:2) afforded the title compound (11.0 mg, 2.60·10$^{-5}$ mol, 39%) as colorless solid.

R$_f$: 0.10 (Cyclohexane/EtOAc 1:1)

$^1$H-NMR (400 MHz, CDCl$_3$): δ=1.20-1.75 (m, 5H, 2×CH$_2$, CH), 2.15-2.22 (m, 1H, CH), 3.17 (ddd, J=13.6, 8.8, 2.8 Hz, 1H, CH$_A$), 3.39 (s, 3H, OCH$_3$), 3.68-3.76 (m, 1H, CH$_B$), 3.85 (ddd, J=10.4, 4.8, 2.8 Hz, 1H, CH), 4.22 (m$_c$, 1H, CH), 4.65 (d, J=7.2 Hz, CH$_A$), 4.66 (m$_c$, 1H, CH), 4.69 (d, J=7.2 Hz, CH$_B$), 6.32 (d$_{br}$, J=7.2 Hz, 1H, NH), 7.58 (d, J=2.0 Hz, 1H, Ar—H), 7.72 (d, J=2.0 Hz, 2H, 2×Ar—H).

$^{13}$C-NMR (100 MHz, CDCl$_3$): δ=16.19, 26.87, 27.26, 43.99, 56.00, 56.50, 57.85, 80.53, 96.69, 125.3, 133.1, 136.6, 144.0, 172.6.

MS (ESI): m/z (%)=423.0 (100) [M+H]$^+$, 846.8 (94) [2M+H]$^+$.

Example 6-7: Preparation of (1S,5S,6R)-10-((3,5-dichlorophenyl)sulfonyl)-3-(2-(3,4-dimethoxyphenoxy)ethyl)-5-hydroxy-3,10-diazabicyclo[4.3.1]decan-2-one H2.3

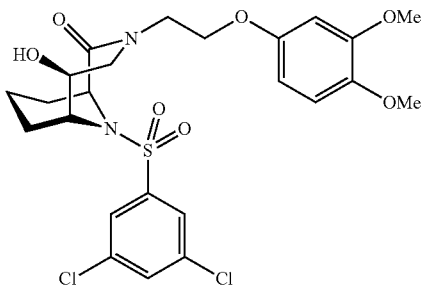

To a solution of H2.2 (11.0 mg, 2.60·10$^{-5}$ mol) in DMF (0.2 mL) was added NaH (1.6 mg, 3.9·10$^{-5}$ mol, 1.5 equiv.). After stirring for 10 min at room temperature, 4-(2-Bromoethoxy)-1,2-dimethoxy benzene (7.50 mg, 2.86·10$^{-5}$ mol, 1.1 equiv.) was added and it was stirred at 80° C. for 2 h. After cooling to room temperature, sat aq. NH$_4$Cl solution (15 mL) was added and the aqueous phase was extracted with Et$_2$O (2×15 mL), dried over MgSO$_4$, and the solvent was evaporated under reduced pressure. Column chromatography on SiO$_2$ (cyclohexane/EtOAc 2:1→1:1) afforded a colorless solid (6.0 mg, 9.94·10$^{-6}$ mol, 38%).

This solid was dissolved in EtOH (0.5 mL), conc. aq. HCl (0.1 mL) was added and it was stirred for 2 d at room temperature. Evaporation of the solvent under reduced pressure and column chromatography on SiO$_2$ (cyclohexane/EtOAc 1:2) afforded the title compound (3.0 mg, 5.36·10$^{-6}$ mol, 54%) as colorless solid.

R$_f$: 0.19 (Cyclohexane/EtOAc 1:1)

$^1$H-NMR (600 MHz, CDCl$_3$): δ=1.27-1.67 (m, 5H, CH, 2×CH$_2$), 2.19-2.24 (m, 1H, CH), 3.47 (dd, J=13.8, 2.4 Hz, 1H, CH), 3.60-3.67 (m, 1H, CH), 3.84 (s, 3H, OMe), 3.86 (s, 3H, OMe), 4.01-4.09 (m, 4H, 2×CH, CH$_2$), 4.10-4.17 (m, 2H, CH$_2$), 4.70 (m$_c$, 1H, CH), 6.39 (dd, J=9.0, 2.4 Hz, 1H, Ar—H), 6.51 (d, J=2.4 Hz, 1H, Ar—H), 6.78 (d, J=9.0 Hz, 1H, Ar—H), 7.51-7.53 (m, 1H, Ar—H), 7.69-7.71 (m, 2H, 2×Ar—H).

MS (ESI): m/z (%)=559.0 (100) [M+H]$^+$.

V. Preparation of Compounds J1-J19

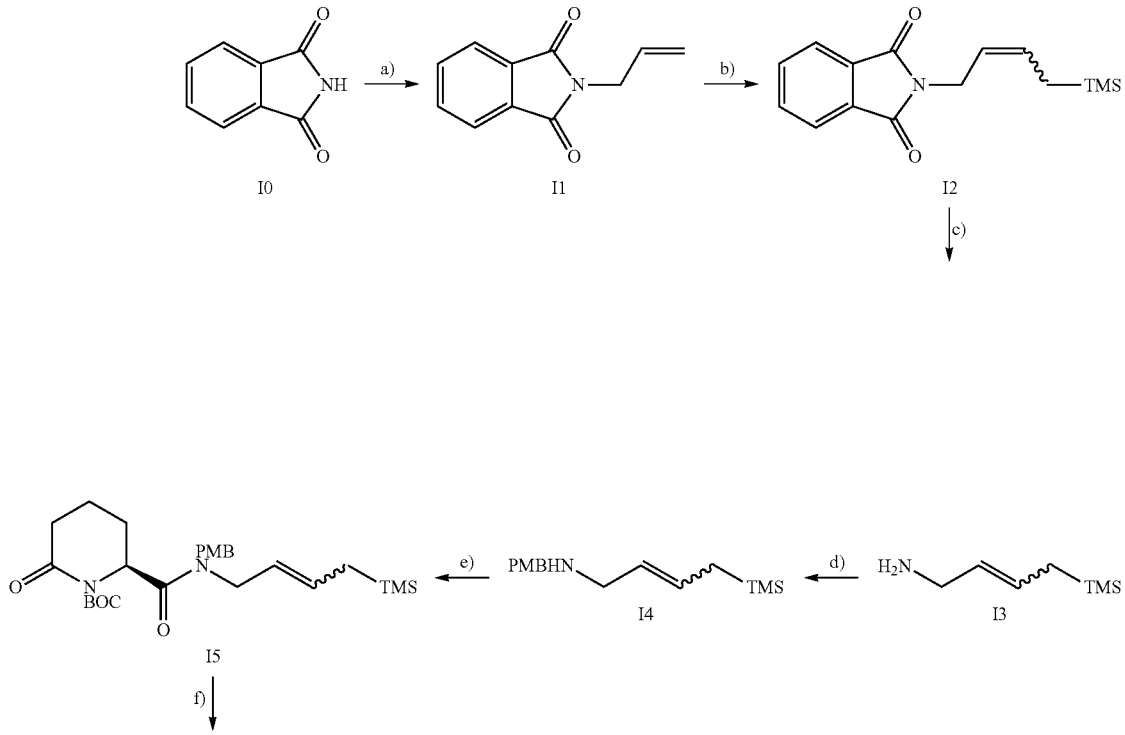

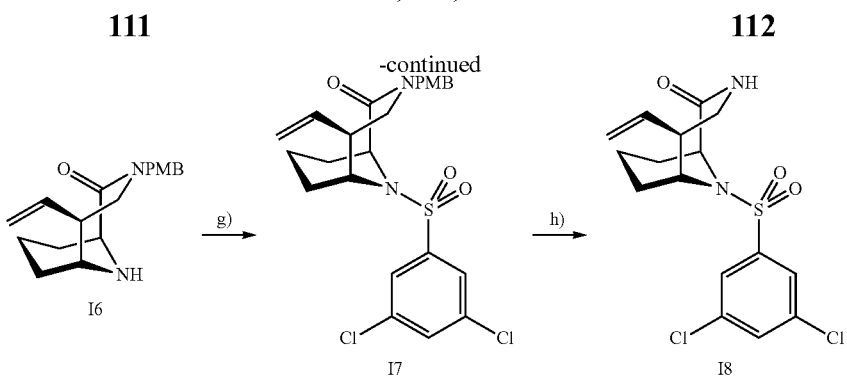

Reagents and conditions; a) K$_2$CO$_3$, allylbromide, DMF, rt, 3 h, quant.; b) AllylTMS, Grubbs I, CH$_2$Cl$_2$, 60° C., 4 h, 79%; c) NH$_2$NH$_2$, MeOH, 70° C., 24 h; d) 4-Methoxybenzaldehyde, NaBH$_4$, EtOH, rt, 4 h, 64% (2 steps); e) 1.) (S)-6-Oxopiperidine-2-carboxylic acid, HOBt, EDC, rt, DMF, 2 h; 2.) Boc$_2$O, DIPEA, DMAP, CH$_2$Cl$_2$, 48 h, 59% (2 steps); f) 1.) DIBAL, THF, −78° C., 15 min; 2.) HF•pyridine, CH$_2$Cl$_2$, −78° C., 1 h, 60% (2 steps); g) 3,5-dichlorobenzene-1-sulfonyl chloride, DIPEA, DMAP, rt, 24 h, 60%; h) CAN, MeCN/H$_2$O, rt, 4 h, 90%;

Scheme J.

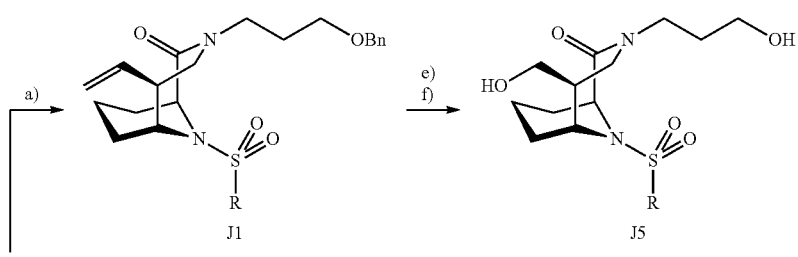

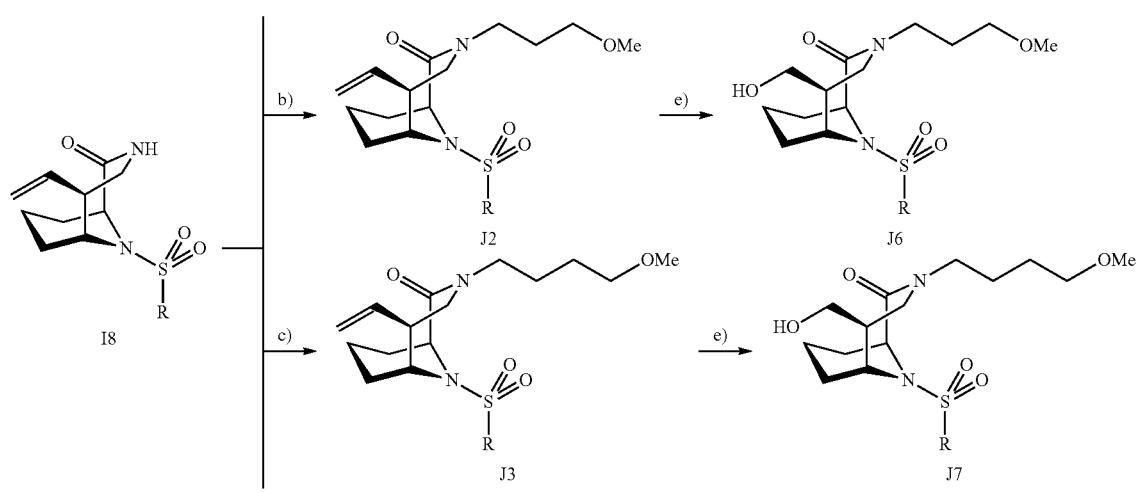

113

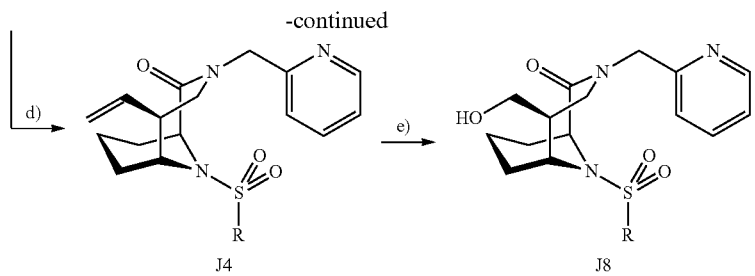

Reagents and conditions: a) NaH, ((3-bromopropoxy)methyl)benzene, DMF, 1 h, 80° C., 64%; b) NaH, 1-bromo-4-methoxypropane, DMF, 1 h, 80° C., 48% c) NaH, 1-bromo-4-methoxybutane, DMF, 1 h, 80° C., 65%; d) NaH, 2-(bromomethyl)pyridine•HBr, DMF, 1 h, 80°, 100%; e) 1.) NaIO$_4$, OsO$_4$, 2,6-lutidine, dioxane/H$_2$O, 20 h, rt; 2.) NaBH$_4$, EtOH rt, 1 h; f) BCl$_3$ SMe$_2$, CH$_2$Cl$_2$, 30 min.

R =

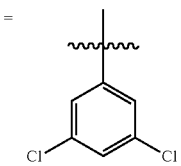

Example 7-1: Preparation of 2-allylisoindoline-1,3-dione I1

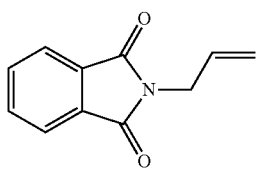

To a solution of Phthalimide (15.0 g, 102 mmol) in DMF (100 mL) was added Allylbromide (12.3 g, 8.82 mL, 102 mmol). After 3 h stirring at room temperature EtO$_2$ (300 mL) was added to the reaction and washed with sat. aq. NaCl solution (3×75 mL). The solvent was removed under reduced pressure affording the title compound (19.0 g, 101 mmol, 99.0%) as a colourless solid, which was used for the next step without further purification.

R$_f$: 0.43 (Cyclohexane/EtOAc=85:15)
$^1$H NMR (300 MHz, CDCl$_3$) δ=4.29 (dt, J=5.7, 1.5 Hz, 2H), 5.15-5.31 (m, 2H), 5.79-5.97 (m, 1H), 7.68-7.76 (m, 2H), 7.80-7.89 (m, 2H).
$^{13}$C-NMR (75.5 MHz, CDCl$_3$) δ=40.03, 117.72, 123.27, 131.50, 132.10, 133.94, 167.88.

Example 7-2: Preparation of 2-(4-(trimethylsilyl)but-2-en-1-yl)isoindoline-1,3-dione I2

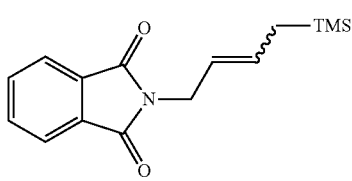

To a solution of 2-allylisoindoline-1,3-dione I1 (13.0 g, 69.4 mmol) in CH$_2$Cl$_2$ (500 mL) was added AllylTMS (79.0 g, 110 mL, 694 mmol) and Grubbs I generation catalyst. The reaction was heated to 60° C. and stirred under reflux for 4 h. Tris(hydroxymethyl)phosphine (1 M solution in i-PrOH, 58 mL) was added and stirred under reflux for 12 h, while the color of the reaction turned from black to orange. Sat. aq. NaCl solution (100 mL) was added to the reaction and the organic phase was separated. The aqueous phase was extracted with CH$_2$Cl$_2$ (3×200 mL). The combined organic layers were dried over MgSO$_4$ and the solvent was removed under reduced pressure. Column chromatography over SiO$_2$ (Cyclohexane/EtOAc=85:15) afforded the title compound (15.0 g, 54.9 mmol, 78.9%) as a yellow resin.

R$_f$: 0.57 (Cyclohexane/EtOAc=85:15)
$^1$H NMR (300 MHz, CDCl$_3$) δ=-0.10-0.09 (m, 9H), 1.44 (d, J=8.2 Hz, 1.6H), 1.72 (d, J=8.8 Hz, 0.4H), 4.21 (d, J=6.5 Hz, 1.6H), 4.29 (dd, J=14.5, 5.9 Hz, 0.4H), 5.26-5.47 (m, 0.8H), 5.56-5.70 (m, 0.2H), 5.70-5.87 (m, 0.8H), 5.94-6.09 (m, 0.2H), 7.65-7.74 (m, 2H), 7.79-7.88 (m, 2H).
$^{13}$C NMR (75 MHz, cdcl$_3$) δ=-2.05, -1.83, -1.43, 18.92, 22.73, 34.72, 39.87, 120.51, 121.30, 123.12, 130.78, 132.24, 133.76, 133.90, 167.99.

Example 7-3: Preparation of 4-(trimethylsilyl)but-2-en-1-amine I3

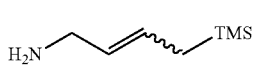

To a solution of 2-(4-(trimethylsilyl)but-2-en-1-yl)isoindoline-1,3-dione I2 (150 mg, 0.549 mmol) in MeOH (5 mL) was added Hydrazine (35.2 mg, 0.034 mL, 1.10 mmol) and the reaction was heated to 75° C. and stirred under reflux for 24 h. CH$_2$Cl$_2$ (90 mL) was added to the solution and washed with NaOH (1 M solution, 3×10 mL). The organic layer was dried over MgSO$_4$ and the solvent was removed under reduced pressure (at room temperature at 150 mbar) affording the title compound as a colourless liquid, which was stored at -20° C.

R$_f$: 0.24 (EtOAc+2% MeOH+2% TEA)
$^1$H NMR (300 MHz, CDCl$_3$) δ=-0.04-0.03 (m, 9H), 1.40-1.50 (m, 2H), 1.69 (s, 2H), 3.14-3.34 (m, 2H), 5.30-5.61 (m, 2H).

¹³C NMR (75 MHz, CDCl₃) δ=−2.02, 22.50, 44.36, 127.19, 129.72

Example 7-4: Preparation of N-(4-methoxybenzyl)-4-(trimethylsilyl)but-2-en-1-amine I4

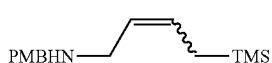

I4

To a solution of 4-(trimethylsilyl)but-2-en-1-amine I3 (7.86 g, 54.8 mmol) in EtOH (250 mL) was added 4-methoxybenzaldehyde (7.47 g, 54.8 mL, 1.10 mmol). After 2 h stirring at room temperature NaBH₄ (3.11 g, 82 mmol) was added to the solution, which was stirred until no more gas evolution was observed. NaOH (1 M solution, 100 mL). was added to the reaction and extracted with CH₂Cl₂ (300 mL). The organic layer was dried over MgSO₄ and the solvent was removed under reduced pressure. Column chromatography (EtOAc+2% MeOH+2% TEA) afforded the title compound (11.2 g, 42.5 mmol, 77.6% over 2 steps) as a slightly yellow oil.

R$_f$: 0.35 (EtOAc+2% MeOH+2% TEA)

MS (ESI): m/z (%)=263.98 [M+H]⁺, 526.24 [2M+H]⁺

Example 7-5: Preparation of (S)—N-(4-methoxybenzyl)-6-oxo-N-(4-(trimethylsilyl)but-2-en-1-yl)piperidine-2-carboxamide I5.1 and (S)-tert-butyl 2-((4-methoxybenzyl)(4-(trimethylsilyl)but-2-en-1-yl)carbamoyl)-6-oxopiperidine-1-carboxylate I5.2

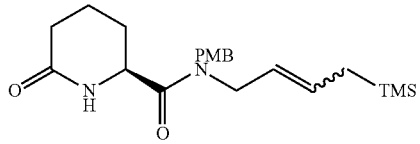

I5.1

To a solution of (S)-6-oxopiperidine-2-carboxylic acid (1.74 g, 12.15 mmol) in DMF (120 mL) were added N-(4-methoxybenzyl)-4-(trimethylsilyl)but-2-en-1-amine I4 (3.20 g, 12.2 mmol), EDC (2.79 g, 14.6 mmol) and HOBt (2.23 g, 14.6 mmol). After 2 h stirring at room temperature EtO₂ (300 mL) was added to the reaction and washed with sat. aq. NaCl solution (3×75 mL). The organic layer was dried over MgSO₄ and the solvent was removed under reduced pressure and the crude compound I5.1 was used for the next step without further purification.

MS (ESI): m/z (%)=389.29 [M+H]⁺, 777.25 [2M+H]⁺

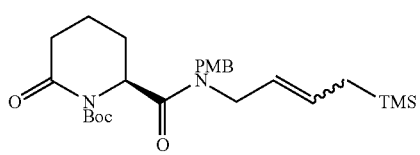

I5.2

Crude compound I5.1 was dissolved in CH₂Cl₂ (120 mL). DIPEA (3.14 g, 4.24 mL, 24.2 mmol), Boc₂O (7.95 g, 36.4 mmol) and DMAP (1.48 g, 12.2 mmol) were added. After 24 h stirring at room temperature sat. aq. NaCl solution (25 mL) was added to the reaction and the organic phase was separated. The aqueous phase was extracted with CH₂Cl₂ (3×100 mL) and the combined organic layers were dried over MgSO₄ and the solvent was removed under reduced pressure. Flash column chromatography (10-30% EtOAc in Cyclohexane) afforded the compound I5.2 (3.50 g, 7.16 mmol, 59% over two steps) as a yellow resin.

R$_f$: 0.14 (Cyclohexane/EtOAc=1:1)

MS (ESI): m/z (%)=389.15 [M+H-Boc]⁺, 999.09 [2M+H]⁺

Example 7-6: Preparation of (1S,5R,6R)-3-(4-methoxybenzyl)-5-vinyl-3,10-diazabicyclo[4.3.1]decan-2-one I6

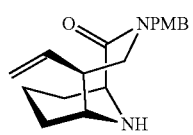

I6

A solution of (6S)-tert-butyl 2-hydroxy-6-((4-methoxybenzyl)((Z)-4-(trimethylsilyl)but-2-en-1-yl)carbamoyl)piperidine-1-carboxylate (3.5 mg, 7.16 mmol) in THF (75 mL) was cooled to −78° C. and then DIBAL-H (1 M solution in CH₂Cl₂, 10.7 mL, 10.7 mmol) was added. After 15 minutes an excess of Glauber's salt (Na₂SO₄ 10H₂O) was added to the reaction. The solution was allowed to warm to room temperature and more Glaubers salt was added and stirred for 15 minutes. The solution was filtered through celite and the solvent was removed under reduced pressure, affording a yellow resin.

The resin resulted from the first step was dissolved in CH₂Cl₂ (300 mL) in a teflon flask and cooled to −78° C. HF (70% in pyridine, 15 mL) was added and the reaction flask was putted in an ice bath at 0° C. After one hour sat. aq. CaCO₃ solution and NaOH (10 M solution) was added to the solution to neutralize the acid and precipitate the fluoride ions as CaF₂. The reaction was extracted three times with CH₂Cl₂, the combined organic layers were dried over MgSO₄ and the solvent removed under reduced pressure. Column chromatography (5% MeOH and 2% TEA in EtOAc) afforded the title compound (1.30 g, 4.33 mmol, 60.6% over two steps) as an orange resin.

¹H NMR (400 MHz, Chloroform-d) δ=1.39-1.55 (m, 2H), 1.60-1.65 (m, 3H), 2.29-2.36 (m, 1H), 2.40-2.50 (m, 1H), 2.76-2.81 (m, 1H), 2.91 (dd, J=13.8, 2.0 Hz, 1H), 3.79 (s, 3H), 3.81-3.85 (m, 1H), 3.89 (dd, J=13.8, 10.8 Hz, 1H), 4.44 (d, J=14.3 Hz, 1H), 4.73 (d, J=14.3 Hz, 1H), 4.77-4.91 (m, 2H), 5.54 (ddd, J=17.0, 10.2, 8.4 Hz, 1H), 6.83-6.88 (m, 2H), 7.19-7.25 (m, 2H).

Example 7-7: Preparation of (1S,5R,6R)-10-((3,5-dichlorophenyl)sulfonyl)-3-(4-methoxybenzyl)-5-vinyl-3,10-diazabicyclo[4.3.1]decan-2-one I7

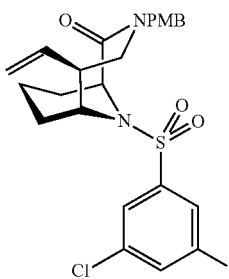

To a solution of (1S,5R,6R)-3-(4-methoxybenzyl)-5-vinyl-3, 10-diazabicyclo[4.3.1]decan-2-one (650 mg, 2.16 mmol) in CH$_2$Cl$_2$ (20 mL) were added 3,5-dichlorobenzene-1-sulfonyl chloride (1.06 g, 4.33 mmol), DMAP (264 mg, 2.16 mmol) and DIPEA (1.13 mL, 6.49 mmol) and the reaction was stirred for 16 hours at room temperature. Sat. aq. NaHCO$_3$ solution (25 mL) was added to the mixture and extracted with CH$_2$Cl$_2$ (250 mL). The organic layer was dried over MgSO$_4$ and the solvent removed under reduced pressure. Flash column chromatography on SiO$_2$ (5-30% EtOAc in Cyclohexane) afforded the title compound (680 mg, 1.33 mmol, 61.7%) as a colorless solid.

$^1$H NMR (400 MHz, CDCl$_3$) δ=1.26 (d, J=7.1 Hz, 2H), 1.46-1.55 (m, 3H), 2.28-2.41 (m, 2H), 2.91 (dd, J=14.3, 1.9 Hz, 1H), 3.80 (s, 3H), 3.90 (dd, J=14.4, 10.9 Hz, 1H), 3.94-3.98 (m, 1H), 4.38 (d, J=14.4 Hz, 1H), 4.77 (dd, J=4.2, 1.8 Hz, 1H), 4.79-4.90 (m, 2H), 5.00 (dd, J=10.1, 1.3 Hz, 1H), 5.66 (ddd, J=17.0, 10.1, 8.9 Hz, 1H), 6.86 (d, J=8.8 Hz, 2H), 7.20 (d, J=8.8 Hz, 2H), 7.54-7.57 (m, 1H), 7.69-7.72 (m, 2H).

Example 7-8: Preparation of (1S,5R,6R)-10-((3,5-dichlorophenyl)sulfonyl)-5-vinyl-3,10-diazabicyclo[4.3.1]decan-2-one I8

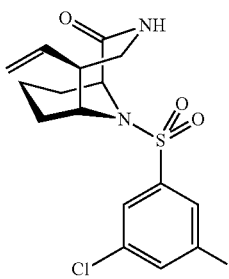

To a solution of (1S,5R,6R)-10-((3,5-dichlorophenyl)sulfonyl)-3-(4-methoxybenzyl)-5-vinyl-3,10-diazabicyclo[4.3.1]decan-2-one (25.0 mg, 0.0491 mmol) in MeCN/H$_2$O (1.5 mL, 2:1) was added CAN (81.0 mg, 0.147 mmol). After 4 h stirring at room temperature sat. aq. NaCl solution (10 mL) was added to the mixture and extracted with CH$_2$Cl$_2$ (90 mL). The organic layer was dried over MgSO$_4$ and the solvent removed under reduced pressure. Flash column chromatography on SiO$_2$ (10-40% EtOAc in Cyclohexane) afforded the title compound (17 mg, 0.0437 mmol, 89.0%) as a colorless solid.

$^1$H NMR (300 MHz, CDCl$_3$) δ=1.29-1.36 (m, 2H), 1.54-1.64 (m, 3H), 2.23 (d, J=13.0 Hz, 2H), 2.68 (d, J=7.8 Hz, 1H), 2.90 (d, J=12.5 Hz, 1H), 3.69-3.85 (m, 1H), 4.04 (s, 1H), 4.66 (d, J=5.1 Hz, 1H), 5.06-5.21 (m, 2H), 5.72-5.87 (m, 1H), 7.57 (t, J=1.8 Hz, 1H), 7.70 (d, J=1.8 Hz, 2H).

$^{13}$C NMR (75 MHz, CDCl$_3$) δ=15.36, 26.48, 26.89, 26.96, 29.67, 45.07, 50.09, 55.47, 117.07, 124.89, 132.75, 136.37, 136.96, 143.97.

Example 7.9

Preparation of (1S,5R,6R)-3-(3-(benzyloxy)propyl)-10-((3,5-dichlorophenyl)sulfonyl)-5-vinyl-3,10-diazabicyclo[4.3.1]decan-2-one J1

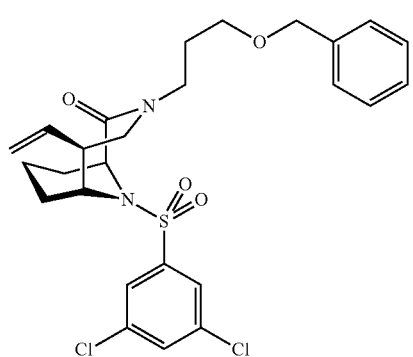

To a solution of (1S,5R,6R)-10-((3,5-dichlorophenyl)sulfonyl)-5-vinyl-3,10 diazabicyclo [4.3.1] decan-2-one (35.0 mg, 0.0899 mmol) in DMF (1.0 mL) was added NaH (5.39 mg, 0.135 mmol). After 20 minutes ((3-bromopropoxy)methyl)benzene (20.6 mg, 0.0899 mmol) was added, the solution was heated to 80° C. and stirred for 1 h. Et$_2$O (90 mL) was added to the solution and washed with sat. aq. NaCl solution (3×10 mL). The organic layer was dried over MgSO$_4$ and the solvent removed under reduced pressure. Column chromatography on SiO$_2$ (Cyclohexane/EtOAc=1:1) afforded the title compound (31.0 mg, 0.0577 mmol, 64.2%) as a colorless solid.

R$_f$ 0.25 (Cyclohexane/EtOAc=7:3)

$^1$H NMR (600 MHz, CDCl$_3$) δ=1.28 (s, 2H), 1.47-1.54 (m, 3H), 1.83-1.92 (m, 2H), 2.23-2.29 (m, 1H), 2.58-2.64 (m, 1H), 2.95-3.00 (m, 1H), 3.49-3.59 (m, 4H), 3.95-4.04 (m, 2H), 4.50 (s, 2H), 4.65 (d, J=6.2 Hz, 1H), 5.09-5.15 (m, 2H), 5.74-5.82 (m, 1H), 7.28 (s, 1H), 7.33 (d, J=1.3 Hz, 4H), 7.56 (s, 1H), 7.69 (d, J=1.8 Hz, 2H).

$^{13}$C NMR (150 MHz, CDCl$_3$) δ=15.42, 26.29, 26.89, 27.36, 28.14, 29.68, 49.16, 49.53, 51.85, 54.83, 56.84, 67.64, 73.08, 116.8, 124.9, 127.6, 127.7, 128.4, 132.6, 136.3, 137.2, 138.2, 144.1, 169.7.

Example 7.10

Preparation of (1S,5R,6R)-10-((3,5-dichlorophenyl)sulfonyl)-3-(3-methoxypropyl)-5-vinyl-3,10-diazabicyclo[4.3.1]decan-2-one J2

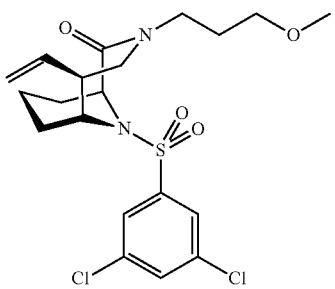

J2

To a solution of (1S,5R,6R)-10-((3,5-dichlorophenyl)sulfonyl)-5-vinyl-3,10-diazabicyclo [4.3.1]decan-2-one (35.0 mg, 0.0899 mmol) in DMF (1.0 mL) was added NaH (5.39 mg, 0.135 mmol). After 20 minutes 1-bromo-4-methoxypropane (13.8 mg, 0.0102 mL, 0.0899 mmol) was added, the solution was heated to 80° C. and stirred for 1 h. Et$_2$O (90 mL) was added to the solution and washed with sat. aq. NaCl solution (3×10 mL). The organic layer was dried over MgSO$_4$ and the solvent removed under reduced pressure. Column chromatography on SiO$_2$ (Cyclohexane/EtOAc=3:7) afforded the title compound (20.0 mg, 0.0433 mmol, 48.2%) as a colorless solid.

R$_f$: 0.57 (Cyclohexane/EtOAc=1:1)

$^1$H NMR (600 MHz, CDCl$_3$) δ=1.27-1.34 (m, 2H), 1.50-1.56 (m, 3H), 1.83 (q, J=6.9 Hz, 2H), 2.26 (d, J=13.4 Hz, 1H), 2.63 (qd, J=8.3, 4.1 Hz, 1H), 2.94-3.00 (m, 1H), 3.33 (s, 3H), 3.41 (t, J=6.2 Hz, 2H), 3.47-3.59 (m, 2H), 3.96-4.04 (m, 2H), 4.65 (d, J=5.7 Hz, 1H), 5.11 (s, 1H), 5.14 (d, J=6.0 Hz, 1H), 5.79 (dt, J=16.7, 9.4 Hz, 1H), 7.56 (s, 1H), 7.69 (s, 2H).

$^{13}$C NMR (150 MHz, CDCl$_3$) δ=15.42, 26.29, 27.36, 28.03, 49.21, 49.53, 51.88, 54.83, 56.84, 58.68, 70.04, 116.8, 124.9, 132.6, 136.3, 137.3, 144.1, 169.7.

Example 7.11

Preparation of (1S,5R,6R)-10-((3,5-dichlorophenyl)sulfonyl)-3-(4-methoxybutyl)-5-vinyl-3,10-diazabicyclo[4.3.1]decan-2-one J3

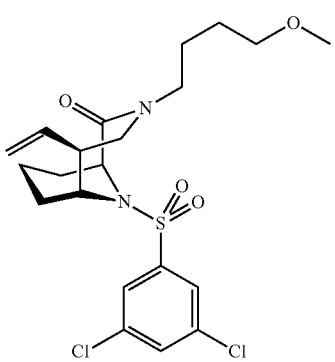

J3

To a solution of (1S,5R,6R)-10-((3,5-dichlorophenyl)sulfonyl)-5-vinyl-3,10-diazabicyclo [4.3.1] decan-2-one (35.0 mg, 0.0899 mmol) in DMF (1.0 mL) was added NaH (5.39 mg, 0.135 mmol). After 20 minutes 1-bromo-4-methoxybutane (15.0 mg, 0.0118 mL, 0.0899 mmol) was added, the solution was heated to 80° C. and stirred for 1 h. Et$_2$O (90 mL) was added to the solution and washed with sat. aq. NaCl solution (3×10 mL). The organic layer was dried over MgSO$_4$ and the solvent removed under reduced pressure. Column chromatography on SiO$_2$ (Cyclohexane/EtOAc=3:7) afforded the title compound (27.8 mg, 0.0584 mmol, 65.1%) as a colorless solid.

R$_f$: 0.16 (Cyclohexane/EtOAc=1:1)

$^1$H NMR (600 MHz, CDCl$_3$) δ=1.24-1.26 (m, 2H), 1.51-1.55 (m, 3H), 1.55-1.64 (m, 4H), 2.26 (dt, J=14.3, 2.4 Hz, 1H), 2.59-2.65 (m, 1H), 2.90-2.95 (m, 1H), 3.33 (d, J=1.0 Hz, 3H), 3.38-3.42 (m, 2H), 3.42-3.50 (m, 2H), 3.96-4.02 (m, 2H), 4.66 (dt, J=5.8, 1.9 Hz, 1H), 5.11-5.16 (m, 2H), 5.76-5.84 (m, 1H), 7.55-7.57 (m, 1H), 7.68-7.69 (m, 2H).

$^{13}$C NMR (150 MHz, CDCl$_3$) δ=15.45, 24.43, 26.31, 26.78, 27.39, 29.67, 49.55, 51.18, 51.43, 54.83, 56.86, 58.53, 72.20, 116.8, 124.9, 132.6, 136.3, 137.3, 144.1, 169.6.

Example 7.12

Preparation of (1S,5R,6R)-10-((3,5-dichlorophenyl)sulfonyl)-3-(pyridin-2-ylmethyl)-5-vinyl-3,10-diazabicyclo[4.3.1]decan-2-one J4

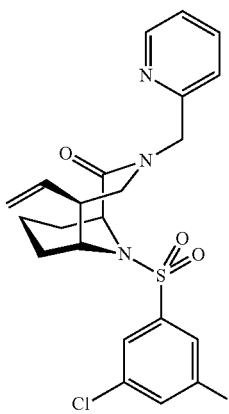

J4

To a solution of (1S,5R,6R)-10-((3,5-dichlorophenyl)sulfonyl)-5-vinyl-3,10 diazabicyclo [4.3.1] decan-2-one (35.0 mg, 0.0899 mmol) in DMF (1.0 mL) was added NaH (5.39 mg, 0.135 mmol). At the same time 2-(bromomethyl)pyridine-hydrobromide (22.7 mg, 0.0899 mmo) in DMF (1 mL) was neutralized with NaH (2.16 mg, 0.0899 mmol). After 20 minutes the solution were united and heated to 80° C. and stirred for 1 h. Et$_2$O (90 mL) was added to the solution and washed with sat. aq. NaCl solution (3×10 mL). The organic layer was dried over MgSO$_4$ and the solvent removed under reduced pressure. Column chromatography on SiO$_2$ (Cyclohexane/EtOAc=1:1) afforded the title compound (43 mg, 0.0899 mmol, 100%) as a colorless solid.

R$_f$: 0.2 (Cyclohexane/EtOAc=1:1)

$^1$H NMR (600 MHz, CDCl$_3$) δ=1.30-1.39 (m, 2H), 1.52-1.63 (m, 3H), 2.26-2.33 (m, 1H), 2.73 (q, J=8.3, 7.9 Hz, 1H), 3.14 (dd, J=14.3, 2.0 Hz, 1H), 4.00-4.06 (m, 2H), 4.74 (dt,

J=6.1, 1.7 Hz, 1H), 4.86 (d, J=15.4 Hz, 1H), 4.90-4.98 (m, 1H), 4.98-5.08 (m, 2H), 5.72 (dddd, J=17.0, 10.0, 8.8, 1.2 Hz, 1H), 7.29 (t, J=6.3 Hz, 1H), 7.41 (d, J=7.9 Hz, 1H), 7.57 (td, J=1.8, 1.0 Hz, 1H), 7.70 (dd, J=1.9, 1.0 Hz, 2H), 7.79 (t, J=7.7 Hz, 1H), 8.49-8.61 (m, 1H).

$^{13}$C NMR (150 MHz, CDCl$_3$) δ=15.46, 26.39, 27.49, 29.67, 49.06, 52.20, 54.89, 55.51, 56.85, 117.02, 122.55, 122.85, 124.84, 132.72, 136.34, 136.93, 143.95, 156.31, 170.56.

Example 7.13: Preparation of (1S,5R,6R)-10-((3,5-dichlorophenyl)sulfonyl)-5-(hydroxymethyl)-3-(3-hydroxypropyl)-3,10-diazabicyclo[4.3.1]decan-2-one J5

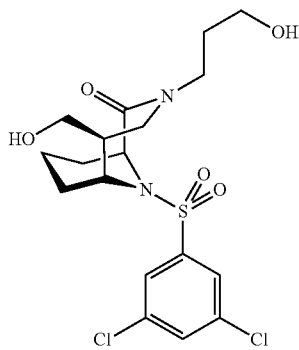

To a solution of (1S,5R,6R)-3-(3-(benzyloxy)propyl)-10-((3,5-dichlorophenyl)sulfonyl)-5-vinyl-3,10-diazabicyclo[4.3.1]decan-2-one (31 mg, 0.0576 mmol) in Dioxane/H$_2$O (0.8 mL, 3:1) was added NaIO$_4$ (52.3 mg, 0.245 mmol), OsO$_4$ (2.5% Solution in tert-Butanol, 0.00122 mmol, 0.015 mL) and 2,6-Lutidine (0.014 mL, 0.122 mmol). The solution was stirred for 18 h at room temperature, then Et$_2$O (90 mL) was added to the reaction and washed with sat. aq. NaCl solution (3×10 mL). The obtained crude product was dissolved in EtOH (1 mL) and NaBH$_4$ (3.47 mg, 0.0917 mmol) was added and stirred for 1 h at room temperature. Et$_2$O (90 mL) was added to the reaction and washed with sat. aq. NaCl solution (3×10 mL). The solvent was removed under reduced pressure and the crude mixture was dissolved in CH$_2$Cl$_2$ (0.5 mL). BCl$_3$ SMe$_2$ (2 M solution in CH$_2$Cl$_2$, 0.144 mL, 0.288 mmol) and the reaction was stirred for 30 minutes. Et$_2$O (90 mL) was added to the reaction and washed with sat. aq. NaCl solution (3×10 mL). The solvent was removed under reduced pressure and flash column chromatography over SiO$_2$ (50-90% EtOAc in Cyclohexane) afforded the title compound (18 mg, 0.0398 mmol, 68.8%) as a colorless wax.

$^1$H NMR (600 MHz, CDCl$_3$) δ=1.36-1.42 (m, 2H), 1.52-1.58 (m, 3H), 1.71-1.80 (m, 2H), 2.19-2.29 (m, 2H), 2.52-2.61 (m, 2H), 3.20-3.24 (m, 1H), 3.49-3.55 (m, 2H), 3.56-3.64 (m, 3H), 3.73 (s, 1H), 3.84 (dd, J=14.3, 10.7 Hz, 1H), 3.88-3.92 (m, 1H), 4.71 (d, J=6.1 Hz, 1H), 7.57 (s, 1H), 7.69 (d, J=1.9 Hz, 2H).

MS (ESI): m/z (%)=451.14 [M+H]$^+$

Example 7.14: Preparation of (1S,5R,6R)-10-((3,5-dichlorophenyl)sulfonyl)-5-(hydroxymethyl)-3-(3-methoxypropyl)-3,10-diazabicyclo[4.3.1]decan-2-one J6

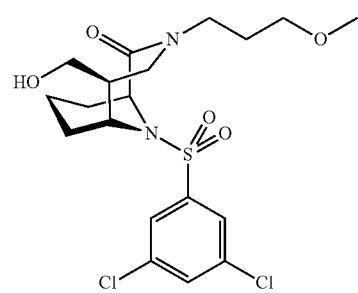

To a solution of (1S,5R,6R)-10-((3,5-dichlorophenyl)sulfonyl)-3-(3-methoxypropyl)-5-vinyl-3,10-diazabicyclo[4.3.1]decan-2-one (14 mg, 0.0299 mmol) in Dioxane/H$_2$O (0.4 mL, 3:1) was added NaIO$_4$ (26.0 mg, 0.121 mmol), OsO$_4$ (2.5% Solution in tert-Butanol, 0.00607 mmol, 0.00761 mL) and 2,6-Lutidine (0.00707 mL, 0.061 mmol). The solution was stirred for 24 h at room temperature, then Et$_2$O (90 mL) was added to the reaction and washed with sat. aq. NaCl solution (3×10 mL). The obtained crude product was dissolved in EtOH (1 mL) and NaBH$_4$ (1.72 mg, 0.046 mmol) was added and stirred for 1 h at room temperature. Et$_2$O (90 mL) was added to the reaction and washed with sat. aq. NaCl solution (3×10 mL). The solvent was removed under reduced pressure and flash column chromatography over SiO$_2$ (50-70% EtOAc in Cyclohexane) afforded the title compound (13.0 mg, 0.0279 mmol, 93%) as a colorless solid.

R$_f$: 0.18 (Cyclohexane/EtOAc=1:4)
MS (ESI): m/z (%)=465.14 [M+H]$^+$

Example 7.15: Preparation of (1S,5R,6R)-10-((3,5-dichlorophenyl)sulfonyl)-5-(hydroxymethyl)-3-(4-methoxybutyl)-3,10-diazabicyclo[4.3.1]decan-2-one J7

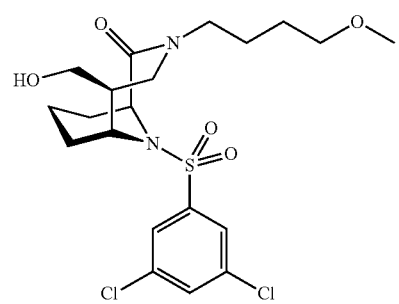

To a solution of (1S,5R,6R)-10-((3,5-dichlorophenyl)sulfonyl)-3-(4-methoxybutyl)-5-vinyl-3,10-diazabicyclo[4.3.1]decan-2-one (24 mg, 0.0499 mmol) in Dioxane/H$_2$O (0.8 mL, 3:1) was added NaIO$_4$ (43.2 mg, 0.202 mmol), OsO$_4$ (2.5% Solution in tert-Butanol, 0.0101 mmol, 0.013 mL) and 2,6-Lutidine (0.012 mL, 0.101 mmol). The solution was stirred for 24 h at room temperature, then Et$_2$O (90 mL)

was added to the reaction and washed with sat. aq. NaCl solution (3×10 mL). The obtained crude product was dissolved in EtOH (1 mL) and NaBH$_4$ (2.86 mg, 0.076 mmol) was added and stirred for 1 h at room temperature. Et$_2$O (90 mL) was added to the reaction and washed with sat. aq. NaCl solution (3×10 mL). The solvent was removed under reduced pressure and flash column chromatography over SiO$_2$ (50-90% EtOAc in Cyclohexane) afforded the title compound (17.5 mg, 0.0365 mmol, 73.0%) as a colorless solid.

R$_f$: 0.18 (Cyclohexane/EtOAc=1:4)
MS (ESI): m/z (%)=479.22 [M+H]$^+$

Example 7-16: Preparation of (1S,5R,6R)-10-((3,5-dichlorophenyl)sulfonyl)-5-(hydroxymethyl)-3-(pyridin-2-ylmethyl)-3,10-diazabicyclo[4.3.1]decan-2-one J8

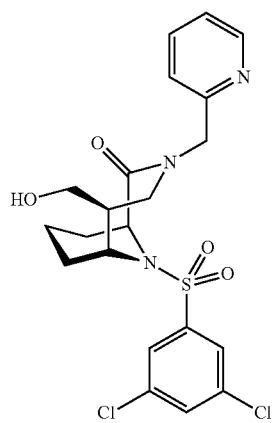

To a solution of (1S,5R,6R)-10-((3,5-dichlorophenyl)sulfonyl)-3-(pyridin-2-ylmethyl)-5-vinyl-3,10-diazabicyclo[4.3.1]decan-2-one (43 mg, 0.0891 mmol) in Dioxane/H$_2$O (0.8 mL, 3:1) was added NaIO$_4$ (76 mg, 0.357 mmol), OsO$_4$ (2.5% Solution in tert-Butanol, 0.00178 mmol, 0.022 mL) and 2,6-Lutidine (0.021 mL, 0.178 mmol). The solution was stirred for 24 h at room temperature, then Et$_2$O (90 mL) was added to the reaction and washed with sat. aq. NaCl solution (3×10 mL). The obtained crude product was dissolved in EtOH (1 mL) and NaBH$_4$ (5.00 mg, 0.132 mmol) was added and stirred for 1 h at room temperature. Et$_2$O (90 mL) was added to the reaction and washed with sat. aq. NaCl solution (3×10 mL). Flash column chromatography over SiO$_2$ (30-70% EtOAc in Cyclohexane) afforded the title compound (16 mg, 0.0330 mmol, 37.1%) as a colorless solid.

$^1$H NMR (600 MHz, CDCl$_3$) δ=1.24-1.30 (m, 2H), 1.49-1.58 (m, 3H), 2.25-2.33 (m, 2H), 3.48-3.56 (m, 3H), 3.86 (dd, J=14.4, 10.6 Hz, 1H), 3.92-3.96 (m, 1H), 4.74-4.77 (m, 1H), 4.87 (d, J=7.9 Hz, 2H), 7.29-7.34 (m, 1H), 7.45 (s, 1H), 7.56 (s, 1H), 7.70 (s, 2H), 7.78-7.83 (m, 1H), 8.54 (dt, J=5.2, 0.9 Hz, 1H).

$^{13}$C NMR (150 MHz, CDCl$_3$) δ=15.51, 27.80, 27.82, 46.93, 49.67, 52.32, 55.22, 57.01, 63.25, 123.10, 123.22, 124.87, 132.71, 136.31, 138.63, 143.91, 147.63, 156.12, 170.54.

Example 7-17: Preparation of ethyl 2-((1S,5R,6R)-10-((3,5-dichlorophenyl)sulfonyl)-2-oxo-5-vinyl-3,10-diazabicyclo[4.3.1]decan-3-yl)acetate J9

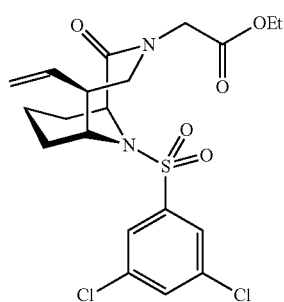

To a solution of (1S,5R,6R)-10-((3,5-dichlorophenyl)sulfonyl)-5-vinyl-3,10-diazabicyclo [4.3.1] decan-2-one I8 (120 mg, 0.308 mmol) in DMF (3.0 mL) was added NaH (14.8 mg, 0.370 mmol). After 20 minutes ethyl 2-bromoacetate (51.5 mg, 0.308 mmol) was, added, the solution was heated to 80° C. and stirred for 1 h. Et$_2$O (90 mL) was added to the solution and washed with sat. aq. NaCl solution (3×10 mL). The organic layer was dried over MgSO$_4$ and the solvent removed under reduced pressure. Column chromatography on SiO$_2$ (Cyclohexane/EtOAc=8:2) afforded the title compound (78.0 mg, 0.164 mmol, 53.3%) as a colorless solid.

R$_f$: 0.71 (Cyclohexane/EtOAc=1:1)
$^1$H NMR (600 MHz, CDCl$_3$) δ=1.19-1.26 (m, 3H), 1.57 (d, J=13.2 Hz, 4H), 1.70-1.81 (m, 1H), 2.27 (dd, J=13.6, 3.2 Hz, 1H), 2.88 (dd, J=14.1, 2.0 Hz, 1H), 3.09-3.16 (m, 1H), 3.65 (d, J=17.4 Hz, 1H), 3.99 (t, J=5.8 Hz, 1H), 4.15-4.24 (m, 3H), 4.73 (d, J=17.5 Hz, 2H), 5.11-5.19 (m, 2H), 5.78 (ddd, J=16.9, 10.0, 8.8 Hz, 1H), 7.57 (s, 1H), 7.70 (dt, J=1.8, 0.7 Hz, 2H).
MS (ESI): m/z (%)=475.03 [M+H]$^+$ Example 7-18: Preparation of 2-((1S,5R,6R)-10-((3,5-dichlorophenyl)sulfonyl)-2-oxo-5-vinyl-3,10-diazabicyclo[4.3.1]decan-3-yl)acetic acid J10

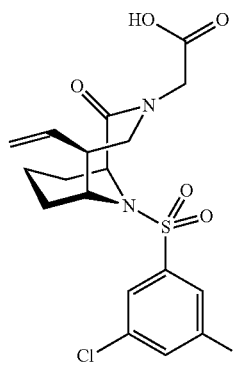

To a solution of ethyl 2-((1S,5R,6R)-10-((3,5-dichlorophenyl)sulfonyl)-2-oxo-5-vinyl-3,10-diazabicyclo[4.3.1]decan-3-yl)acetate J9 (70.0 mg, 0.147 mmol) in THF/H$_2$O (1.5 mL, 2:1) was added aq. NaOH (10 M aq. sol., 0.147 mL).

After 20 h the solution was diluted with CH₂Cl₂ (100 mL) and washed with aq. HCl (1 M, 15 mL). The organic phase was dried with MgSO₄ and solvent was removed under reduced pressure affording the title compound (65.0 mg, 0.145 mmol, 98.6%) as a white solid.

¹H NMR (600 MHz, CDCl₃) δ=1.18-1.36 (m, 3H), 1.49-1.60 (m, 1H), 1.63-1.76 (m, 1H), 2.21-2.32 (m, 1H), 2.91 (dd, J=14.0, 2.0 Hz, 1H), 2.98-3.12 (m, 1H), 3.77 (d, J=17.6 Hz, 1H), 3.95-4.07 (m, 1H), 4.16 (dd, J=14.1, 10.7 Hz, 1H), 4.65-4.76 (m, 2H), 5.09-5.19 (m, 2H), 5.77 (ddd, J=17.0, 10.1, 8.8 Hz, 1H), 7.57 (t, J=1.8 Hz, 1H), 7.70 (d, J=1.8 Hz, 2H).

¹³C NMR (150 MHz, CDCl₃) δ=15.38, 26.23, 27.49, 48.55, 53.17, 53.71, 54.95, 56.68, 117.28, 124.90, 132.78, 136.38, 137.01, 143.91, 171.50, 173.11.

MS (ESI): m/z (%)=447.02 [M+H]⁺

Example 7-19: Preparation of 2-((1S,5R,6R)-10-((3,5-dichlorophenyl)sulfonyl)-2-oxo-5-vinyl-3,10-diazabicyclo[4.3.1]decan-3-yl)acetamide J11

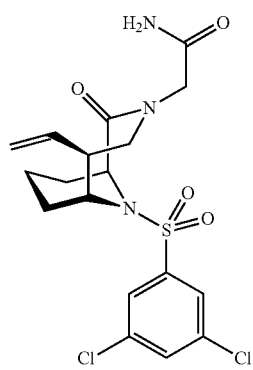

J11

To a solution of 2-((1S,5R,6R)-10-((3,5-dichlorophenyl)sulfonyl)-2-oxo-5-vinyl-3,10-diazabicyclo[4.3.1]decan-3-yl)acetic acid J10 (57 mg, 0.127 mmol) in EtOAc (1 mL) was added CDI (31.0 mg, 0.191 mmol). After 30 min aq. NH₃ (7 M, 364 mL, 2.55 mmol) was added. After 1 h sat. aq. NH₄Cl solution (15 mL) was added to the solution and extracted with EtOAc (100 mL). The organic phase was dried over MgSO₄ and the solvent was removed under reduced pressure. Column chromatography on SiO₂ (Cyclohexane/EtOAc=3:7) afforded the title compound (43.7 mg, 0.0979 mmol, 77.1%) as a colorless wax.

¹H NMR (600 MHz, CDCl₃) δ=1.32-1.42 (m, 2H), 1.52-1.58 (m, 1H), 1.60-1.68 (m, 2H), 2.23-2.29 (m, 1H), 2.94-3.00 (m, 1H), 3.05 (dd, J=14.3, 2.0 Hz, 1H), 4.05 (td, J=6.1, 4.9, 2.0 Hz, 1H), 4.08-4.19 (m, 3H), 4.61 (dt, J=6.1, 1.9 Hz, 1H), 5.13-5.21 (m, 2H), 5.52 (s, 1H), 5.78 (ddd, J=17.0, 10.1, 8.8 Hz, 1H), 6.22 (s, 1H), 7.58 (t, J=1.8 Hz, 1H), 7.69 (d, J=1.8 Hz, 2H).

¹³C NMR (150 MHz, CDCl₃) δ=15.38, 26.30, 27.21, 48.47, 53.75, 54.98, 55.18, 56.62, 117.52, 124.88, 132.90, 136.40, 136.65, 143.64, 170.68, 171.40.

MS (ESI): m/z (%)=445.82 [M+H]⁺

Example 7-20: Preparation of (1S,5R,6R)-10-((3,5-dichlorophenyl)sulfonyl)-3-(prop-2-yn-1-yl)-5-vinyl-3,10-diazabicyclo[4.3.1]decan-2-one J12

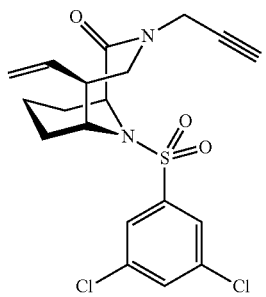

J12

To a solution of (1S,5R,6R)-10-((3,5-dichlorophenyl)sulfonyl)-5-vinyl-3,10-diazabicyclo [4.3.1] decan-2-one I8 (50.0 mg, 0.128 mmol) in DMF (1.0 mL) was added NaH (5.65 mg, 0.128 mmol). After 20 minutes propargylbromide (19.1 mg, 0.014 mL 0.128 mmol) was added, the solution was heated to 80° C. and stirred for 1 h. Et₂O (90 mL) was added to the solution and washed with sat. aq. NaCl solution (3×10 mL). The organic layer was dried over MgSO₄ and the solvent removed under reduced pressure. Column chromatography on SiO₂ (Cyclohexane/EtOAc=7:3) afforded the title compound (44.0 mg, 0.103 mmol, 80.4%) as a colorless solid.

R_f: 0.61 (Cyclohexane/EtOAc=3:2)

¹H NMR (600 MHz, CDCl₃) δ=1.26-1.34 (m, 3H), 1.53-1.57 (m, 2H), 2.22 (tt, J=2.5, 0.7 Hz, 1H), 2.26-2.32 (m, 1H), 2.68-2.75 (m, 1H), 3.18-3.23 (m, 1H), 3.91 (ddt, J=17.2, 2.9, 0.8 Hz, 1H), 3.97-4.03 (m, 2H), 4.66 (ddd, J=17.2, 2.4, 1.0 Hz, 1H), 4.70-4.73 (m, 1H), 5.13-5.19 (m, 2H), 5.82 (dddd, J=17.1, 10.0, 8.8, 1.0 Hz, 1H), 7.57 (dq, J=1.9, 1.0 Hz, 1H), 7.69 (dt, J=1.9, 0.7 Hz, 2H).

¹³C NMR (150 MHz, CDCl₃) δ=15.41, 26.21, 26.90, 27.52, 39.32, 49.32, 50.86, 54.92, 56.86, 71.69, 117.14, 124.88, 132.73, 136.36, 137.03, 143.97, 169.93.

MS (ESI): m/z (%)=427.09 [M+H]⁺

Example 7-21: Preparation of (1S,5R,6R)-3-((1H-1,2,3-triazol-4-yl)methyl)-10-((3,5-dichlorophenyl)sulfonyl)-5-vinyl-3,10-diazabicyclo[4.3.1]decan-2-one J13

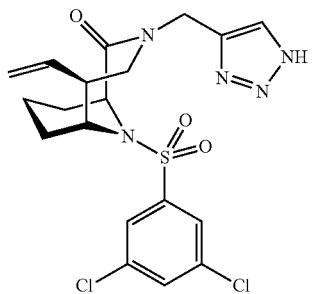

J13

To a solution of (1S,5R,6R)-10-((3,5-dichlorophenyl)sulfonyl)-3-(prop-2-yn-1-yl)-5-vinyl-3,10-diazabicyclo[4.3.1]

decan-2-one J12 (25.0 mg, 0.0590 mmol) in DMF/MeOH (0.55 mL, 9:1) were added TMS-azide (10.1 mg, 0.012 mL, 0.0880 mmol) and CuI (0.557 mg, 2.93 µmol). After 8 h Et$_2$O (90 mL) was added to the solution and washed with sat. aq. NaHCO$_3$ solution (3×10 mL). The organic layer was dried over MgSO$_4$ and the solvent removed under reduced pressure. Column chromatography on SiO$_2$ (Cyclohexane/EtOAc=6:4) afforded the title compound (14.5 mg, 0.0308 mmol, 52.2%) as a colorless solid.

R$_f$ 0.6 (EtOAc)

$^1$H NMR (600 MHz, CDCl$_3$) δ=1.28-1.40 (m, 3H), 1.44-1.48 (m, 1H), 1.55-1.61 (m, 1H), 2.26 (d, J=13.9 Hz, 1H), 2.53 (q, J=9.2 Hz, 1H), 3.21 (d, J=14.2 Hz, 1H), 3.58-3.75 (m, 2H), 3.98 (q, J=7.0, 6.0 Hz, 1H), 4.07 (dd, J=14.7, 10.5 Hz, 1H), 4.66-4.74 (m, 2H), 5.03-5.11 (m, 2H), 5.74 (dt, J=17.9, 9.3 Hz, 1H), 7.57 (q, J=1.6 Hz, 1H), 7.69 (t, J=1.4 Hz, 2H), 7.90 (d, J=32.0 Hz, 1H).

$^{13}$C NMR (150 MHz, CDCl$_3$) δ=15.40, 22.67, 26.17, 27.33, 29.68, 45.50, 49.13, 52.25, 54.81, 56.78, 117.31, 124.86, 132.82, 136.38, 136.64, 143.83, 171.11.

MS (ESI): m/z (%)=470.12 [M+H]$^+$

Example 7-22: Preparation of (1S,5R,6R)-10-((3,5-dichlorophenyl)sulfonyl)-3-(pyrazin-2-ylmethyl)-5-vinyl-3,10-diazabicyclo[4.3.1]decan-2-one J14

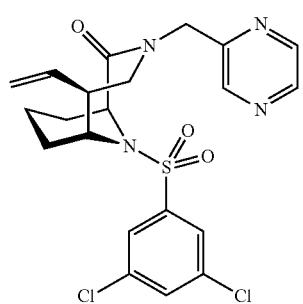

J14

To a solution of (1S,5R,6R)-10-((3,5-dichlorophenyl)sulfonyl)-5-vinyl-3,10-diazabicyclo [4.3.1] decan-2-one I8 (35.0 mg, 0.0899 mmol) in DMF (1.0 mL) was added NaH (4.67 mg, 0.117 mmol). After 20 minutes 2-(chloromethyl)pyrazine (23.1 mg, 0.180 mmol) was added, the solution was heated to 80° C. and stirred for 1 h. Et$_2$O (90 mL) was added to the solution and washed with sat. aq. NaCl solution (3×10 mL). The organic layer was dried over MgSO$_4$ and the solvent removed under reduced pressure. Column chromatography on SiO$_2$ (Cyclohexane/EtOAc=7:3) afforded the title compound (40.0 mg, 0.0831 mmol, 92.4%) as a colorless solid.

$^1$H NMR (300 MHz, CDCl$_3$) δ=1.26-1.39 (m, 3H), 1.55 (s, 2H), 2.27 (d, J=13.4 Hz, 1H), 2.75 (q, J=8.9 Hz, 1H), 3.08-3.17 (m, 1H), 3.56-3.76 (m, 2H), 4.00 (dd, J=6.8, 4.9 Hz, 1H), 4.59 (d, J=15.5 Hz, 1H), 4.74 (dt, J=6.2, 2.0 Hz, 1H), 4.99-5.09 (m, 2H), 5.67-5.81 (m, 1H), 7.56 (td, J=1.9, 0.5 Hz, 1H), 7.70 (dd, J=1.9, 0.5 Hz, 2H), 8.52 (d, J=1.9 Hz, 2H), 8.62-8.67 (m, 1H).

$^{13}$C NMR (75 MHz, CDCl$_3$) δ=15.49, 26.31, 27.47, 49.10, 52.59, 54.24, 54.84, 56.83, 70.17, 70.50, 71.26, 72.46, 116.98, 124.89, 132.73, 136.35, 137.06, 143.88, 143.98, 170.61, 170.63.

MS (ESI): m/z (%)=481.28 [M+H]$^+$

Example 7-23: Preparation of (1S,5R,6R)-10-((3,5-dichlorophenyl)sulfonyl)-3-(pyrimidin-4-ylmethyl)-5-vinyl-3,10-diazabicyclo[4.3.1]decan-2-one J15

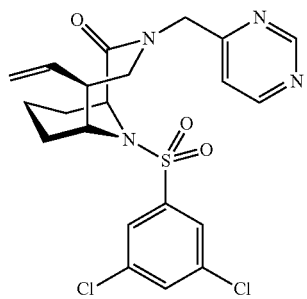

J15

To a solution of (1S,5R,6R)-10-((3,5-dichlorophenyl)sulfonyl)-5-vinyl-3,10-diazabicyclo [4.3.1] decan-2-one I8 (35.0 mg, 0.0899 mmol) in DMF (1.0 mL) was added NaH (4.67 mg, 0.117 mmol). After 20 minutes 2-(chloromethyl)pyrimidine (23.1 mg, 0.180 mmol) was added, the solution was heated to 80° C. and stirred for 1 h. Et$_2$O (90 mL) was added to the solution and washed with sat. aq. NaCl solution (3×10 mL). The organic layer was dried over MgSO$_4$ and the solvent removed under reduced pressure. Column chromatography on SiO$_2$ (Cyclohexane/EtOAc=7:3) afforded the title compound (4.00 mg, 0.0831 mmol, 9.2%) as a colorless solid.

$^1$H NMR (300 MHz, CDCl$_3$) δ=1.26-1.39 (m, 3H), 1.55 (s, 2H), 2.27 (d, J=13.4 Hz, 1H), 2.75 (q, J=8.9 Hz, 1H), 3.08-3.17 (m, 1H), 3.56-3.76 (m, 2H), 4.00 (dd, J=6.8, 4.9 Hz, 1H), 4.59 (d, J=15.5 Hz, 1H), 4.74 (dt, J=6.2, 2.0 Hz, 1H), 4.99-5.09 (m, 2H), 5.67-5.81 (m, 1H), 7.56 (td, J=1.9, 0.5 Hz, 1H), 7.70 (dd, J=1.9, 0.5 Hz, 2H), 8.52 (d, J=1.9 Hz, 2H), 8.62-8.67 (m, 1H).

$^{13}$C NMR (75 MHz, CDCl$_3$) δ=15.49, 26.31, 27.47, 49.10, 52.59, 54.24, 54.84, 56.83, 70.17, 70.50, 71.26, 72.46, 116.98, 124.89, 132.73, 136.35, 137.06, 143.88, 143.98, 170.61, 170.63.

MS (ESI): m/z (%)=481.18

Example 7-24: Preparation of 2-((1S,5R,6R)-10-((3,5-dichlorophenyl)sulfonyl)-2-oxo-5-vinyl-3,10-diazabicyclo[4.3.1]decan-3-yl)acetonitrile J16

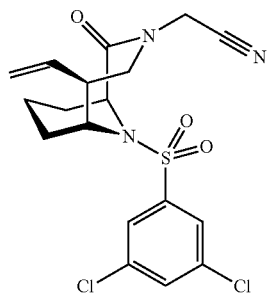

J16

To a solution of (1S,5R,6R)-10-((3,5-dichlorophenyl)sulfonyl)-5-vinyl-3,10-diazabicyclo [4.3.1] decan-2-one I8 (23.0 mg, 0.0590 mmol) in DMF (1.0 mL) was added NaH (2.84 mg, 0.0710 mmol). After 20 minutes 2-bromoacetonitrile (7.09 mg, 0.004 mL 0.0590 mmol) was added, the solution was heated to 80° C. and stirred for 1 h. Et$_2$O (90 mL) was added to the solution and washed with sat. aq. NaCl solution (3×10 mL). The organic layer was dried over MgSO$_4$ and the solvent removed under reduced pressure. Column chromatography on SiO$_2$ (Cyclohexane/EtOAc=7:3) afforded the title compound (12.0 mg, 0.0280 mmol, 47.5%) as a colorless solid.

$^1$H NMR (600 MHz, CDCl$_3$) δ=1.26-1.33 (m, 3H), 1.56-1.59 (m, 2H), 2.24-2.31 (m, 1H), 2.72-2.79 (m, 1H), 3.11 (dd, J=14.3, 2.0 Hz, 1H), 3.94 (d, J=17.2 Hz, 1H), 3.99-4.03 (m, 1H), 4.18 (dd, J=14.3, 10.9 Hz, 1H), 4.73 (dt, J=6.1, 1.9 Hz, 1H), 4.83 (d, J=17.2 Hz, 1H), 5.18-5.25 (m, 2H), 5.81 (ddd, J=17.0, 10.1, 8.8 Hz, 1H), 7.58 (t, J=1.9 Hz, 1H), 7.69 (d, J=1.8 Hz, 2H).

$^{13}$C NMR (150 MHz, CDCl$_3$) δ=15.35, 25.96, 27.38, 29.68, 38.31, 49.01, 52.45, 54.87, 56.71, 118.10, 124.84, 132.96, 136.21, 136.49, 170.99.

MS (ESI): m/z (%)=428.00

Example 7-25: Preparation of (1S,5R,6R)-10-((3,5-dichlorophenyl)sulfonyl)-3-(furan-2-ylmethyl)-5-vinyl-3,10-diazabicyclo[4.3.1]decan-2-one J17

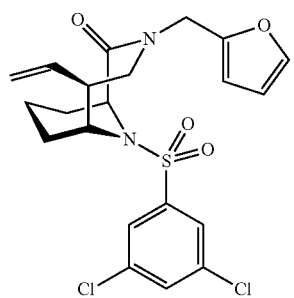

To a solution of (1S,5R,6R)-10-((3,5-dichlorophenyl)sulfonyl)-5-vinyl-3,10-diazabicyclo [4.3.1] decan-2-one I8 (50.0 mg, 0.128 mmol) in DMF (1.0 mL) was added NaH (7.71 mg, 0.193 mmol). After 20 minutes furfurylchloride (29.9 mg, 0.257 mmol) was added, the solution was heated to 80° C. and stirred for 1 h. Et$_2$O (90 mL) was added to the solution and washed with sat. aq. NaCl solution (3×10 mL). The organic layer was dried over MgSO$_4$ and the solvent removed under reduced pressure. Column chromatography on SiO$_2$ (Cyclohexane/EtOAc=8:2) afforded the title compound (41.0 mg, 0.0873 mmol, 68.2%) as a colorless solid.

R$_f$: 0.75 (Cyclohexane/EtOAc=1:1)

$^1$H NMR (600 MHz, CDCl$_3$) δ=1.24-1.34 (m, 3H), 1.48-1.51 (m, 2H), 2.28-2.34 (m, 1H), 2.34-2.42 (m, 1H), 3.07 (dd, J=14.4, 2.0 Hz, 1H), 3.95-4.02 (m, 2H), 4.25 (d, J=15.2 Hz, 1H), 4.73 (dt, J=5.7, 1.8 Hz, 1H), 4.94-5.08 (m, 3H), 5.69-5.77 (m, 1H), 6.27-6.36 (m, 2H), 7.37 (dd, J=2.0, 1.0 Hz, 1H), 7.55-7.58 (m, 1H), 7.69 (t, J=1.5 Hz, 2H).

$^{13}$C NMR (150 MHz, CDCl$_3$) δ=15.38, 26.35, 27.68, 46.59, 49.33, 50.99, 54.91, 56.92, 108.62, 110.45, 116.91, 124.86, 132.66, 136.31, 137.19, 142.31, 144.01, 150.55, 169.95.

MS (ESI): m/z (%)=469.06 [M+H]$^+$

Example 7-26: Preparation of ((1S,5R,6R)-10-((3,5-dichlorophenyl)sulfonyl)-3-(thiophen-2-ylmethyl)-5-vinyl-3,10-diazabicyclo[4.3.1]decan-2-one J18

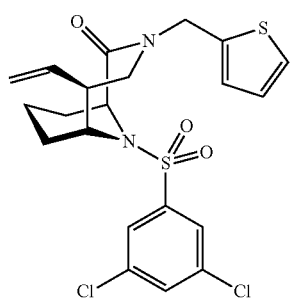

To a solution of (1S,5R,6R)-10-((3,5-dichlorophenyl)sulfonyl)-5-vinyl-3,10-diazabicyclo [4.3.1] decan-2-one I8 (25.0 mg, 0.0640 mmol) in DMF (1.0 mL) was added NaH (3.08 mg, 0.0769 mmol). After 20 minutes 2-(chloromethyl)thiophene (25.5 mg, 0.193 mmol) was added, the solution was heated to 80° C. and stirred for 1 h. Et$_2$O (90 mL) was added to the solution and washed with sat. aq. NaCl solution (3×10 mL). The organic layer was dried over MgSO$_4$ and the solvent removed under reduced pressure. Column chromatography on SiO$_2$ (Cyclohexane/EtOAc=7:3) afforded the title compound (14.0 mg, 0.0288 mmol, 45.1%) as a colorless solid.

R$_f$: 0.83 (Cyclohexane/EtOAc=3:2)

$^1$H NMR (600 MHz, CDCl$_3$) δ=1.23-1.31 (m, 3H), 1.49-1.54 (m, 2H), 2.32-2.40 (m, 2H), 3.03 (dd, J=14.3, 2.0 Hz, 1H), 3.94-4.02 (m, 2H), 4.34 (d, J=14.9 Hz, 1H), 4.72-4.75 (m, 1H), 4.90 (dt, J=17.0, 1.0 Hz, 1H), 5.03 (dd, J=10.2, 1.2 Hz, 1H), 5.22 (dd, J=15.0, 1.0 Hz, 1H), 5.69 (ddd, J=17.0, 10.1, 8.8 Hz, 1H), 6.94 (dd, J=5.1, 3.5 Hz, 1H), 6.98-7.00 (m, 1H), 7.24 (dd, J=5.1, 1.2 Hz, 1H), 7.55 (t, J=1.9 Hz, 1H), 7.69 (d, J=1.8 Hz, 2H).

$^{13}$C NMR (150 MHz, CDCl$_3$) δ=15.48, 26.24, 27.57, 48.98, 49.55, 50.94, 54.88, 56.87, 117.05, 124.88, 125.70, 126.55, 126.90, 132.68, 136.33, 137.09, 139.48, 144.03, 170.02.

MS (ESI): m/z (%)=485.05 [M+H]$^+$

Example 7-27: Preparation of (1S,5R,6R)-10-((3,5-dichlorophenyl)sulfonyl)-3-(2-(methylamino)ethyl)-5-vinyl-3,10-diazabicyclo[4.3.1]decan-2-one J19

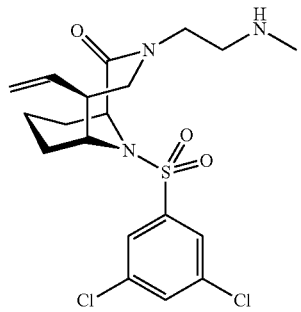

To a solution of (1S,5R,6R)-10-((3,5-dichlorophenyl)sulfonyl)-3-(2-(methylamino)ethyl)-5-vinyl-3,10-diazabicyclo[4.3.1]decan-2-one (50.0 mg, 0.116 mmol) in MeOH (1 mL) were added AcOH (0.02 mL) and methanamine (0.058 mL, 0.116 mmol) and the solution was stirred for 1 h at room temperature. Sodiumtriacetoxyborohydride (49.1 mg, 0.232 mmol) was added to the solution. After 1 h sat. aq. NaHCO₃ sol. (5 ml) was added to the mixture and then extracted with CH₂Cl₂ (3×10 mL). The combined organic layers were dried over MgSO₄ and the solvent was removed under reduced pressure. Column chromatography over SiO₂ (EtOAc+3% TEA) afforded the title compound (20.0 mg, 0.0448 mmol, 39%).

¹H NMR (300 MHz, Chloroform-d) δ 1.25-1.38 (m, 2H), 1.44-1.60 (m, 3H), 2.14-2.28 (m, 2H), 2.45 (s, 3H), 2.65-2.87 (m, 3H), 2.92-3.00 (m, 1H), 3.47-3.69 (m, 2H), 3.94-4.16 (m, 2H), 4.64 (dt, J=6.1, 1.9 Hz, 1H), 5.05-5.17 (m, 2H), 5.78 (ddd, J=16.9, 10.2, 8.9 Hz, 1H), 7.55 (t, J=1.8 Hz, 1H), 7.68 (d, J=1.8 Hz, 2H).

VI. Preparation of Compounds K1-K29

For the synthesis of examples of different $R^B$ substituents, the synthetic procedure of Scheme I was slightly modified from I3:

Scheme K.

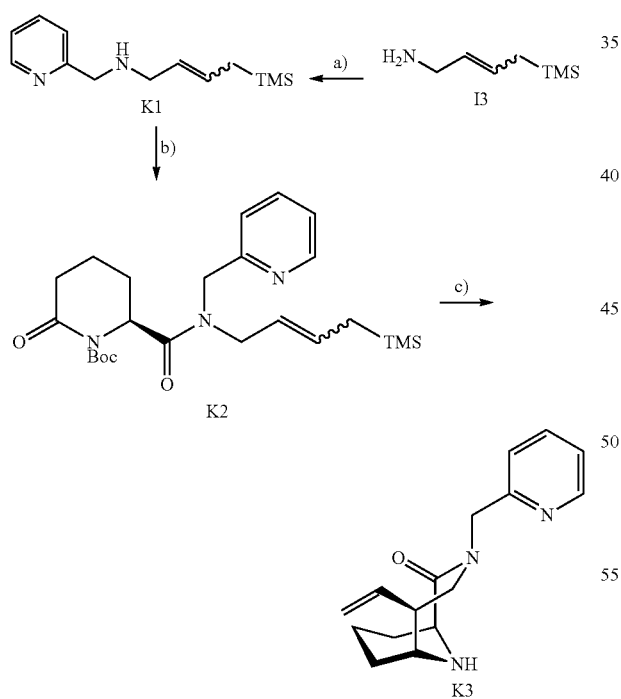

Reagents and conditions: a) Picolinaldehyde, NaBH₄, EtOH, rt, 4 h, 76% (2 steps); b) 1.) (S)-6-Oxopiperidine-2-carboxylic acid, HOBt, EDC, rt, DMF, 2 h; 2.) Boc₂O, DIPEA, DMAP, CH₂Cl₂, 48 h, 70% (2 steps); c) 1.) DIBAL, THF, -78° C., 15 min; 2.) HF pyridine, CH₂Cl₂, -78° C. to 0° C., 1 h, 41% (2 steps).

General Procedure K for the preparation of the sulfonamides K4-K29:

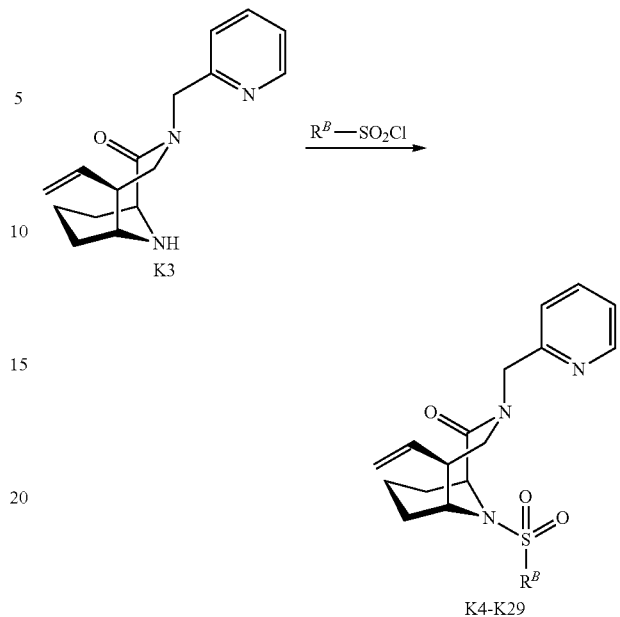

To a solution of (1S,5R,6R)-3-(pyridin-2-ylmethyl)-5-vinyl-3,10-diazabicyclo[4.3.1]decan-2-one K3 (25 mg, 0.092 mmol) in CH₂Cl₂ (1 mL) were added sulfonylchloride ($R^B$—SO₂Cl, 1.5 Equiv) and DIPEA (0.032 mL) and the reaction was stirred for 16 hours at room temperature. Sat. aq. NaHCO₃ solution (5 mL) was added to the mixture and extracted with CH₂Cl₂ (25 mL). The organic layer was dried over MgSO₄ and the solvent removed under reduced pressure. Column chromatography on SiO₂ afforded the title compounds.

Example 8-1: Preparation of 6-(((1S,5R,6R)-2-oxo-3-(pyridin-2-ylmethyl)-5-vinyl-3,10-diazabicyclo[4.3.1]decan-10-yl)sulfonyl)benzo[d]thiazol-2(3H)-one (K4)

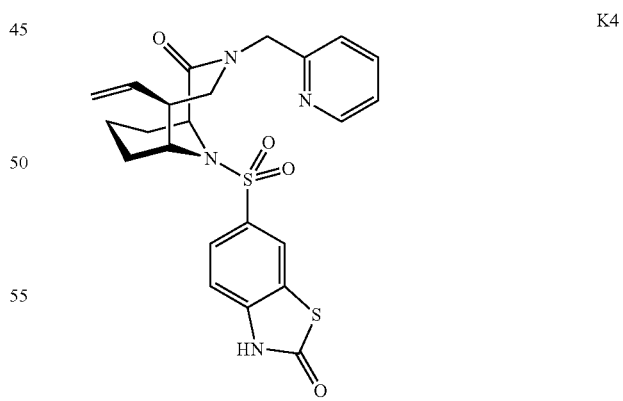

¹H NMR (600 MHz, CDCl₃) δ 1.28-1.34 (m, 2H), 1.43-1.55 (m, 3H), 2.26 (d, J=13.4 Hz, 1H), 2.64 (s, 1H), 2.66-2.73 (m, 1H), 3.07-3.12 (m, 1H), 4.00-4.04 (m, 1H), 4.04-4.10 (m, 1H), 4.76-4.87 (m, 3H), 4.96-5.05 (m, 2H), 5.67-5.76 (m, 1H), 7.18-7.23 (m, 2H), 7.31-7.34 (m, 1H), 7.66-7.70 (m, 1H), 7.71-7.74 (m, 1H), 7.89-7.91 (m, 1H), 8.51-8.54 (m, 1H).

$^{13}$C NMR (150 MHz, CDCl$_3$) δ 15.58, 26.27, 27.42, 29.67, 49.07, 52.13, 54.53, 56.22, 56.74, 111.53, 116.66, 121.38, 122.00, 122.44, 125.17, 136.11, 136.93, 137.34, 138.40, 156.91, 170.54, 170.88.

MS (ESI): m/z (%)=485.19 [M+H]$^+$

Example 8-2: Preparation of (1S,5R,6R)-10-((3-bromophenyl)sulfonyl)-3-(pyridin-2-ylmethyl)-5-vinyl-3,10-diazabicyclo[4.3.1]decan-2-one (K5)

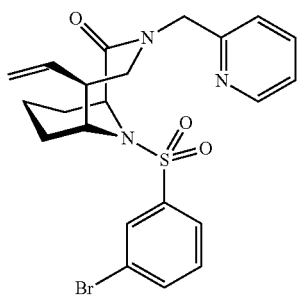

K5

$^1$H NMR (400 MHz, CDCl$_3$) δ 1.18-1.36 (m, 3H), 1.46-1.54 (m, 2H), 2.24-2.31 (m, 1H), 2.64-2.73 (m, 1H), 3.09 (dd, J=14.2, 2.0 Hz, 1H), 3.98-4.07 (m, 2H), 4.75-4.87 (m, 3H), 4.95-5.06 (m, 2H), 5.71 (ddd, J=16.9, 10.2, 8.8 Hz, 1H), 7.20 (ddd, J=7.5, 4.9, 1.2 Hz, 1H), 7.33 (d, J=7.9, 1.1 Hz, 1H), 7.40 (t, J=7.9 Hz, 1H), 7.66-7.73 (m, 2H), 7.74-7.78 (m, 1H), 7.98 (t, J=1.8 Hz, 1H), 8.51-8.55 (m, 1H).

$^{13}$C NMR (100 MHz, CDCl$_3$) δ 14.55, 25.23, 26.39, 48.08, 51.05, 53.65, 55.12, 55.78, 115.70, 121.04, 121.45, 122.30, 124.01, 128.46, 129.83, 134.73, 136.06, 136.29, 142.05, 148.02, 155.91, 169.66.

MS (ESI): m/z (%)=490.41 [M+H]$^+$

Example 8-3: Preparation of (1S,5R,6R)-10-((2-methylbenzo[d]thiazol-6-yl)sulfonyl)-3-(pyridin-2-ylmethyl)-5-vinyl-3,10-diazabicyclo[4.3.1]decan-2-one (K6)

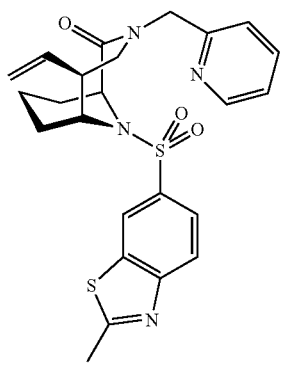

K6

$^1$H NMR (300 MHz, CDCl$_3$) δ 1.24-1.32 (m, 3H), 1.41-1.50 (m, 2H), 2.19-2.27 (m, 1H), 2.68 (q, J=8.9 Hz, 1H), 2.90 (s, 3H), 3.08 (dd, J=14.2, 1.9 Hz, 1H), 4.01-4.12 (m, 2H), 4.73-4.87 (m, 3H), 4.93-5.05 (m, 2H), 5.72 (ddd, J=17.0, 10.2, 8.8 Hz, 1H), 7.18 (ddd, J=7.5, 4.9, 1.2 Hz, 1H), 7.31 (dt, J=7.9, 1.1 Hz, 1H), 7.66 (td, J=7.7, 1.8 Hz, 1H), 7.86 (dd, J=8.6, 1.9, 0.7 Hz, 1H), 8.04 (dd, J=8.6, 0.6 Hz, 1H), 8.37 (dt, J=1.9, 0.6 Hz, 1H), 8.51 (ddd, J=4.9, 1.8, 0.9 Hz, 1H).

$^{13}$C NMR (75 MHz, CDCl$_3$) δ 15.56, 20.46, 26.21, 27.35, 29.66, 49.08, 52.08, 54.54, 56.16, 56.76, 116.56, 120.91, 121.99, 122.38, 123.21, 123.91, 136.20, 136.91, 137.42, 137.44, 149.09, 155.74, 157.01, 170.83, 171.54.

MS (ESI): m/z (%)=483.18 [M+H]$^+$

Example 8-4: Preparation of 3-(((1S,5R,6R)-2-oxo-3-(pyridin-2-ylmethyl)-5-vinyl-3,10-diazabicyclo[4.3.1]decan-10-yl)sulfonyl)benzonitrile (K7)

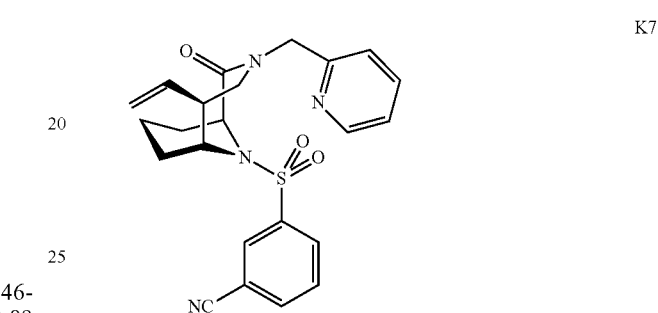

K7

$^1$H NMR (400 MHz, CDCl$_3$) δ 1.14-1.29 (m, 3H), 1.46-1.58 (m, 2H), 2.26-2.35 (m, 1H), 2.66-2.77 (m, 1H), 3.12 (dd, J=14.3, 2.0 Hz, 1H), 3.97-4.07 (m, 2H), 4.71-4.90 (m, 3H), 4.94-5.08 (m, 2H), 5.71 (ddd, J=17.0, 10.1, 8.8 Hz, 1H), 7.20 (ddd, J=7.6, 4.9, 1.2 Hz, 1H), 7.32 (dt, J=8.0, 1.1 Hz, 1H), 7.65-7.73 (m, 2H), 7.87 (dt, J=7.8, 1.3 Hz, 1H), 8.03-8.09 (m, 1H), 8.09-8.16 (m, 1H), 8.50-8.56 (m, 1H).

$^{13}$C NMR (101 MHz, CDCl$_3$) δ 14.47, 25.40, 26.58, 48.03, 51.04, 53.87, 55.18, 55.85, 113.01, 115.90, 115.96, 121.07, 121.48, 129.05, 129.44, 134.79, 135.97, 136.09, 141.96, 148.13, 155.83, 169.30.

MS (ESI): m/z (%)=437.21 [M+H]$^+$

Example 8-5: Preparation of (1S,5R,6R)-10-((3,5-dichloro-4-hydroxyphenyl)sulfonyl)-3-(pyridin-2-ylmethyl)-5-vinyl-3,10-diazabicyclo[4.3.1]decan-2-one (K8)

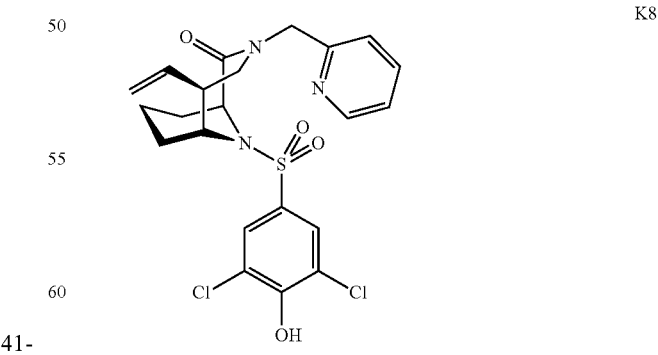

K8

$^1$H NMR (300 MHz, CDCl$_3$) δ 1.29-1.35 (m, 1H), 1.48-1.67 (m, 4H), 2.29 (d, J=14.1 Hz, 1H), 2.63-2.72 (m, 1H), 3.09 (dd, J=14.1, 2.0 Hz, 1H), 3.95-4.07 (m, 2H), 4.70-4.75 (m, 1H), 4.81 (s, 2H), 4.92-5.06 (m, 2H), 5.70 (ddd, J=16.9, 10.1, 8.7 Hz, 1H), 7.17-7.22 (m, 1H), 7.28-7.35 (m, 1H), 7.61-7.80 (m, 3H), 8.49-8.55 (m, 1H).

$^{13}$C NMR (75 MHz, CDCl$_3$) δ 15.55, 26.37, 27.49, 29.66, 49.05, 52.08, 54.69, 56.08, 56.77, 116.76, 122.07, 122.25, 122.50, 126.79, 133.97, 137.11, 137.21, 148.98, 151.86, 156.82, 170.68.

MS (ESI): m/z (%)=496.22 [M+H]$^+$

Example 8-6: Preparation of (1S,5R,6R)-10-(benzo[d]thiazol-6-ylsulfonyl)-3-(pyridin-2-ylmethyl)-5-vinyl-3,10-diazabicyclo[4.3.1]decan-2-one (K9)

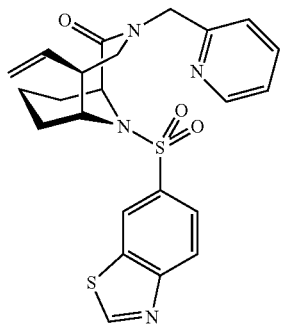

K9

$^1$H NMR (400 MHz, CDCl$_3$) δ 1.13-1.32 (m, 3H), 1.38-1.51 (m, 2H), 2.17-2.27 (m, 1H), 2.63-2.72 (m, 1H), 3.08 (dd, J=14.2, 2.0 Hz, 1H), 4.01-4.13 (m, 2H), 4.73-4.86 (m, 3H), 4.92-5.04 (m, 2H), 5.71 (ddd, J=17.0, 10.1, 8.8 Hz, 1H), 7.12-7.20 (m, 1H), 7.27-7.33 (m, 1H), 7.61-7.69 (m, 1H), 7.92 (dd, J=8.6, 1.9 Hz, 1H), 8.24 (dd, J=8.6, 0.6 Hz, 1H), 8.46-8.55 (m, 2H), 9.19 (s, 1H).

13C NMR (100 MHz, CDCl$_3$) δ 15.54, 26.26, 27.40, 49.07, 52.09, 54.62, 56.18, 56.79, 116.61, 121.55, 121.99, 122.39, 124.04, 124.62, 134.35, 136.89, 137.38, 138.43, 149.11, 155.43, 156.97, 157.89, 170.75.

MS (ESI): m/z (%)=496.20 [M+H]$^+$

Example 8-7: Preparation of (1S,5R,6R)-10-((3-chloro-4-methoxyphenyl)sulfonyl)-3-(pyridin-2-ylmethyl)-5-vinyl-3,10-diazabicyclo[4.3.1]decan-2-one (K10)

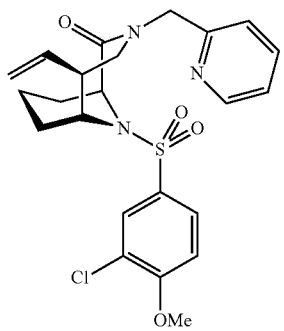

K10

$^1$H NMR (400 MHz, CDCl$_3$) δ 1.11-1.26 (m, 3H), 1.39-1.47 (m, 2H), 2.20 (d, J=13.4 Hz, 1H), 2.56-2.64 (m, 1H), 2.96-3.08 (m, 1H), 3.89-4.05 (m, 5H), 4.64-4.82 (m, 3H), 4.85-5.02 (m, 2H), 5.55-5.73 (m, 1H), 6.89-6.98 (m, 1H), 7.08-7.17 (m, 1H), 7.23-7.30 (m, 1H), 7.57-7.71 (m, 2H), 7.72-7.81 (m, 1H), 8.42-8.52 (m, 1H).

MS (ESI): m/z (%)=476.38 [M+H]$^+$

Example 8-8: Preparation of (1S,5R,6R)-10-((3-chlorophenyl)sulfonyl)-3-(pyridin-2-ylmethyl)-5-vinyl-3,10-diazabicyclo[4.3.1]decan-2-one (K11)

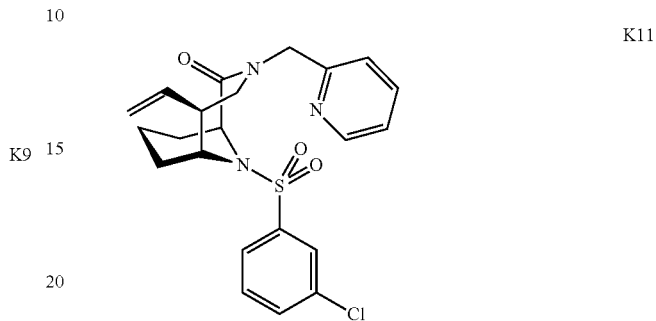

K11

$^1$H NMR (300 MHz, CDCl$_3$) δ 1.19-1.33 (m, 3H), 1.44-1.53 (m, 2H), 2.22-2.31 (m, 1H), 2.62-2.73 (m, 1H), 3.08 (dd, J=14.3, 2.0 Hz, 1H), 3.97-4.07 (m, 2H), 4.73-4.87 (m, 3H), 4.92-5.04 (m, 2H), 5.70 (ddd, J=16.9, 10.2, 8.8 Hz, 1H), 7.18 (ddd, J=7.6, 4.9, 1.2 Hz, 1H), 7.31 (dt, J=7.9, 1.1 Hz, 1H), 7.41-7.49 (m, 1H), 7.51-7.57 (m, 1H), 7.63-7.73 (m, 2H), 7.81 (t, J=1.9 Hz, 1H), 8.51 (ddd, J=4.9, 1.9, 1.0 Hz, 1H).

$^{13}$C NMR (75 MHz, CDCl$_3$) δ 15.54, 26.24, 27.40, 49.06, 52.04, 54.65, 56.14, 56.79, 116.66, 122.02, 122.42, 124.59, 126.64, 130.60, 132.79, 135.54, 136.98, 137.30, 142.93, 149.06, 156.94, 170.65.

MS (ESI): m/z (%)=446.20 [M+H]$^+$

Example 8-9: Preparation of (1S,5R,6R)-10-((2,3-dihydrobenzofuran-5-yl)sulfonyl)-3-(pyridin-2-ylmethyl)-5-vinyl-3,10-diazabicyclo[4.3.1]decan-2-one (K12)

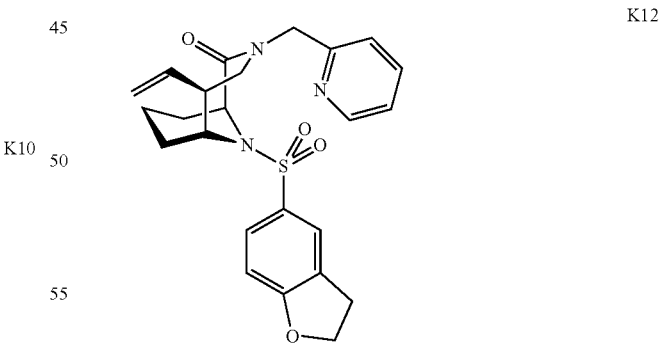

K12

$^1$H NMR (600 MHz, CDCl$_3$) δ 1.31-1.40 (m, 1H), 1.51-1.79 (m, 4H), 2.21-2.26 (m, 1H), 2.62-2.69 (m, 1H), 3.05 (dd, J=14.1, 2.0 Hz, 1H), 3.24-3.29 (m, 2H), 3.98-4.03 (m, 1H), 4.04-4.09 (m, 1H), 4.69 (t, J=8.9 Hz, 2H), 4.75 (dt, J=6.0, 1.9 Hz, 1H), 4.80 (s, 2H), 4.93-5.02 (m, 2H), 5.71 (ddd, J=17.0, 10.1, 8.8 Hz, 1H), 6.84 (d, J=8.4 Hz, 1H), 7.19 (ddd, J=7.5, 4.9, 1.1 Hz, 1H), 7.32 (d, J=7.9, 1.0 Hz, 1H), 7.59-7.63 (m, 1H), 7.65-7.70 (m, 2H), 8.52 (ddd, J=4.9, 1.8, 0.9 Hz, 1H).

¹³C NMR (151 MHz, CDCl₃) δ 15.70, 26.15, 27.28, 29.06, 49.12, 52.09, 54.20, 56.15, 56.60, 72.24, 109.69, 116.37, 121.96, 122.35, 123.94, 128.08, 128.42, 132.87, 136.92, 137.61, 149.07, 157.09, 163.72, 171.17.

MS (ESI): m/z (%)=454.20 [M+H]⁺

Example 8-10: Preparation of (1S,5R,6R)-10-(phenylsulfonyl)-3-(pyridin-2-ylmethyl)-5-vinyl-3,10-diazabicyclo[4.3.1]decan-2-one (K13)

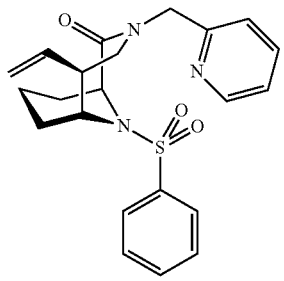

K13

¹H NMR (300 MHz, CDCl₃) δ 1.23-1.34 (m, 2H), 1.41-1.61 (m, 3H), 2.22 (d, J=13.4 Hz, 1H), 2.61-2.73 (m, 1H), 3.06 (dd, J=14.2, 2.0 Hz, 1H), 3.98-4.07 (m, 2H), 4.72-4.81 (m, 2H), 4.88-5.05 (m, 3H), 5.71 (ddd, J=16.9, 10.2, 8.7 Hz, 1H), 7.22-7.29 (m, 1H), 7.36-7.42 (m, 1H), 7.47-7.61 (m, 3H), 7.72-7.86 (m, 3H), 8.53-8.58 (m, 1H).

¹³C NMR (75 MHz, CDCl₃) δ 15.58, 26.11, 27.22, 49.09, 52.24, 54.40, 55.58, 56.67, 116.62, 122.42, 122.73, 126.52, 129.31, 132.70, 137.31, 138.09, 141.15, 148.06, 156.57, 171.13.

MS (ESI): m/z (%)=412.20 [M+H]⁺

Example 8-11: Preparation of (1S,5R,6R)-3-(pyridin-2-ylmethyl)-10-(pyridin-2-ylsulfonyl)-5-vinyl-3,10-diazabicyclo[4.3.1]decan-2-one (K14)

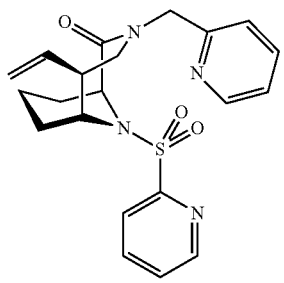

K14

¹H NMR (300 MHz, CDCl₃) δ 1.35-1.58 (m, 5H), 2.21-2.30 (m, 1H), 2.63-2.74 (m, 1H), 3.09 (dd, J=14.1, 2.0 Hz, 1H), 4.07-4.15 (m, 2H), 4.80 (d, J=3.3 Hz, 2H), 4.84-4.89 (m, 1H), 4.92-5.01 (m, 2H), 5.72 (ddd, J=16.9, 10.2, 8.8 Hz, 1H), 7.17 (dddd, J=7.6, 4.9, 1.2, 0.6 Hz, 1H), 7.33 (d, J=8.0, 1.6, 0.7 Hz, 1H), 7.48 (dddd, J=7.5, 4.7, 1.3, 0.5 Hz, 1H), 7.62-7.71 (m, 2H), 7.89 (tdd, J=7.8, 1.7, 0.5 Hz, 1H), 7.94-8.01 (m, 1H), 8.51 (ddt, J=5.0, 1.7, 0.7 Hz, 1H), 8.70 (ddt, J=4.7, 1.6, 0.7 Hz, 1H).

¹³C NMR (75 MHz, CDCl₃) δ 15.65, 26.15, 27.37, 49.20, 52.18, 54.87, 56.21, 57.20, 116.44, 122.01, 122.04, 122.35, 126.64, 136.90, 137.48, 138.00, 149.09, 150.23, 157.14, 158.16, 170.97.

MS (ESI): m/z (%)=413.19 [M+H]⁺

Example 8-12: Preparation of (1S,5R,6R)-10-((3-fluorophenyl)sulfonyl)-3-(pyridin-2-ylmethyl)-5-vinyl-3,10-diazabicyclo[4.3.1]decan-2-one (K15)

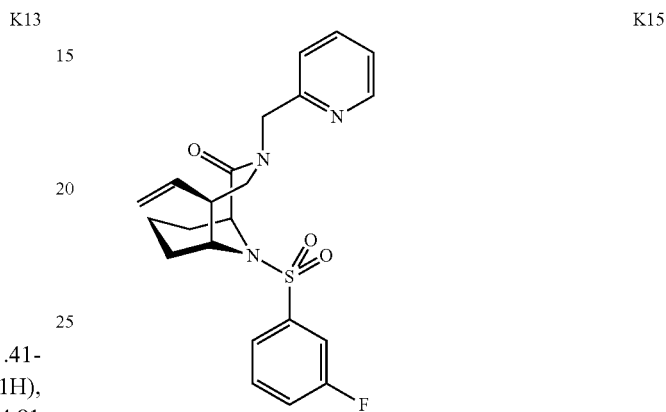

K15

¹H NMR (300 MHz, CDCl₃) δ 1.24-1.34 (m, 2H), 1.43-1.63 (m, 3H), 2.26 (d, J=13.3 Hz, 1H), 2.57-2.76 (m, 1H), 3.08 (dd, J=14.2, 2.0 Hz, 1H), 3.95-4.05 (m, 2H), 4.70-4.89 (m, 3H), 4.92-5.06 (m, 2H), 5.70 (ddd, J=17.0, 10.2, 8.8 Hz, 1H), 7.13-7.22 (m, 1H), 7.24-7.34 (m, 2H), 7.44-7.57 (m, 2H), 7.58-7.71 (m, 2H), 8.51 (ddd, J=4.9, 1.8, 0.9 Hz, 1H).

¹³C NMR (75 MHz, CDCl₃) δ 15.55, 26.22, 27.39, 49.06, 52.04, 54.65, 56.18, 56.81, 113.79, 114.11, 116.64, 119.75, 120.03, 122.01, 122.30, 122.34, 122.40, 131.09, 131.19, 136.90, 137.33, 143.20, 143.28, 149.13, 156.99, 164.21, 170.65.

MS (ESI): m/z (%)=430.17 [M+H]⁺

Example 8-13: Preparation of (1S,5R,6R)-10-((3,5-dibromophenyl)sulfonyl)-3-(pyridin-2-ylmethyl)-5-vinyl-3,10-diazabicyclo[4.3.1]decan-2-one (K16)

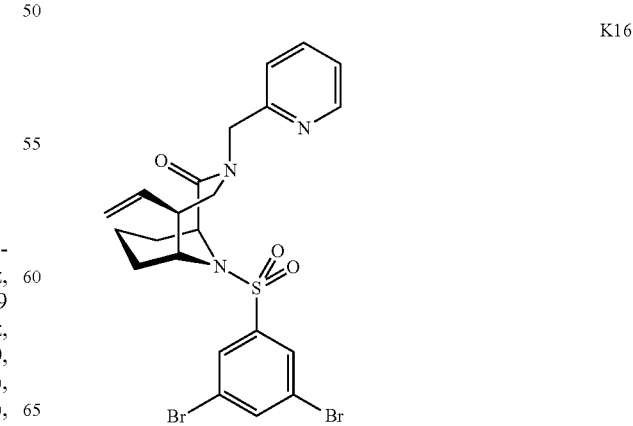

K16

Example 8-14: Preparation of 3-(((1S,5R,6R)-2-oxo-3-(pyridin-2-ylmethyl)-5-vinyl-3,10-diazabicyclo[4.3.1]decan-10-yl)sulfonyl)benzamide (K17)

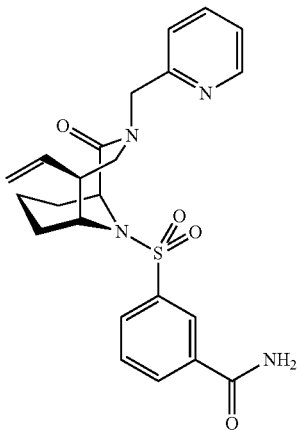
K17

¹H NMR (400 MHz, CDCl₃) δ 1.09-1.22 (m, 1H), 1.26-1.33 (m, 1H), 1.41-1.62 (m, 3H), 2.23 (d, J=13.4 Hz, 1H), 2.60-2.75 (m, 1H), 3.08 (dd, J=14.2, 2.0 Hz, 1H), 3.96-4.06 (m, 2H), 4.70-4.90 (m, 3H), 4.91-5.04 (m, 2H), 5.70 (ddd, J=17.0, 10.1, 8.8 Hz, 1H), 6.07 (s, 1H), 6.72 (s, 1H), 7.19 (ddd, J=7.6, 4.9, 1.2 Hz, 1H), 7.30 (dt, J=7.9, 1.0 Hz, 1H), 7.55-7.73 (m, 2H), 7.97 (ddd, J=7.9, 1.8, 1.1 Hz, 1H), 8.05-8.14 (m, 1H), 8.31 (td, J=1.8, 0.5 Hz, 1H), 8.52 (ddd, J=4.9, 1.8, 0.9 Hz, 1H).

¹³C NMR (100 MHz, CDCl₃) δ 15.55, 26.23, 27.42, 49.08, 52.17, 54.66, 56.21, 56.79, 116.74, 122.05, 122.50, 125.32, 129.53, 129.89, 131.99, 134.82, 136.97, 137.30, 141.84, 149.22, 156.88, 167.32.

MS (ESI): m/z (%)=455.18 [M+H]⁺

Example 8-15: Preparation of 3-bromo-5-(((1S,5R,6R)-2-oxo-3-(pyridin-2-ylmethyl)-5-vinyl-3,10-diazabicyclo[4.3.1]decan-10-yl)sulfonyl)benzamide (K18)

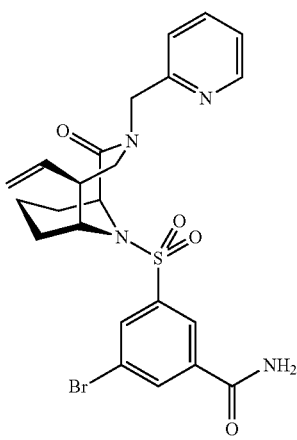
K18

¹H NMR (400 MHz, CDCl₃) δ 1.26-1.33 (m, 2H), 1.48-1.64 (m, 3H), 2.26 (d, J=13.6 Hz, 1H), 2.67-2.78 (m, 1H), 3.10 (dd, J=14.2, 2.0 Hz, 1H), 3.98-4.07 (m, 2H), 4.70-5.07 (m, 5H), 5.70 (ddd, J=16.9, 10.1, 8.7 Hz, 1H), 6.00 (s, 1H), 6.73 (s, 1H), 7.21 (ddd, J=7.5, 4.9, 1.2 Hz, 1H), 7.30 (dt, J=7.8, 1.1 Hz, 1H), 7.68 (td, J=7.7, 1.8 Hz, 1H), 8.09 (t, J=1.7 Hz, 1H), 8.24 (p, J=1.6 Hz, 2H), 8.53 (ddd, J=5.0, 1.9, 1.0 Hz, 1H).

¹³C NMR (100 MHz, CDCl₃) δ 15.50, 22.70, 26.37, 27.54, 29.37, 29.66, 29.70, 31.93, 49.06, 52.19, 54.89, 56.18, 56.87, 116.93, 122.12, 122.58, 123.73, 123.86, 132.21, 135.11, 136.42, 137.08, 137.13, 143.48, 149.17, 156.72, 165.83.

MS (ESI): m/z (%)=535.09 [M+H]⁺

Example 8-16: Preparation of 3-chloro-5-(((1S,5R,6R)-2-oxo-3-(pyridin-2-ylmethyl)-5-vinyl-3,10-diazabicyclo[4.3.1]decan-10-yl)sulfonyl)benzamide (K19)

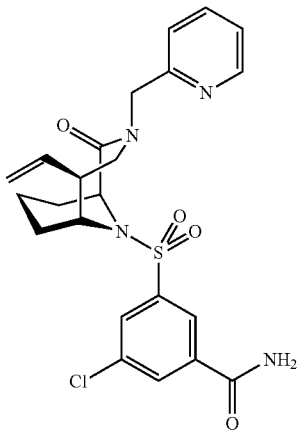
K19

¹H NMR (400 MHz, CDCl₃) δ 1.26-1.32 (m, 2H), 1.47-1.63 (m, 3H), 2.23 (dd, J=13.7, 2.9 Hz, 1H), 2.65-2.78 (m, 1H), 3.10 (dd, J=14.2, 2.0 Hz, 1H), 3.99-4.07 (m, 2H), 4.75-4.93 (m, 3H), 4.94-5.07 (m, 2H), 5.70 (ddd, J=16.9, 10.1, 8.7 Hz, 1H), 6.26 (s, 1H), 7.01 (s, 1H), 7.22 (ddd, J=7.5, 5.0, 1.2 Hz, 1H), 7.31 (d, J=7.8 Hz, 1H), 7.70 (td, J=7.7, 1.8 Hz, 1H), 7.94 (t, J=1.8 Hz, 1H), 8.07-8.13 (m, 1H), 8.21 (t, J=1.6 Hz, 1H), 8.54 (ddd, J=5.1, 1.7, 0.9 Hz, 1H).

¹³C NMR (100 MHz, CDCl₃) δ 15.47, 26.34, 27.51, 29.70, 49.02, 52.27, 54.86, 56.05, 56.75, 117.00, 122.20, 122.70, 123.31, 129.32, 132.38, 136.28, 136.32, 137.03, 137.34, 143.32, 148.96, 156.51, 163.86, 166.26.

MS (ESI): m/z (%)=489.18 [M+H]⁺

Example 8-17: Preparation of N-(2-bromo-4-(((1S, 5R,6R)-2-oxo-3-(pyridin-2-ylmethyl)-5-vinyl-3,10-diazabicyclo[4.3.1]decan-10-yl)sulfonyl)phenyl)acetamide (K20)

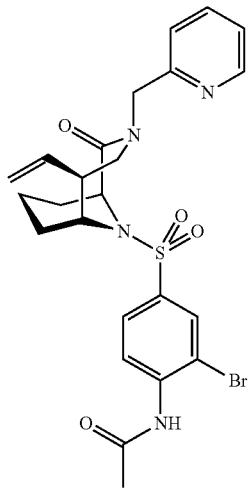

Example 8-18: Preparation of N-(2-chloro-4-(((1S, 5R,6R)-2-oxo-3-(pyridin-2-ylmethyl)-5-vinyl-3,10-diazabicyclo[4.3.1]decan-10-yl)sulfonyl)phenyl)acetamide (K21)

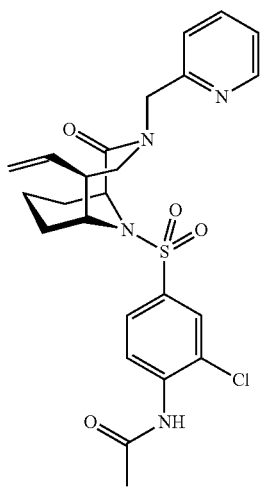

Example 8-19: Preparation of N-(2,6-dichloro-4-(((1S,5R,6R)-2-oxo-3-(pyridin-2-ylmethyl)-5-vinyl-3,10-diazabicyclo[4.3.1]decan-10-yl)sulfonyl)phenyl)acetamide (K22)

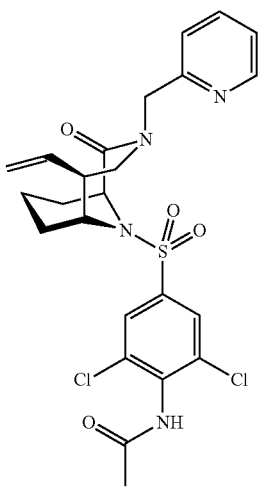

Example 8-20: Preparation of methyl 3-(((1S,5R, 6R)-2-oxo-3-(pyridin-2-ylmethyl)-5-vinyl-3,10-diazabicyclo[4.3.1]decan-10-yl)sulfonyl)benzoate (K23)

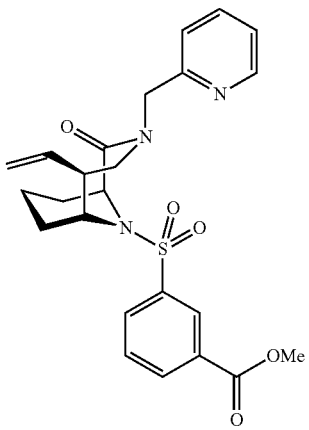

$^1$H NMR (300 MHz, CDCl$_3$) δ 1.13-1.21 (m, 1H), 1.25-1.32 (m, 1H), 1.42-1.65 (m, 3H), 2.25 (d, J=13.5 Hz, 1H), 2.62-2.75 (m, 1H), 3.09 (dd, J=14.2, 2.0 Hz, 1H), 3.96 (s, 3H), 4.01-4.13 (m, 2H), 4.73-5.05 (m, 5H), 5.72 (ddd, J=16.9, 10.1, 8.8 Hz, 1H), 7.19 (ddd, J=7.5, 4.9, 1.2 Hz, 1H), 7.32 (dt, J=7.9, 1.1 Hz, 1H), 7.57-7.71 (m, 2H), 8.01 (ddd, J=7.9, 2.0, 1.2 Hz, 1H), 8.24 (ddd, J=7.8, 1.7, 1.2 Hz, 1H), 8.44-8.49 (m, 1H), 8.52 (ddd, J=4.9, 1.8, 1.0 Hz, 1H).

$^{13}$C NMR (75 MHz, CDCl$_3$) δ 15.55, 26.23, 27.37, 49.11, 52.10, 52.66, 54.62, 56.15, 56.78, 116.66, 122.03, 122.42, 127.56, 129.59, 130.52, 131.58, 133.51, 136.99, 137.34, 141.93, 149.05, 156.96, 165.31, 170.72.

MS (ESI): m/z (%)=470.18 [M+H]$^+$

Example 8-21: Preparation of methyl 3-bromo-5-((((1S,5R,6R)-2-oxo-3-(pyridin-2-ylmethyl)-5-vinyl-3,10-diazabicyclo[4.3.1]decan-10-yl)sulfonyl)benzoate K24)

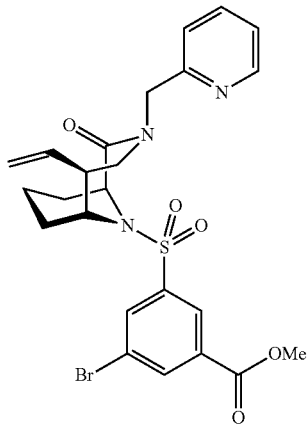

Example 8-22: Preparation of methyl 3-chloro-5-((((1S,5R,6R)-2-oxo-3-(pyridin-2-ylmethyl)-5-vinyl-3,10-diazabicyclo[4.3.1]decan-10-yl)sulfonyl)benzoate (K25)

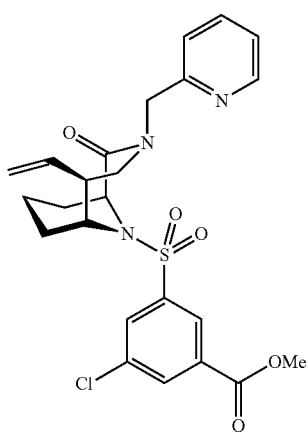

Example 8-23: Preparation of (1S,5R,6R)-3-(pyridin-2-ylmethyl)-10-(pyridin-3-ylsulfonyl)-5-vinyl-3,10-diazabicyclo[4.3.1]decan-2-one (K26)

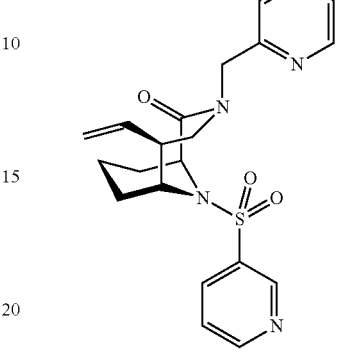

$^1$H NMR (600 MHz, CDCl$_3$) δ 1.27-1.34 (m, 2H), 1.46-1.64 (m, 3H), 2.25-2.34 (m, 1H), 2.65-2.75 (m, 1H), 3.12 (dd, J=14.3, 2.0 Hz, 1H), 4.00-4.08 (m, 2H), 4.73-4.89 (m, 3H), 4.96-5.06 (m, 2H), 5.72 (ddd, J=17.0, 10.1, 8.8 Hz, 1H), 7.20 (ddd, J=7.5, 4.9, 1.2 Hz, 1H), 7.32 (dt, J=7.8, 1.1 Hz, 1H), 7.47 (ddd, J=8.0, 4.8, 0.9 Hz, 1H), 7.68 (td, J=7.7, 1.8 Hz, 1H), 8.12 (ddd, J=8.0, 2.4, 1.6 Hz, 1H), 8.53 (ddd, J=4.9, 1.9, 1.0 Hz, 1H), 8.82 (dd, J=4.8, 1.6 Hz, 1H), 9.06 (dd, J=2.4, 0.9 Hz, 1H).

$^{13}$C NMR (150 MHz, CDCl$_3$) δ 15.54, 26.37, 27.56, 29.68, 49.04, 52.09, 54.70, 56.22, 56.77, 116.79, 122.04, 122.44, 123.84, 134.17, 136.93, 137.20, 137.84, 147.51, 149.16, 153.26, 156.92, 170.46.

MS (ESI): m/z (%)=413.17 [M+H]$^+$

Example 8-24: Preparation of (1S,5R,6R)-10-((6-phenylpyridin-3-yl)sulfonyl)-3-(pyridin-2-ylmethyl)-5-vinyl-3,10-diazabicyclo[4.3.1]decan-2-one (K27)

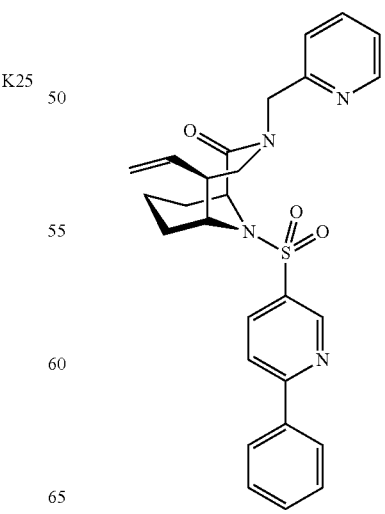

Example 8-25: Preparation of (1S,5R,6R)-3-(pyridin-2-ylmethyl)-10-((4-(pyrimidin-2-yl)phenyl)sulfonyl)-5-vinyl-3,10-diazabicyclo[4.3.1]decan-2-one (K28)

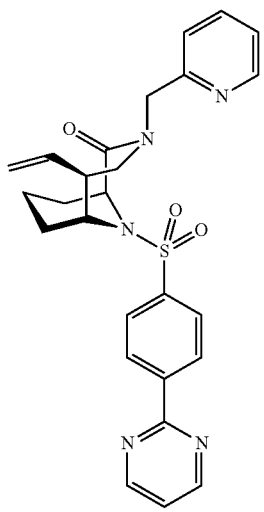

K28

¹H NMR (600 MHz, CDCl₃) δ 1.27-1.35 (m, 2H), 1.43-1.53 (m, 3H), 2.22-2.27 (m, 1H), 2.65-2.72 (m, 1H), 3.09 (dd, J=14.1, 1.9 Hz, 1H), 4.03-4.10 (m, 2H), 4.78-4.90 (m, 3H), 4.96-5.06 (m, 2H), 5.73 (ddd, J=17.0, 10.1, 8.7 Hz, 1H), 7.20-7.23 (m, 1H), 7.29 (t, J=4.8 Hz, 1H), 7.36 (d, J=7.9 Hz, 1H), 7.72 (t, J=7.6 Hz, 1H), 7.93-7.99 (m, 2H), 8.52-8.55 (m, 1H), 8.59-8.64 (m, 2H), 8.87 (d, J=4.8 Hz, 2H).

¹³C NMR (150 MHz, CDCl₃) δ 15.51, 25.99, 27.15, 29.59, 49.02, 52.09, 54.44, 55.89, 56.70, 116.54, 119.93, 122.12, 122.45, 126.70, 128.95, 137.30, 141.48, 142.75, 157.35, 162.90, 170.88.

MS (ESI): m/z (%)=490.18 [M+H]⁺

Example 8-26: Preparation of (1S,5R,6R)-10-((1H-benzo[d]imidazol-2-yl)sulfonyl)-3-(pyridin-2-ylmethyl)-5-vinyl-3,10-diazabicyclo[4.3.1]decan-2-one (K29)

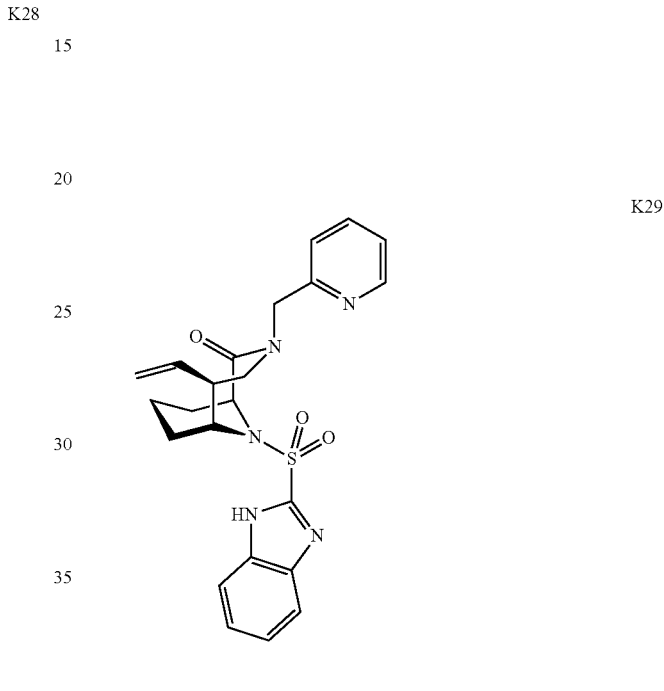

K29

VII. Preparation of Compounds M1-M6

From J4 further examples for R^C modifications (M1-M6) were prepared:

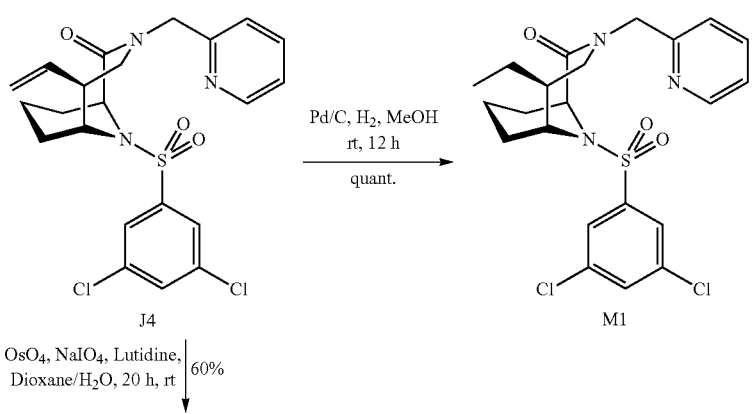

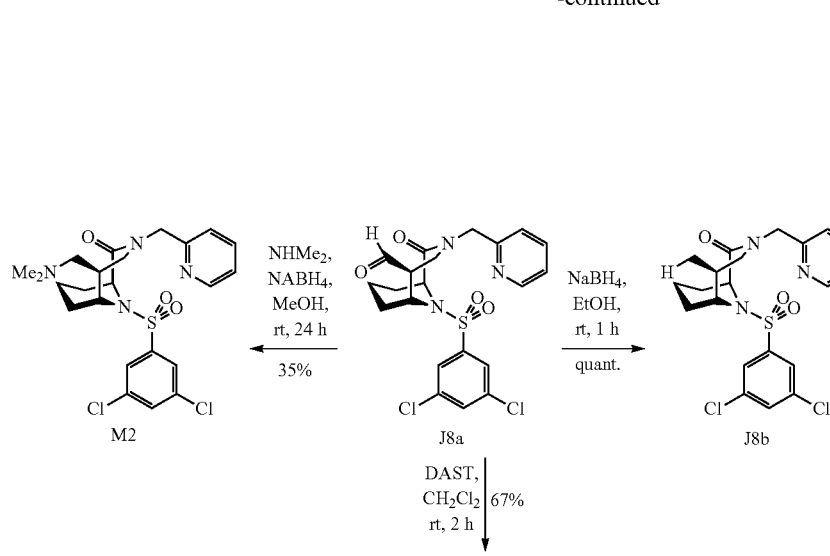
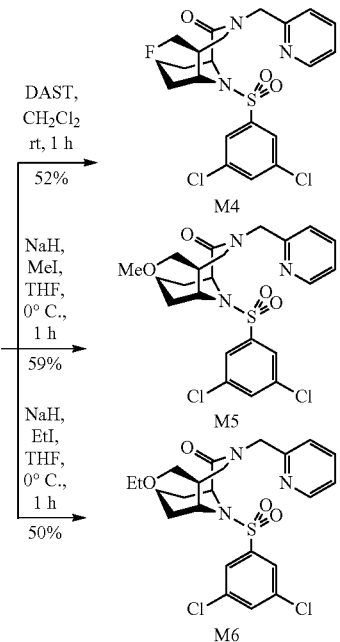

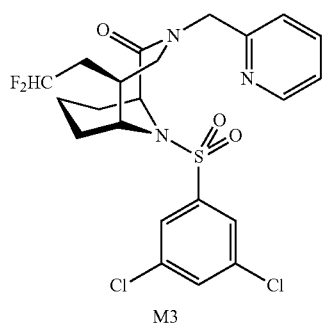

Example 9-1: Preparation of (1S,5R,6R)-10-((3,5-dichlorophenyl)sulfonyl)-5-ethyl-3-(pyridin-2-ylmethyl)-3,10-diazabicyclo[4.3.1]decan-2-one M1

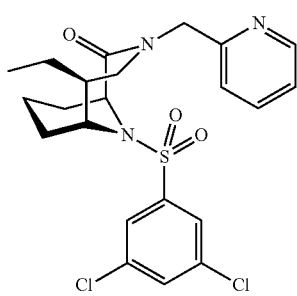

M1

To a solution of (1S,5R,6R)-10-((3,5-dichlorophenyl)sulfonyl)-3-(pyridin-2-ylmethyl)-5-vinyl-3,10-diazabicyclo[4.3.1]decan-2-one (35.0 mg, 0.0730 mmol) in MeOH (1 mL) was added Pd/C (10%, 7.75 mg, 0.00729 mmol) and the solution was saturated with $H_2$. After 2 h the mixture was filtered through Celite and washed with EtOAc. The solvent was removed under reduced pressure and column chromatography over $SiO_2$ (Cyclohexane/EtOAc=2:3) afforded the title compound (35.1 mg, 0.0730 mmol, quant.) as a white solid.

$R_f$: 0.33 (Cyclohexane/EtOAc=2:3)

$^1$H NMR (300 MHz, CDCl$_3$) δ 0.78 (t, J=7.4 Hz, 3H), 1.22-1.37 (m, 4H), 1.42-1.62 (m, 3H), 1.79-1.92 (m, 1H), 2.30 (d, J=13.5 Hz, 1H), 3.11 (dd, J=14.4, 1.8 Hz, 1H), 3.73-3.86 (m, 2H), 4.64 (d, J=15.0 Hz, 1H), 4.71-4.77 (m, 1H), 4.93 (d, J=15.0 Hz, 1H), 7.15-7.21 (m, 1H), 7.28-7.34 (m, 1H), 7.53-7.56 (m, 1H), 7.62-7.71 (m, 3H), 8.49-8.54 (m, 1H).

$^{13}$C NMR (75 MHz, CDCl$_3$) δ 11.46, 15.62, 26.16, 27.39, 27.62, 45.56, 50.89, 55.54, 56.02, 56.90, 122.16, 122.44, 124.90, 132.57, 136.27, 136.87, 144.17, 149.13, 157.09, 170.39.

MS (ESI): m/z (%)=482.49 [M+H]$^+$

Example 9-2: Preparation of (1S,5S,6R)-10-((3,5-dichlorophenyl)sulfonyl)-5-((dimethylamino)methyl)-3-(pyridin-2-ylmethyl)-3,10-diazabicyclo[4.3.1]decan-2-one M2

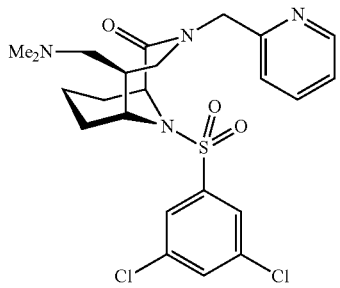

To a solution of (1S,5S,6R)-10-((3,5-dichlorophenyl)sulfonyl)-2-oxo-3-(pyridin-2-ylmethyl)-3,10-diazabicyclo[4.3.1]decane-5-carbaldehyde (35 mg, 0.0730 mmol) in MeOH (1 mL) was added dimethylamine (0.109 mL, 0.218 mmol). After 2 h NaBH$_4$ to the mixture and stirred for 1 h. The solvent was removed under reduced pressure and the mixture was loaded on SiO$_2$. Column chromatography over SiO$_2$ (CH$_2$Cl$_2$+MeOH 4%) afforded the title compound (13.0 mg, 0.0254 mmol, 35%).

$^1$H NMR (600 MHz, CDCl$_3$) δ 1.19-1.26 (m, 1H), 1.32-1.41 (m, 1H), 1.44-1.56 (m, 2H), 1.56-1.66 (m, 1H), 2.06 (s, 6H), 2.12-2.19 (m, 1H), 2.22-2.33 (m, 3H), 3.32-3.40 (m, 1H), 3.74-3.89 (m, 2H), 4.64 (d, J=15.2 Hz, 1H), 4.72-4.77 (m, 1H), 4.96 (d, J=15.2 Hz, 1H), 7.18 (dt, J=12.8, 6.2 Hz, 1H), 7.30 (t, J=8.6 Hz, 1H), 7.53-7.56 (m, 1H), 7.63-7.68 (m, 1H), 7.67-7.72 (m, 2H), 8.49-8.53 (m, 1H).

$^{13}$C NMR (151 MHz, CDCl$_3$) δ 15.69, 28.07, 28.13, 42.25, 45.47, 50.30, 54.35, 56.18, 57.03, 62.45, 122.01, 122.31, 124.87, 132.59, 136.27, 136.81, 144.15, 149.09, 149.15, 157.06, 170.34.

MS (ESI): m/z (%)=511.25 [M+H]$^+$

Example 9-3: Preparation of (1S,5S,6R)-10-((3,5-dichlorophenyl)sulfonyl)-5-(difluoromethyl)-3-(pyridin-2-ylmethyl)-3,10-diazabicyclo[4.3.1]decan-2-one M3

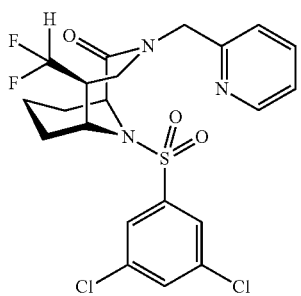

A solution of (1S,5S,6R)-10-((3,5-dichlorophenyl)sulfonyl)-2-oxo-3-(pyridin-2-ylmethyl)-3,10-diazabicyclo[4.3.1]decane-5-carbaldehyde (50 mg, 0.104 mmol) in CH$_2$Cl$_2$ (1 mL) was cooled to 0° C. and then DAST (0.016 mL, 20.0 mg, 0.124 mmol) was added. After 2 h sat. aq. K$_2$CO$_3$ sol. (5 mL) was added to the mixture and extracted with CH$_2$Cl$_2$ (3×25 mL). The collected organic layers were dried over MgSO$_4$ and the solvent was removed under reduced pressure. Column chromatography over SiO$_2$ (Cyclohexane/EtOAc=3/7) afforded the title compound (35.0 mg, 0.0693 mmol, 67%).

$^1$H NMR (400 MHz, CDCl$_3$) δ 1.27-1.30 (m, 1H), 1.47-1.59 (m, 4H), 2.27-2.35 (m, 1H), 2.62-2.76 (m, 1H), 3.30-3.37 (m, 1H), 3.90-3.99 (m, 1H), 4.29-4.35 (m, 1H), 4.58 (d, J=15.2 Hz, 1H), 4.75-4.79 (m, 1H), 5.00 (d, J=15.2 Hz, 1H), 5.58-5.86 (m, 1H), 7.17-7.21 (m, 1H), 7.25-7.29 (m, 1H), 7.53-7.57 (m, 1H), 7.64-7.69 (m, 1H), 7.69-7.72 (m, 2H), 8.50-8.53 (m, 1H).

$^{13}$C NMR (100 MHz, CDCl$_3$) δ 15.16, 28.11, 28.76, 29.66, 48.29, 49.35, 49.37, 56.10, 57.06, 122.15, 122.60, 124.91, 132.90, 136.44, 136.94, 143.61, 149.28, 156.32, 169.86.

MS (ESI): m/z (%)=504.36 [M+H]$^+$

Example 9-4: Preparation of (1S,5S,6R)-10-((3,5-dichlorophenyl)sulfonyl)-5-(fluoromethyl)-3-(pyridin-2-ylmethyl)-3,10-diazabicyclo[4.3.1]decan-2-one M4

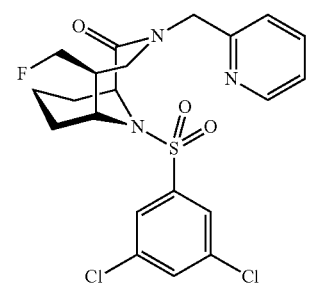

A solution of (1S,5S,6R)-10-((3,5-dichlorophenyl)sulfonyl)-5-(hydroxymethyl)-3-(pyridin-2-ylmethyl)-3,10-diazabicyclo[4.3.1]decan-2-one (25 mg, 0.0520 mmol) in CH$_2$Cl$_2$ (1 mL) was cooled to 0° C. and then DAST (0.016 mL, 20.0 mg, 0.124 mmol) was added. After 2 h sat. aq. K$_2$CO$_3$ sol. (5 mL) was added to the mixture and extracted with CH$_2$Cl$_2$ (3×25 mL). The collected organic layers were dried over MgSO$_4$ and the solvent was removed under reduced pressure. Column chromatography over SiO$_2$ (Cyclohexane/EtOAc=3/7) afforded the title compound (13 mg, 0.0268 mmol, 52%).

R$_f$: 0.29 (Cyclohexane/EtOAc=3:7)

$^1$H NMR (600 MHz, CDCl$_3$) δ 1.40-1.46 (m, 2H), 1.50-1.59 (m, 3H), 2.33 (d, J=13.3 Hz, 1H), 2.49-2.57 (m, 1H), 3.29 (dd, J=14.4, 2.0 Hz, 1H), 3.88 (dd, J=14.3, 10.7 Hz, 1H), 3.99 (t, J=5.7 Hz, 1H), 4.24-4.35 (m, 2H), 4.71 (d, J=152 Hz, 1H), 4.77-4.80 (m, 1H), 4.90 (d, J=15.2 Hz, 1H), 7.17-7.22 (m, 1H), 7.30 (d, J=7.9 Hz, 1H), 7.56-7.58 (m, 1H), 7.67-7.72 (m, 3H), 8.53 (d, J=5.0 Hz, 1H).

$^{13}$C NMR (150 MHz, CDCl$_3$) δ 15.41, 27.90, 28.02, 29.67, 45.01, 45.12, 48.56, 48.60, 51.28, 51.33, 56.14, 57.02, 80.72, 82.46, 83.61, 122.04, 122.51, 123.12, 124.89, 132.78, 133.76, 136.37, 136.91, 143.81, 149.28, 156.63, 170.12.

MS (ESI): m/z (%)=486.28 [M+H]$^+$

Example 9-5: Preparation of (1S,5R,6R)-10-((3,5-dichlorophenyl)sulfonyl)-5-(methoxymethyl)-3-(pyridin-2-ylmethyl)-3,10-diazabicyclo[4.3.1]decan-2-one M5

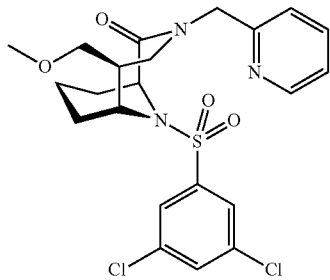

A solution of (1S,5S,6R)-10-((3,5-dichlorophenyl)sulfonyl)-5-(hydroxymethyl)-3-(pyridin-2-ylmethyl)-3,10-diazabicyclo[4.3.1]decan-2-one (14.0 mg, 0.0290 mmol) in DMF (1 mL) was cooled to 0° C. and then NaH (60% dispersion in mineral oil, 2.3 mg, 0.058 mmol) was added and stirred for 20 minutes. CH$_3$I (8.20 mg, 3.6 µL, 0.0.058 mmol) was added. After 16 h at room temperature the solvent was removed under reduced pressure and column chromatography over SiO$_2$ (Cyclohexane/EtOAc=3/7) afforded the title compound (8.5 mg, 0.0171 mmol, 59%) as a yellow oil.

R$_f$: 0.2 (Cyclohexane/EtOAc=3:7)

$^1$H-NMR (600 MHz, CDCl$_3$) δ=1.46 (dt, J=13.3, 5.0 Hz, 1H), 1.52-1.64 (m, 4H), 2.27-2.33 (m, 1H), 2.37 (dtd, J=13.1, 8.6, 7.6, 5.8 Hz, 1H), 2.88 (s, 1H), 2.95 (s, 1H), 3.22-3.31 (m, 5H), 3.76 (dd, J=14.4, 10.8 Hz, 1H), 4.00 (td, J=5.0, 2.4 Hz, 1H), 4.75 (dt, J=6.2, 1.8 Hz, 1H), 4.82 (d, J=15.7 Hz, 1H), 7.39 (s, 1H), 7.45-7.51 (m, 1H), 7.56 (d, J=1.9 Hz, 1H), 7.70 (d, J=1.8 Hz, 2H), 7.90 (t, J=7.5 Hz, 1H), 8.57 (d, J=5.0 Hz, 1H).

$^{13}$C-NMR (150 MHz, CDCl$_3$) δ=1.00, 15.50, 27.94, 28.09, 29.63, 29.66, 36.45, 44.59, 49.94, 52.68, 56.96, 59.00, 73.17, 123.17, 123.26, 124.91, 132.70, 136.27, 143.85, 170.74.

MS (ESI): m/z (%)=498.46 [M+H]$^+$

Example 9-6: Preparation of (1S,5S,6R)-10-((3,5-dichlorophenyl)sulfonyl)-5-(ethoxymethyl)-3-(pyridin-2-ylmethyl)-3,10-diazabicyclo[4.3.1]decan-2-one M6

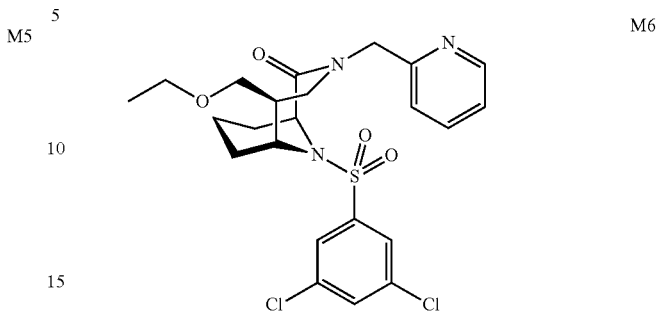

A solution of (1S,5S,6R)-10-((3,5-dichlorophenyl)sulfonyl)-5-(hydroxymethyl)-3-(pyridin-2-ylmethyl)-3,10-diazabicyclo[4.3.1]decan-2-one (25.0 mg, 0.0520 mmol) in THF (1 mL) was cooled to 0° C. and then NaH (60% dispersion in mineral oil, 2.3 mg, 0.058 mmol) was added and stirred for 20 minutes. Iodoethane (8.20 mg, 3.6 µL, 0.0.058 mmol) was added. After 2 h at room temperature the solvent was removed under reduced pressure and column chromatography over SiO$_2$ (Cyclohexane/EtOAc=3/7) afforded the title compound (13.0 mg, 0.0254 mmol, 50%) as a yellow oil.

R$_f$: 0.5 (EtOAc)

$^1$H NMR (600 MHz, CDCl$_3$) δ 1.10-1.14 (m, 3H), 1.41-1.43 (m, 1H), 1.51-1.65 (m, 4H), 2.27-2.34 (m, 2H), 3.20-3.28 (m, 3H), 3.35-3.41 (m, 2H), 3.73 (dd, J=14.2, 10.9 Hz, 1H), 3.91-3.95 (m, 1H), 4.73-4.82 (m, 3H), 7.16-7.20 (m, 1H), 7.27 (d, J=7.9 Hz, 1H), 7.53-7.56 (m, 1H), 7.64-7.71 (m, 3H), 8.52 (d, J=4.8 Hz, 1H).

$^{13}$C NMR (151 MHz, CDCl$_3$) δ 14.95, 15.59, 27.98, 44.57, 49.55, 52.72, 56.14, 57.03, 66.58, 71.06, 121.89, 122.38, 124.94, 132.61, 136.23, 136.94, 144.00, 149.16, 156.92, 170.36.

MS (ESI): m/z (%)=512.24 [M+H]$^+$

VIII. Preparation of Compounds N1-N32 further examples for R$^B$ modifications (N1-N32) are prepared from I6 according to the following synthesis procedure (Scheme N)

Scheme N

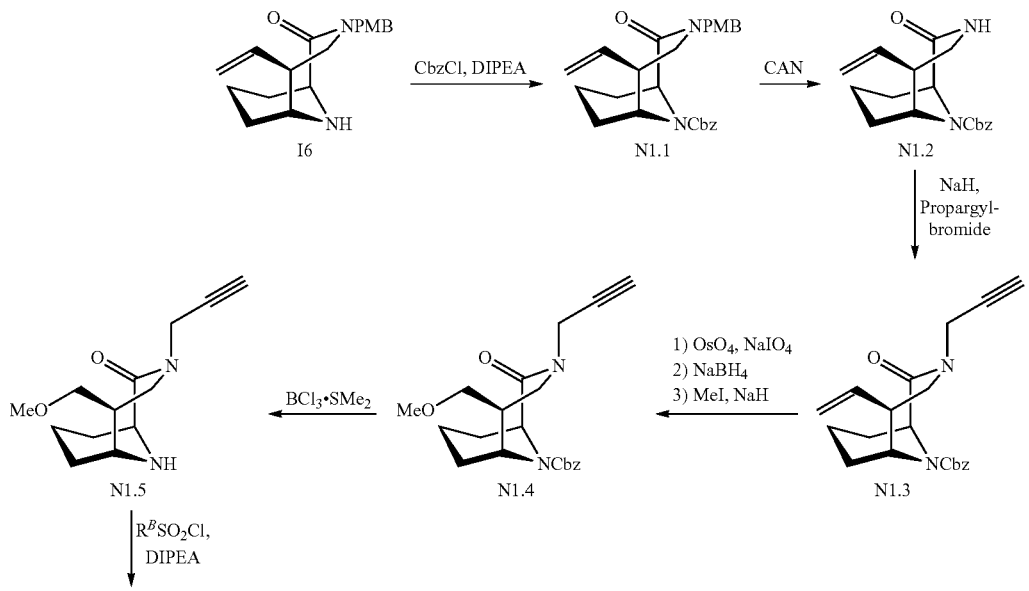

-continued

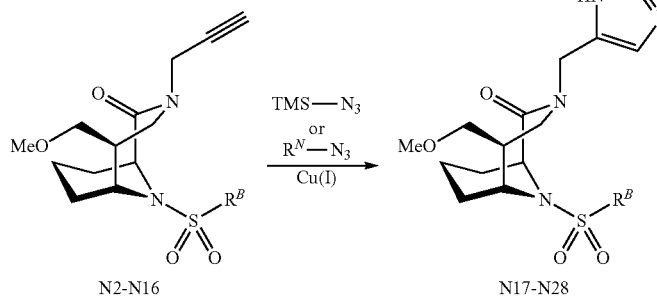

N2-N16 → N17-N28 or N29-N32

Example 10-1: Preparation of (1S,5S,6R)-5-(methoxymethyl)-3-(prop-2-yn-1-yl)-3,10-diazabicyclo[4.3.1]decan-2-one (N1.5)

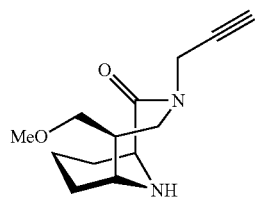

N1.5

Example 10-2: Preparation of (1S,5S,6R)-10-((3-fluorophenyl)sulfonyl)-5-(methoxymethyl)-3-(prop-2-yn-1-yl)-3,10-diazabicyclo[4.3.1]decan-2-one (N2)

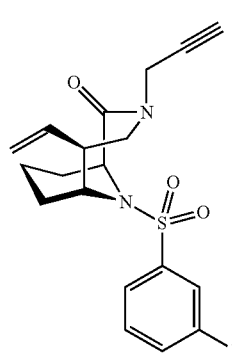

N2

Example 10-3: Preparation of (1S,5S,6R)-10-((3,5-dibromophenyl)sulfonyl)-5-(methoxymethyl)-3-(prop-2-yn-1-yl)-3,10-diazabicyclo[4.3.1]decan-2-one (N3)

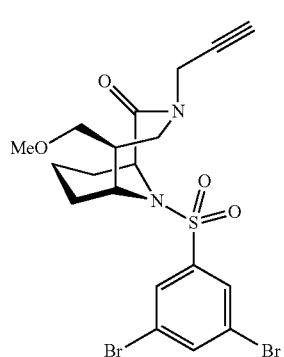

N3

Example 10-4: Preparation of 3-(((1S,5S,6R)-5-(methoxymethyl)-2-oxo-3-(prop-2-yn-1-yl)-3,10-diazabicyclo[4.3.1]decan-10-yl)sulfonyl)benzamide (N4)

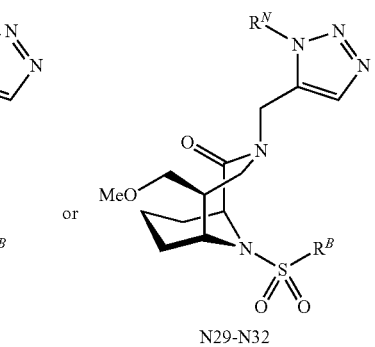

N4

Example 10-5: Preparation of 3-bromo-5-(((1S,5S,6R)-5-(methoxymethyl)-2-oxo-3-(prop-2-yn-1-yl)-3,10-diazabicyclo[4.3.1]decan-10-yl)sulfonyl)benzamide (N5)

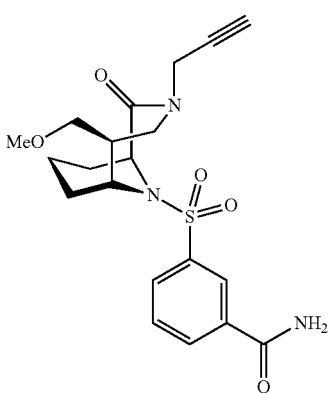

N5

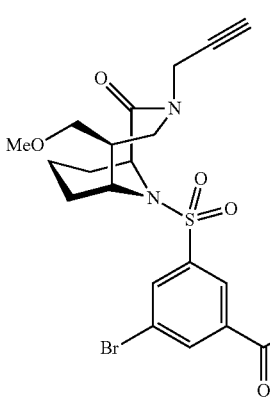

Example 10-6: Preparation of 3-chloro-5-((((1S,5S,6R)-5-(methoxymethyl)-2-oxo-3-(prop-2-yn-1-yl)-3,10-diazabicyclo[4.3.1]decan-10-yl)sulfonyl)benzamide (N6)

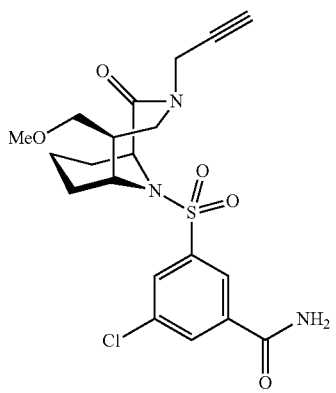

Example 10-7: Prep. of N-(2-bromo-4-((((1S,5S,6R)-5-(methoxymethyl)-2-oxo-3-(prop-2-yn-1-yl)-3,10-diazabicyclo[4.3.1]decan-10-yl)sulfonyl)phenyl)acetamide (N7)

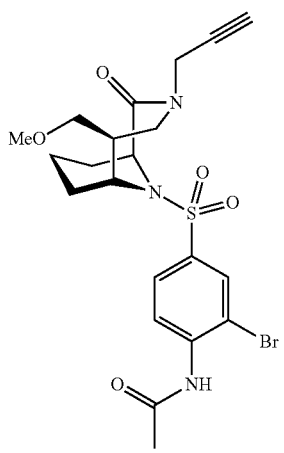

Example 10-8: Prep. of N-(2-chloro-4-((((1S,5S,6R)-5-(methoxymethyl)-2-oxo-3-(prop-2-yn-1-yl)-3,10-diazabicyclo[4.3.1]decan-10-yl)sulfonyl)phenyl)acetamide (N8)

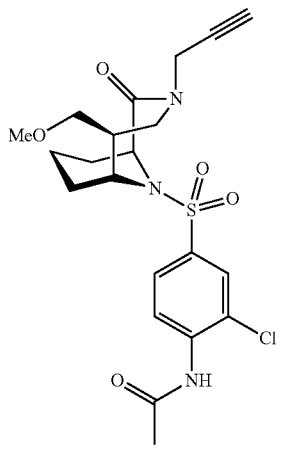

Example 10-9: Preparation of N-(2,6-dichloro-4-((((1S,5S,6R)-5-(methoxymethyl)-2-oxo-3-(prop-2-yn-1-yl)-3,10-diazabicyclo[4.3.1]decan-10-yl)sulfonyl)phenyl)acetamide (N9)

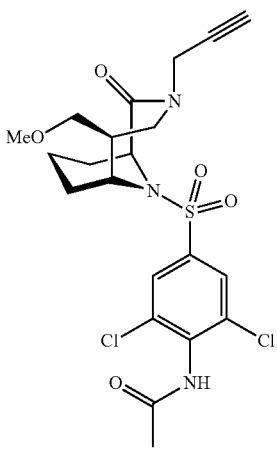

Example 10-10: Preparation of methyl 3-((((1S,5S,6R)-5-(methoxymethyl)-2-oxo-3-(prop-2-yn-1-yl)-3,10-diazabicyclo[4.3.1]decan-10-yl)sulfonyl)benzoate (N10)

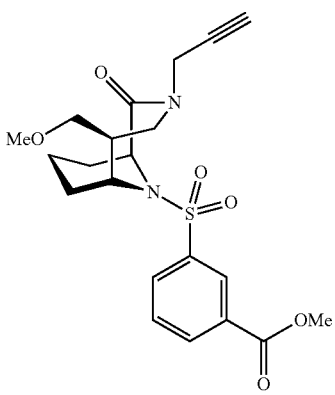

Example 10-11: Preparation of methyl 3-bromo-5-((((1S,5S,6R)-5-(methoxymethyl)-2-oxo-3-(prop-2-yn-1-yl)-3,10-diazabicyclo[4.3.1]decan-10-yl)sulfonyl)benzoate (N11)

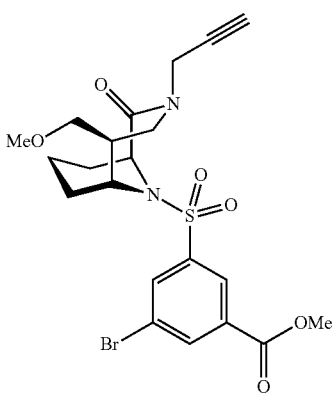

Example 10-12: Preparation of methyl 3-chloro-5-(((1S,5S,6R)-5-(methoxymethyl)-2-oxo-3-(prop-2-yn-1-yl)-3,10-diazabicyclo[4.3.1]decan-10-yl)sulfonyl)benzoate (N12)

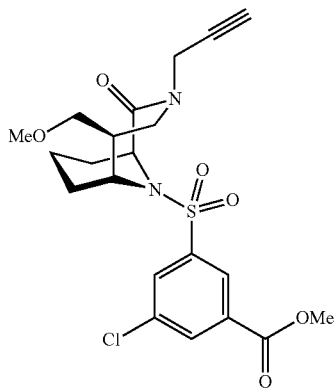

Example 10-13: Preparation of (1S,5S,6R)-5-(methoxymethyl)-3-(prop-2-yn-1-yl)-10-(pyridin-3-ylsulfonyl)-3, 10-diazabicyclo[4.3.1]decan-2-one (N13)

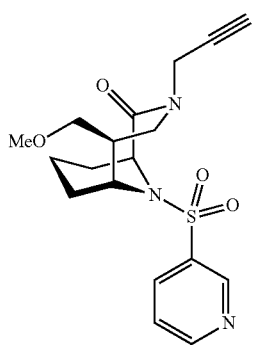

Example 10-14: Preparation of (1S,5S,6R)-5-(methoxymethyl)-10-((6-phenylpyridin-3-yl)sulfonyl)-3-(prop-2-yn-1-yl)-3,10-diazabicyclo[4.3.1]decan-2-one (N14)

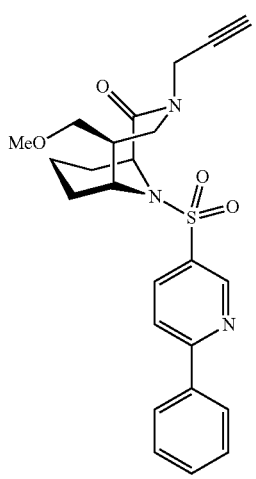

Example 10-15: Preparation of (1S,5S,6R)-5-(methoxymethyl)-3-(prop-2-yn-1-yl)-10-((4-(pyrimidin-2-yl)phenyl)sulfonyl)-3,10-diazabicyclo[4.3.1]decan-2-one (N15)

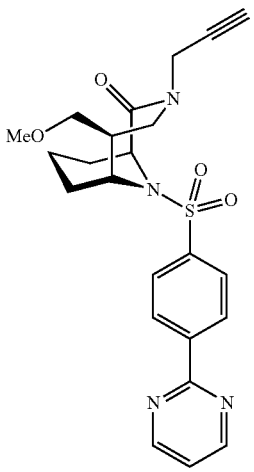

Example 10-16: Preparation of (1S,5S,6R)-10-((1H-benzo[d]imidazol-2-yl)sulfonyl)-5-(methoxymethyl)-3-(prop-2-yn-1-yl)-3,10-diazabicyclo[4.3.1]decan-2-one (N16)

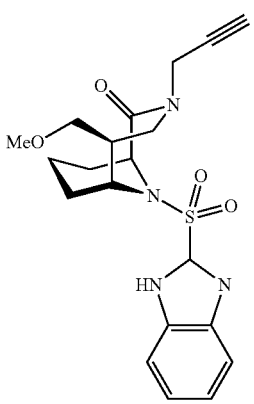

Example 10-17: Preparation of (1S,5S,6R)-3-((1H-1,2,3-triazol-5-yl)methyl)-10-((3-fluorophenyl)sulfonyl)-5-(methoxymethyl)-3,10-diazabicyclo[4.3.1]decan-2-one (N17)

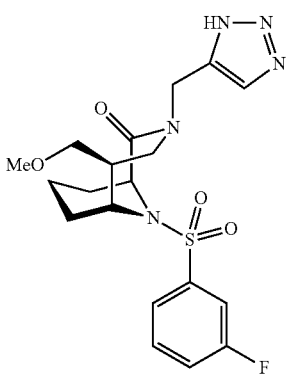

Example 10-18: Preparation of (1S,5S,6R)-3-((1H-1,2,3-triazol-5-yl)methyl)-10-((3,5-dibromophenyl)sulfonyl)-5-(methoxymethyl)-3,10-diazabicyclo[4.3.1]decan-2-one (N18)

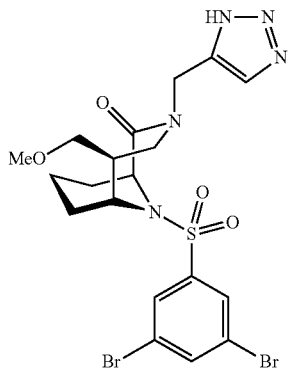

Example 10-19: Preparation of 3-(((1S,5S,6R)-3-((1H-1,2,3-triazol-5-yl)methyl)-5-(methoxymethyl)-2-oxo-3,10-diazabicyclo[4.3.1]decan-10-yl)sulfonyl)benzamide (N19)

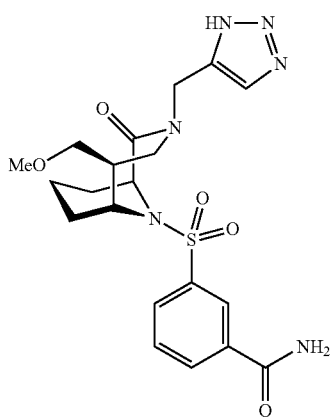

Example 10-20: Preparation of 3-(((1S,5S,6R)-3-((1H-1,2,3-triazol-5-yl)methyl)-5-(methoxymethyl)-2-oxo-3,10-diazabicyclo[4.3.1]decan-10-yl)sulfonyl)-5-bromobenzamide (N20)

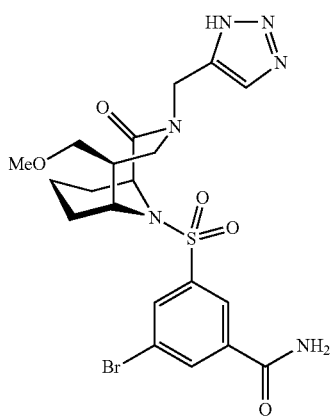

Example 10-21: Preparation of 3-(((1S,5S,6R)-3-((1H-1,2,3-triazol-5-yl)methyl)-5-(methoxymethyl)-2-oxo-3,10-diazabicyclo[4.3.1]decan-10-yl)sulfonyl)-5-chlorobenzamide (N21)

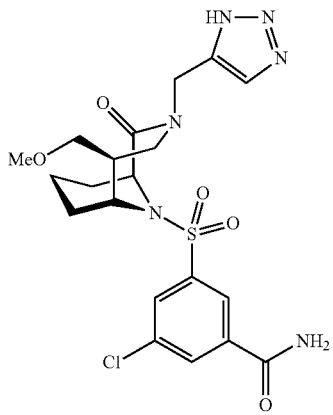

Example 10-22: Preparation of N-(4-(((1S,5S,6R)-3-((1H-1,2,3-triazol-5-yl)methyl)-5-(methoxymethyl)-2-oxo-3,10-diazabicyclo[4.3.1]decan-10-yl)sulfonyl)-2-bromophenyl)acetamide (N22)

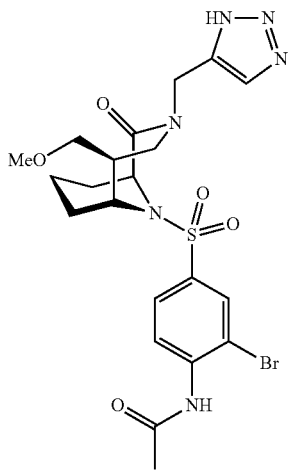

Example 10-23: Preparation of N-(4-(((1S,5S,6R)-3-((1H-1,2,3-triazol-5-yl)methyl)-5-(methoxymethyl)-2-oxo-3,10-diazabicyclo[4.3.1]decan-10-yl)sulfonyl)-2-chlorophenyl)acetamide (N23)

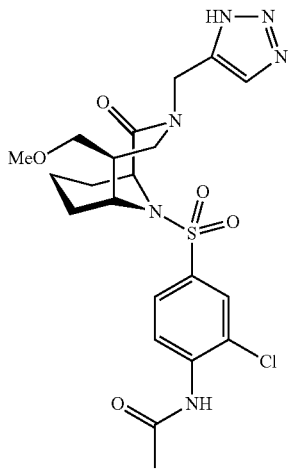

Example 10-24: Preparation of N-(4-(((1S,5S,6R)-3-((1H-1,2,3-triazol-5-yl)methyl)-5-(methoxymethyl)-2-oxo-3,10-diazabicyclo[4.3.1]decan-10-yl)sulfonyl)-2,6-dichlorophenyl)acetamide (N24)

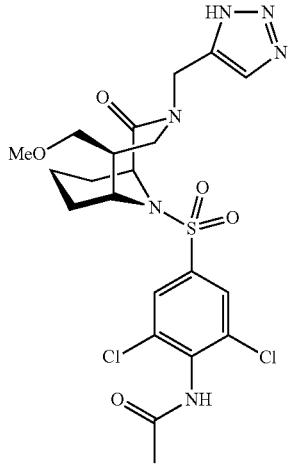

Example 10-25: Preparation of (1S,5S,6R)-3-((1H-1,2,3-triazol-5-yl)methyl)-5-(methoxymethyl)-10-(pyridin-3-ylsulfonyl)-3,10-diazabicyclo[4.3.1]decan-2-one (N25)

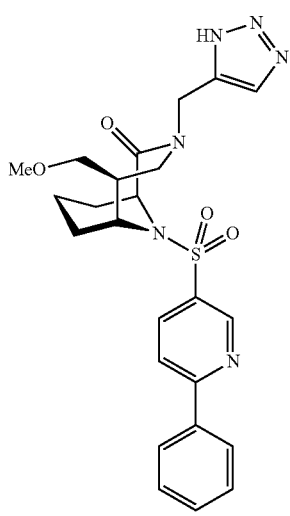

Example 10-26: Preparation of (1S,5S,6R)-3-((1H-1,2,3-triazol-5-yl)methyl)-5-(methoxymethyl)-10-((6-phenylpyridin-3-yl)sulfonyl)-3,10-diazabicyclo[4.3.1]decan-2-one (N26)

Example 10-27: Preparation of (1S,5S,6R)-3-((1H-1,2,3-triazol-5-yl)methyl)-5-(methoxymethyl)-10-((4-(pyrimidin-2-yl)phenyl)sulfonyl)-3,10-diazabicyclo[4.3.1]decan-2-one (N27)

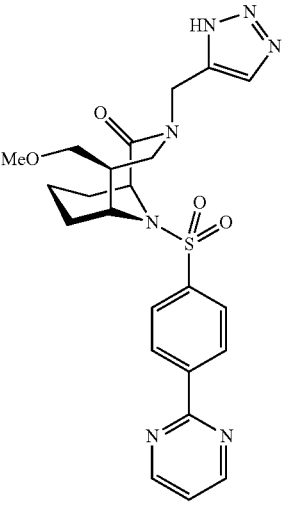

Example 10-28: Preparation of (1S,5S,6R)-3-((1H-1,2,3-triazol-5-yl)methyl)-10-((1H-benzo[d]imidazol-2-yl)sulfonyl)-5-(methoxymethyl)-3,10-diazabicyclo[4.3.1]decan-2-one (N28)

Example 10-29: Preparation of (1S,5R,6R)-10-((3-fluorophenyl)sulfonyl)-5-(methoxymethyl)-3-((1-phenyl-1H-1,2,3-triazol-5-yl)methyl)-3,10-diazabicyclo[4.3.1]decan-2-one (N29)

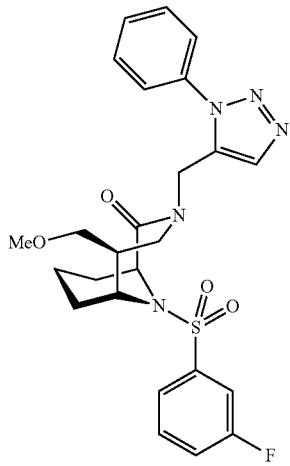

N29

Example 10-30: Preparation of (1S,5S,6R)-3-((1-benzyl-1H-1,2,3-triazol-5-yl)methyl)-10-((3-fluorophenyl)sulfonyl)-5-(methoxymethyl)-3,10-diazabicyclo[4.3.1]decan-2-one (N30)

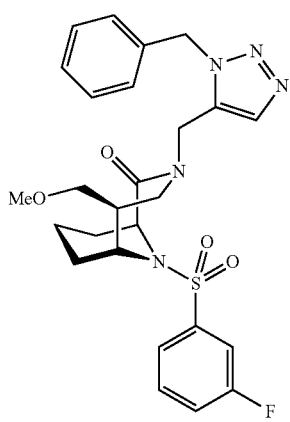

N30

Example 10-12: Preparation of (1S,5S,6R)-3-((1-benzoyl-1H-1,2,3-triazol-5-yl)methyl)-10-((3-fluorophenyl)sulfonyl)-5-(methoxymethyl)-3,10-diazabicyclo[4.3.1]decan-2-one (N31)

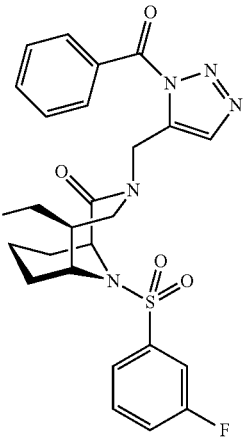

N31

Example 10-12: Preparation of (1S,5S,6R)-10-((3-fluorophenyl)sulfonyl)-5-(methoxymethyl)-3-((1-(phenylsulfonyl)-1H-1,2,3-triazol-5-yl)methyl)-3,10-diazabicyclo[4.3.1]decan-2-one (N32)

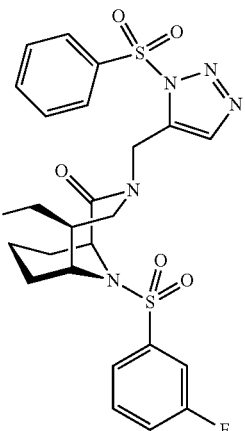

N32

Example 11: Fluorescence Polarization (FP) Assays

In-vitro fluorescence polarization assays were performed to determine the binding affinities for FKBP51 and 52 according to a literature procedure (Kozany, C.; Marz, A.; Kress, C.; Hausch, F., Fluorescent probes to characterise FK506-binding proteins. *Chembiochem* 2009, 10, (8), 1402-10).

For fluorescence polarization assays the fluorescent ligand 2b was dissolved in HEPES (20 mm, pH 8), Triton-X100 (0.01%), at double the concentration required for the final sample. The target protein was also diluted in this assay buffer at double the highest concentration required for the final sample. This protein stock was used for a 1:1 serial dilution.

The fluorescent ligand 2b was diluted in assay buffer to a concentration double the final concentration (20 nM 2b). The inventive compound was dissolved in DMSO to reach a 100-times concentrated stock solution. This was used for a 1:1 serial dilution in DMSO. Every sample of this serial dilution was diluted by a factor of 50 in assay buffer supplemented with ligand 2b to achieve a 2× concentrated mixture of ligand 2b and the inventive compound. To this competitive ligand double the protein concentration for 2b assay: FKBP51FK1 560 nM (2×280 nM) or FKBP52FK1 800 nM (2×400 nM) diluted in assay buffer was added.

The samples were transferred to black 384-well assay plates (No.: 3575; Corning Life Sciences). After incubation at room temperature for 30 min the fluorescence anisotropy was measured (GENios Pro, Tecan, Männedorf, Switzerland) by using an excitation filters of 485/20 nm and emission filters of 535/25 nm. The binding assays were performed in duplicates in the plate format.

The competition curves were analyzed by using Sigma-Plot9. Data were fitted to a four parameter logistic curve to deduce the $IC_{50}$ values. For the analysis of $K_1$ values, data were fitted to the following equation (Z. X. Wang, FEBS Lett. 1995, 360, 111-114).

$$A=(A_{max}-A_{min})/[L]_t \times(([L]_t\times((2\times((K_{lig}+K_{comp}+[L]_t+[I]_t-[R]_t)^2-3\times(K_{comp}\times([L]_t-[R]_t)+K_{lig}\times([I]_t-[R]_t)+K_{lig}\times K_{comp}))^{\wedge}0.5\times COS(ARCCOS((-2\times(K_{lig}+K_{comp}+[L]_t+[I]_t-[R]_t)^{\wedge}3+9\times(K_{lig}+K_{comp}+[L]_t+[I]_t-[R]_t)\times(K_{comp}\times([L]_t-[R]_t)+K_{lig}\times([I]_t-[R]_t)+K_{lig}\times K_{comp})-27\times(-1\times K_{lig}\times K_{comp}\times[R]_t))/(2\times(((K_{lig}+K_{comp}+[L]_t+[I]_t-[R]_t)^2-3\times(K_{comp}\times([L]_t-[R]_t)+K_{lig}\times([I]_t-[R]_t)+K_{lig}\times K_{comp}))^{\wedge}3)^{\wedge}0.5)))/3))-(K_{lig}+K_{comp}+[L]_t+[I]_t-[R]_t)))/((3\times K_{lig})+((2\times((K_{lig}+K_{comp}+[L]_t+[I]_t-[R]_t)^2-3\times(K_{comp}\times([L]_t-[R]_t)+K_{lig}\times([I]_t-[R]_t)+K_{lig}\times K_{comp}))^{\wedge}0.5\times COS(ARCCOS((-2\times(K_{lig}+K_{comp}+[L]_t+[I]_t-[R]_t)^{\wedge}3+9\times(K_{lig}+K_{comp}+[L]_t+[I]_t-[R]_t)\times(K_{comp}\times([L]_t-[R]_t)+K_{lig}\times([I]_t-[R]_t)+K_{lig}\times K_{comp})-27\times(-1\times K_{lig}\times K_{comp}\times[R]_t))/(2\times(((K_{lig}+K_{comp}+[L]_t+[I]_t-[R]_t)^2-3\times(K_{comp}\times([L]_t-[R]_t)+K_{lig}\times([I]_t-[R]_t)+K_{lig}\times K_{comp}))^{\wedge}3)^{\wedge}0.5)))/3))-(K_{lig}+K_{comp}+[L]_t+[I]_t-[R]_t)))+A_{min}$$

In this equation $K_{lig}$ and $K_{comp}$ stand for the $K_d$ values of the used tracer or competing inhibitor, $[I]_t$ is referring to the total concentration of the titrated inhibitor.

These assays revealed that substitutents $R^C$ significantly increased the affinity to FKBP51/52 compared to known FKBP51 ligands (Ref.1-Ref.4). Table 1 summarize the binding data of exemplary compounds.

The compounds B3-N32 and Ref. 1-Ref. 4 are FKBP51/52 inhibitors of which Ki values are:

| | |
|---|---|
| $K_i \leq 0.1\ \mu M$ | ++++ |
| $0.1\ \mu M < K_i \leq 0.5\ \mu M$ | +++ |
| $0.5\ \mu M < K_i \leq 1\ \mu M$ | ++ |
| $1\ \mu M < K_i \leq 5\ \mu M$ | + |
| $5\ \mu M < K_i$ | ○ |

TABLE 1

Chemical compounds according to formula (I) tested for binding to the FK506-binding domain of FKBP51/52 using fluorescence polarization assay (Kozany et al, ChemBioChem 2009, 10, 1402)

| Compound | FKBP51 $K_i$ [μM] | FKBP52 $K_i$ [μM] |
|---|---|---|
| B3 | ++++ | ++++ |
| B4&B5 | +++ | ++++ |
| B6 | ++++ | ++++ |
| B7 | ++++ | ++++ |
| B8 | +++ | +++ |
| B9 | +++ | +++ |
| B11 | +++ | +++ |
| B12 | +++ | +++ |
| B13 | ++++ | +++ |
| B14 | ++++ | +++ |
| B15 | ++++ | ++++ |
| C1 | ++++ | ++++ |
| C2(C2a/b) | ++++ | ++++ |
| C3 | +++ | +++ |
| D3 | ++++ | ++++ |
| D4 | ++++ | ++++ |
| D5 | ++++ | ++++ |
| D6 | ++++ | ++++ |
| D7 | ++++ | ++++ |
| D8 | ++++ | ++++ |
| G6 | ++ | +++ |
| H1.2 | + | + |
| H1.3 | ++ | ++ |
| H1.4 | + | + |
| H2.1 | +++ | +++ |
| H2.2 | ++ | ++ |
| H2.3 | ++++ | +++ |
| I8 | ++ | ++ |
| J1 | +++ | +++ |
| J2 | ++ | ++ |
| J3 | ++ | ++ |

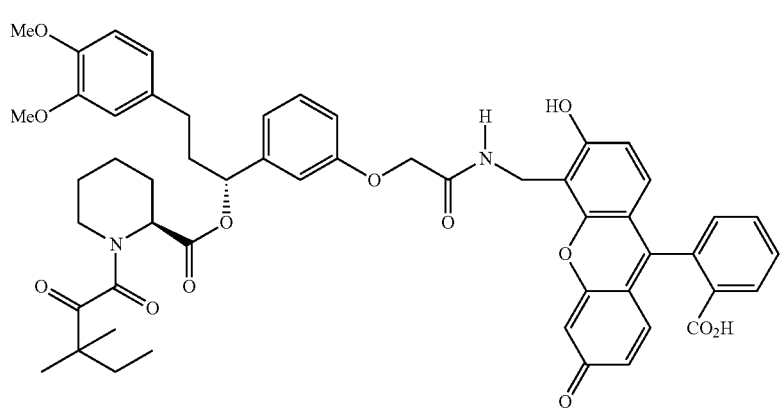

2b

TABLE 1-continued

Chemical compounds according to formula (I) tested for binding to the FK506-binding domain of FKBP51/52 using fluorescence polarization assay (Kozany et al, ChemBioChem 2009, 10, 1402)

| Compound | FKBP51 $K_i$ [µM] | FKBP52 $K_i$ [µM] |
|---|---|---|
| J4 | +++ | +++ |
| J5 | ++ | ++ |
| J6 | +++ | ++ |
| J7 | ++ | ++ |
| J8 | ++++ | ++++ |
| J9 | +++ | +++ |
| J10 | +++ | +++ |
| J11 | +++ | +++ |
| J12 | +++ | +++ |
| J13 | ++++ | ++++ |
| J14 | +++ | +++ |
| J15 | +++ | +++ |
| J16 | +++ | +++ |
| J17 | + | + |
| J19 | +++ | +++ |
| K4 | ++++ | ++++ |
| K5 | ++++ | ++++ |
| K6 | ++++ | ++++ |
| K7 | +++ | +++ |
| K8 | +++ | +++ |
| K9 | +++ | +++ |
| K10 | +++ | +++ |
| K11 | +++ | +++ |
| K12 | ++ | ++ |
| K13 | ++ | ++ |
| K15 | +++ | +++ |
| K16 | ++++ | ++++ |
| K17 | +++ | +++ |
| K18 | +++ | +++ |
| K19 | +++ | +++ |
| K20 | +++ | +++ |
| K21 | +++ | +++ |
| K22 | ++++ | ++++ |
| K23 | ++ | ++ |
| K24 | ++++ | ++++ |
| K25 | ++++ | ++++ |
| K26 | +++ | +++ |
| K27 | +++ | +++ |
| K28 | ++++ | ++++ |
| K29 | ++++ | ++++ |
| M1 | ++++ | ++++ |
| M2 | ++++ | ++++ |
| M3 | ++++ | ++++ |
| M4 | ++++ | ++++ |
| M5 | ++++ | ++++ |
| M6 | ++++ | ++++ |
| N2 | +++ | +++ |
| N3 | +++ | +++ |
| N4 | +++ | +++ |
| N5 | +++ | +++ |
| N6 | +++ | +++ |
| N7 | +++ | +++ |
| N8 | +++ | +++ |
| N9 | +++ | +++ |
| N10 | +++ | +++ |
| N11 | +++ | +++ |
| N12 | +++ | +++ |
| N13 | ++ | ++ |
| N14 | +++ | +++ |
| N15 | +++ | +++ |
| N16 | +++ | +++ |
| N17 | ++++ | ++++ |
| N18 | ++++ | ++++ |
| N19 | ++++ | ++++ |
| N20 | ++++ | ++++ |
| N21 | ++++ | ++++ |
| N22 | ++++ | ++++ |
| N23 | ++++ | ++++ |
| N24 | ++++ | ++++ |
| N25 | ++++ | ++++ |
| N26 | ++++ | ++++ |
| N27 | ++++ | ++++ |
| N28 | ++++ | ++++ |
| N29 | +++ | +++ |
| N30 | +++ | +++ |
| N31 | +++ | +++ |
| N32 | +++ | +++ |
| Ref. 1 | + | + |
| Ref. 2 | + | + |
| Ref. 3 | + | + |
| Ref. 4 | ○ | ○ |

Reference compounds Ref.1-Ref. 4 and FK506 have the following structures:

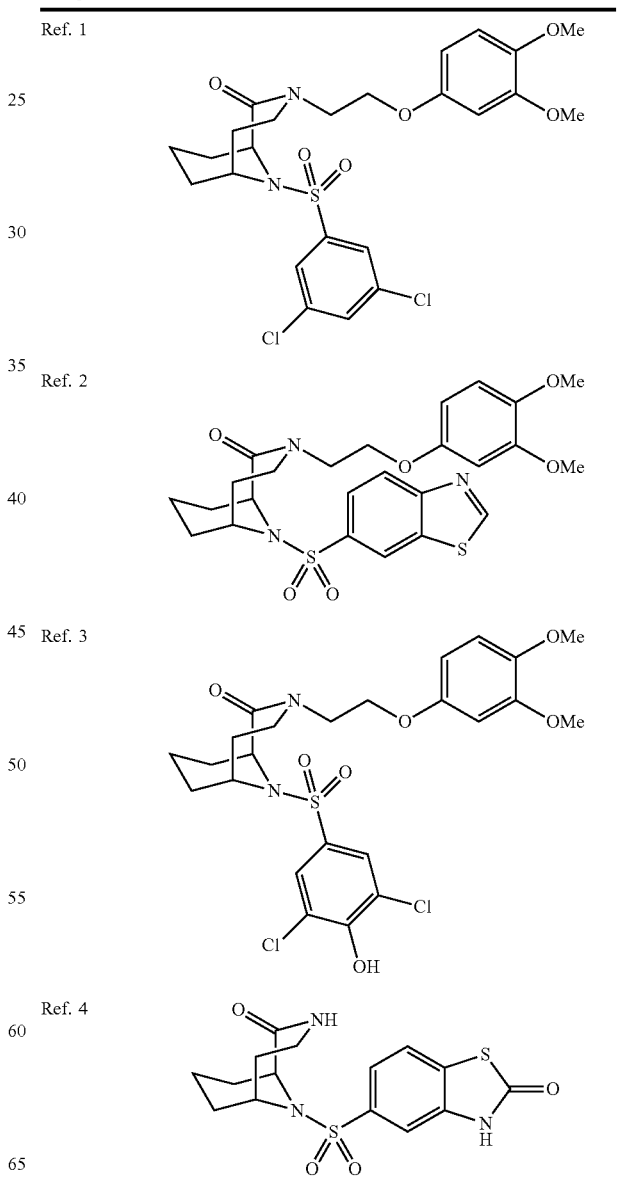

| Compound | Structure |
|---|---|
| FK506 | (structure shown) |

Example 12: N2a Cellular Assay

At day one N2a cells were plated into 24-well plates with cover slips (pretreated with polylysine) at a density of 35,000 cells/well and cultured with DMEM (incl. FCS 10% and Pen/Strep 1%) for 24 h. Next, cells were transfected with 80 ng expression plasmids encoding Venus as well as 720 ng pRK5 (mock transfection) in a total volume of 500 µl starvation media containing different concentrations of compounds or DMSO for 36 h (media without FCS; induction of neurite outgrowth). Therefore media was removed and replaced by 400 µl DMEM (empty). Next an equivalent volume of plasmids were given to 50 µl OPTIMEM and incubated for 5 min at RT. Additionally 1.5 µl Lipofectamine 2000 was separately dissolved in 50 µl OPTIMEM. After 5 min both solutions (plasmids and Lipofectamine 2000 containing media) were combined and incubated again for another 20 min. After that 100 µl of this mixture was given to 400 µl media per well. (See also protocol of the provider—Life Technologies).

On the next day cells were washed with PBS and incubated for 30 min with 300 µl PFA (4%) and sucrose (5%) to fix cells. After fixation cells were washed three times, mounted onto microscope slides using 4 µl Vectashield (mounting media) and analyzed by fluorescence microscopy. Each bar represents the mean of the neurite length of 30-50 cells after the indicated treatment (FIG. 1).

FK506 was included (see FIG. 1 (c)). None of the Reference compounds 1-4 are good enough that a cellular N2a experiment would be warranted.

The invention claimed is:
1. Compound of the general formula (I):

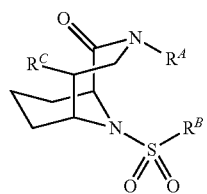

(I)

wherein
$R^A$ represents —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_7$H$_{15}$, —C$_8$H$_{17}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —CH$_2$OH, —C$_2$H$_4$OH, —C$_3$H$_6$OH, —C$_4$H$_8$OH, —CH(CH$_3$)—C$_2$H$_4$OH, —C$_5$H$_{10}$H, —CH$_2$OCH$_3$, —C$_2$H$_4$OCH$_3$, —C$_3$H$_6$OCH$_3$, —C$_4$H$_8$OCH$_3$, —CH(CH$_3$)—C$_2$H$_4$OCH$_3$, —C$_5$H$_{10}$CH$_3$, —CH$_2$NH$_2$, —C$_2$H$_4$NH$_2$, —C$_3$H$_6$NH$_2$, —C$_4$H$_8$NH$_2$, —CH(CH$_3$)—C$_2$H$_4$NH$_2$, —C$_5$H$_{10}$NH$_2$, —C$_2$H$_4$NHCH$_3$, —C$_2$H$_4$N(CH$_3$)$_2$, —C$_2$H$_4$N(CH$_3$)$_2$, —C$_2$H$_4$NHCH(CH$_3$)$_2$, —C$_2$H$_4$NH(CH$_2$CH$_3$), —C$_2$H$_4$N(CH$_2$CH$_3$)$_2$, —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$, —CH=CH—C$_2$H$_5$, —CH$_2$—C(CH$_3$)=CH$_2$, —CH(CH$_3$)—CH=CH, —CH=C(CH$_3$)$_2$, —C(CH$_3$)=CH—CH$_3$, —CH=CH—CH=CH$_2$, —C$_3$H$_6$—CH=CH$_2$, —C$_2$H$_4$—CH=CH—CH$_3$, —CH$_2$—CH=CH—C$_2$H$_5$, —CH=CH—C$_3$H$_7$, —CH$_2$—CH=CH—CH=CH$_2$, —CH=CH—CH=CH—CH$_3$, —CH=CH—CH$_2$—CH=CH$_2$, —C(CH$_3$)=CH—CH=CH$_2$, —CH=C(CH$_3$)—CH=CH$_2$, —CH=CH—C(CH$_3$)=CH$_2$, —C$_2$H$_4$—C(CH$_3$)=CH$_2$, —CH$_2$—CH(CH$_3$)—CH=CH$_2$, —CH(CH$_3$)—CH$_2$—CH=CH$_2$, —CH$_2$—CH=C(CH$_3$)$_2$, —CH$_2$—C(CH$_3$)=CH—CH$_3$, —CH(CH$_3$)—CH=CH—CH$_3$, —CH=CH—CH(CH$_3$)$_2$, —CH=C(CH$_3$)—C$_2$H$_5$, —C(CH$_3$)=CH—C$_2$H$_5$, —C(CH$_3$)=C(CH$_3$)$_2$, —C(CH$_3$)$_2$—CH=CH$_2$, —CH(CH$_3$)—C(CH$_3$)=CH$_2$, —C(CH$_3$)$_2$—CH=CH—CH$_2$, —CH=C(CH$_3$)—CH=CH$_2$, —CH=C(CH$_3$)—CH=CH$_2$, —CH(CH$_3$)—CH=CH$_2$, —CH$_2$—CH=C(CH$_3$)—C$_2$H$_5$, —CH$_2$—C(CH$_3$)=CH—C$_2$H$_5$, —CH(CH$_3$)—CH=CH—C$_2$H$_5$, —CH=CH—CH$_2$—CH(CH$_3$)$_2$, —CH=CH—CH(CH$_3$)—C$_2$H$_5$, —CH=C(CH$_3$)—C$_3$H$_7$, —C(CH$_3$)=CH—C$_3$H$_7$, —CH$_2$—CH(CH$_3$)—C(CH$_3$)=CH$_2$, —C[C(CH$_3$)$_3$]=CH$_2$, —CH(CH$_3$)—CH$_2$—C(CH$_3$)=CH$_2$, —CH(CH$_3$)—CH(CH$_3$)—CH=CH$_2$, —CH=CH—C$_2$H$_4$—CH=CH$_2$, —CH$_2$—C(CH$_3$)$_2$—CH=CH$_2$, —C(CH$_3$)$_2$—CH$_2$—CH=CH$_2$, —CH$_2$—C(CH$_3$)=C(CH$_3$)$_2$, —CH(CH$_3$)—CH=C(CH$_3$)$_2$, —C(CH$_3$)$_2$—CH=CH—CH$_3$, —CH=CH—CH$_2$—CH=CH—CH$_3$, —CH(CH$_3$)—C(CH$_3$)=CH—CH$_3$, —CH=C(CH$_3$)—CH(CH$_3$)$_2$, —C(CH$_3$)=CH—CH(CH$_3$)$_2$, —CH=CH—C(CH$_3$)$_3$, —C(CH$_3$)$_2$—C(CH$_3$)=CH$_2$, —CH(C$_2$H$_5$)—C(CH$_3$)=CH$_2$, —C(CH$_3$)(C$_2$H$_5$)—CH=CH$_2$, —CH(CH$_3$)—C(C$_2$H$_5$)=CH$_2$, —CH$_2$—C(C$_3$H$_7$)=CH$_2$, —CH$_2$—C(C$_2$H$_5$)=CH—CH$_3$, —CH —(C₂H₅)—CH=CH—CH₃, —C(C₄H₉)=CH₂, —C(C₃H₇)=CH—CH₃, —C(C₂H₅)=CH—C₂H₅, —C(C₂H₅)=C(CH₃)₂, —C[CH(CH₃)(C₂H₅)]=CH₂, —C[CH₂—CH(CH₃)₂]=CH₂, —C₂H₄—CH=CH—CH=CH₂, —CH₂—CH=CH—CH₂—CH=CH₂, —C₃H₆—C=C—CH₃, —CH₂—CH=CH—CH=CH—CH₃, —CH=CH—CH=CH—C₂H₅, —CH₂—CH=CH—C(CH₃)=CH₂, —CH₂—CH=C(CH₃)—CH=CH₂, —CH₂—C(CH₃)=CH—CH=CH₂, —CH(CH₃)—CH₂—C≡CH, —CH(CH₃)—CH=CH—CH=CH₂, —CH=CH—CH₂—C(CH₃)=CH₂, —CH(CH₃)—C≡C—CH₃, —CH=CH—CH(CH₃)—CH=CH₂, —CH=C(CH₃)—CH₂—CH=CH₂, —C₂H₄—CH(CH₃)—C≡CH, —C(CH₃)=CH—CH₂—CH=CH₂, —CH=CH—CH=C(CH₃)₂, —CH₂—CH(CH₃)—CH₂—C≡CH, —CH=CH—C(CH₃)=CH—CH₃, —CH=C(CH₃)—CH=CH—CH₃, —CH₂—CH(CH₃)—C≡CH, —C(CH₃)=CH—CH=CH—CH₃, —CH=C(CH₃)—C(CH₃)=CH₂, —C(CH₃)=CH—C(CH₃)=CH₂, —C(CH₃)=C(CH₃)—CH=CH₂, —CH=CH—CH=CH—CH=CH₂, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —C₄H₈—C≡CH, —C₂H₄—C≡C—C₂H₅, —CH₂—C≡C—C₃H₇, —C≡C—C₄H₉, —C≡C—C(CH₃)₃, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —C≡C—CH₂—CH(CH₃)₂, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —CH₂-Ph, —CH₂-L₁-R^D,

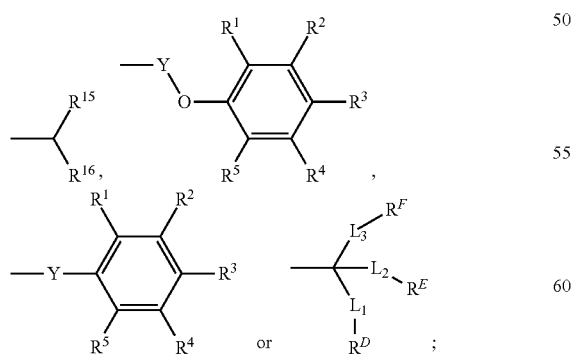

Y represents CH₂, —CH₂—CH₂—, —CH₂—CH₂—CH₂—, —CH=CH—, —CH=CH—CH₂—, —CH₂—CH=CH—, —CH(CH₃)—, —CH(CH₃)—CH₂—, —CH₂—CH(CH₃)—CH₂—, —CH₂—CH(CH₃)—CH₂—, or —CH₂—O—CH₂—;

R^D represents: R²² or

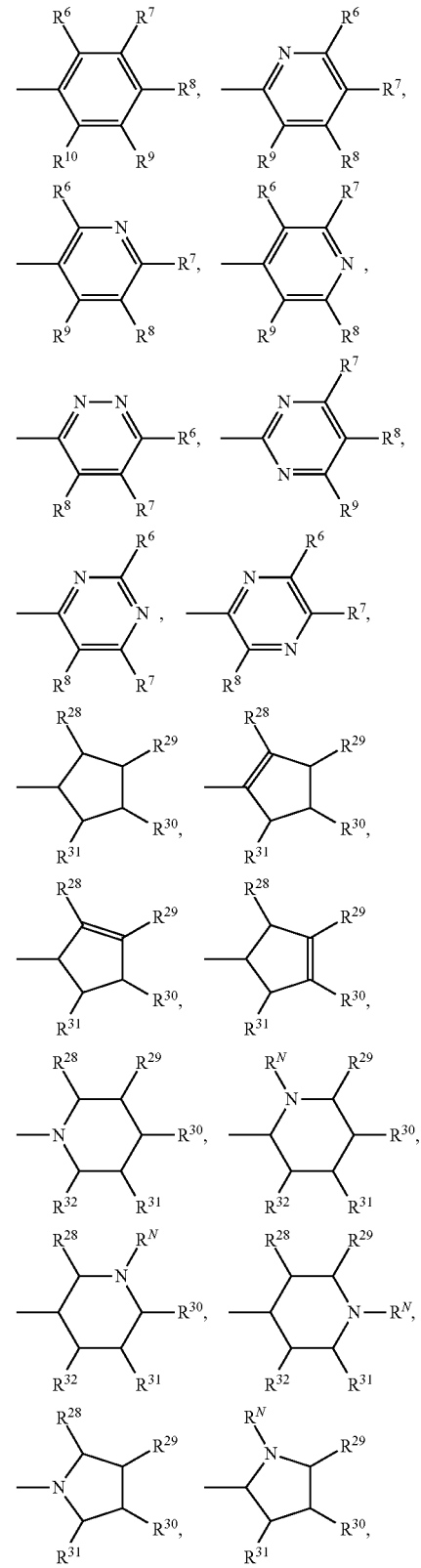

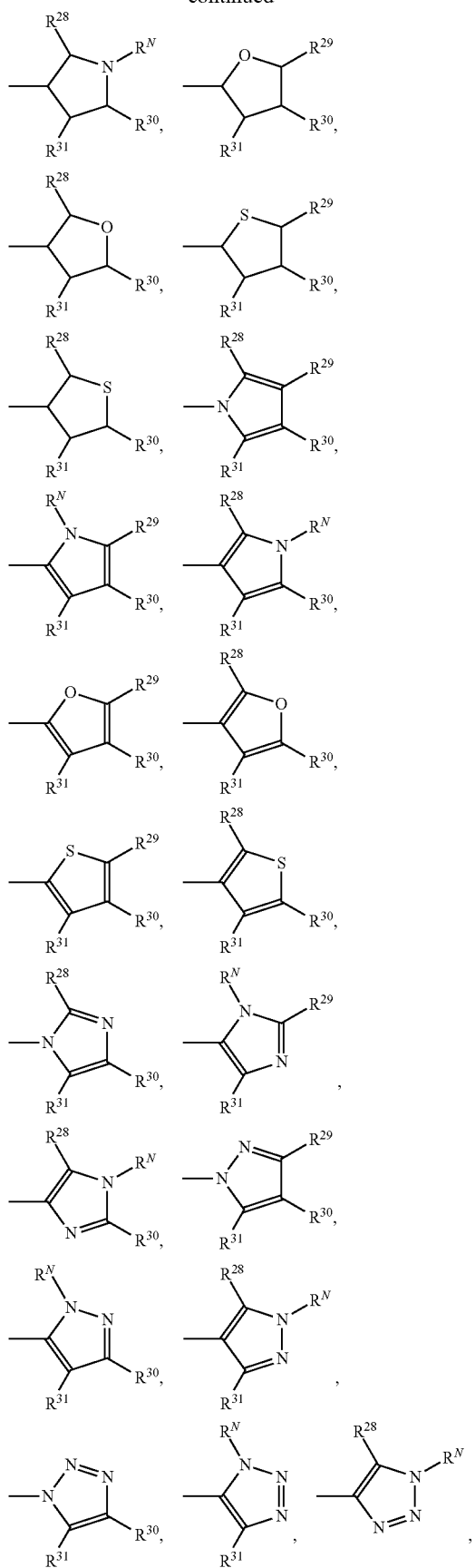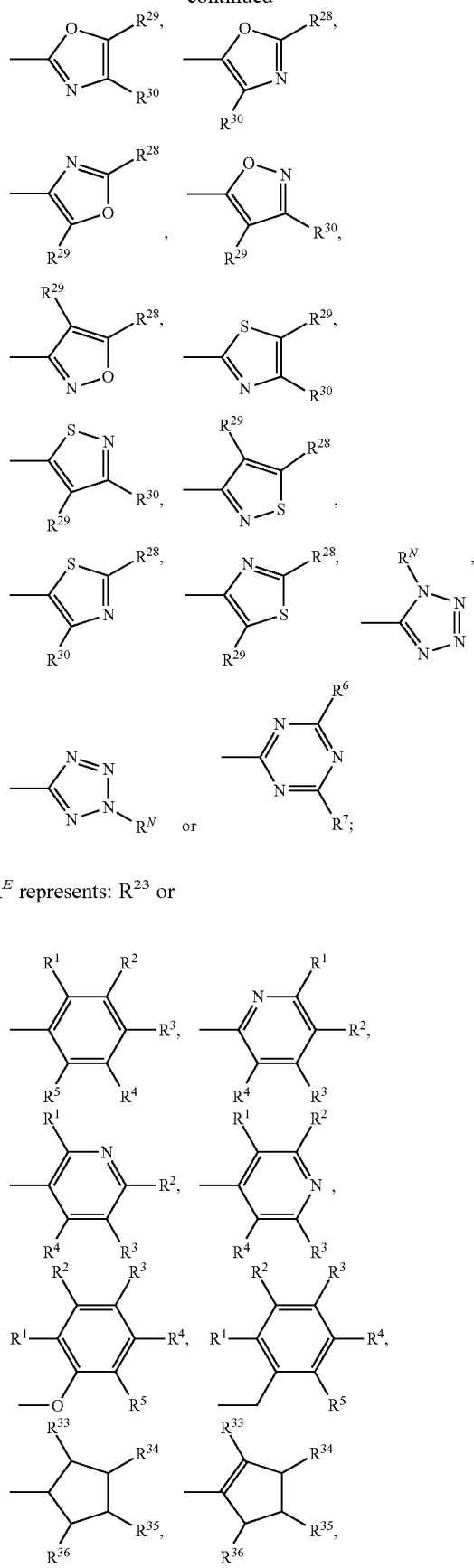
$R^E$ represents: $R^{23}$ or

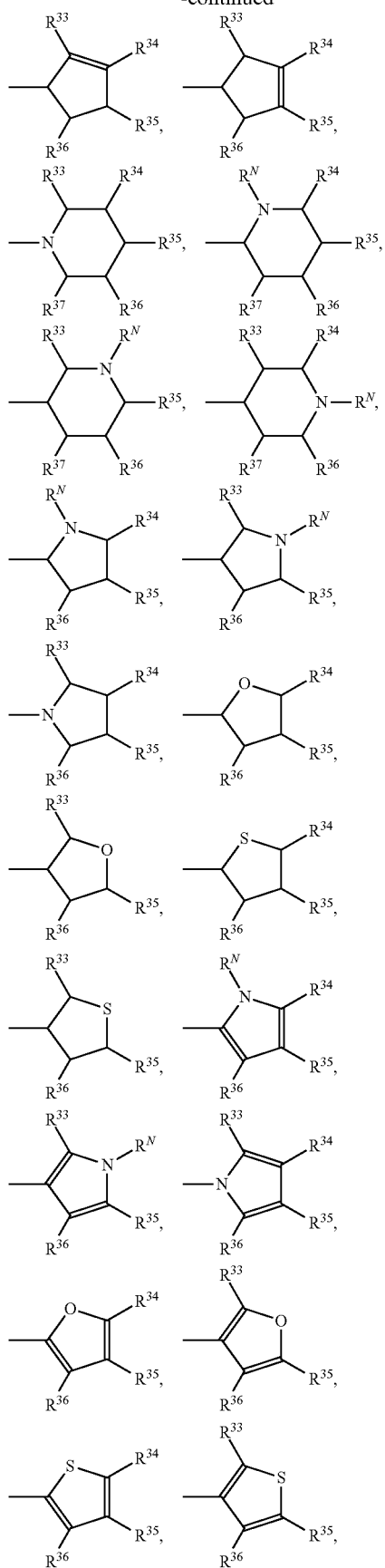
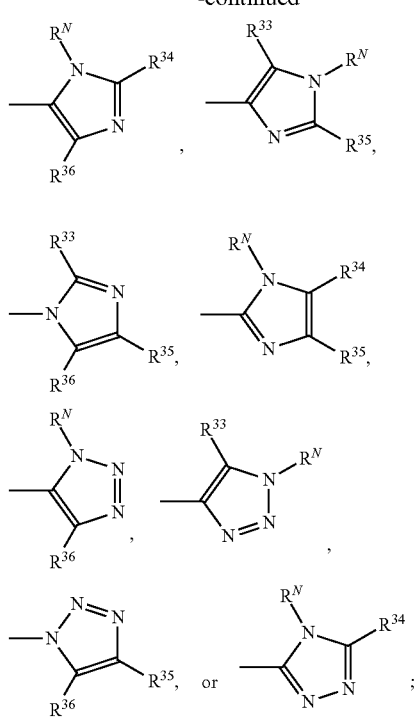
$R^F$ represents: $R^{24}$ or
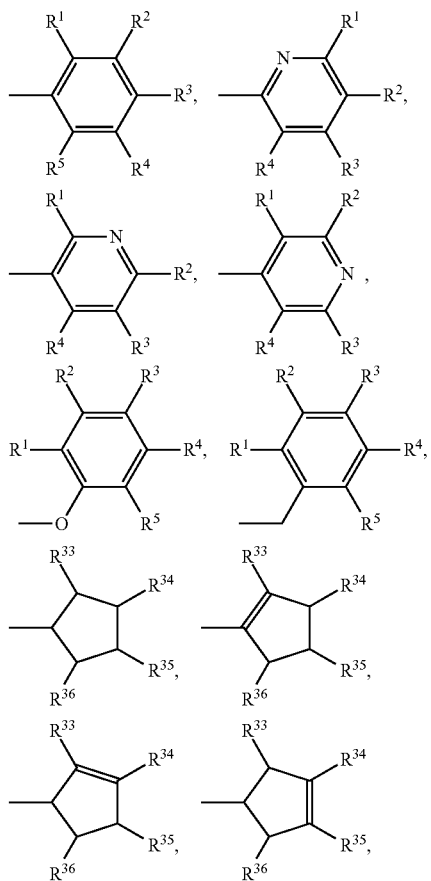

-continued

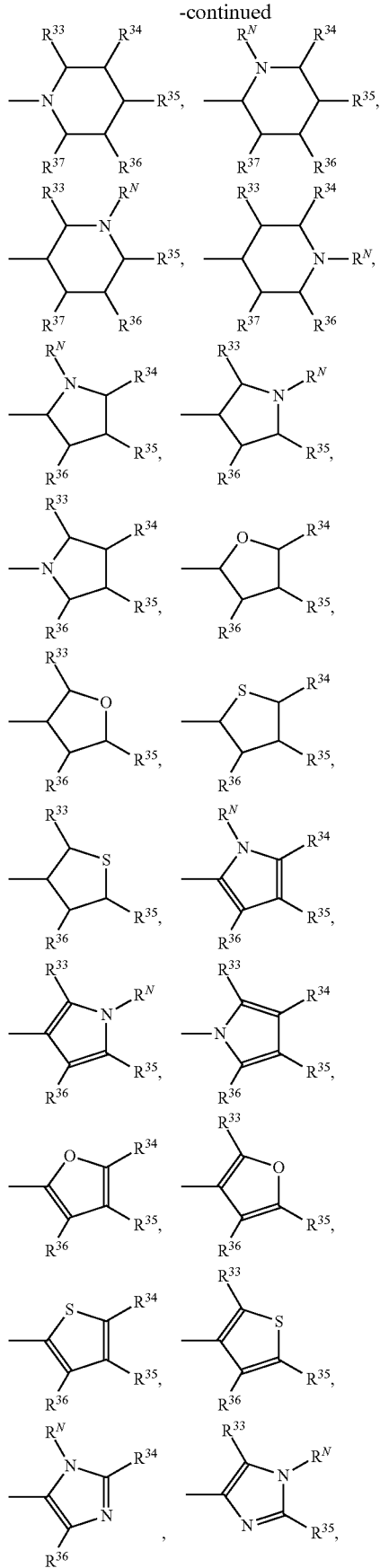

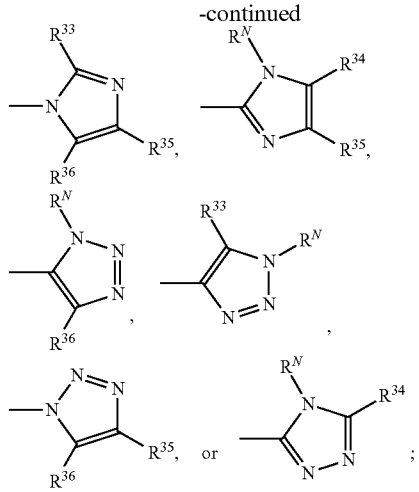

$L^1$, $L^2$ and $L^3$ represent independently of each other: a bond, —CH$_2$—, —C$_2$H$_4$—, —C$_3$H$_6$—, —C$_4$H$_8$—, —C$_6$H$_{10}$—, —C$_6$H$_{12}$—, —C$_7$H$_{14}$—, —C$_8$H$_{16}$—, —C$_9$H$_{18}$—, —C$_{10}$H$_{20}$—, —CH(CH$_3$)—, —C[(CH$_3$)$_2$]—, —CH$_2$—CH(CH$_3$)—, —CH(CH$_3$)—CH$_2$—, —CH(CH$_3$)—C$_2$H$_4$—, —CH$_2$—CH(CH$_3$)—CH$_2$—, —C$_2$H$_4$—CH(CH$_3$)—, —CH$_2$—C[(CH$_3$)$_2$]—, —C[(CH$_3$)$_2$]—CH$_2$—, —CH(CH$_3$)—CH(CH$_3$)—, —C[(C$_2$H$_6$)(CH$_3$)]—, —CH(C$_3$H$_7$)—, —(CH$_2$)$_m$O—, —(CH$_2$)$_p$OCH$_2$—, —(CH$_2$—CH$_2$—O)$_n$—CH$_2$—CH$_2$—, —CH═CH—, —C(CH$_3$)═CH—, —CH═C(CH$_3$)—, —CH$_2$—CH═CH—, —CH$_2$—C(CH$_3$)═CH—, —CH$_2$—CH═C(CH$_3$)—, —CH═CH—CH$_2$—, —C(CH$_3$)═CH—CH$_2$—, —CH═C(CH$_3$)—CH$_2$—, —C(CH$_3$)═CH—C(CH$_3$)═CH—, —C$_2$H$_4$—CH═CH—CH═CH—, —CH$_2$—CH═CH—CH$_2$—CH═CH—, —C$_3$H$_6$—C≡C—CH$_2$—, —CH$_2$—CH═CH—CH═CH—CH$_2$—, —CH═CH—CH═CH—C$_2$H$_4$—, —CH$_2$—CH═CH—C(CH$_3$)═CH—, —CH$_2$—CH═C(CH$_3$)—CH═CH—, —CH$_2$—C(CH$_3$)═CH—CH═CH—, —CH(CH$_3$)—CH═CH—CH═CH—, —CH═CH—CH$_2$—C(CH$_3$)═CH—, —CH(CH$_3$)—C≡C—CH$_2$—, —CONH—, —NHCO—, —CH$_2$—CONH—, —CONH—CH$_2$—, —NHCO—CH$_2$—, —CH$_2$—NHCO—;

wherein n, m, p are independently an integer from 1 to 10; or $L_1$-$R^D$ and $L_2$-$R^E$ or $L_1$-$R^D$ and $L_3$-$R^F$ or $L_2$-$R^E$ and $L_3$-$R^F$ can form together a cyclic ring selected from the group consisting of:

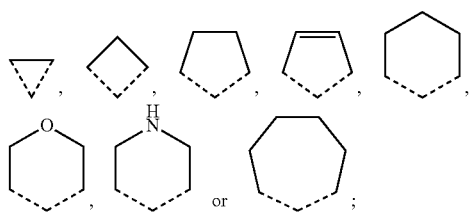

$R^N$ represents —H, —CH$_2$—OCH$_3$, —C$_2$H$_4$—OCH$_3$, —C$_3$H$_6$—OCH$_3$, —CH$_2$—OC$_2$H$_5$, —C$_2$H$_4$—OC$_2$H$_5$, —C$_3$H$_6$—OC$_2$H$_5$, —CH$_2$—OC$_3$H$_7$, —C$_2$H$_4$—OC$_3$H$_7$, —C$_3$H$_6$—OC$_3$H$_7$, —CH$_2$—O-cyclo-C$_3$H$_5$, —C$_2$H$_4$—O-cyclo-C$_3$H$_5$, —C$_3$H$_6$—O-cyclo-C$_3$H$_5$, —CH$_2$—

OCH(CH₃)₂, —C₂H₄—OCH(CH₃)₂, —C₃H₆—OCH(CH₃)₂, —CH₂—OC(CH₃)₃, —C₂H₄—OC(CH₃)₃, —C₃H₆—OC(CH₃)₃, —CH₂—OC₄H₉, —C₂H₄—OC₄H₉, —C₃H₆—OC₄H₉, —CH₂—OPh, —C₂H₄—OPh, —C₃H₆—OPh, —CH₂—OCH₂-Ph, —C₂H₄—OCH₂-Ph, —C₃H₆—OCH₂-Ph, —CHO, —COCH₃, —COC₂H₅, —COC₃H₇, —CO-cyclo-C₃H₅, —COCH(CH₃)₂, —COC(CH₃)₃, —COPh, —COCN, —COOCH₃, —COOC₂H₅, —COOC₃H₇, —COO-cyclo-C₃H₅, —COOCH(CH₃)₂, —COOC(CH₃)₃, —COCH₂Ph, —CONH₂, —CONHCH₃, —CONHC₂H₅, —CONHC₃H₇, —CONH-cyclo-C₃H₅, —CONH[CH(CH₃)₂], —CONH[C(CH₃)₃], —CON(CH₃)₂, —CON(C₂H₅)₂, —CON(C₃H₇)₂, —CON(cyclo-C₃H₅)₂, —CON[CH(CH₃)₂]₂, —CON[C(CH₃)₃]₂, —SO₂CH₃, —SO₂C₂H₅, —SO₂CH₂Ph, —SO₂C₃H₇, —SO₂-cyclo-C₃H₅, —SO₂CH(CH₃)₂, —SO₂C(CH₃)₃, —SO₂Ph, —CH₂—OCF₃, —C₂H₄—OCF₃, —C₃H₆—OCF₃, —OC₂F₅, —CH₂—OC₂F₅, —C₂H₄—OC₂F₅, —C₃H₆—OC₂F₅, —CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, -cyclo-C₈H₁₅, -Ph, —CH₂-Ph, —CH₂—CH₂-Ph, —CH=CH-Ph, —CPh₃, —CH₃, —C₂H₅, —C₃H₇, —CH(CH₃)₂, —C₄H₉, —CH₂—CH(CH₃)₂, —CH(CH₃)—C₂H₅, —C(CH₃)₃, C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₇H₁₅, —C₈H₁₇, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —CH=CH₂, —CH₂—CH=CH₂, —C(CH₃)=CH₂, —CH=CH—CH₃, —C₂H₄—CH=CH₂, —CH₂—CH=CH—CH₃, —CH=CH—C₂H₅, —CH₂—C(CH₃)=CH₂, —CH(CH₃)—CH=CH, —CH=C(CH₃)₂, —C(CH₃)=CH—CH₃, —CH=CH—CH=CH₂, —C₃H₆—CH=CH₂, —C₂H₄—CH=CH—CH₃, —CH₂—CH=CH—C₂H₅, —CH=CH—C₃H₇, —CH₂—CH=CH—CH=CH₂, —CH=CH—CH=CH—CH₃, —CH₂—CH=CH—CH=CH₂, —C(CH₃)=CH—CH=CH₂, —CH=C(CH₃)—CH=CH₂, —CH=CH—C(CH₃)=CH₂, —C₂H₄—C(CH₃)=CH₂, —CH₂—CH(CH₃)—CH=CH₂, —CH(CH₃)—CH₂—CH=CH₂, —CH₂—CH=C(CH₃)₂, —CH₂—C(CH₃)=CH—CH₃, —CH(CH₃)—CH=CH—CH₃, —CH=CH—CH(CH₃)₂, —CH=C(CH₃)—C₂H₅, —C(CH₃)=CH—C₂H₅, —C(CH₃)=C(CH₃)₂, —C(CH₃)₂—CH=CH₂, —CH(CH₃)—C(CH₃)=CH₂, —C(CH₃)—CH—CH₂, —CH=C(CH₃)—CH=CH₂, —CH=CH—C(CH₃)=CH₂, —C₄H₈—CH=CH₂, —C₃H₆—CH=CH—CH₃, —C₂H₄—CH=CH—C₂H₅, —CH=CH—C₃H₇, —CH—CH—C₄H₉, —C₃H₆—C(CH₃)=CH₂, —C₂H₄—CH(CH₃)—CH=CH₂, —CH₂—CH(CH₃)—CH₂—CH=CH₂, —C₂H₄—CH=C(CH₃)₂, —CH(CH₃)—C₂H₄—CH=CH₂, —C₂H₄—C(CH₃)=CH—CH₃, —CH₂—CH(CH₃)—CH=CH—CH₃, —CH(CH₃)—CH₂—CH=CH—CH₃, —CH₂—CH=CH—CH(CH₃)₂, —CH₂—CH=C(CH₃)—C₂H₅, —CH₂—C(CH₃)=CH—C₂H₅,
—CH(CH₃)—CH=CH—C₂H₅, —CH=CH—CH₂—CH(CH₃)₂, —CH=CH—CH(CH₃)—C₂H₅, —CH=C(CH₃)—C₃H₇, —C(CH₃)=CH—C₃H₇, —CH₂—CH(CH₃)—C(CH₃)=CH₂, —C[C(CH₃)₃]=CH₂, —CH(CH₃)—CH₂—C(CH₃)=CH₂, —CH(CH₃)—CH(CH₃)—CH=CH₂, —CH=CH—C₂H₄—CH=CH₂, —CH₂—C(CH₃)₂—CH=CH₂, —C(CH₃)₂—CH₂—CH=CH₂, —CH₂—C(CH₃)=C(CH₃)₂, —CH(CH₃)—CH=C(CH₃)₂, —C(CH₃)₂—CH=CH—CH₃, —CH=CH—CH₂—CH=CH—CH₃, —CH(CH₃)—C(CH₃)=CH—CH₃, —CH=C(CH₃)—CH(CH₃)₂, —C(CH₃)=CH—CH(CH₃)₂, —C(CH₃)=C(CH₃)—C₂H₅, —CH=CH—C(CH₃)₃, —C(CH₃)₂—C(CH₃)=CH₂, —CH(C₂H₅)—C(CH₃)=CH₂, —C(CH₃)(C₂H₅)—CH=CH₂, —CH(CH₃)—C(C₂H₅)=CH₂, —CH₂—C(C₃H₇)=CH₂, —CH₂—C(C₂H₅)=CH—CH₃, —CH(C₂H₅)—CH=CH—CH₃, —C(C₄H₉)=CH₂, —C(C₃H₇)=CH—CH₃, —C(C₂H₅)=CH—C₂H₅, —C(C₂H₅)=C(CH₃)₂, —C[CH(CH₃)(C₂H₅)]=CH₂, —C[CH₂—CH(CH₃)₂]=CH₂, —C₂H₄—CH=CH—CH=CH₂, —CH₂—CH=CH—CH₂—CH=CH₂, —C₃H₆—C≡C—CH₃, —CH₂—CH=CH—CH=CH—CH₃, —CH=CH—CH=CH—C₂H₅, —CH₂—CH=CH—C(CH₃)=CH₂, —CH₂—CH=C(CH₃)—CH=CH₂, —CH₂—C(CH₃)=CH—CH=CH₂, —CH(CH₃)—CH₂—C≡CH, —CH(CH₃)—CH=CH—CH=CH₂, —CH=CH—CH₂—C(CH₃)=CH₂, —CH(CH₃)—C≡C—CH₃, —CH=CH—CH(CH₃)—CH=CH₂, —CH=C(CH₃)—CH₂—CH=CH₂, —C₂H₄—CH(CH₃)—C≡CH, —C(CH₃)=CH—CH₂—CH=CH₂, —CH₂—C≡C—C₂H₅, —CH=CH—CH=C(CH₃)₂, —CH₂—CH(CH₃)—CH₂—C≡CH, —C₂H₄—C≡C—CH₃, —CH=CH—CH=CH—CH₃, —CH=C(CH₃)—CH=CH—CH₃, —CH₂—CH(CH₃)—C≡CH, —C(CH₃)=CH—CH=CH—CH₃, —CH=C(CH₃)—C(CH₃)=CH₂, —C(CH₃)=CH—C(CH₃)=CH₂, —C(CH₃)=C(CH₃)—CH=CH₂, —CH=CH—CH=CH—CH=CH₂, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C≡C—C₃H₇, —CH(CH₃)—C≡CH, —C₄H₈—C≡CH, —C₂H₄—C≡C—C₂H₅, —CH₂—C≡C—C₃H₇, —C≡C—C₄H₉, —C≡C—C(CH₃)₃, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —C≡C—CH₂—CH(CH₃)₂, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —CH₂—CH(C≡CH)₂, —C≡C—C≡CH, —CH₂—C≡C—C≡CH, —C≡C—C≡C—CH₃, —CH(C≡CH)₂, —C₂H₄—C≡C—C≡CH, —CH₂—C≡C—CH₂—C≡CH, —C≡C—C₂H₄—C≡CH, —CH₂—C≡C—C≡C—CH₃, —C≡C—CH₂—C≡C—CH₃, —C≡C—C≡C—C₂H₅, —C(C≡CH)₂—CH₃, —C≡C—CH(CH₃)—C≡CH, —CH(CH₃)—C≡C—C≡CH, —CH(C≡CH)—CH₂—C≡CH, or —CH(C≡CH)—C≡C—CH₃;

$R^B$ represents
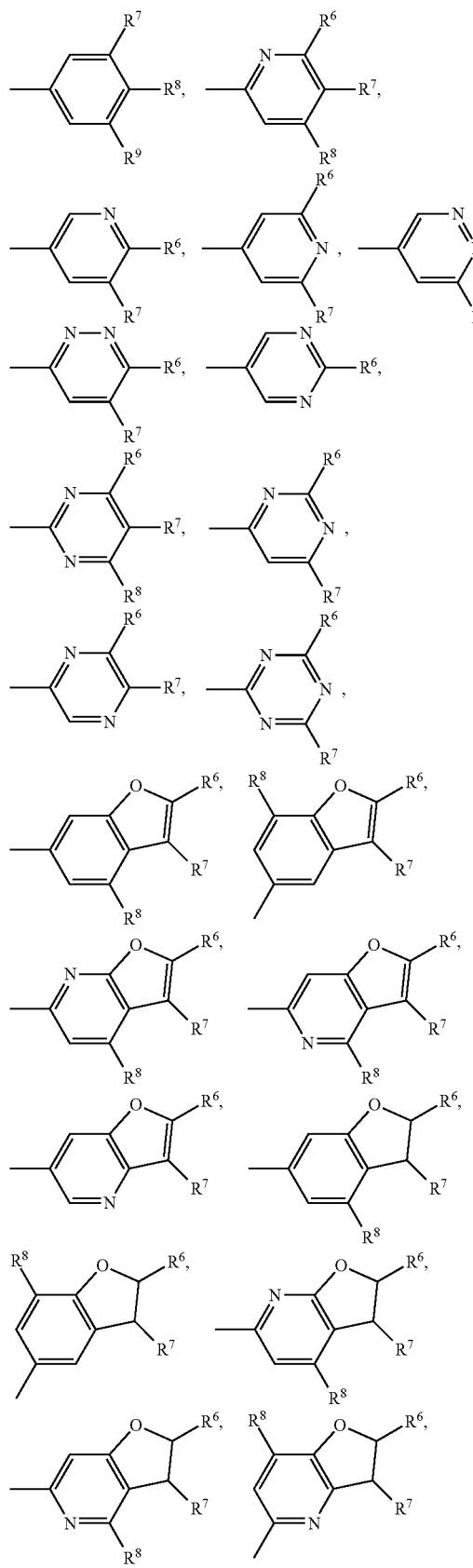
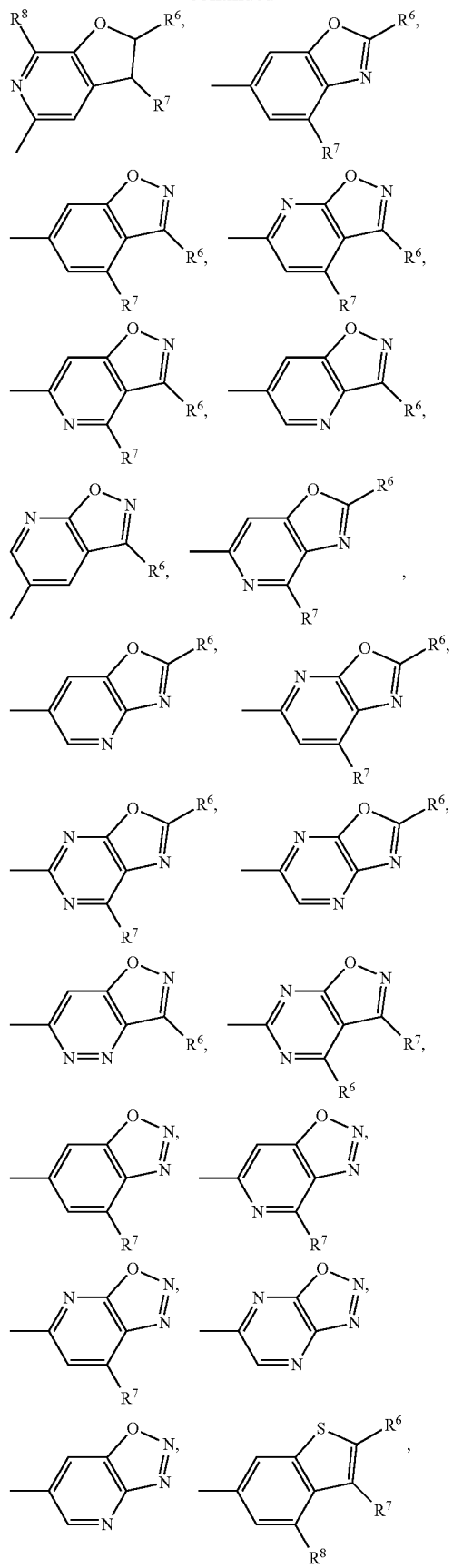

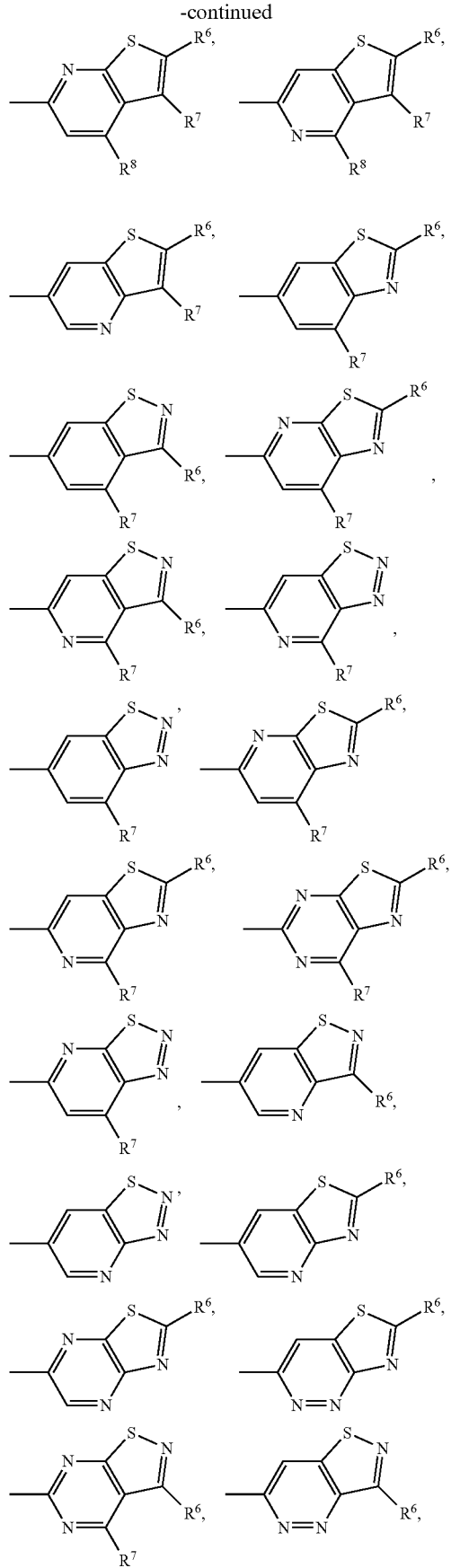
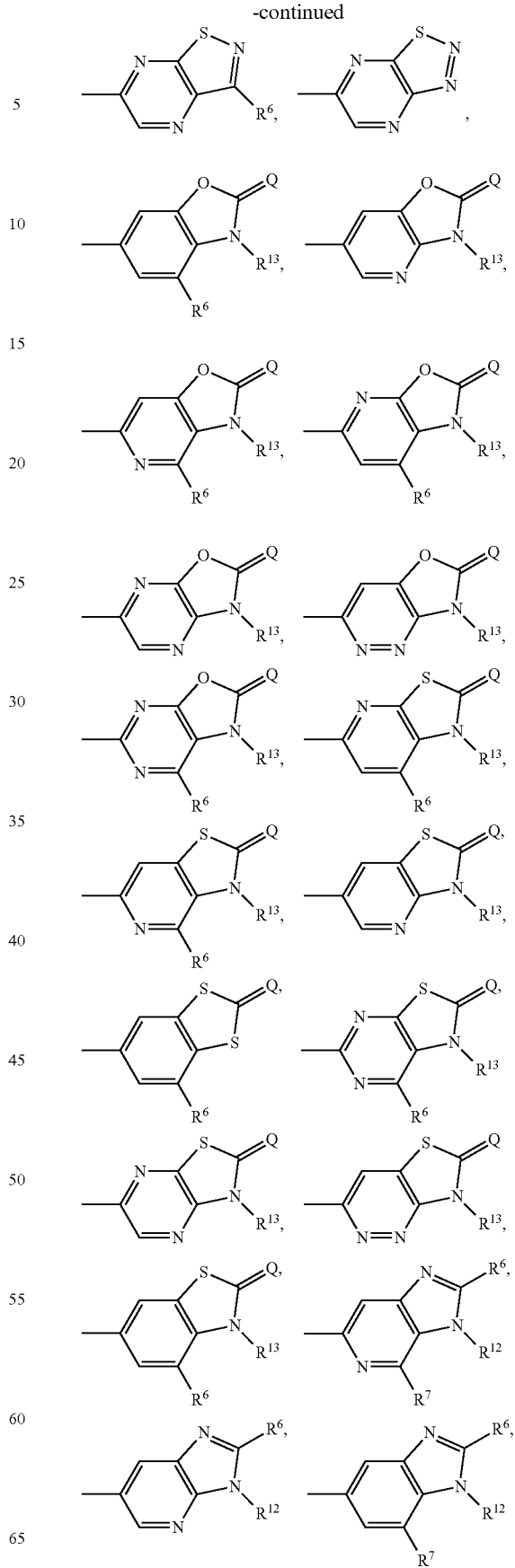

-continued
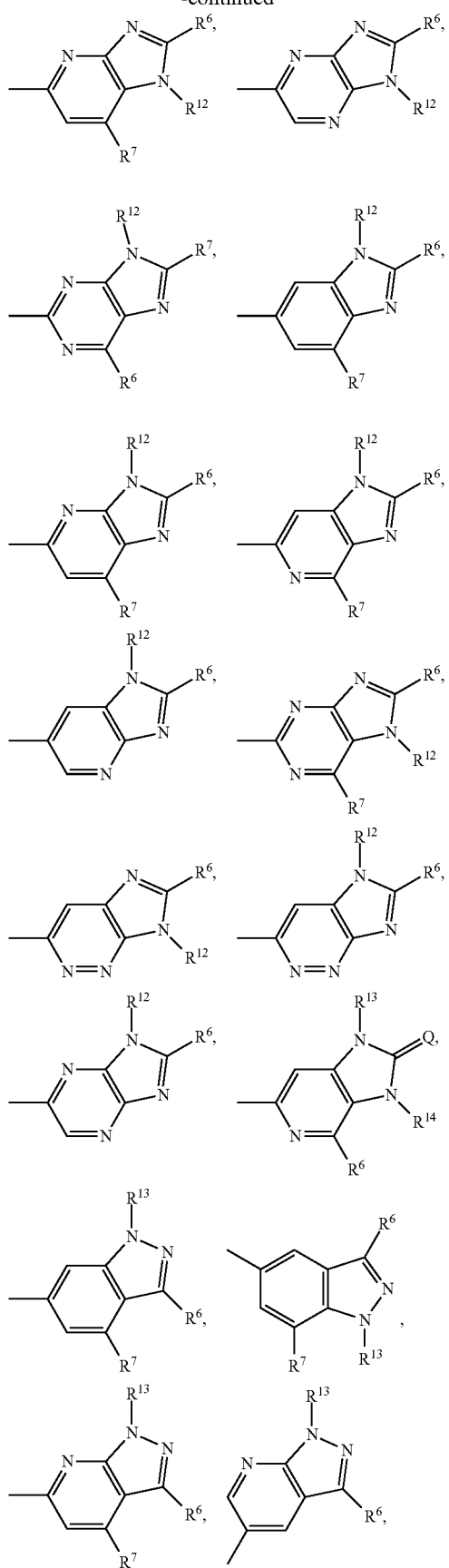
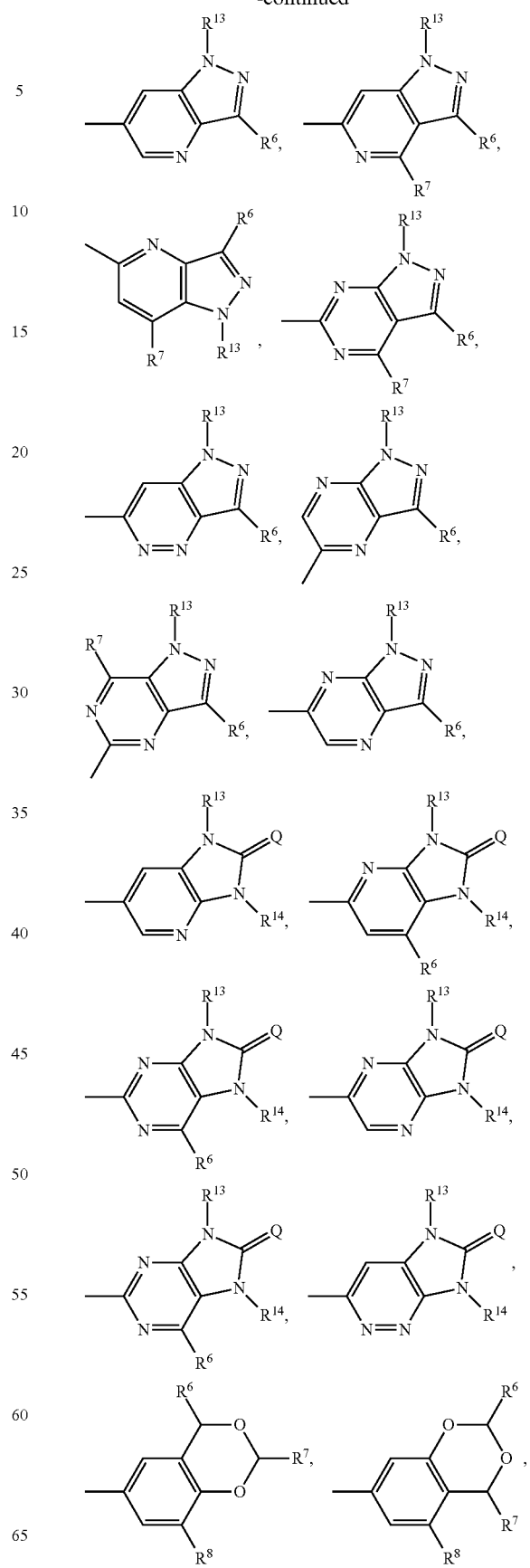

-continued

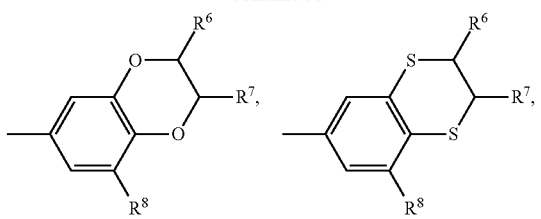

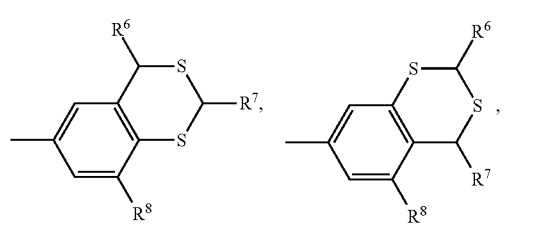

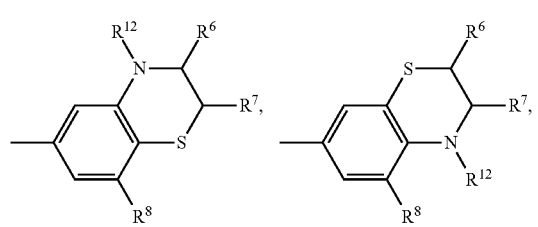

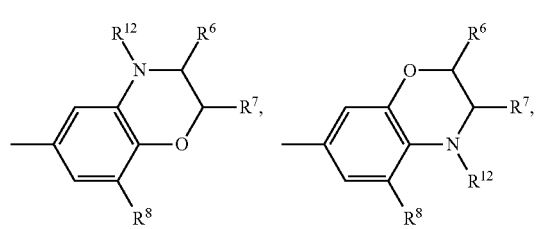

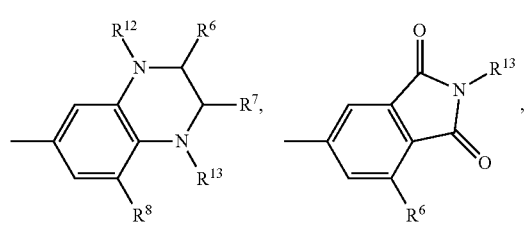

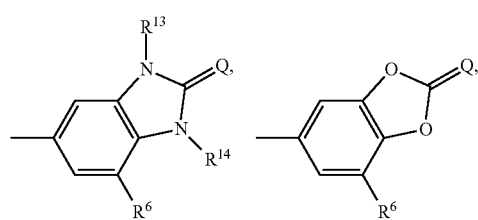

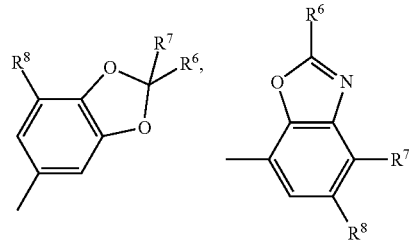

-continued

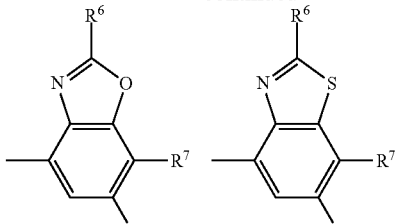

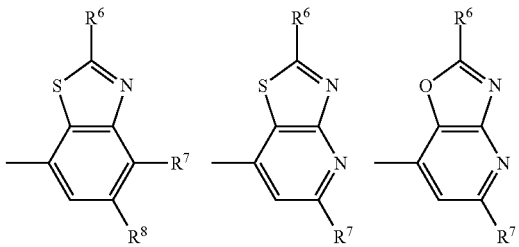

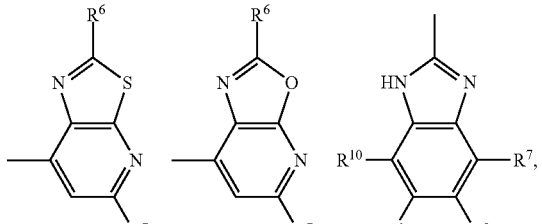

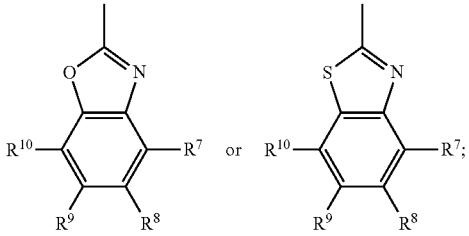

Q represents =O, =S, or =N—R$^{12}$;
R$^C$ represents —OH, —CH$_2$—OH, —CHO, —CH$_2$CHO, —CH$_2$CH$_2$CHO, —C$_2$H$_4$—OH, —C$_3$H$_6$—OH, —O—CH$_3$, —O—C$_2$H$_5$, —O—CH$_2$—OH, —O—CH(CH$_3$)$_2$, —O—CH$_2$—O—CH$_3$, —O—C$_2$H$_4$—O—CH$_3$, —CH$_2$—O—CH$_3$, —CH$_2$—O—CH$_2$—OH, —CH$_2$O—C$_2$H$_5$, —CH$_2$—O—CH(CH$_3$)$_2$, —CH$_2$—O—C$_3$H$_7$, —CO—CH$_3$, —CH$_2$—CO—CH$_3$, —CO—CH$_2$—OH, —CH(OH)—CH$_3$, —C(OH)(CH$_3$)$_2$, —CH(CH$_3$)CH$_2$OH, —CH(OH)—CH$_2$—OH, —CH$_2$—CH(OH)—CH$_3$, —CH$_2$—CH(OH)—CH$_2$—OH, —CH(OCH$_3$)—CH$_2$OH, —CH(OC$_2$H$_5$)—CH$_2$OH, —CH(OCH$_3$)—CH$_2$OCH$_3$, —CH(OC$_2$H$_5$)—CH$_2$OCH$_3$, —CH(OC$_2$H$_5$)—CH$_2$OC$_2$H$_5$, —CH(OAc)—CH$_2$OH, —CH(OAc)—CH$_2$OAc, —CH(OH)—CH$_2$OAc, —CH(OH)—CH$_2$—NH$_2$, —CH$_2$—CH(OH)—CH$_2$—NH$_2$, —CH(OCH$_3$)—CH$_2$—NH$_2$, —CH(OC$_2$H$_5$)—CH$_2$—NH$_2$, —CH$_2$—CH(OCH$_3$)—CH$_2$—NH$_2$, —CH$_2$—CH(OC$_2$H$_5$)—CH$_2$—NH$_2$, —CH(OH)—CH$_2$—NHCH$_3$, —CH(OH)—CH$_2$—NHC$_2$H$_5$, —CH$_2$—CH(OH)—CH$_2$—NHCH$_3$, —CO—C$_3$H$_7$, —CH$_2$—CH(OH)—CH$_2$—NHC$_2$H$_5$, —CH(OCH$_3$)—CH$_2$NHCH$_3$, —CO—C$_2$H$_5$, —CO—CH(CH$_3$)$_2$, —CH(OC$_2$H$_5$)—CH$_2$NHCH$_3$, —CH$_2$—CH(OCH$_3$)—CH$_2$—NHCH$_3$, —O—C$_3$H$_7$, —CH$_2$—CH(OC$_2$H$_5$)—CH$_2$—NHCH$_3$, —CH(OCH$_3$)—CH$_2$NHC$_2$H$_5$, —CH(OC$_2$H$_5$)—CH$_2$NHC$_2$H$_5$, —CH(OCH$_3$)—CH$_2$N(CH$_3$)$_2$, —CH(OC$_2$H$_5$)—CH$_2$N(CH$_3$)$_2$, —NH$_2$, —NHCH₃, —N(CH₃)₂, —CH₂—NH₂, —CH₂—NHCH₃, —CH₂—N(CH₃)₂, —C₂H₄—NH₂, —C₂H₄—NHCH₃, —C₂H₄—N(CH₃)₂, —CH(NHCH₃)CH₃, —CH(NHC₂H₅)CH₃, —CH(N(CH₃)₂)CH₃, —CH(N(C₂H₅)₂)CH₃, —CH(NH₂)CH₂OH, —CH(NHCH₃)CH₂OH, —CH(NHC₂H₅)CH₂OH, —CH(N(CH₃)₂)CH₂OH, —CH(N(C₂H₅)₂)CH₂OH, —CH(NH₂)CH₂OCH₃, —CH(NHCH₃)CH₂OCH₃, —CH(NHC₂H₅)CH₂OCH₃, —CH(N(CH₃)₂)CH₂OCH₃, —CH(N(C₂H₅)₂)CH₂OCH₃, —CH(NH₂)CH₂OC₂H₅, —CH(NHCH₃)CH₂OC₂H₅, —CH(NHC₂H₅)CH₂OC₂H₅, —CH(N(CH₃)₂)CH₂OC₂H₅, —CH(N(C₂H₅)₂)CH₂OC₂H₅, —CH(NH₂)CH₂OAc, —CH(NHCH₃)CH₂OAc, —CH(NHC₂H₅)CH₂OAc, —CH(N(CH₃)₂)CH₂OAc, —CH(N(C₂H₅)₂)CH₂OAc, —CH₂—CH(NHAc)CH₂OH, —CH₂—CH(NHAc)CH₂OCH₃, —CH₂—CH(NHAc)CH₂OC₂H₅, —CH₂—CH(NHCH₃)CH₃, —CH₂—CH(NHC₂H₅)CH₃, —CH₂—CH(N(CH₃)₂)CH₃, —CH₂—CH(N(C₂H₅)₂)CH₃, —CH₂—CH(NH₂)CH₂OH, —CH₂—CH(NHCH₃)CH₂OH, —CH₂—CH(NHC₂H₅)CH₂OH, —CH₂—CH(N(CH₃)₂)CH₂OH, —CH₂—CH(N(C₂H₅)₂)CH₂OH, —CH₂—CH(NH₂)CH₂OCH₃, —CH₂—CH(NHCH₃)CH₂OCH₃, —CH₂—CH(NHC₂H₅)CH₂OCH₃, —CH₂—CH(N(CH₃)₂)CH₂OCH₃, —CH₂—CH(N(C₂H₅)₂)CH₂OCH₃, —CH₂—CH(NH₂)CH₂OC₂H₅, —CH₂—CH(NHCH₃)CH₂OC₂H₅, —CH₂—CH(NHC₂H₅)CH₂OC₂H₅, —CH₂—CH(N(CH₃)₂)CH₂OC₂H₅, —CH₂—CH(N(C₂H₅)₂)CH₂OC₂H₅, —CH₂—CH(NH₂)CH₂OAc, —CH₂—CH(NHCH₃)CH₂OAc, —CH₂—CH(NHC₂H₅)CH₂OAc, —CH₂—CH(N(CH₃)₂)CH₂OAc, —CH₂—CH(N(C₂H₅)₂)CH₂OAc, —CH₂—CH(NHAc)CH₂OH, —CH₂—CH(NHAc)CH₂OCH₃, —CH₂—CH(NHAc)CH₂OC₂H₅, —NHCOCH₃, —CH₂—NHCOCH₃, —C₂H₄—NHCOCH₃, —NHCHO, —CH₂—NHCHO, —C₂H₄—NHCHO, —NHSO₂CH₃, —NHSO₂CF₃, —NHSO₂CH₂CF₃, —CH₂—NHSO₂CH₃, —CH₂—NHSO₂CF₃, —CH₂—NHSO₂CH₂CF₃, —C₂H₄—NHSO₂CH₃, —C₂H₄—NHSO₂CF₃, —C₂H₄—NHSO₂CH₂CF₃, —CONH₂, —CONHCH₃, —CONHC₂H₅, —CONHC₃H₇, —NH(C₂H₅), —N(C₂H₅)₂, —CH₂—NH(C₂H₅), —CH₂—N(C₂H₅)₂, —C₂H₄—NH(C₂H₅), —C₂H₄—N(C₂H₅)₂, —NO₂, —CH₂—NO₂, —C₂H₄—NO₂, —CH(OH)—NO₂, —CH(NO₂)—OH, —CO₂H, —CH₂—CO₂H, —C₂H₄—CO₂H, —CH=CH—CO₂H, —CO₂CH₃, —CO₂C₂H₅, —CO₂CH(CH₃)₂, —CH₂—CO₂CH₃, —CH₂—CO₂C₂H₅, —CH₂—CO₂CH(CH₃)₂, —C₂H₄—CO₂CH₃, —C₂H₄—CO₂C₂H₅, —C₂H₄—CO₂CH(CH₃)₂, —CO₂NH₂, —CO₂NHCH₃, —CO₂N(CH₃)₂, —CH₂—CO₂NH₂, —CH₂—CO₂NHCH₃, —CH₂—CO₂N(CH₃)₂, —C₂H₄—CO₂NH₂, —C₂H₄—CO₂NHCH₃, —C₂H₄—CO₂N(CH₃)₂, —O—Si(CH₃)₃, —O—Si(C₂H₅)₃, —CO—CHO, —CO—CO—CH₃, —C(OH)—CO—CH₃, —CO—C(OH)—CH₃, —CO—CH₂—CO—CH₃, —C(OH)—CH₂—CO—CH₃, —CO—CH₂—C(OH)—CH₃, —C(OH)—CH₂—C(OH)—CH₃, —F, —Cl, —Br, —CH₂—F, —CHF₂, —CF₃, —C₂H₄—F, —CH₂—CF₃, —CF₂—CF₃, —O—CHF₂, —O—CF₃, —O—CH₂—CF₃, —O—C₂F₅, —CH₃, —CH₂CH₃, —C₃H₇, —CH(CH₃)₂;

R¹-R¹⁰ represent independently of each other —H, —OH, —OCH₃, —OC₂H₅, —OC₃H₇, —O-cyclo-C₃H₅, —OCH(CH₃)₂, —OC(CH₃)₃, —OC₄H₉, —OCH₂—COOH, —OPh, —OCH₂-Ph, —OCPh₃, —CH₂—OCH₃, —CH₂—OH, —C₂H₄—OCH₃, —C₃H₆—OCH₃, —CH₂—OC₂H₅, —C₂H₄—OC₂H₅, —C₃H₆—OC₂H₅, —CH₂—OC₃H₇, —C₂H₄—OC₃H₇, —C₃H₆—OC₃H₇, —CH₂—O-cyclo-C₃H₅, —C₂H₄—O-cyclo-C₃H₅, —C₃H₆—O-cyclo-C₃H₅, —CH₂—OCH(CH₃)₂, —C₂H₄—OCH(CH₃)₂, —C₃H₆—OCH(CH₃)₂, —CH₂—OC(CH₃)₃, —C₂H₄—OC(CH₃)₃, —C₃H₆—OC(CH₃)₃, —CH₂—OC₄H₉, —C₂H₄—OC₄H₉, —C₃H₆—OC₄H₉, —CH₂—OPh, —C₂H₄—OPh, —C₃H₆—OPh, —CH₂—OCH₂-Ph, —C₂H₄—OCH₂-Ph, —C₃H₆—OCH₂-Ph, —SH, —SCH₃, —SC₂H₅, —SC₃H₇, —S-cyclo-C₃H₆, —SCH(CH₃)₂, —SC(CH₃)₃, —NO₂, —F, —Cl, —Br, —I, —P(O)(OH)₂, —P(O)(OCH₃)₂, —P(O)(OC₂H₅)₂, —P(O)(OCH(CH₃)₂)₂, —C(OH)[P(O)(OH)₂]₂, —Si(CH₃)₂(C(CH₃)₃), —Si(C₂H₅)₃, —Si(CH₃)₃, —N₃, —CN, —OCN, —NCO, —SCN, —NCS, —CHO, —COCH₃, —COC₂H₅, —COC₃H₇, —CO-cyclo-C₃H₅, —COCH(CH₃)₂, —COC(CH₃)₃, —COOH, —COCN, —COOCH₃, —COOC₂H₅, —COOC₃H₇, —COO-cyclo-C₃H₅, —COOCH(CH₃)₂, —COOC(CH₃)₃, —OOC—CH₃, —OOC—C₂H₅, —OOC—C₃H₇, —OOC-cyclo-C₃H₅, —OOC—CH(CH₃)₂, —OOC—C(CH₃)₃, —CONH₂, —CONHCH₃, —CONHC₂H₅, —CONHC₃H₇, —CONH-cyclo-C₃H₅, —CONH[CH(CH₃)₂], —CONH[C(CH₃)₃], —CON(CH₃)₂, —CON(C₂H₅)₂, —CON(C₃H₇)₂, —CON(cyclo-C₃H₅)₂, —CON[CH(CH₃)₂]₂, —CON[C(CH₃)₃]₂, —NHCOCH₃, —NHCOC₂H₅, —NHCOC₃H₇, —NHCO-cyclo-C₃H₅, —NHCO—CH(CH₃)₂, —NHCO—C(CH₃)₃, —NHCO—OCH₃, —NHCO—OC₂H₅, —NHCO—OC₃H₇, —NHCO—O-cyclo-C₃H₅, —NHCO—OCH(CH₃)₂, —NHCO—OC(CH₃)₃, —NH₂, —NHCH₃, —NHC₂H₅, —NHC₃H₇, —NH-cyclo-C₃H₅, —NHCH(CH₃)₂, —NHC(CH₃)₃, —N(CH₃)₂, —N(C₂H₅)₂, —N(C₃H₇)₂, —N(cyclo-C₃H₅)₂, —N[CH(CH₃)₂]₂, —N[C(CH₃)₃]₂, —SOCH₃, —SOC₂H₅, —SOC₃H₇, —SO-cyclo-C₃H₅, —SOCH(CH₃)₂, —SOC(CH₃)₃, —SO₂CH₃, —SO₂C₂H₅, —SO₂C₃H₇, —SO₂-cyclo-C₃H₆, —SO₂CH(CH₃)₂, —SO₂C(CH₃)₃, —SO₃H, —SO₃CH₃, —SO₃C₂H₅, —SO₃C₃H₇, —SO₃-cyclo-C₃H₅, —SO₃CH(CH₃)₂, —SO₃C(CH₃)₃, —SO₂NH₂, —SO₂NHCH₃, —SO₂NHC₂H₅, —SO₂NHC₃H₇, —SO₂NH-cyclo-C₃H₅, —SO₂NHCH(CH₃)₂, —SO₂NHC(CH₃)₃, —SO₂N(CH₃)₂, —SO₂N(C₂H₅)₂, —SO₂N(C₃H₇)₂, —SO₂N(cyclo-C₃H₅)₂, —SO₂N[CH(CH₃)₂]₂, —SO₂N[C(CH₃)₃]₂, —O—S(=O)CH₃, —O—S(=O)C₂H₅, —O—S(=O)C₃H₇, —O—S(=O)-cyclo-C₃H₅, —O—S(=O)CH(CH₃)₂, —O—S(=O)C(CH₃)₃, —S(=O)(=NH)CH₃, —S(=O)(=NH)C₂H₅, —S(=O)(=NH)C₃H₇, —S(=O)(=NH)-cyclo-C₃H₅, —S(=O)(=NH)CH(CH₃)₂, —S(=O)(=NH)C(CH₃)₃, —NH—SO₂—CH₃, —NH—SO₂—C₂H₆, —NH—SO₂—C₃H₇, —NH—SO₂-cyclo-C₃H₆, —NH—SO₂—CH(CH₃)₂, —NH—SO₂—C(CH₃)₃, —O—SO₂—CH₃, —O—SO₂—C₂H₅, —O—SO₂—C₃H₇, —O—SO₂-cyclo-C₃H₅, —O—SO₂—CH(CH₃)₂, —O—SO₂—C(CH₃)₃, —OCF₃, —CH₂—OCF₃, —C₂H₄—OCF₃, —C₃H₆—OCF₃, —OC₂F₅, —CH₂—OC₂F₅, —C₂H₄—OC₂F₅, —C₃H₆—OC₂F₅, —O—COOCH₃, —O—COOC₂H₅, —O—COOC₃H₇, —O—COO-cyclo-C₃H₅, —O—COOCH(CH₃)₂, —O—COOC(CH₃)₃, —NH—CO—NH₂, —NH—CO—NHCH₃, —NH—CO—NHC₂H₅, —NH—CS—N(C₃H₇)₂, —NH—CO—NHC₃H₇, —NH—CO—N(C₃H₇)₂, —NH—CO—NH[CH(CH₃)₂], —NH—

—CO—NH[C(CH₃)₃], —NH—CO—N(CH₃)₂, —NH—CO—N(C₂H₅)₂, —NH—CO—NH-cyclo-C₃H₅, —NH—CO—N(cyclo-C₃H₅)₂, —NH—CO—N[CH(CH₃)₂]₂, —NH—CS—N(C₂H₅)₂, —NH—CO—N[C(CH₃)₃]₂, —NH—CS—NH₂, —NH—CS—NHCH₃, —NH—CS—N(CH₃)₂, —NH—CS—NHC₂H₅, —NH—CS—NHC₃H₇, —NH—CS—NH-cyclo-C₃H₅, —NH—CS—NH[CH(CH₃)₂], —NH—CS—NH[C(CH₃)₃], —NH—CS—N(cyclo-C₃H₅)₂, —NH—CS—N[CH(CH₃)₂]₂, —NH—CS—N[C(CH₃)₃]₂, —NH—C(=NH)—NH₂, —NH—C(=NH)—NHCH₃, —NH—C(=NH)—NHC₂H₅, —NH—C(=NH)—NHC₃H₇, —O—CO—NH-cyclo-C₃H₅, —NH—C(=NH)—NH-cyclo-C₃H₅, —NH—C(=NH)—NH[CH(CH₃)₂], —O—CO—NH[CH(CH₃)₂], —NH—C(=NH)—NH[C(CH₃)₃], —NH—C(=NH)—N(CH₃)₂, —NH—C(=NH)—N(C₂H₅)₂, —NH—C(=NH)—N(C₃H₇)₂, —NH—C(=NH)—N(cyclo-C₃H₅)₂, —O—CO—NHC₃H₇, —NH—C(=NH)—N[CH(CH₃)₂]₂, —NH—C(=NH)—N[C(CH₃)₃]₂, —O—CO—NH₂, —O—CO—NHCH₃, —O—CO—NHC₂H₅, —O—CO—NH[C(CH₃)₃], —O—CO—N(CH₃)₂, —O—CO—N(C₂H₅)₂, —O—CO—N(C₃H₇)₂, —O—CO—N(cyclo-C₃H₅)₂, —O—CO—N[CH(CH₃)₂]₂, —O—CO—N[C(CH₃)₃]₂, —O—CO—OCH₃, —O—CO—OC₂H₅, —O—CO—OC₃H₇, —O—CO—O-cyclo-C₃H₅, —O—CO—OCH(CH₃)₂, —O—CO—OC(CH₃)₃, —CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, -cyclo-C₃H₅, -cyclo-C₄H₇, -cyclo-C₅H₉, -cyclo-C₆H₁₁, -cyclo-C₇H₁₃, -cyclo-C₈H₁₅, -Ph, —CH₂-Ph, —CH₂—CH₂-Ph, —CH=CH-Ph, —CPh₃, —CH₃, —C₂H₅, —C₃H₇, —CH(CH₃)₂, —C₄H₉, —CH₂—CH(CH₃)₂, —CH(CH₃)—C₂H₅, —C(CH₃)₃, C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₇H₁₅, —C₈H₁₇, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—CH(C₂H₅)₂, —CH(CH₃)—C(CH₃)₃, —CH=CH₂, —CH₂—CH=CH₂, —C(CH₃)=CH₂, —CH=CH—CH₃, —C₂H₄—CH=CH₂, —CH₂—CH=CH—CH₃, —CH=CH—C₂H₅, —CH₂—C(CH₃)=CH₂, —CH(CH₃)—CH=CH, —CH=C(CH₃)₂, —C(CH₃)=CH—CH₃, —CH=CH—CH=CH₂, —C₃H₆—CH=CH₂, —C₂H₄—CH=CH—CH₃, —CH₂—CH=CH—C₂H₅, —CH=CH—C₃H₇, —CH₂—CH=CH—CH=CH₂, —CH=CH—CH=CH—CH₃, —CH=CH—CH₂—CH=CH₂, —C(CH₃)=CH—CH=CH₂, —CH=C(CH₃)—CH=CH₂, —CH=CH—C(CH₃)=CH₂, —C₂H₄—C(CH₃)=CH₂, —CH₂—CH(CH₃)—CH=CH₂, —CH(CH₃)—CH₂—CH=CH₂, —CH₂—CH=C(CH₃)₂, —CH₂—C(CH₃)=CH—CH₃, —CH(CH₃)—CH=CH—CH₃, —CH=CH—CH(CH₃)₂, —CH=CH—C(CH₃)₂, —CH(CH₃)=C(CH₃)₂, —C(CH₃)₂—CH=CH₂, —CH(CH₃)—C(CH₃)=CH₂, —C(CH₃)₂—CH=CH—CH₃, —CH₂—C(CH₃)=CH—CH₃, —C₂H₄—CH=CH—C₂H₅, —CH₂—CH=CH—C₃H₇, —CH=CH—C₃H₇, —CH=CH—C₄H₉, —C₃H₆—C(CH₃)=CH₂, —C₂H₄—CH(CH₃)—CH=CH₂, —CH₂—CH(CH₃)—CH₂—CH=CH₂, —C₂H₄—CH=C(CH₃)₂, —CH(CH₃)—C₂H₄—CH=CH₂, —C₂H₄—C(CH₃)=CH—CH₃, —CH₂—CH(CH₃)—CH=CH—CH₃, —CH(CH₃)—CH₂—CH=CH—CH₃, —CH₂—CH=CH—CH(CH₃)₂, —CH₂—CH=C(CH₃)—C₂H₅, —CH(CH₃)—CH=CH—C₂H₅, —CH=CH—CH₂—CH(CH₃)₂, —CH=CH—CH(CH₃)—C₂H₅, —CH=C(CH₃)—C₃H₇, —C(CH₃)=CH—C₃H₇, —CH₂—CH(CH₃)—C(CH₃)=CH₂, —C[C(CH₃)₃]=CH₂, —CH(CH₃)—CH₂—C(CH₃)=CH₂, —CH(CH₃)—CH(CH₃)—CH=CH₂, —CH₂—C(CH₃)₂—CH=CH₂, —C(CH₃)₂—CH₂—CH=CH₂, —CH₂—C(CH₃)=C(CH₃)₂, —CH(CH₃)—CH=C(CH₃)₂, —C(CH₃)₂—CH=CH—CH₃, —CH(CH₃)—C(CH₃)=CH—CH₃, —CH=C(CH₃)—CH(CH₃)₂, —C(CH₃)=CH—CH(CH₃)₂, —C(CH₃)=C(CH₃)—C₂H₅, —CH=CH—C(CH₃)₃, —C(CH₃)₂—C(CH₃)=CH₂, —CH(C₂H₅)—C(CH₃)=CH₂, —C(CH₃)(C₂H₅)—CH=CH₂, —CH(CH₃)—C(C₂H₅)=CH₂, —CH₂—C(C₃H₇)=CH₂, —CH₂—C(C₂H₅)=CH—CH₃, —CH(C₂H₅)—CH=CH—CH₃, —C(C₄H₉)=CH₂, —C(C₃H₇)=CH—CH₃, —C(C₂H₅)=CH—C₂H₅, —C(C₂H₅)=C(CH₃)₂, —C[CH(CH₃)(C₂H₅)]=CH₂, —C[CH₂—CH(CH₃)₂]=CH₂, —C₃H₆—C≡C—CH₃, —CH(CH₃)—CH₂—C≡CH, —CH(CH₃)—C≡C—CH₃, —C₂H₄—CH(CH₃)—C≡CH, —CH₂—CH(CH₃)—CH₂—C≡CH, —CH₂—CH(CH₃)—C≡CH, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —C₄H₈—C≡CH, —C₂H₄—C≡C—C₂H₅, —CH₂—C≡C—C₃H₇, —C≡C—C₄H₉, —C≡C—C(CH₃)₃, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —C≡C—CH₂—CH(CH₃)₂, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —CH₂—CH(C≡CH)₂,

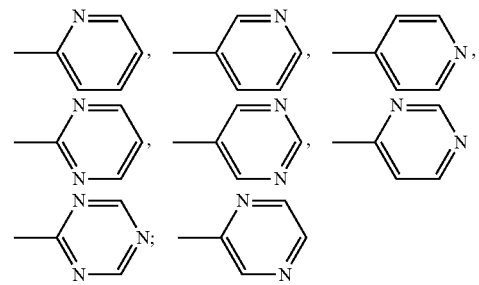

R¹⁵ represents —R²⁰, —CN, —CH₂—CN, —CH₂—OR¹⁷, —CH₂—CH₂—OR¹⁷, —CH₂—NR¹⁷R¹⁸, —CH₂—NR¹⁷COR¹⁹, —CH₂—NR¹⁷R¹⁸, —CH₂—NR¹⁷COR¹⁹, —CO₂R¹⁷, —CO—NR¹⁷R¹⁸, —CH₂—CO₂R¹⁷, or —CH₂—CO—NR¹⁷R¹⁸;

$R^{16}$ represents —$R^{21}$, —H, —$CH_3$, —$C_2H_5$, —$C_3H_7$, —$CH(CH_3)_2$, —$C_4H_9$, —$CH_2$—$CH(CH_3)_2$, —$CH(CH_3)$—$C_2H_5$, —$C(CH_3)_3$, $C_5H_{11}$, —$CH(CH_3)$—$C_3H_7$, —$CH_2$—$CH(CH_3)$—$C_2H_5$, —$CH(CH_3)$—$CH(CH_3)_2$, —$C(CH_3)_2$—$C_2H_5$, —$C(CH_3)_3$, —$CH(C_2H_5)_2$, —$C_2H_4$—$CH(CH_3)_2$, —$C_6H_{13}$, —$C_7H_{15}$, —$C_8H_{17}$, —$C_3H_6$—$CH(CH_3)_2$, —$C_2H_4$—$CH(CH_3)$—$C_2H_5$, —$CH(CH_3)$—$C_4H_9$, —$CH_2$—$CH(CH_3)$—$C_3H_7$, —$CH(CH_3)$—$CH_2$—$CH(CH_3)_2$, —$CH(CH_3)$—$CH(CH_3)$—$C_2H_5$, —$CH_2$—$CH(CH_3)$—$CH(CH_3)_2$, —$CH_2$—$C(CH_3)_2$—$C_2H_5$, —$C(CH_3)_2$—$C_3H_7$, —$C(CH_3)_2$—$CH(CH_3)_2$, —$C_2H_4$—$C(CH_3)_3$, —$CH(CH_3)$—$C(CH_3)_3$, —$CH_2OH$, —$CH_2$—SH, —$CH(OH)CH_3$, —$C_2H_4OH$, —$C_3H_6OH$, —$C_4H_8OH$, —$CH(CH_3)$—$C_2H_4OH$, —$C_5H_{10}OH$, —$CH_2$—S—$CH_3$, —$CH_2$—$CH_2$—S—$CH_3$, —$C_3H_6$—S—$CH_3$, —$CH_2OCH_3$, —$C_2H_4OCH_3$, —$C_3H_6OCH_3$, —$C_4H_8OCH_3$, —$CH(CH_3)$—$C_2H_4OCH_3$, —$C_5H_{10}OCH_3$, —$CH_2NH_2$, —$C_2H_4NH_2$, —$C_3H_6NH_2$, —$C_4H_8NH_2$, —$CH(CH_3)$—$C_2H_4NH_2$, —$C_5H_{10}NH_2$, —$CH_2$—$CH_2$—$CH_2$—NH—C(NH)$NH_2$, —$CH_2$—$CO_2H$, —$CH_2$—$CONH_2$, —$CH_2$—$CH_2$—$CO_2H$, —$CH_2$—$CH_2$—$CONH_2$, —$CH_2$—$CO_2CH_3$, —$CH_2$—$CONHCH_3$, —$CH_2$—$CON(CH_3)_2$, —$CH_2$—$CH_2$—$CO_2CH_3$, —$CH_2$—$CH_2$—$CONHCH_3$, —$CH_2$—$CH_2$—$CONH(CH_3)_2$, —CH=CH—$CO_2H$, —CH=CH—$CO_2CH_3$, —CH=CH—$CONHCH_3$, —CH=CH—$CONHC_2H_5$, —CH=CH—$CON(CH_3)_2$, —CH=CH—$CON(C_2H_5)_2$, —$CH_2$—CH=CH—$CO_2H$, —$CH_2$—CH=CH—$CO_2CH_3$, —$CH_2$—CH=CH—$CONHCH_3$, —$CH_2$—CH=CH—$CON(CH_3)_2$, —$CH_2$—CH=CH—$CONHC_2H_5$, —$CH_2$—CH=CH—$CON(C_2H_5)_2$, —CH=$CH_2$, —$CH_2$—CH=$CH_2$, —C($CH_3$)=$CH_2$, —CH=CH—$CH_3$, —$C_2H_4$—CH=$CH_2$, —$CH_2$—CH=CH—$CH_3$, —CH=CH—$C_2H_5$, —$CH_2$—C($CH_3$)=$CH_2$, —CH($CH_3$)—CH=$CH$, —CH=C($CH_3$)$_2$, —C($CH_3$)=CH—$CH_3$, —CH=CH—CH=$CH_2$, —$C_3H_6$—CH=$CH_2$, —$C_2H_4$—CH=CH—$CH_3$, —$CH_2$—CH=CH—$C_2H_5$, —CH=CH—$C_3H_7$, —$CH_2$—CH=CH—CH=$CH_2$, —CH=CH—CH=CH—$CH_3$, —CH=CH—$CH_2$—C($CH_3$)=CH—CH=$CH_2$, —CH=C($CH_3$)—CH=$CH_2$, —CH=C($CH_3$)—CH=$CH_2$, —C($CH_3$)=CH—CH=$CH_2$, —$C_2H_4$—C($CH_3$)=$CH_2$, —$CH_2$—CH($CH_3$)—CH=$CH_2$, —CH($CH_3$)—$CH_2$—CH=$CH_2$, —$CH_2$—CH=C($CH_3$)$_2$, —$CH_2$—C($CH_3$)=CH—$CH_3$, —CH($CH_3$)—CH=CH—$CH_3$, —CH=CH—CH($CH_3$)$_2$, —CH=C($CH_3$)—$C_2H_5$, —C($CH_3$)=CH—$C_2H_5$, —C($CH_3$)=C($CH_3$)$_2$, —C($CH_3$)$_2$—CH=$CH_2$, —CH($CH_3$)—C($CH_3$)=$CH_2$, —C($CH_3$)=CH—CH=$CH_2$, —CH=C($CH_3$)—CH=$CH_2$, —CH=CH—C($CH_3$)=$CH_2$, —$C_4H_8$—CH=$CH_2$, —$C_3H_6$—CH=CH—$CH_3$, —$C_2H_4$—CH=CH—$C_2H_5$, —$CH_2$—CH=CH—$C_3H_7$, —CH=CH—$C_4H_9$, —$C_3H_6$—C($CH_3$)=$CH_2$, —$C_2H_4$—CH($CH_3$)—CH=$CH_2$, —$CH_2$—CH($CH_3$)—$CH_2$—CH=$CH_2$, —$C_2H_4$—CH=C($CH_3$)$_2$, —CH($CH_3$)—$C_2H_4$—CH=$CH_2$, —$C_2H_4$—C($CH_3$)=CH—$CH_3$, —$CH_2$—CH($CH_3$)—CH=CH—$CH_3$, —$CH_2$—CH=CH—CH($CH_3$)$_2$, —$CH_2$—CH=CH—$C_2H_5$, —$CH_2$—CH=CH—$CH_2$—CH($CH_3$)$_2$, —CH=CH—CH($CH_3$)—$C_2H_5$, —CH=C($CH_3$)—$C_3H_7$, —$CH_2$—CH($CH_3$)—C($CH_3$)=$CH_2$, —$CH_2$—C[C($CH_3$)$_3$]=$CH_2$, —CH($CH_3$)—$CH_2$—C($CH_3$)=$CH_2$, —CH($CH_3$)—CH (CH$_3$)—CH=$CH_2$, —CH=CH—$C_2H_4$—CH=$CH_2$, —$CH_2$—C($CH_3$)$_2$—CH=$CH_2$, —C($CH_3$)$_2$—CH=$CH_2$, —$CH_2$—C($CH_3$)=C($CH_3$)$_2$, —CH(CH$_3$)—CH=C($CH_3$)$_2$, —C($CH_3$)$_2$—CH=CH—$CH_3$, —CH=CH—$CH_2$—CH=CH—$CH_3$, —CH(CH$_3$)—C($CH_3$)=CH—$CH_3$, —CH=C($CH_3$)—CH(CH$_3$)$_2$, —C($CH_3$)=CH—CH(CH$_3$)$_2$, —C($CH_3$)=C($CH_3$)—$C_2H_5$, —CH=CH—C($CH_3$)$_3$, —C($CH_3$)$_2$—C($CH_3$)=$CH_2$, —CH($C_2H_5$)—C($CH_3$)=$CH_2$, —C($CH_3$)($C_2H_5$)—CH=$CH_2$, —CH(CH$_3$)—C($C_2H_5$)=$CH_2$, —$CH_2$—C($C_3H_7$)=$CH_2$, —$CH_2$—C($C_2H_5$)=CH—$CH_3$, —CH($C_2H_5$)—CH=CH—$CH_3$, —C($C_4H_9$)=$CH_2$, —C($C_3H_7$)=CH—$CH_3$, —C($C_2H_5$)=CH—$C_2H_5$, —C($C_2H_5$)=C($CH_3$)$_2$, —C[CH(CH$_3$)($C_2H_5$)]=$CH_2$, —C[$CH_2$—CH(CH$_3$)$_2$]=$CH_2$, —$C_2H_4$—CH=CH—CH=$CH_2$, —$CH_2$—CH=CH—$CH_2$—CH=$CH_2$, —$C_3H_6$—C≡C—$CH_3$, —$CH_2$—CH=CH—CH=CH—$CH_3$, —CH=CH—CH=CH—$C_2H_5$, —$CH_2$—CH=CH—C($CH_3$)=$CH_2$, —$CH_2$—CH=C($CH_3$)—CH=$CH_2$, —$CH_2$—C($CH_3$)=CH—CH=$CH_2$, —CH(CH$_3$)—$CH_2$—C≡CH, —CH(CH$_3$)—CH=CH—CH=$CH_2$, —CH=CH—$CH_2$—C($CH_3$)=$CH_2$, —CH(CH$_3$)—C≡C—$CH_3$, —CH=CH—CH(CH$_3$)—CH=$CH_2$, —CH=C($CH_3$)—$CH_2$—CH=$CH_2$, —$C_2H_4$—CH(CH$_3$)—C≡CH, —C($CH_3$)—$CH_2$—CH=$CH_2$, —CH=CH—CH=C($CH_3$)$_2$, —$CH_2$—CH(CH$_3$)—$CH_2$—C≡CH, —CH=CH—C($CH_3$)=CH—$CH_3$, —CH=C($CH_3$)—CH=CH—$CH_3$, —$CH_2$—CH(CH$_3$)—C≡CH, —C($CH_3$)=CH—CH=CH—$CH_3$, —CH=C($CH_3$)—C($CH_3$)=$CH_2$, —C($CH_3$)=CH—C($CH_3$)=$CH_2$, —C($CH_3$)=C($CH_3$)—CH=$CH_2$, —CH=CH—CH=CH—CH=$CH_2$, —C≡CH, —C≡C—$CH_3$, —$CH_2$—C≡CH, —$C_2H_4$—C≡CH, —$CH_2$—C≡C—$CH_3$, —C≡C—$C_2H_5$, —$C_3H_6$—C≡CH, —$C_2H_4$—C≡C—$CH_3$, —$CH_2$—C≡C—$C_2H_5$, —C≡C—$C_3H_7$, —CH(CH$_3$)—C≡CH, —$C_4H_8$—C≡CH, —$C_2H_4$—C≡C—$C_2H_5$, —C≡C—$C_3H_7$, —C≡C—$C_4H_9$, —C≡C—C($CH_3$)$_3$, —CH(CH$_3$)—$C_2H_4$—C≡CH, —$CH_2$—CH(CH$_3$)—C≡C—$CH_3$, —CH(CH$_3$)—$CH_2$—C≡C—$CH_3$, —CH(CH$_3$)—C≡C—$C_2H_5$, —$CH_2$—C≡C—CH(CH$_3$)$_2$, —C≡C—CH(CH$_3$)—$C_2H_5$, —C≡C—$CH_2$—CH(CH$_3$)$_2$, —CH($C_2H_5$)—C≡C—$CH_3$, —C($CH_3$)$_2$—C≡C—$CH_3$, —CH($C_2H_5$)—$CH_2$—C≡CH, —$CH_2$—CH($C_2H_5$)—C≡CH, —C($CH_3$)$_2$—$CH_2$—C≡CH, —$CH_2$—C($CH_3$)$_2$—C≡CH, —CH(CH$_3$)—CH(CH$_3$)—C≡CH, —CH($C_3H_7$)—C≡CH, —C($CH_3$)($C_2H_5$)—C≡CH, —$CH_2$-Ph,

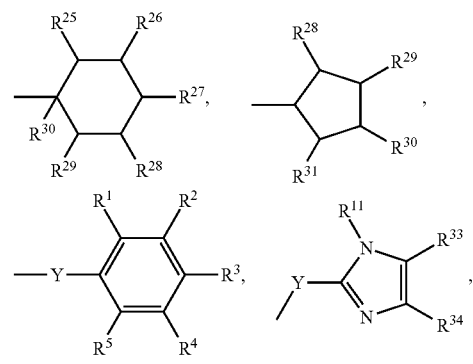

-continued

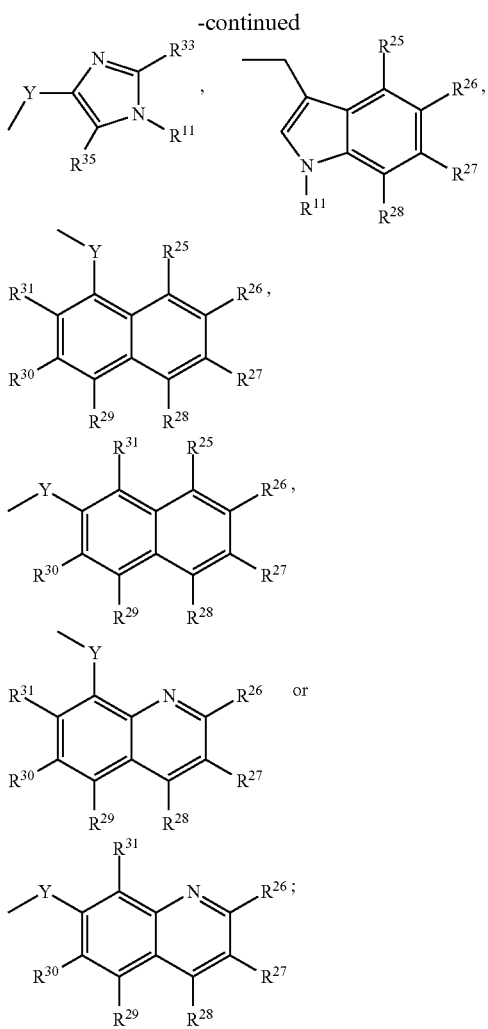

$R^{11}$-$R^{14}$ and $R^{17}$-$R^{21}$ represent independently of each other —H, —CH$_2$F, —CHF$_2$, —CH$_2$—OCH$_3$, —CH$_2$—OH, —C$_2$H$_4$—OCH$_3$, —C$_3$H$_6$—OCH$_3$, —CH$_2$—OC$_2$H$_5$, —C$_2$H$_4$—OC$_2$H$_5$, —C$_3$H$_6$—OC$_2$H$_5$, —CH$_2$—OC$_3$H$_7$, —C$_2$H$_4$—OC$_3$H$_7$, —C$_3$H$_6$—OC$_3$H$_7$, —CH$_2$—O-cyclo-C$_3$H$_5$, —C$_2$H$_4$—O-cyclo-C$_3$H$_5$, —C$_3$H$_6$—O-cyclo-C$_3$H$_5$, —CH$_2$—OCH(CH$_3$)$_2$, —C$_2$H$_4$—OCH(CH$_3$)$_2$, —C$_3$H$_6$—OCH(CH$_3$)$_2$, —CH$_2$—OC(CH$_3$)$_3$, —C$_2$H$_4$—OC(CH$_3$)$_3$, —C$_3$H$_6$—OC(CH$_3$)$_3$, —CH$_2$—OC$_4$H$_9$, —C$_2$H$_4$—OC$_4$H$_9$, —C$_3$H$_6$—OC$_4$H$_9$, —CH$_2$—OPh, —C$_2$H$_4$—OPh, —C$_3$H$_6$—OPh, —CH$_2$—OCH$_2$-Ph, —C$_2$H$_4$—OCH$_2$-Ph, —C$_3$H$_6$—OCH$_2$-Ph, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, -cyclo-C$_3$H$_5$, -cyclo-C$_4$H$_7$, -cyclo-C$_5$H$_9$, -cyclo-C$_6$H$_{11}$, -cyclo-C$_7$H$_{13}$, -cyclo-C$_8$H$_{15}$, -Ph, —CH$_2$-Ph, —CH$_2$—CH$_2$-Ph, —CH=CH-Ph, —CPh$_3$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_7$H$_{15}$, —C$_8$H$_{17}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —CH$_2$—CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$, —CH=CH—C$_2$H$_5$, —CH$_2$—C(CH$_3$)=CH$_2$, —CH(CH$_3$)—CH=CH, —CH=C(CH$_3$)$_2$, —C(CH$_3$)=CH—CH$_3$, —CH=CH—CH=CH$_2$, —C$_3$H$_6$—CH=CH$_2$, —C$_2$H$_4$—CH=CH—CH$_3$, —CH$_2$—CH=CH—C$_2$H$_5$, —CH=CH—C$_3$H$_7$, —CH$_2$—CH=CH—CH=CH$_2$, —CH=CH—CH=CH—CH$_3$, —CH=CH—CH$_2$—CH=CH$_2$, —C(CH$_3$)=CH—CH=CH$_2$, —CH=C(CH$_3$)—CH=CH$_2$, —CH=CH—C(CH$_3$)=CH$_2$, —C$_2$H$_4$—C(CH$_3$)=CH$_2$, —CH$_2$—CH(CH$_3$)—CH=CH$_2$, —CH(CH$_3$)—CH$_2$—CH=CH$_2$, —CH$_2$—CH=C(CH$_3$)$_2$, —CH$_2$—C(CH$_3$)=CH—CH$_3$, —CH(CH$_3$)—CH=CH—CH$_3$, —CH=CH—CH(CH$_3$)$_2$, —CH=C(CH$_3$)—C$_2$H$_5$, —C(CH$_3$)=CH—C$_2$H$_5$, —C(CH$_3$)=C(CH$_3$)$_2$, —C(CH$_3$)$_2$—CH=CH$_2$, —CH(CH$_3$)—C(CH$_3$)=CH$_2$, —C(CH$_3$)=CH—CH=CH$_2$, —CH=C(CH$_3$)—CH=CH$_2$, —CH=CH—C(CH$_3$)=CH$_2$, —C$_4$H$_8$—CH=CH$_2$, —C$_3$H$_6$—CH=CH—CH$_3$, —C$_2$H$_4$—CH=CH—C$_2$H$_5$, —CH$_2$—CH=CH—C$_3$H$_7$, —CH=CH—C$_4$H$_9$, —C$_3$H$_6$—C(CH$_3$)=CH$_2$, —C$_2$H$_4$—CH(CH$_3$)—CH=CH$_2$, —CH$_2$—CH(CH$_3$)—CH$_2$—CH=CH$_2$, —C$_2$H$_4$—CH=C(CH$_3$)$_2$, —CH(CH$_3$)—C$_2$H$_4$—CH=CH$_2$, —C$_2$H$_4$—C(CH$_3$)=CH—CH$_3$, —CH$_2$—CH(CH$_3$)—CH=CH—CH$_3$, —CH(CH$_3$)—CH$_2$—CH=CH—CH$_3$, —CH$_2$—CH=CH—CH(CH$_3$)$_2$, —CH$_2$—CH=C(CH$_3$)—C$_2$H$_5$, —CH$_2$—C(CH$_3$)=CH—C$_2$H$_5$, —CH(CH$_3$)—CH=CH—C$_2$H$_5$, —CH=CH—CH$_2$—CH(CH$_3$)$_2$, —CH=CH—CH(CH$_3$)—C$_2$H$_5$, —CH=C(CH$_3$)—C$_3$H$_7$, —C(CH$_3$)=CH—C$_3$H$_7$, —CH$_2$—CH(CH$_3$)—C(CH$_3$)=CH$_2$, —C[C(CH$_3$)$_3$]=CH$_2$, —CH(CH$_3$)—CH$_2$—C(CH$_3$)=CH$_2$, —CH(CH$_3$)—CH(CH$_3$)—CH=CH$_2$, —CH$_2$—C(CH$_3$)$_2$—CH=CH$_2$, —C(CH$_3$)$_2$—CH$_2$—CH=CH$_2$, —CH$_2$—C(CH$_3$)=C(CH$_3$)$_2$, —CH(CH$_3$)—CH=C(CH$_3$)$_2$, —C(CH$_3$)$_2$—CH=CH—CH$_3$, —CH(CH$_3$)—C(CH$_3$)=CH—CH$_3$, —CH=C(CH$_3$)—CH(CH$_3$)$_2$, —C(CH$_3$)=CH—CH(CH$_3$)$_2$, —C(CH$_3$)=C(CH$_3$)—C$_2$H$_5$, —CH=CH—C(CH$_3$)$_3$, —C(CH$_3$)$_2$—C(CH$_3$)=CH$_2$, —CH(C$_2$H$_5$)—C(CH$_3$)=CH$_2$, —C(CH$_3$)(C$_2$H$_5$)—CH=CH$_2$, —CH(CH$_3$)—C(C$_2$H$_5$)=CH$_2$, —CH$_2$—C(C$_3$H$_7$)=CH$_2$, —CH$_2$—C(C$_2$H$_5$)=CH—CH$_3$, —CH(C$_2$H$_5$)—CH=CH—CH$_3$, —C(C$_4$H$_9$)=CH$_2$, —C(C$_3$H$_7$)=CH—CH$_3$, —C(C$_2$H$_5$)=CH—C$_2$H$_5$, —C(C$_2$H$_5$)=C(CH$_3$)$_2$, —C[CH(CH$_3$)(C$_2$H$_5$)]=CH$_2$, —C[CH$_2$—CH(CH$_3$)$_2$]=CH$_2$, —C$_3$H$_6$—C≡C—CH$_3$, —CH(CH$_3$)—CH$_2$—C≡CH, —CH(CH$_3$)—C≡C—CH$_3$, —C$_2$H$_4$—CH(CH$_3$)—C≡CH, —CH$_2$—CH(CH$_3$)—CH$_2$—C≡CH, —CH$_2$—CH(CH$_3$)—C≡CH, —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —C$_3$H$_6$—C≡CH, —C$_2$H$_4$—C≡C—CH$_3$, —CH$_2$—C≡C—C$_2$H$_5$, —C≡C—C$_3$H$_7$, —CH(CH$_3$)—C≡CH, —C$_4$H$_8$—C≡CH, —C$_2$H$_4$—C≡C—C$_2$H$_5$, —CH$_2$—C≡C—C$_3$H$_7$, —C≡C—C$_4$H$_9$, —C≡C—C(CH$_3$)$_3$, —CH(CH$_3$)—C$_2$H$_4$—C≡CH, —CH$_2$—CH(CH$_3$)—C≡C—CH$_3$, —CH(CH$_3$)—CH$_2$—C≡C—CH$_3$, —CH(CH$_3$)—C≡C—C$_2$H$_5$, —CH$_2$—C≡C—CH(CH$_3$)$_2$, —C≡C—CH(CH$_3$)—C$_2$H$_5$, —CH$_2$—C$_2$H$_5$, —C≡C—CH$_2$—CH(CH$_3$)$_2$, —CH(C$_2$H$_5$)—C≡C—CH$_3$, —C(CH$_3$)$_2$—C≡C—CH$_3$, —CH($C_2H_5$)—$CH_2$—C≡CH, —$CH_2$—CH($C_2H_5$)—C≡CH, —C($CH_3$)$_2$—$CH_2$—C≡CH, —$CH_2$—C($CH_3$)$_2$—C≡CH, —CH($CH_3$)—CH($CH_3$)—C≡CH, —CH($C_3H_7$)—C≡CH, —C($CH_3$)($C_2H_5$)—C≡CH, or —$CH_2$—CH(C≡CH)$_2$;

$R^{22}$-$R^{37}$ represent independently of each other —H, —OH, —$OCH_3$, —$OC_2H_5$, —$OC_3H_7$, —O-cyclo-$C_3H_5$, —OCH($CH_3$)$_2$, —OC($CH_3$)$_3$, —$OC_4H_9$, —$OCH_2$—COOH, —OPh, —$OCH_2$-Ph, —$OCPh_3$, —$CH_2$—OH, —$C_2H_4$—OH, —$C_3H_6$—OH, —CH(OH)—$CH_2$—OH, —$CH_2$—$OCH_3$, —$C_2H_4$—$OCH_3$, —$C_3H_6$—$OCH_3$, —$CH_2$—$OC_2H_5$, —$C_2H_4$—$OC_2H_5$, —$C_3H_6$—$OC_2H_5$, —$CH_2$—$OC_3H_7$, —$C_2H_4$—$OC_3H_7$, —$C_3H_6$—$OC_3H_7$, —$CH_2$—O-cyclo-$C_3H_5$, —$C_2H_4$—O-cyclo-$C_3H_5$, —$C_3H_6$—O-cyclo-$C_3H_5$, —$CH_2$—OCH($CH_3$)$_2$, —$C_2H_4$—OCH($CH_3$)$_2$, —$C_3H_6$—OCH($CH_3$)$_2$, —$CH_2$—OC($CH_3$)$_3$, —$C_2H_4$—OC($CH_3$)$_3$, —$C_3H_6$—OC($CH_3$)$_3$, —$CH_2$—$OC_4H_9$, —$C_2H_4$—$OC_4H_9$, —$C_3H_6$—$OC_4H_9$, —$CH_2$—OPh, —$C_2H_4$—OPh, —$C_3H_6$—OPh, —$CH_2$—$OCH_2$-Ph, —$C_2H_4$—$OCH_2$-Ph, —$C_3H_6$—$OCH_2$-Ph, —SH, —$SCH_3$, —$SC_2H_5$, —$SC_3H_7$, —S-cyclo-$C_3H_5$, —SCH($CH_3$)$_2$, —SC($CH_3$)$_3$, —$NO_2$, —F, —Cl, —Br, —I, —P(O)(OH)$_2$, —P(O)(OCH$_3$)$_2$, —P(O)(OC$_2$H$_5$)$_2$, —P(O)(OCH($CH_3$)$_2$)$_2$, —C(OH)[P(O)(OH)$_2$]$_2$, —Si($CH_3$)$_2$(C($CH_3$)$_3$), —Si($C_2H_5$)$_3$, —Si($CH_3$)$_3$, —$N_3$, —CN, —OCN, —NCO, —SCN, —NCS, —CHO, —$COCH_3$, —$COC_2H_5$, —$COC_3H_7$, —CO-cyclo-$C_3H_5$, —COCH($CH_3$)$_2$, —COC($CH_3$)$_3$, —COOH, —COCN, —$COOCH_3$, —$COOC_2H_5$, —$COOC_3H_7$, —COO-cyclo-$C_3H_5$, —COOCH($CH_3$)$_2$, —COOC($CH_3$)$_3$, —OOC—$CH_3$, —OOC—$C_2H_5$, —OOC—$C_3H_7$, —OOC-cyclo-$C_3H_5$, —OOC—CH($CH_3$)$_2$, —OOC—C($CH_3$)$_3$, —$CONH_2$, —$CH_2$—$CONH_2$, —$CONHCH_3$, —$CONHC_2H_5$, —$CONHC_3H_7$, —CONH-cyclo-$C_3H_5$, —CONH[CH($CH_3$)$_2$], —CONH[C($CH_3$)$_3$], —CON($CH_3$)$_2$, —CON($C_2H_5$)$_2$, —CON($C_3H_7$)$_2$, —CON(cyclo-$C_3H_5$)$_2$, —CON[CH($CH_3$)$_2$]$_2$, —CON[C($CH_3$)$_3$]$_2$, —$NHCOCH_3$, —$NHCOC_2H_5$, —$NHCOC_3H_7$, —NHCO-cyclo-$C_3H_5$, —NHCO—CH($CH_3$)$_2$, —NHCO—C($CH_3$)$_3$, —NHCO—$OCH_3$, —NHCO—$OC_2H_5$, —NHCO—$OC_3H_7$, —NHCO—O-cyclo-$C_3H_5$, —NHCO—OCH($CH_3$)$_2$, —NHCO—OC($CH_3$)$_3$, —$NH_2$, —$NHCH_3$, —$NHC_2H_5$, —$NHC_3H_7$, —NH-cyclo-$C_3H_5$, —NHCH($CH_3$)$_2$, —NHC($CH_3$)$_3$, —N($CH_3$)$_2$, —N($C_2H_5$)$_2$, —N($C_3H_7$)$_2$, —N(cyclo-$C_3H_5$)$_2$, —N[CH($CH_3$)$_2$]$_2$, —N[C($CH_3$)$_3$]$_2$, —$SOCH_3$, —$SOC_2H_5$, —$SOC_3H_7$, —SO-cyclo-$C_3H_5$, —SOCH($CH_3$)$_2$, —SOC($CH_3$)$_3$, —$SO_2CH_3$, —$SO_2C_2H_5$, —$SO_2C_3H_7$, —$SO_2$-cyclo-$C_3H_5$, —$SO_2$CH($CH_3$)$_2$, —$SO_2$C($CH_3$)$_3$, —$SO_3$H, —$SO_3CH_3$, —$SO_3C_2H_5$, —$SO_3C_3H_7$, —$SO_3$-cyclo-$C_3H_5$, —$SO_3$CH($CH_3$)$_2$, —$SO_3$C($CH_3$)$_3$, —$SO_2NH_2$, —$SO_2NHCH_3$, —$SO_2NHC_2H_5$, —$SO_2NHC_3H_7$, —$SO_2$NH-cyclo-$C_3H_5$, —$SO_2$NHCH($CH_3$)$_2$, —$SO_2$NHC($CH_3$)$_3$, —$SO_2$N($CH_3$)$_2$, —$SO_2$N($C_2H_5$)$_2$, —$SO_2$N($C_3H_7$)$_2$, —$SO_2$N(cyclo-$C_3H_5$)$_2$, —$SO_2$N[CH($CH_3$)$_2$]$_2$, —$SO_2$N[C($CH_3$)$_3$]$_2$, —O—S(=O)$CH_3$, —O—S(=O)$C_2H_5$, —O—S(=O)$C_3H_7$, —O—S(=O)-cyclo-$C_3H_5$, —O—S(=O)CH($CH_3$)$_2$, —O—S(=O)C($CH_3$)$_3$, —S(=O)(=NH)$CH_3$, —S(=O)(=NH)$C_2H_5$, —S(=O)(=NH)$C_3H_7$, —S(=O)(=NH)-cyclo-$C_3H_5$, —S(=O)(=NH)CH($CH_3$)$_2$, —S(=O)(=NH)C($CH_3$)$_3$, —NH—$SO_2$—$CH_3$, —NH—$SO_2$—$C_2H_5$, —NH—$SO_2$—$C_3H_7$, —NH—$SO_2$-cyclo-$C_3H_5$, —NH—$SO_2$—CH($CH_3$)$_2$, —NH—$SO_2$—C($CH_3$)$_3$, —O—$SO_2$—$CH_3$, —O—$SO_2$—$C_2H_5$, —O—$SO_2$—$C_3H_7$, —O—$SO_2$-cyclo-$C_3H_5$, —O—$SO_2$—CH($CH_3$)$_2$, —O—$SO_2$—C($CH_3$)$_3$, —$OCF_3$, —$CH_2$—$OCF_3$, —$C_2H_4$—$OCF_3$, —$C_3H_6$—$OCF_3$, —$OC_2F_5$, —$CH_2$—$OC_2F_5$, —$C_2H_4$—$OC_2F_5$, —$C_3H_6$—$OC_2F_5$, —O—COOCH$_3$, —O—$COOC_2H_5$, —O—$COOC_3H_7$, —O—COO-cyclo-$C_3H_5$, —O—COOCH($CH_3$)$_2$, —O—COOC($CH_3$)$_3$, —NH—CO—$NH_2$, —NH—CO—$NHCH_3$, —NH—CO—$NHC_2H_5$, —NH—CS—N($C_3H_7$)$_2$, —NH—CO—$NHC_3H_7$, —NH—CO—N($C_3H_7$)$_2$, —NH—CO—NH[CH($CH_3$)$_2$], —NH—CO—NH[C($CH_3$)$_3$], —NH—CO—N($CH_3$)$_2$, —NH—CO—N($C_2H_5$)$_2$, —NH—CO—NH-cyclo-$C_3H_5$, —NH—CO—N(cyclo-$C_3H_5$)$_2$, —NH—CO—N[CH($CH_3$)$_2$]$_2$, —NH—CS—N($C_2H_5$)$_2$, —NH—CO—N[C($CH_3$)$_3$]$_2$, —NH—CS—$NH_2$, —NH—CS—$NHCH_3$, —NH—CS—N($CH_3$)$_2$, —NH—CS—$NHC_2H_5$, —NH—CS—$NHC_3H_7$, —NH—CS—NH-cyclo-$C_3H_5$, —NH—CS—NH[CH($CH_3$)$_2$], —NH—CS—NH[C($CH_3$)$_3$], —NH—CS—N(cyclo-$C_3H_5$)$_2$, —NH—CS—N[CH($CH_3$)$_2$]$_2$, —NH—CS—N[C($CH_3$)$_3$]$_2$, —NH—C(=NH)—$NH_2$, —NH—C(=NH)—$NHCH_3$, —NH—C(=NH)—$NHC_2H_5$, —NH—C(=NH)—$NHC_3H_7$, —O—CO—NH-cyclo-$C_3H_5$, —NH—C(=NH)—N H-cyclo-$C_3H_5$, —NH—C(=NH)—NH[CH($CH_3$)$_2$] —O—CO—NH[CH($CH_3$)$_2$], —NH—C(=NH)—NH[C($CH_3$)$_3$], —NH—C(=NH)—N($CH_3$)$_2$, —NH—C(=NH)—N($C_2H_5$)$_2$, —NH—C(=NH)—N($C_3H_7$)$_2$, —NH—C(=NH)—N(cyclo-$C_3H_5$)$_2$, —O—CO—$NHC_3H_7$, —NH—C(=NH)—N[CH($CH_3$)$_2$]$_2$, —NH—C(=NH)—N[C($CH_3$)$_3$]$_2$, —O—CO—$NH_2$, —O—CO—$NHCH_3$, —O—CO—$NHC_2H_5$, —O—CO—NH[C($CH_3$)$_3$], —O—CO—N($CH_3$)$_2$, —O—CO—N($C_2H_5$)$_2$, —O—CO—N($C_3H_7$)$_2$, —O—CO—N(cyclo-$C_3H_5$)$_2$, —O—CO—N[CH($CH_3$)$_2$]$_2$, —O—CO—N[C($CH_3$)$_3$]$_2$, —O—CO—$OCH_3$, —O—CO—$OC_2H_5$, —O—CO—$OC_3H_7$, —O—CO—O-cyclo-$C_3H_5$, —O—CO—OCH($CH_3$)$_2$, —O—CO—OC($CH_3$)$_3$, —$CH_2$F, —$CHF_2$, —$CF_3$, —$CH_2$Cl, —$CH_2$Br, —$CH_2$I, —$CH_2$—$CH_2$F, —$CH_2$—$CHF_2$, —$CH_2$—$CF_3$, —$CH_2$—$CH_2$Cl, —$CH_2$—$CH_2$Br, —$CH_2$—$CH_2$I, -cyclo-$C_5H_9$, -cyclo-$C_6H_{11}$, —$CH_2$-cyclo-$C_6H_{11}$, —$CH_2$—$CH_2$-cyclo-$C_6H_{11}$, -cyclo-$C_7H_{13}$, -cyclo-$C_8H_{15}$, -Ph, —$CH_2$-Ph, —$CH_2$—$CH_2$-Ph, —CH=CH-Ph, —$CPh_3$, —$CH_3$, —$C_2H_5$, —$C_3H_7$, —CH($CH_3$)$_2$, -$C_4H_9$, —$CH_2$—CH($CH_3$)$_2$, —CH($CH_3$)—$C_2H_5$, —C($CH_3$)$_3$, —$C_5H_{11}$, —CH($CH_3$)—$C_3H_7$, —$CH_2$—CH($CH_3$)—$C_2H_5$, —CH($CH_3$)—CH($CH_3$)$_2$, —C($CH_3$)$_2$—$C_2H_5$, —$CH_2$—C($CH_3$)$_3$, —CH($C_2H_5$)$_2$, —$C_2H_4$—CH($CH_3$)$_2$, —$C_6H_{13}$, —$C_7H_{15}$, —$C_8H_{17}$, —$C_3H_6$—CH($CH_3$)$_2$, —$C_2H_4$—CH($CH_3$)—$C_2H_5$, —CH($CH_3$)—$C_4H_9$, —$CH_2$—CH($CH_3$)—$C_3H_7$, —CH($CH_3$)—$CH_2$—CH($CH_3$)$_2$, —CH($CH_3$)—CH($CH_3$)—$C_2H_5$, —$CH_2$—CH($CH_3$)—CH($CH_3$)$_2$, —$CH_2$—C($CH_3$)$_2$—$C_2H_5$, —C($CH_3$)$_2$—$C_3H_7$, —C($CH_3$)$_2$—CH($CH_3$)$_2$, —$C_2H_4$—C($CH_3$)$_3$, —CH($CH_3$)—C($CH_3$)$_3$, —CH=$CH_2$, —$CH_2$—CH=$CH_2$, —C($CH_3$)=$CH_2$, —CH=CH—$CH_3$, —$C_2H_4$—CH=$CH_2$, —$CH_2$—CH=CH—$CH_3$, —CH=CH—$C_2H_5$, —$CH_2$—C($CH_3$)=$CH_2$, —CH($CH_3$)—CH=CH, —CH=C($CH_3$)$_2$, —C($CH_3$)=CH—$CH_3$, —CH=CH—CH=$CH_2$, —$C_3H_6$—CH=$CH_2$, —$C_2H_4$—CH=CH—$CH_3$, —$CH_2$—CH=CH—$C_2H_5$, —CH=CH—$C_3H_7$, —$CH_2$—CH=CH—CH=$CH_2$, —CH=CH—CH=CH—$CH_3$, —$CH_2$—CH=CH—CH=$CH_2$, —C($CH_3$)=CH—CH=$CH_2$, —CH=C($CH_3$)—CH=$CH_2$, —CH=CH—C(CH₃)=CH₂, —C₂H₄—C(CH₃)=CH₂, —CH₂—CH(CH₃)—CH=CH₂, —CH(CH₃)—CH₂—CH=CH₂, —CH₂—CH=C(CH₃)₂, —CH₂—C(CH₃)=CH—CH₃, —CH(CH₃)—CH=CH—CH₃, —CH=CH—CH(CH₃)₂, —CH=C(CH₃)—C₂H₅, —C(CH₃)=CH—C₂H₅, —C(CH₃)=C(CH₃)₂, —C(CH₃)₂—CH=CH₂, —CH(CH₃)—C(CH₃)=CH₂, —C(CH₃)=CH—CH=CH₂, —CH=C(CH₃)—CH=CH₂, —CH=CH—C(CH₃)=CH₂, —C₄H₈—CH=CH₂, —C₃H₆—CH=CH—CH₃, —C₂H₄—CH=CH—C₂H₅, —CH₂—CH=CH—C₃H₇, —CH=CH—C₄H₉, —C₃H₆—C(CH₃)=CH₂, —C₂H₄—CH(CH₃)—CH=CH₂, —CH₂—CH(CH₃)—CH₂—CH=CH₂, —C₂H₄—CH=C(CH₃)₂, —CH(CH₃)—C₂H₄—CH=CH₂, —C₂H₄—C(CH₃)=CH—CH₃, —CH₂—CH(CH₃)—CH=CH—CH₃, —CH(CH₃)—CH₂—CH=CH—CH₃, —CH₂—CH=CH—CH(CH₃)₂, —CH₂—CH=C(CH₃)—C₂H₅, —CH₂—C(CH₃)=CH—C₂H₅, —CH(CH₃)—CH=CH—C₂H₅, —CH=CH—CH₂—CH(CH₃)₂, —CH=CH—CH(CH₃)—C₂H₅, —CH=C(CH₃)—C₃H₇, —C(CH₃)=CH—C₃H₇, —CH₂—CH(CH₃)—C(CH₃)=CH₂, —C[C(CH₃)₃]=CH₂, —CH(CH₃)—CH₂—C(CH₃)=CH₂, —CH(CH₃)—CH(CH₃)—CH=CH₂, —CH—C(CH₃)₂—CH=CH—C₂H₄—CH=CH₂, —CH₂—C(CH₃)₂—CH=CH₂, —C(CH₃)₂—CH₂—CH=CH₂, —CH₂—C(CH₃)=C(CH₃)₂, —CH(CH₃)—CH=C(CH₃)₂, —C(CH₃)₂—CH=CH—CH₃, —CH=CH—CH₂—CH=CH—CH₃, —CH(CH₃)—C(CH₃)=CH—CH₃, —CH=C(CH₃)—CH(CH₃)₂, —C(CH₃)=CH—CH(CH₃)₂, —C(CH₃)=C(CH₃)—C₂H₅, —CH=CH—C(CH₃)₃, —C(CH₃)₂—C(CH₃)=CH₂, —CH(C₂H₅)—C(CH₃)=CH₂, —C(CH₃)(C₂H₅)—CH=CH₂, —CH(CH₃)—C(C₂H₅)=CH₂, —CH₂—C(C₃H₇)=CH₂, —CH₂—C(C₂H₅)=CH—CH₃, —CH(C₂H₅)—CH=CH—CH₃, —C(C₄H₉)=CH₂, —C(C₃H₇)=CH—CH₃, —C(C₂H₅)=CH—C₂H₅, —C(C₂H₅)=C(CH₃)₂, —C[CH(CH₃)(C₂H₅)]=CH₂, —C[CH₂—CH(CH₃)₂]=CH₂, —C₂H₄—CH=CH—CH=CH₂, —CH₂—CH=CH—CH₂—CH=CH₂, —C₃H₆—C≡C—CH₃, —CH₂—CH=CH—CH=CH—CH₃, —CH=CH—CH=CH—C₂H₅, —CH₂—CH=CH—C(CH₃)=CH₂, —CH₂—CH=C(CH₃)—CH=CH₂, —CH₂—C(CH₃)=CH—CH=CH₂, —CH(CH₃)—CH₂—C≡CH, —CH(CH₃)—CH=CH—CH=CH₂, —CH(CH₃)—CH—CH=CH₂, —CH(CH₃)—C≡C—CH₃, —CH=CH—CH(CH₃)—CH=CH₂, —CH=C(CH₃)—CH₂—CH=CH₂, —C₂H₄—CH(CH₃)—C≡CH, —C(CH₃)=CH—CH₂—CH=CH₂, —CH=CH—CH=C(CH₃)₂, —CH₂—CH(CH₃)—CH₂—C≡CH, —CH=CH—C(CH₃)=CH—CH₃, —CH=C(CH₃)—CH=CH—CH₃, —CH₂—CH(CH₃)—C≡CH, —C(CH₃)=CH—CH=CH—CH₃, —CH=C(CH₃)—C(CH₃)=CH₂, —C(CH₃)=CH—C(CH₃)=CH₂, —C(CH₃)=C(CH₃)—CH=CH₂, —CH=CH—CH=CH—CH=CH₂, —C=CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —C₄H₈—C≡CH, —C₂H₄—C≡C—C₂H₅, —CH₂—C≡C—C₃H₇, —C≡C—C₄H₉, —C≡C—C(CH₃)₃, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —C≡C—CH₂—CH(CH₃)₂, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH(CH₃)—CH(CH₃)—C≡CH, —CH(C₃H₇)—C≡CH, —C(CH₃)(C₂H₅)—C≡CH, —CH₂—CH(C≡CH)₂, —C≡C—C≡CH, —CH₂—C≡C—C≡CH, —C≡C—C≡C—CH₃, —CH(C≡CH)₂, —C₂H₄—C≡C—C≡CH, —CH₂—C≡C—CH₂—C≡CH, —C≡C—C₂H₄—C≡CH, —CH₂—C≡C—C≡C—CH₃, —C≡C—CH₂—C≡C—CH₃, —C≡C—C≡C—C₂H₅, —C(C≡CH)₂—CH₃, —C≡C—CH(CH₃)—C≡CH, —CH(CH₃)—C≡C—C≡CH, —CH(C≡CH)—CH₂—C≡CH, —CH(C≡CH)—C≡C—CH₃,

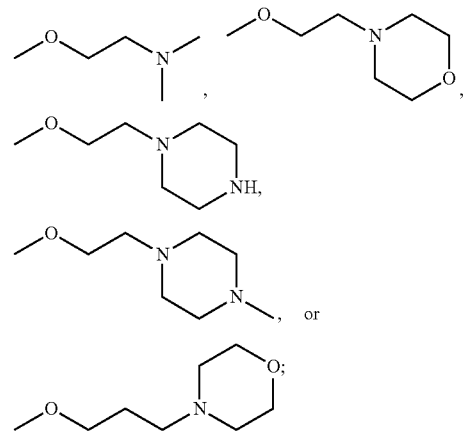

and enantiomers, stereoisomeric forms, mixtures of enantiomers, anomers, deoxy-forms, diastereomers, mixtures of diastereomers, tautomers, or racemates of the above mentioned compounds or pharmaceutically acceptable salts.

2. Compound according to claim 1 of the general formula (II):

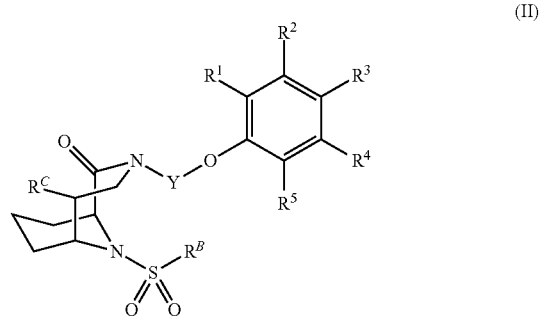

wherein Y, $R^B$, $R^C$ and $R^1$-$R^5$ have the meanings as defined in claim 1.

3. Compound according to claim 1 of the general formula (VII):

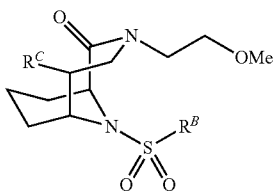

(VII)

wherein $R^B$ and $R^C$ have the meanings as defined in claim 1.

4. Compound selected from the group consisting of:
(1S,5S,6R)-5-acetyl-10-((3,5-dichlorophenyl)sulfonyl)-3-(2-methoxyethyl)-3,10-diazabicyclo[4.3.1]decan-2-one,
2-((1S,5S,6R)-10-((3,5-dichlorophenyl)sulfonyl)-3-(2-methoxyethyl)-2-oxo-3,10-diazabicyclo[4.3.1]decan-5-yl)acetaldehyde,
(1S,5S,6R)-10-((3,5-dichlorophenyl)sulfonyl)-5-(2-hydroxypropan-2-yl)-3-(2-methoxyethyl)-3,10-diazabicyclo[4.3.1]decan-2-one,
(1S,5S,6R)-10-((3,5-dichlorophenyl)sulfonyl)-5-((R)-1-hydroxyethyl)-3-(2-methoxyethyl)-3,10-diazabicyclo[4.3.1]decan-2-one,
(1S,5S,6R)-10-((3,5-dichlorophenyl)sulfonyl)-5-((S)-1-hydroxyethyl)-3-(2-methoxyethyl)-3,10-diazabicyclo[4.3.1]decan-2-one,
(1S,5S,6R)-10-((3,5-dichlorophenyl)sulfonyl)-5-(2-hydroxyethyl)-3-(2-methoxyethyl)-3,10-diazabicyclo[4.3.1]decan-2-one,
(1S,5S,6R)-10-((3,5-dichlorophenyl)sulfonyl)-3-(2-methoxyethyl)-2-oxo-3,10-diazabicyclo[4.3.1]decane-5-carbaldehyde,
(1S,5S,6R)-10-((3,5-dichlorophenyl)sulfonyl)-3-(2-methoxyethyl)-2-oxo-3,10-diazabicyclo[4.3.1]decane-5-carboxylic acid,
(1S,5S,6R)-10-((3,5-dichlorophenyl)sulfonyl)-3-(2-methoxyethyl)-2-oxo-3,10-diazabicyclo[4.3.1]decane-5-carboxamide,
(1S,5R,6R)-10-((3,5-dichlorophenyl)sulfonyl)-3-(2-methoxyethyl)-5-((methylamino)methyl)-3,10-diazabicyclo[4.3.1]decan-2-one,
(1S,5R,6R)-10-((3,5-dichlorophenyl)sulfonyl)-5-(hydroxymethyl)-3-(2-methoxyethyl)-3,10-diazabicyclo[4.3.1]decan-2-one,
(1S,5R,6R)-10-((3,5-dichlorophenyl)sulfonyl)-3-(2-methoxyethyl)-5-(methoxymethyl)-3,10-diazabicyclo[4.3.1]decan-2-one,
(1S,5S,6R)-10-((3,5-dichlorophenyl)sulfonyl)-5-ethyl-3-(2-methoxyethyl)-3,10-diazabicyclo[4.3.1]decan-2-one,
(1S,5R,6R)-10-((3,5-dichlorophenyl)sulfonyl)-3-(2-hydroxyethyl)-5-(hydroxymethyl)-3,10-diazabicyclo[4.3.1]decan-2-one,
(1S,5S,6R)-10-((3,5-dichlorophenyl)sulfonyl)-5-(1,2-dihydroxyethyl)-3-(2-(3,4-dimethoxyphenoxy)ethyl)-3,10-diazabicyclo[4.3.1]decan-2-one,
(1S,5S,6R)-10-((3,5-dichlorophenyl)sulfonyl)-5-(1,2-dihydroxyethyl)-3-(2-ethoxyethyl)-3,10-diazabicyclo[4.3.1]decan-2-one,
(1S,5S,6R)-5-acetyl-10-((3,5-dichlorophenyl)sulfonyl)-3-(2-(3,4-dimethoxyphenoxy)ethyl)-3,10-diazabicyclo[4.3.1]decan-2-one,
2-((1S,5S,6R)-10-((3,5-dichlorophenyl)sulfonyl)-3-(2-(3,4-dimethoxyphenoxy)ethyl)-2-oxo-3,10-diazabicyclo[4.3.1]decan-5-yl)acetaldehyde,
(1S,5S,6R)-10-((3,5-dichlorophenyl)sulfonyl)-3-(2-(3,4-dimethoxyphenoxy) ethyl)-5-(2-hydroxypropan-2-yl)-3,10-diazabicyclo[4.3.1]decan-2-one,
(1S,5S,6R)-10-((3,5-dichlorophenyl)sulfonyl)-3-(2-(3,4-dimethoxyphenoxy) ethyl)-5-(2-hydroxypropyl)-3,10-diazabicyclo[4.3.1]decan-2-one,
(1S,5S,6R)-10-((3,5-dichlorophenyl)sulfonyl)-3-(2-(3,4-dimethoxyphenoxy) ethyl)-5-(2-hydroxypropyl)-3,10-diazabicyclo[4.3.1]decan-2-one,
(1S,5S,6R)-10-((3,5-dichlorophenyl)sulfonyl)-3-(2-(3,4-dimethoxyphenoxy) ethyl)-5-((R)-1-hydroxyethyl)-3,10-diazabicyclo[4.3.1]decan-2-one,
(1S,5S,6R)-10-((3,5-dichlorophenyl)sulfonyl)-3-(2-(3,4-dimethoxyphenoxy) ethyl)-5-((R)-1-hydroxyethyl)-3,10-diazabicyclo[4.3.1]decan-2-one,
(1S,5S,6R)-10-((3,5-dichlorophenyl)sulfonyl)-3-(2-(3,4-dimethoxyphenoxy) ethyl)-5-(2-hydroxyethyl)-3,10-diazabicyclo[4.3.1]decan-2-one,
(1S,5S,6R)-10-((3,5-dichlorophenyl)sulfonyl)-5-hydroxy-3,10-diazabicyclo-[4.3.1]decan-2-one,
(1S,5R,6R)-5-amino-10-((3,5-dichlorophenyl)sulfonyl)-3,10-diazabicyclo-[4.3.1]decan-2-one,
(1S,5S,6R)-10-((3,5-dichlorophenyl)sulfonyl)-5-methoxy-3-methyl-3,10-diazabicyclo[4.3.1]decan-2-one,
(1S,5R,6R)-10-((3,5-dichlorophenyl)sulfonyl)-5-hydroxy-3,10-diazabicyclo-[4.3.1]decan-2-one,
(1S,5S,6R)-10-((3,5-dichlorophenyl)sulfonyl)-5-(2-methoxyethoxy)-3-(2-methoxy-ethyl)-3,10-diazabicyclo[4.3.1]decan-2-one,
(1S,5S,6R)-10-((3,5-dichlorophenyl)sulfonyl)-5-(methoxymethoxy)-3,10-diaza-bicyclo[4.3.1]decan-2-one,
(1S,5S,6R)-10-((3,5-dichlorophenyl)sulfonyl)-3-(2-(3,4-dimethoxyphenoxy) ethyl)-5-hydroxy-3,10-diazabicyclo[4.3.1]decan-2-one,
(1S,5R,6R)-10-((3,5-dichlorophenyl)sulfonyl)-5-(hydroxymethyl)-3-(3-hydroxypropyl)-3,10-diazabicyclo[4.3.1]decan-2-one,
(1S,5R,6R)-10-((3,5-dichlorophenyl)sulfonyl)-5-(hydroxymethyl)-3-(3-methoxypropyl)-3,10-diazabicyclo[4.3.1]decan-2-one,
(1S,5R,6R)-10-((3,5-dichlorophenyl)sulfonyl)-5-(hydroxymethyl)-3-(4-methoxybutyl)-3,10-diazabicyclo[4.3.1]decan-2-one, and
(1S,5R,6R)-10-((3,5-dichlorophenyl)sulfonyl)-5-(hydroxymethyl)-3-(pyridin-2-ylmethyl)-3,10-diazabicyclo[4.3.1]decan-2-one,
(1S,5R,6R)-10-((3,5-dichlorophenyl)sulfonyl)-5-ethyl-3-(pyridin-2-ylmethyl)-3,10-diazabicyclo[4.3.1]decan-2-one,
(1S,5S,6R)-10-((3,5-dichlorophenyl)sulfonyl)-5-((dimethylamino)methyl)-3-(pyridin-2-ylmethyl)-3,10-diazabicyclo[4.3.1]decan-2-one,
(1S,5S,6R)-10-((3,5-dichlorophenyl)sulfonyl)-5-(difluoromethyl)-3-(pyridin-2-ylmethyl)-3,10-diazabicyclo[4.3.1]decan-2-one,
(1S,5S,6R)-10-((3,5-dichlorophenyl)sulfonyl)-5-(fluoromethyl)-3-(pyridin-2-ylmethyl)-3,10-diazabicyclo[4.3.1]decan-2-one,
(1S,5R,6R)-10-((3,5-dichlorophenyl)sulfonyl)-5-(methoxymethyl)-3-(pyridin-2-ylmethyl)-3,10-diazabicyclo[4.3.1]decan-2-one,
(1S,5S,6R)-10-((3,5-dichlorophenyl)sulfonyl)-5-(ethoxymethyl)-3-(pyridin-2-ylmethyl)-3,10-diazabicyclo[4.3.1]decan-2-one, (1S,5S,6R)-10-((3-fluorophenyl)sulfonyl)-5-(methoxymethyl)-3-(prop-2-yn-1-yl)-3,10-diazabicyclo[4.3.1]decan-2-one, (1S,5S,6R)-10-((3,5-dibromophenyl)sulfonyl)-5-(methoxymethyl)-3-(prop-2-yn-1-yl)-3,10-diazabicyclo[4.3.1]decan-2-one, 3-(((1S,5S,6R)-5-(methoxymethyl)-2-oxo-3-(prop-2-yn-1-yl)-3,10-diazabicyclo[4.3.1]decan-10-yl)sulfonyl)benzamide, 3-bromo-5-(((1S,5S,6R)-5-(methoxymethyl)-2-oxo-3-(prop-2-yn-1-yl)-3,10-diazabicyclo[4.3.1]decan-10-yl)sulfonyl)benzamide, 3-chloro-5-(((1S,5S,6R)-5-(methoxymethyl)-2-oxo-3-(prop-2-yn-1-yl)-3,10-diazabicyclo[4.3.1]decan-10-yl)sulfonyl)benzamide, N-(2-bromo-4-(((1S,5S,6R)-5-(methoxymethyl)-2-oxo-3-(prop-2-yn-1-yl)-3,10-diazabicyclo[4.3.1]decan-10-yl)sulfonyl)phenyl)acetamide, N-(2-chloro-4-(((1S,5S,6R)-5-(methoxymethyl)-2-oxo-3-(prop-2-yn-1-yl)-3,10-diazabicyclo[4.3.1]decan-10-yl)sulfonyl)phenyl)acetamide, N-(2,6-dichloro-4-(((1S,5S,6R)-5-(methoxymethyl)-2-oxo-3-(prop-2-yn-1-yl)-3,10-diazabicyclo[4.3.1]decan-10-yl)sulfonyl)phenyl)acetamido, methyl 3-(((1S,5S,6R)-5-(methoxymethyl)-2-oxo-3-(prop-2-yn-1-yl)-3,10-diazabicyclo[4.3.1]decan-10-yl)sulfonyl)benzoate, methyl 3-bromo-5-(((1S,5S,6R)-5-(methoxymethyl)-2-oxo-3-(prop-2-yn-1-yl)-3,10-diazabicyclo[4.3.1]decan-10-yl)sulfonyl)benzoate, methyl 3-chloro-5-(((1S,5S,6R)-5-(methoxymethyl)-2-oxo-3-(prop-2-yn-1-yl)-3,10-diazabicyclo[4.3.1]decan-10-yl)sulfonyl)benzoate, 1S,5S,6R)-5-(methoxymethyl)-3-(prop-2-yn-1-yl)-10-(pyridin-3-ylsulfonyl)-3,10-diazabicyclo[4.3.1]decan-2-one, (1S,5S,6R)-5-(methoxymethyl)-10-((6-phenylpyridin-3-yl)sulfonyl)-3-(prop-2-yn-1-yl)-3,10-diazabicyclo[4.3.1]decan-2-one, (1S,5S,6R)-5-(methoxymethyl)-3-(prop-2-yn-1-yl)-10-((4-(pyrimidin-2-yl)phenyl)sulfonyl)-3,10-diazabicyclo[4.3.1]decan-2-one, (1S,5S,6R)-10-((1H-benzo[d]imidazol-2-yl)sulfonyl)-5-(methoxymethyl)-3-(prop-2-yn-1-yl)-3,10-diazabicyclo[4.3.1]decan-2-one, (1S,5S,6R)-3-((1H-1,2,3-triazol-5-yl)methyl)-10-((3-fluorophenyl)sulfonyl)-5-(methoxymethyl)-3,10-diazabicyclo[4.3.1]decan-2-one, 1S,5S,6R)-3-((1H-1,2,3-triazol-5-yl)methyl)-10-((3,5-dibromophenyl)-sulfonyl)-5-(methoxymethyl)-3,10-diazabicyclo[4.3.1]decan-2-one, 3-(((1S,5S,6R)-3-((1H-1,2,3-triazol-5-yl)methyl)-5-(methoxymethyl)-2-oxo-3,10-diazabicyclo[4.3.1]decan-10-yl)sulfonyl)benzamide, 3-(((1S,5S,6R)-3-((1H-1,2,3-triazol-5-yl)methyl)-5-(methoxymethyl)-2-oxo-3,10-diazabicyclo[4.3.1]decan-10-yl)sulfonyl)-5-bromobenzamide, 3-(((1S,5S,6R)-3-((1H-1,2,3-triazol-5-yl)methyl)-5-(methoxymethyl)-2-oxo-3,10-diazabicyclo[4.3.1]decan-10-yl)sulfonyl)-5-chlorobenzamide, N-(4-(((1S,5S,6R)-3-((1H-1,2,3-triazol-5-yl)methyl)-5-(methoxymethyl)-2-oxo-3,10-diazabicyclo[4.3.1]decan-10-yl)sulfonyl)-2-bromophenyl)acetamide, N-(4-(((1S,5S,6R)-3-((1H-1,2,3-triazol-5-yl)methyl)-5-(methoxymethyl)-2-oxo-3,10-diazabicyclo[4.3.1]decan-10-yl)sulfonyl)-2-chlorophenyl)acetamide, N-(4-(((1S,5S,6R)-3-((1H-1,2,3-triazol-5-yl)methyl)-5-(methoxymethyl)-2-oxo-3,10-diazabicyclo[4.3.1]decan-10-yl)sulfonyl)-2,6-dichlorophenyl)acetamide, (1S,5S,6R)-3-((1H-1,2,3-triazol-5-yl)methyl)-5-(methoxymethyl)-10-(pyridin-3-ylsulfonyl)-3,10-diazabicyclo[4.3.1]decan-2-one, (1S,5S,6R)-3-((1H-1,2,3-triazol-5-yl)methyl)-5-(methoxymethyl)-10-((6-phenylpyridin-3-yl)sulfonyl)-3,10-diazabicyclo[4.3.1]decan-2-one, (1S,5S,6R)-3-((1H-1,2,3-triazol-5-yl)methyl)-5-(methoxymethyl)-10-((4-(pyrimidin-2-yl)phenyl)sulfonyl)-3,10-diazabicyclo[4.3.1]decan-2-one, (1S,5S,6R)-3-((1H-1,2,3-triazol-5-yl)methyl)-10-((1H-benzo[d]imidazol-2-yl)sulfonyl)-5-(methoxymethyl)-3,10-diazabicyclo[4.3.1]decan-2-one, (1S,5R,6R)-10-((3-fluorophenyl)sulfonyl)-5-(methoxymethyl)-3-((1-phenyl-1H-1,2,3-triazol-5-yl)methyl)-3,10-diazabicyclo[4.3.1]decan-2-one, (1S,5S,6R)-3-((1-benzyl-1H-1,2,3-triazol-5-yl)methyl)-10-((3-fluorophenyl)-sulfonyl)-5-(methoxymethyl)-3,10-diazabicyclo[4.3.1]decan-2-one, (1S,5S,6R)-3-((1-benzoyl-1H-1,2,3-triazol-5-yl)methyl)-10-((3-fluorophenyl)-sulfonyl)-5-(methoxymethyl)-3,10-diazabicyclo[4.3.1]decan-2-one, and (1S,5S,6R)-10-((3-fluorophenyl)sulfonyl)-5-(methoxymethyl)-3-((1-(phenylsulfonyl)-1H-1,2,3-triazol-5-yl)methyl)-3,10-diazabicyclo[4.3.1]decan-2-one.

5. A method for inhibiting FK506-binding proteins comprising contacting a cell with an effective amount of a compound according to claim 1.

6. The method according to claim 5, wherein the FK506-binding proteins are FK506-binding protein 51 and/or FK506-binding protein 52.

7. A method for stimulating neurite growth comprising administering to a patient in need thereof a dose-effective amount of a compound according to claim 1.

8. Pharmaceutical composition comprising at least one compound according to claim 1 together with at least one pharmaceutically acceptable carrier, solvent or excipient or together with at least one pharmaceutically acceptable carrier, solvent or excipient and at least one active agent selected from the group consisting of an anti-depressant and other psychotropic drugs.

9. Pharmaceutical composition according to claim 8, wherein the anti-depressant is selected from amitriptyline, amioxide clomipramine, doxepine, duloxetine, imipramine trimipramine, mirtazapine, reboxetine, citaloprame, fluoxetine, moclobemide and sertraline.

10. Method for preparation of compound of the general formula (I) comprising the following steps:
(a) providing an intermediate compound of formula (I-A1)

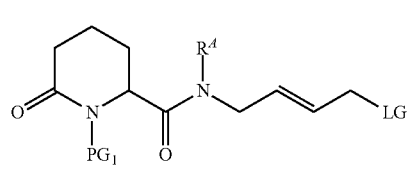

(I-A1)

wherein $R^A$ has the meanings as defined in claim 1, LG refers to a leaving group, and $PG_1$ refers to a protecting group for amine;
(b) performing a cyclization reaction and deprotecting $PG_1$ to yield compound of formula (I-B1)

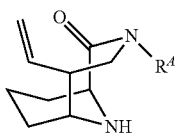
(I-B1)

(c) introducing a moiety —SO$_2$—R$^B$ to yield compound of formula (I-C)

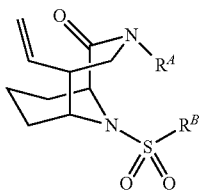
(I-C)

(d) transforming the vinyl group of compound (I-C) into the substituent R$^C$ to yield compound of the formula (I)

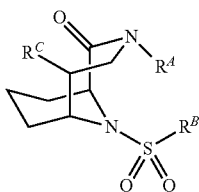
(I)

wherein R$^A$, R$^B$ and R$^C$ have the meanings as defined in claim 1.

11. Method for preparation of compound of the general formula (I) comprising the following steps:
(a) providing an intermediate compound of the formula (I-A2)

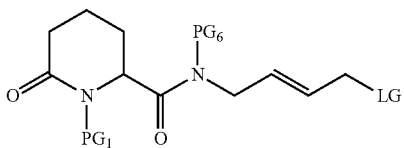
(I-A2)

wherein R$^A$ has the meanings as defined herein, LG refers to a leaving group, and PG$_1$ and PG$_6$ refer to protecting groups for amines;
(b) performing a cyclization reaction and deprotecting PG$_1$ to yield compound of the formula (I-B1)

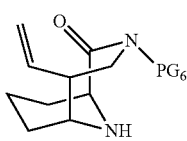
(I-B2)

(c) introducing the moiety —SO$_2$—R$^B$ to yield compound of the formula (I-B3)

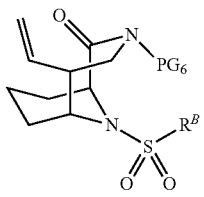
(I-B3)

wherein R$^B$ has the meanings as defined herein;
(d) deprotecting PG$_6$ and introducing the moiety R$^A$ to yield compound of the formula (I-C)

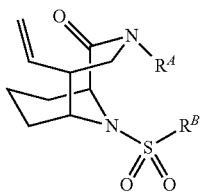
(I-C)

(e) transforming the vinyl group of compound (I-C) into the substituent R$^C$ to yield compound of the formula (I)

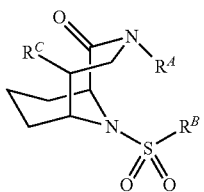
(I)

wherein R$^A$, R$^B$ and R$^C$ have the meanings as defined herein.

12. Method for preparation of compound of the general formula (I) comprising the following steps:
(a) providing an intermediate compound of formula (I-E)

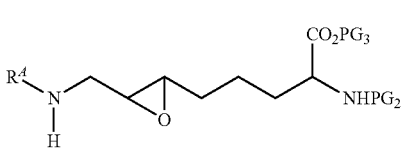
(I-E)

wherein R$^A$ has the meanings as defined in claim 1, PG$_2$ refers to a protecting group for amine, and PG$_3$ refers to a protecting group for carboxylic acid;
(b) deprotecting PG$_2$, performing a piperidine ring formation reaction and introducing PG$_4$ to yield compound of formula (I-F)

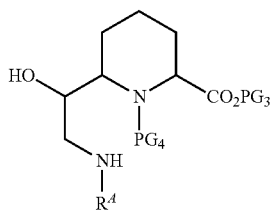

(I-F)

wherein PG$_4$ refers to a protecting group for amine;
(c) introducing PG$_5$, deprotecting PG$_3$ and performing an amide coupling reaction to yield compound of formula (I-G)

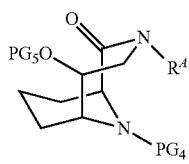

(I-G)

wherein PG$_5$ refers to a protecting group for hydroxyl group;
(d) deprotecting PG$_4$ and introducing a moiety —SO$_2$—R$^B$ to yield compound of formula (I-H)

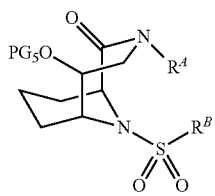

(I-H)

wherein R$^B$ has the meanings as defined in claim 1;

(e) transforming a hydroxyl group obtained by deprotecting PG$_5$ to yield compound of the formula (I)

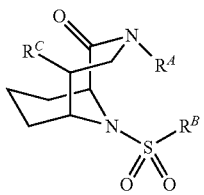

(I)

wherein R$^A$, R$^B$ and R$^C$ have the meanings as defined in claim 1;

the protecting groups PG$_1$-PG$_4$, and PG$_6$ for amines represent independently of each other carbobenzyloxy, p-methoxybenzyl carbonyl, tert-butyloxycarbonyl, 9-fluorenylmethyloxycarbonyl, allyloxycarbonyl, 2,2,2-trichlorethoxycarbonyl, trifluoroacetyl, 2-(trimethylsilyl)ethoxycarbonyl, p-methoxy-benzyl or phthalimide;

the protecting group PG$_3$ for carboxylic acid selected from the group consisting of methyl, ethyl, isopropyl, tert-butyl, allyl, and benzyl; and the protecting group PG$_5$ for hydroxyl group is selected from the group consisting of trimethylsilyl, triethylsilyl, tert-butyldimethylsilyl, tert-butyldiphenylsilyl, allyl, benzyl, tert-butyl, methoxylmethyl, methoxyethyl, tetrahydropyranyl, acetyl, benzoyl and pivalic.

* * * * *